(12) United States Patent
Rubbert et al.

(10) Patent No.: US 8,121,718 B2
(45) Date of Patent: Feb. 21, 2012

(54) INTERACTIVE ORTHODONTIC CARE SYSTEM BASED ON INTRA-ORAL SCANNING OF TEETH

(75) Inventors: Rüdger Rubbert, Berlin (DE); Thomas Weise, Berlin (DE); Friedrich Riemeier, Berlin (DE); Rohit Sachdeva, Plano, TX (US); Werner Butscher, Berlin (DE); Peer Sporbert, Berlin (DE); Hans Imgrund, Berlin (DE); Lutz Pfeil, Berlin (DE); Hans-Florian Geerdes, Berlin (DE); Dimitrij Kouzian, Berlin (DE); Mario Leichner, Hohen Neuendorf (DE); Stephan Maetzel, Berlin (DE); Peter See, Berlin (DE); Jens Troeger, Berlin (DE)

(73) Assignee: Orametrix, Inc., Richardson, TX (US)

( * ) Notice: Subject to any disclaimer, the term of this patent is extended or adjusted under 35 U.S.C. 154(b) by 0 days.

(21) Appl. No.: 12/510,921

(22) Filed: Jul. 28, 2009

(65) Prior Publication Data

US 2009/0291417 A1 Nov. 26, 2009

Related U.S. Application Data

(60) Continuation of application No. 11/285,629, filed on Nov. 22, 2005, now Pat. No. 7,590,462, which is a continuation of application No. 10/951,119, filed on Sep. 27, 2004, now Pat. No. 7,013,191, which is a division of application No. 10/280,758, filed on Oct. 24, 2002, now Pat. No. 7,029,275, which is a division of application No. 09/835,039, filed on Apr. 13, 2001, now Pat. No. 6,648,640, and a continuation-in-part of application No. 09/560,643, filed on Apr. 28, 2000, now Pat. No. 6,464,496, and a continuation-in-part of application No. 09/560,131, filed on Apr. 28, 2000, now Pat. No. 6,744,914, and a continuation-in-part of (Continued)

(51) Int. Cl.
*G06F 19/00* (2011.01)
*G06F 17/50* (2006.01)
(52) U.S. Cl. ............... 700/98; 703/1; 703/11; 433/214
(58) Field of Classification Search ............ 700/97, 700/98, 117; 433/3, 24, 213, 214, 215; 703/1, 703/6, 11
See application file for complete search history.

(56) References Cited

U.S. PATENT DOCUMENTS 6,227,850 B1 * 5/2001 Chishti et al. .................. 433/24

(Continued)

*Primary Examiner* — Charles Kasenge
(74) *Attorney, Agent, or Firm* — McDonnell Boehnen Hulbert & Berghoff LLP

(57) ABSTRACT

Interactive, computer based orthodontist treatment planning, appliance design and appliance manufacturing is described. A scanner is described which acquires images of the dentition which are converted to three-dimensional frames of data. The data from the several frames are registered to each other to provide a complete three-dimensional virtual model of the dentition. Individual tooth objects are obtained from the virtual model. A computer-interactive software program provides for treatment planning, diagnosis and appliance from the virtual tooth models. A desired occlusion for the patient is obtained from the treatment planning software. The virtual model of the desired occlusion and the virtual model of the original dentition provide a base of information for custom manufacture of an orthodontic appliance. A variety of possible appliance and appliance manufacturing systems are contemplated, including customized archwires and customized devices for placement of off-the shelf brackets on the archwires, and removable orthodontic appliances.

14 Claims, 91 Drawing Sheets

Related U.S. Application Data application No. 09/560,132, filed on Apr. 28, 2000, now Pat. No. 6,771,809, and a continuation-in-part of application No. 09/560,583, filed on Apr. 28, 2000, now Pat. No. 6,738,508, and a continuation-in-part of application No. 09/560,645, filed on Apr. 28, 2000, now Pat. No. 6,728,423, and a continuation-in-part of application No. 09/560,644, filed on Apr. 28, 2000, now Pat. No. 6,413,084, and a continuation-in-part of application No. 09/560,133, filed on Apr. 28, 2000, now Pat. No. 6,744,932, and a continuation-in-part of application No. 09/560,129, filed on Apr. 28, 2000, now Pat. No. 6,318,995, and a continuation-in-part of application No. 09/560,642, filed on Apr. 28, 2000, now Pat. No. 6,688,885, and a continuation-in-part of application No. 09/560,641, filed on Apr. 28, 2000, now Pat. No. 6,512,994, and a continuation-in-part of application No. 09/560,134, filed on Apr. 28, 2000, now Pat. No. 6,851,949, and a continuation-in-part of application No. 09/560,640, filed on Apr. 28, 2000, now abandoned, and a continuation-in-part of application No. 09/560,584, filed on Apr. 28, 2000, now Pat. No. 7,068,836, and a continuation-in-part of application No. 09/560,128, filed on Apr. 28, 2000, now abandoned, and a continuation-in-part of application No. 09/560,647, filed on Apr. 28, 2000, now abandoned, and a continuation-in-part of application No. 09/560,646, filed on Apr. 28, 2000, now abandoned, and a continuation-in-part of application No. 09/560,130, filed on Apr. 28, 2000, now Pat. No. 6,736,638, and a continuation-in-part of application No. 09/560,127, filed on Apr. 28, 2000, now Pat. No. 6,554,613, and a continuation-in-part of application No. 09/552,189, filed on Apr. 19, 2000, now abandoned, and a continuation-in-part of application No. 09/552,190, filed on Apr. 19, 2000, now abandoned, and a continuation-in-part of application No. 09/451,637, filed on Nov. 30, 1999, now Pat. No. 6,471,512, and a continuation-in-part of application No. 09/451,564, filed on Nov. 30, 1999, now Pat. No. 6,350,120, and a continuation-in-part of application No. 09/452,038, filed on Nov. 30, 1999, now Pat. No. 6,315,553, and a continuation-in-part of application No. 09/452,033, filed on Nov. 30, 1999, now Pat. No. 6,587,828, and a continuation-in-part of application No. 09/452,034, filed on Nov. 30, 1999, now abandoned, and a continuation-in-part of application No. 09/452,031, filed on Nov. 30, 1999, now Pat. No. 6,431,870, and a continuation-in-part of application No. 09/451,560, filed on Nov. 30, 1999, now Pat. No. 6,540,512, and a continuation-in-part of application No. 09/451,609, filed on Nov. 30, 1999, now Pat. No. 6,250,918, and a continuation-in-part of application No. 09/616,093, filed on Jul. 13, 2000, now Pat. No. 6,532,299.

(56) References Cited

U.S. PATENT DOCUMENTS

| | | | |
|---|---|---|---|
| 6,334,853 B1 * | 1/2002 | Kopelman et al. | 433/214 |
| 6,457,972 B1 * | 10/2002 | Chishti et al. | 433/24 |
| 6,783,360 B2 * | 8/2004 | Chishti | 433/6 |

* cited by examiner

3-DIMENSIONAL IMAGE CAPTURE
(PER FRAME)

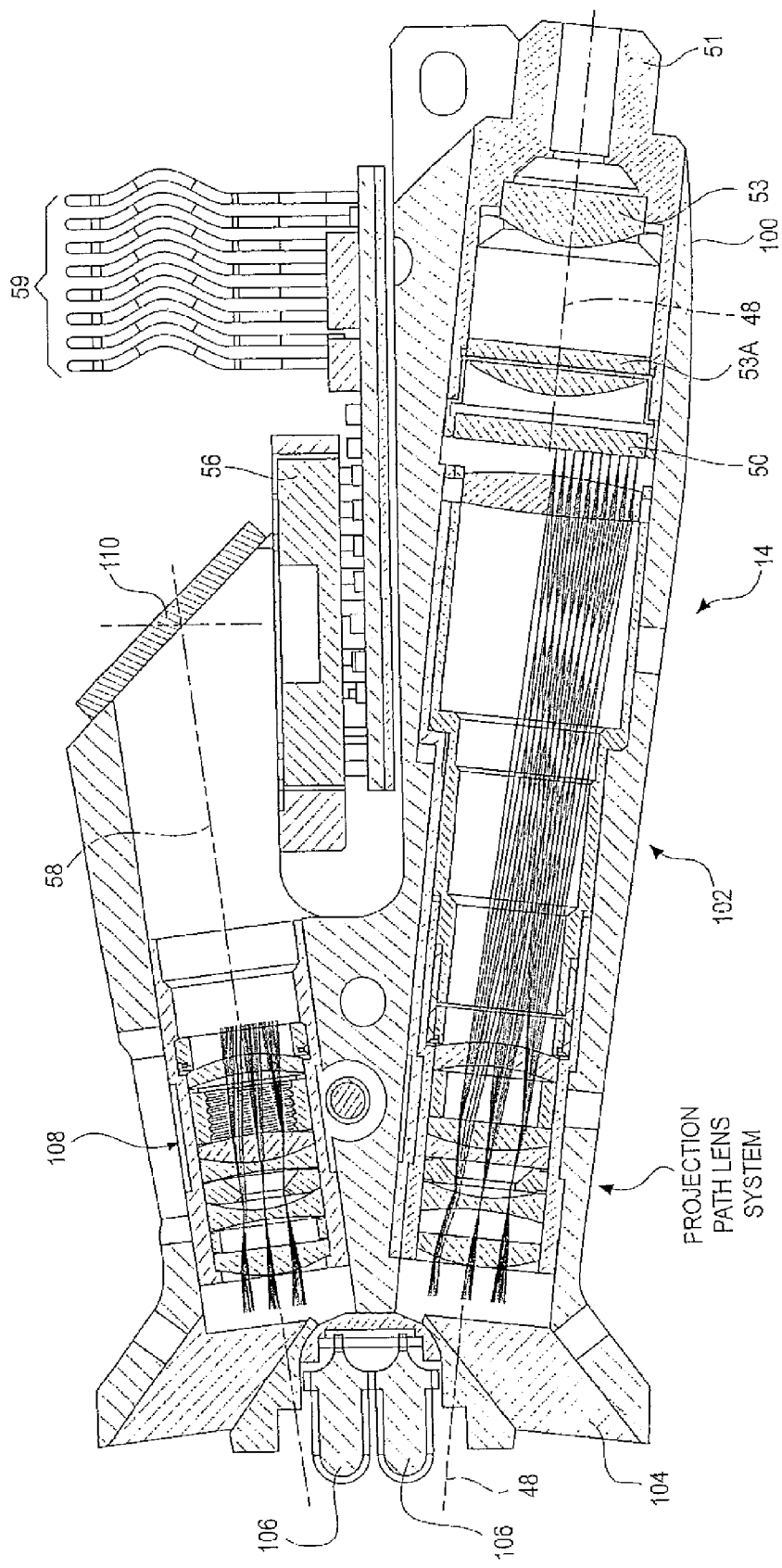

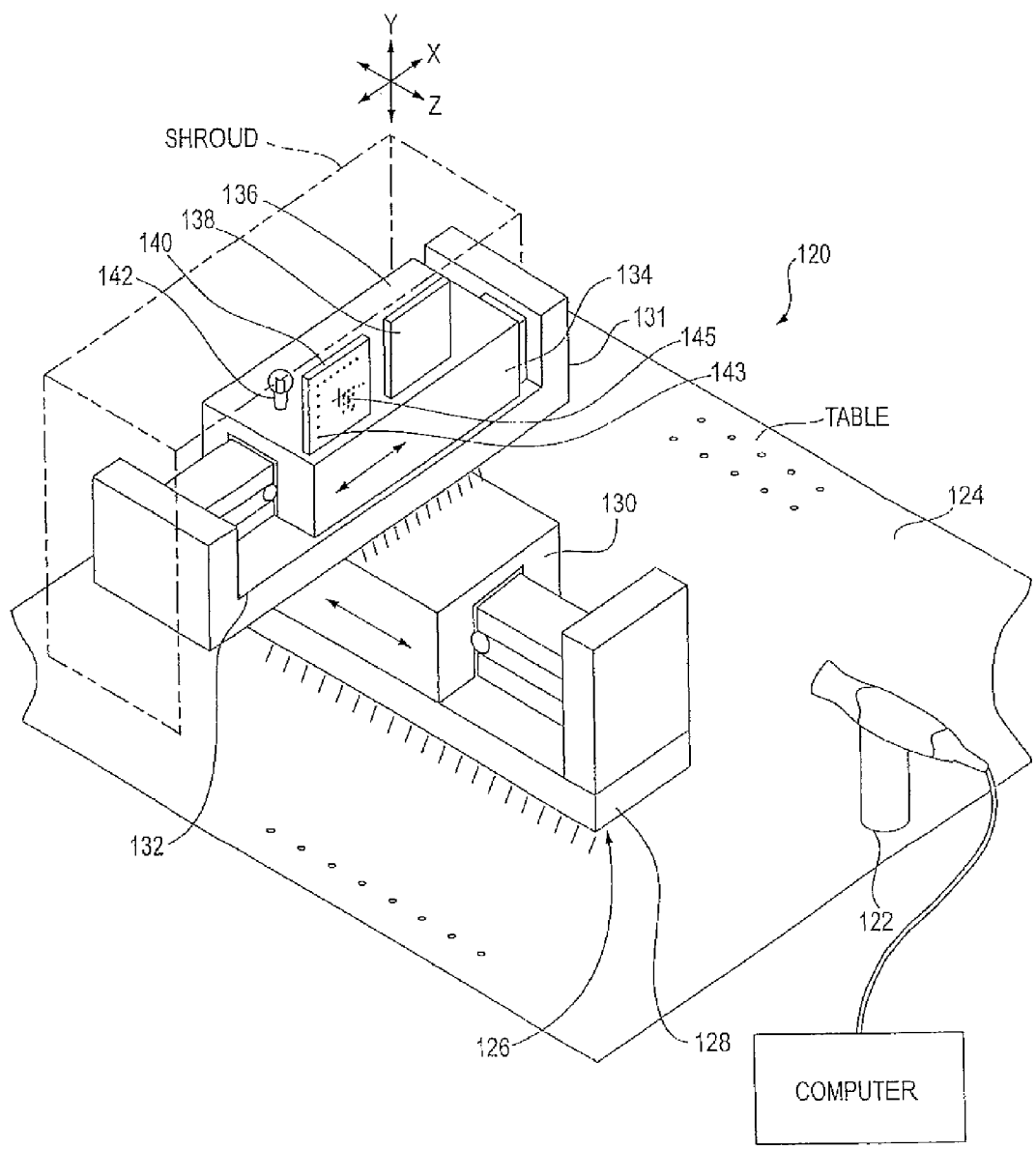

PIXEL COORDINATES FOR PORTIONS OF THE PATTERN ASSIGNED TO A CERTAIN Z-LEVEL

FIG. 24

CCD$_X$, CCD$_Y$ = PIXEL #, IN SUBPIXEL RESOLUTION

CALIBRATION TABLE #1 (BEFORE)

| | | LINE 1 | | | | | LINE 2 | | | | | LINE N | | |
|---|---|---|---|---|---|---|---|---|---|---|---|---|---|---|
| | | ROW 1 | ROW 2 | ROW 3 | ROW 4 | ... | ROW M | ROW 1 | ROW 2 | ROW 3 | ROW 4 | ... | ROW 1 | ROW 2 | ... | ROW M |
| $z_1$ | CCD$_X$ | 1.0 | 1.1 | 1.5 | 2.1 | | | 27.1 | 29.5 | 30.2 | 37.1 | | | | | |
| | MM DIST. | | | | | | | | | | | | | | | |
| | CCD$_Y$ | 10.2 | 20.4 | 32.8 | 44.5 | | | 11.5 | 21.6 | 36.2 | 44 | | | | | |
| | MM DIST. | | | | | | | | | | | | | | | |
| $z_2$ | CCD$_X$ | 3.9 | 4.5 | 6.8 | 12.2 | | | 34.0 | 41.1 | 43.0 | 46 | | | | | |
| | MM DIST. | | | | | | | | | | | | | | | |
| | CCD$_Y$ | 12.1 | 21.5 | 30.4 | 46.3 | | | 13.2 | 21.8 | 31.0 | 48.2 | | | | | |
| | MM DIST. | | | | | | | | | | | | | | | |

FIG. 25

CALIBRATION TABLE #2

QUADRANT I

|  |  | (0,0) | (1,0) | (2,0) | (3,0) | ... | ROW 0 (Q/2 − ΔQ,0) | ... | (Q/210) | ROW 1 (0,1) | (1,1) | (2,1) | ... | (Q,P) | ... | ROW + P/2 (0, P/2) | (1, P/2) | ... | (Q/2, P/2) |
|---|---|---|---|---|---|---|---|---|---|---|---|---|---|---|---|---|---|---|---|
| $z_1$ | CCDx | 640.1 | 700.2 | 760.6 | 820.5 | ... | ... | ... | — | 640.1 | 700.2 | ... | ... | ... | ... | ... | ... | ... | 1,279.5 |
|  | CCDy | 640.1 | 640.1 | 640.3 | 640.4 | ... | ... | ... | — | | 701.2 | 701.5 | ... | ... | ... | ... | ... | ... | 1,279.4 |
| $z_2$ | CCDx | 640.2 | 680.3 | 741.2 | 801.6 | ... | ... | ... | 1,279.5 | | | 681.2 | ... | ... | ... | ... | ... | ... | 1,256.4 |
|  | CCDy | 640.2 | 640.3 | 640.1 | 640.1 | ... | ... | ... | 640.2 | | | 680.9 | ... | ... | ... | ... | ... | ... | 1,251.5 |

QUADRANT II

|  |  | (−1,0) | (−2,0) | (−3,0) | (−4, 0) | ... | ROW 0 (−Q/2 − ΔQ,0) | ... | (−Q/210) | ROW 1 (−1,1) | (−2,1) | (−3,1) | ... | ... | ... | RCW +P/2 (−1, P/2) | (−2, P/2) | ... | (−Q/2, P/2) |
|---|---|---|---|---|---|---|---|---|---|---|---|---|---|---|---|---|---|---|---|
| $z_1$ | CCDx | | | | | | | | | | | | | | | | | | |
|  | CCDy | | | | | | | | | | | | | | | | | | |
| $z_2$ | CCDx | | | | | | | | | | | | | | | | | | |
|  | CCDy | | | | | | | | | | | | | | | | | | |

QUADRANT III
...

QUADRANT IV
...

|  |  | (−1,−1) | (−2,−1) | ... |
|---|---|---|---|---|
| $z_1$ | CCDx | — | — | |
|  | CCDy | — | — | |
| $z_2$ | CCDx | — | — | |
|  | CCDy | — | — | |

|  |  | (0,−1) | (1,−1) | ... |
|---|---|---|---|---|
| $z_1$ | CCDx | — | — | |
|  | CCDy | — | — | |
| $z_2$ | CCDx | — | — | |
|  | CCDy | — | — | |

FIG. 26

CCD$_X$, CCD$_Y$ = PIXEL #, IN SUBPIXEL RESOLUTION

CALIBRATION TABLE #1 (AFTER)

| PATTERN | LINE 1 | | | | | | LINE 2 | | | | | | LINE N | | | |
|---|---|---|---|---|---|---|---|---|---|---|---|---|---|---|---|---|
| | ROW 1 | ROW 2 | ROW 3 | ROW 4 | ... | ROW M | ROW 1 | ROW 2 | ROW 3 | ROW 4 | ... | ROW M | ROW 1 | ROW 2 | ... | ROW M |
| $z_1$ CCD$_X$ | 1.0 | 1.1 | 1.5 | 2.1 | | | 27.1 | 29.5 | 30.2 | 37.1 | | | | | | |
| MM DIST. | | | | | | | | | | | | | | | | |
| CCD$_Y$ | 10.2 | 20.4 | 32.8 | 44.5 | | | 11.5 | 21.6 | 36.2 | 44 | | | | | | |
| MM DIST. | | | | | | | | | -14.6 | | | | | | | |
| $z_2$ CCD$_X$ | 3.9 | 4.5 | 6.8 | 12.2 | | | 34.0 | 41.1 | 43.0 | 46 | | | | | | |
| MM DIST. | | | | | | | | | -14.4 | | | | | | | |
| CCD$_Y$ | 12.1 | 21.5 | 30.4 | 46.3 | | | 13.2 | 21.8 | 31.0 | 48.2 | | | | | | |
| MM DIST. | | | | | | | | | -14.8 | | | | | | | |
| | | | | | | | | | -15.8 | | | | | | | |

L = 1.0 mm

△ = POINTS OF FRAME i
+ = POINTS OF FRAME i + 1
○ = POINTS OF FRAME i + 2

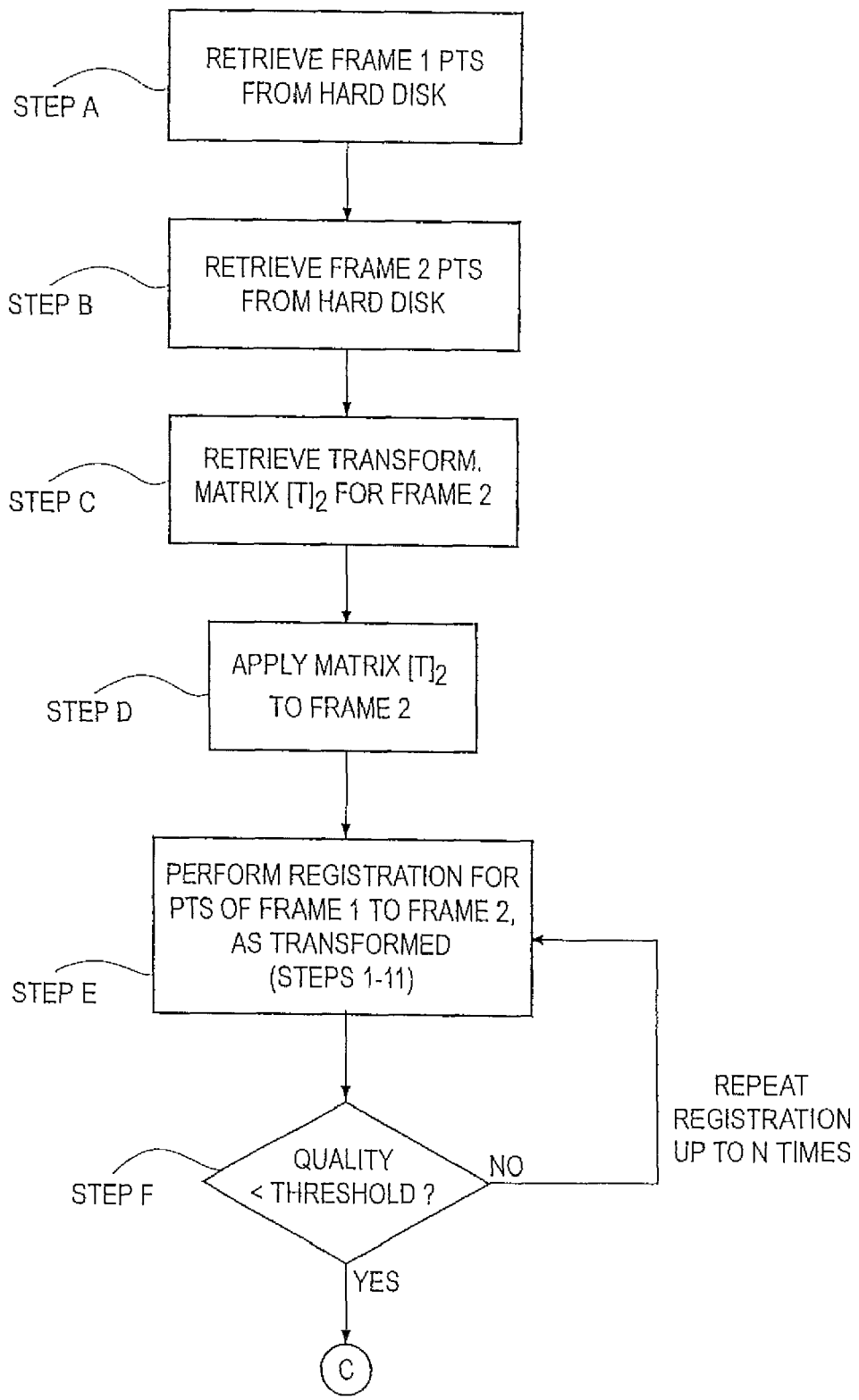

| | | | FRAME 1 | | FRAME 2 |
|---|---|---|---|---|---|
| 12 | F1 | | X | | X |
| 10 | F2 | 1 | Y | 1 | Y |
| 2 | F3 | | Z | | Z |
| 3 | F4 | | X | | X |
| 9 | F5 | 2 | Y | 2 | Y |
| 6 | F6 | | Z | | Z |
| 1 | F7 | | X | | X |
| 7 | F8 | 3 | Y | 3 | Y |
| 13 | F9 | | Z | | Z |
| 11 | F10 | | X | | X |
| 4 | F11 | 4 | Y | 4 | Y |
| 5 | F12 | | Z | | Z |
| 8 | F13 | ... | ... | ... | ... |
| | | | X | | X |
| | | N | Y | N' | Y |
| | | | Z | | Z |

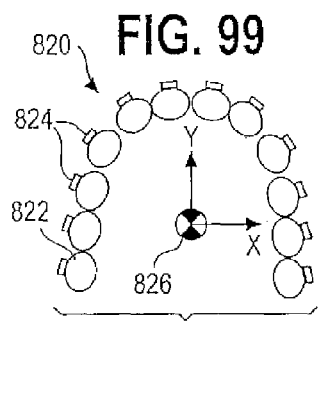
FIG. 99
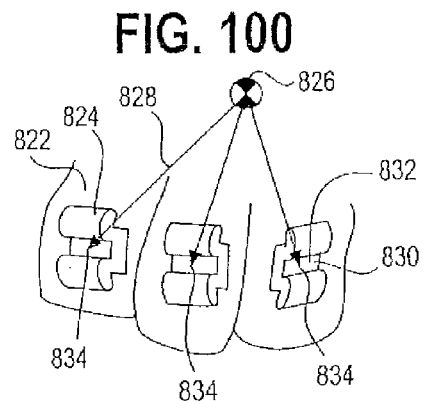
FIG. 100
FIG. 101
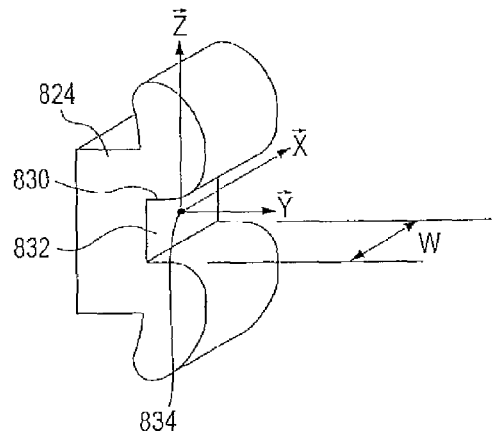
FIG. 102
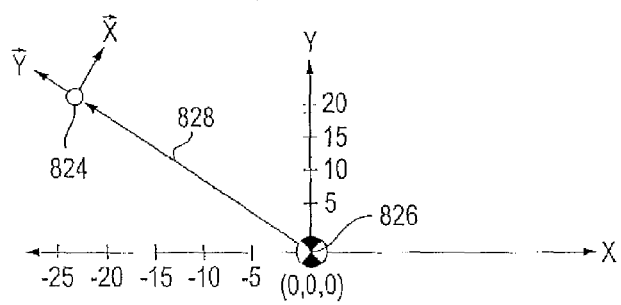
FIG. 103
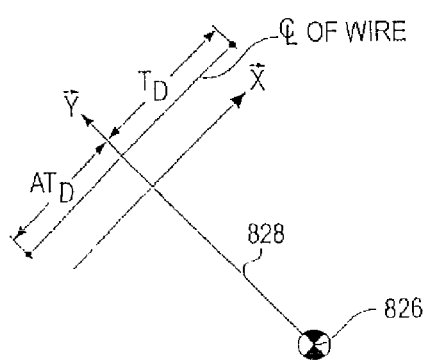

FIG. 104
$$\begin{bmatrix} 0.4 & -0.7 & 0 & -22 \\ 0.9 & 0.7 & 0 & 21 \\ 0 & 0.14 & 0 & 2 \\ 0 & 0 & 0 & 1 \end{bmatrix}$$
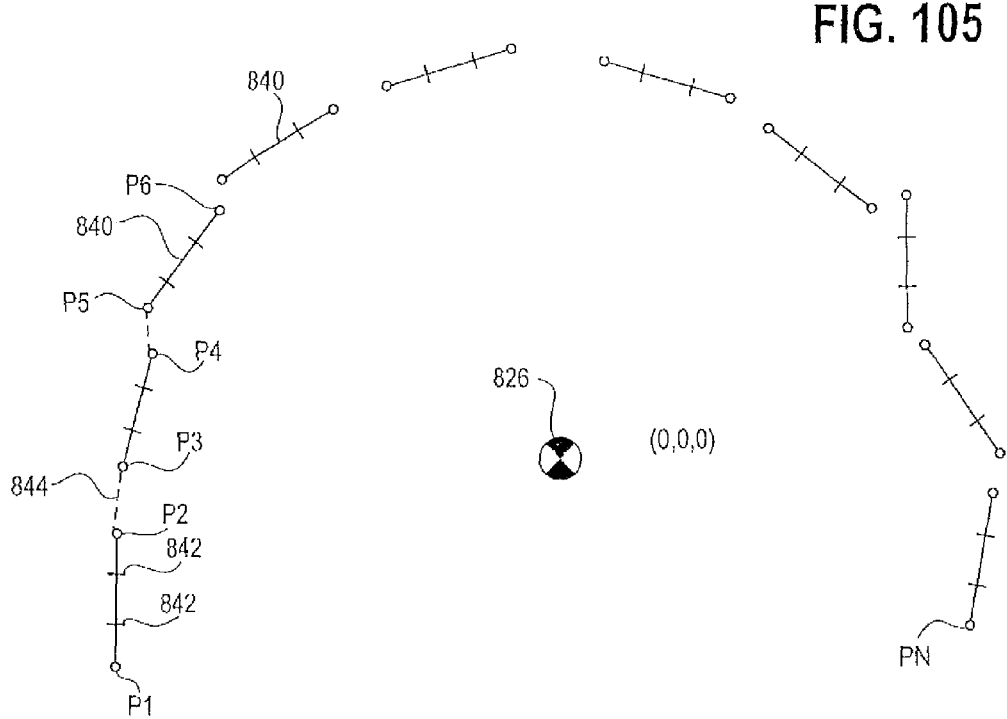
FIG. 105
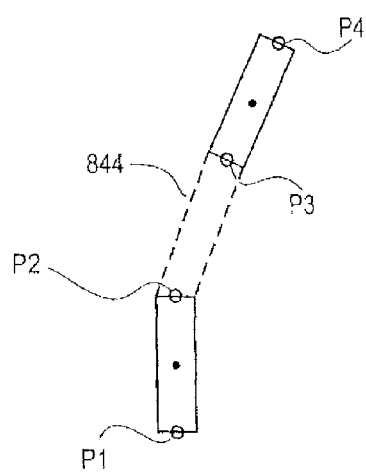
FIG. 106

1ST MOTION

2ND MOTION

INTERACTIVE ORTHODONTIC CARE SYSTEM BASED ON INTRA-ORAL SCANNING OF TEETH

CROSS-REFERENCE TO RELATED APPLICATIONS

This is a continuation application of application Ser. No. 11/285,629, filed Nov. 22, 2005, now U.S. Pat. No. 7,590,462, which is a continuation application of application Ser. No. 10/951,119, filed Sep. 27, 2004, now issued as U.S. Pat. No. 7,013,191, which is a divisional application of Ser. No. 10/280,758, filed Oct. 24, 2002, now issued as U.S. Pat. No. 7,029,275, which in turn is a divisional application of Ser. No. 09/835,039 filed Apr. 13, 2001, now issued as U.S. Pat. No. 6,648,640, a continuation-in-part application of the following U.S. patent applications:
Ser. No. 09/560,643 filed Apr. 28, 2000, now issued as U.S. Pat. No. 6,464,496;
Ser. No. 09/560,131 filed Apr. 28, 2000, now issued as U.S. Pat. No. 6,744,914;
Ser. No. 09/560,132 filed Apr. 28, 2000, now issued as U.S. Pat. No. 6,771,809;
Ser. No. 09/560,583 filed Apr. 28, 2000, now issued as U.S. Pat. No. 6,738,508;
Ser. No. 09/560,645 filed Apr. 28, 2000, now issued as U.S. Pat. No. 6,728,423;
Ser. No. 09/560,644 filed Apr. 28, 2000, now issued as U.S. Pat. No. 6,413,084;
Ser. No. 09/560,133 filed Apr. 28, 2000, now issued as U.S. Pat. No. 6,744,932;
Ser. No. 09/560,129 filed Apr. 28, 2000, now issued as U.S. Pat. No. 6,318,995;
Ser. No. 09/560,642 filed Apr. 28, 2000, now issued as U.S. Pat. No. 6,688,885;
Ser. No. 09/560,641 filed Apr. 28, 2000, now issued as U.S. Pat. No. 6,512,994;
Ser. No. 09/560,134 filed Apr. 28, 2000, now issued as U.S. Pat. No. 6,851,949;
Ser. No. 09/560,640 filed Apr. 28, 2000, abandoned;
Ser. No. 09/560,584 filed Apr. 28, 2000, now issued as U.S. Pat. No. 7,068,836;
Ser. No. 09/560,128 filed Apr. 28, 2000, abandoned;
Ser. No. 09/560,647 filed Apr. 28, 2000, abandoned;
Ser. No. 09/560,646 filed Apr. 28, 2000, abandoned;
Ser. No. 09/560,130 filed Apr. 28, 2000, now issued as U.S. Pat. No. 6,736,638;
Ser. No. 09/560,127 filed Apr. 28, 2000, now issued as U.S. Pat. No. 6,554,613;
Ser. No. 09/552,189 filed Apr. 19, 2000, abandoned;
Ser. No. 09/552,190 filed Apr. 19, 2000, abandoned;
Ser. No. 09/451,637 filed Nov. 30, 1999, now issued as U.S. Pat. No. 6,471,512;
Ser. No. 09/451,564 filed Nov. 30, 1999, now issued as U.S. Pat. No. 6,350,120;
Ser. No. 09/452,038 filed Nov. 30, 1999, now issued as U.S. Pat. No. 6,315,553;
Ser. No. 09/452,033 filed Nov. 30, 1999, now issued as U.S. Pat. No. 6,587,828;
Ser. No. 09/452,034 filed Nov. 30, 1999, abandoned;
Ser. No. 09/452,031 filed Nov. 30, 1999, now issued as U.S. Pat. No. 6,431,870;
Ser. No. 09/451,560 filed Nov. 30, 1999, now issued as U.S. Pat. No. 6,540,512;
Ser. No. 09/451,609 filed Nov. 30, 1999, now issued as U.S. Pat. No. 6,250,918;
Ser. No. 09/616,093, filed Jul. 13, 2000, now issued as U.S. Pat. No. 6,532,299.

The entire contents of each of the above-referenced patent applications is incorporated by reference herein.

NOTICE REGARDING COPYRIGHT

A portion of the disclosure of this patent document contains material which is subject to copyright protection. The copyright owner has no objection to the facsimile reproduction by anyone of the patent disclosure, at it appears in the Patent and Trademark Office files or records, but otherwise reserves all copyright rights whatsoever.

BACKGROUND OF THE INVENTION

A. Field of the Invention

This invention relates generally to the field of orthodontics. More particularly, the invention relates to a computerized, interactive method and associated system for orthodontic treatment. The system includes a hand-held optical scanner capturing 3-dimensional information of objects, interactive computer-based treatment planning using three-dimensional tooth objects and user specified simulation of tooth movement, and appliance manufacturing apparatus, including bending machines.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 5,431,562 to Andreiko et al. describes a computerized, appliance-driven approach to orthodontics. In this method, first certain shape information of teeth is acquired. A uniplanar target archform is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

The art has lacked an effective, computer-based interactive orthodontic treatment planning system that provides the necessary tools to allow the orthodontist to quickly and efficiently design a treatment plan for a patient. The art has also lacked a treatment planning system in which the orthodontist-derived parameters for the treatment can be translated into a design of an orthodontic appliance in real time, while the patient is in the chair. Real-time appliance design as described herein also allows for real-time communication of the treatment plan or appliance design to occur with the patient, or transmitted over a communications link and shared with a colleague or remote appliance manufacturing facility. Alternatively, the treatment planning can be performed remotely and a digital treatment plan sent to the orthodontist for review, interactive modification, or approval.

Scanners are devices for capturing and recording information from a surface of an object. Scanners for obtaining information from a two-dimensional surface, such as reading bar codes or characters printed on a piece of paper, are widely known. Several scanners have been proposed for recording three-dimensional information as well, including the field of dentistry.

U.S. Pat. No. 4,837,732 and U.S. Pat. No. 4,575,805 to Brandestini and Moermann propose a scanning system for in vivo, non-contact scanning of teeth. The patents describe a procedure for optically mapping a prepared tooth with a non-contact scan-head. The scan-head delivers the contour data, converted to electrical format, to be stored in a memory. A computer reads the memory following a line scan pattern. A milling device is slaved to follow this pattern by means of position control signals and mills an implant for the prepared tooth cavity.

The scan-head of the '732 and '805 patents includes a light emitting diode, with integral lens that radiates light onto the cavity. Before reaching the object, the rays of light are reflected by a mirror and pass through a ruling consisting of a plurality of parallel slits, or an alternating pattern of parallel opaque and transparent stripes. The reflected light is focused by a lens onto a charge-coupled device (CCD) sensor. Depth information is determined in accordance with a principle known as "active triangulation," using parameters shown in FIG. 9 of this document and described subsequently. Basically, the object is viewed under an angle different from the incident rays due to a parallax effect. Each light stripe will have an apparent positional shift and the amount of the shift at each point along each light stripe is proportional to the vertical height of the corresponding portion of the surface on the object.

U.S. Pat. No. 5,372,502 to Massen et al. describes an optical probe for measuring teeth that works on a similar principle. As noted in the Massen et al. patent, the Brandestini et al. technique is difficult to use when there are large variations in surface topography since such large jumps displace the pattern by an amount larger than the phase constant of the pattern, making it difficult to reconstruct the pattern of lines. Furthermore, precise knowledge of the angle of incidence and angle of reflection, and the separation distance between the light source and the detector, are needed to make accurate determinations of depth. Furthermore, the scanner has to be rather carefully positioned with respect to the tooth and would be unable to make a complete model of the dentition.

U.S. Pat. No. 5,027,281 to Rekow et al. describes a scanning method using a three axis positioning head with a laser source and detector, a rotational stage and a computer controller. The computer controller positions both the rotational stage and the positioning head. An object is placed on the rotational stage and the laser beam reflects from it. The reflected laser beam is used to measure the distance between the object and the laser source. X and Y coordinates are obtained by movement of the rotational stage or the positioning head. A three-dimensional virtual model of the object is created from the laser scanning. The '281 patent describes using this scanning method for scanning a plaster model of teeth for purposes of acquiring shape of the teeth to form a dental prosthesis. The system of the '281 patent is not particularly flexible, since it requires the object to be placed on the rotational stage and precise control of the relative position of the object and the positioning head is required at all times. It is unsuited for in vivo scanning of the teeth.

U.S. Pat. No. 5,431,562 to Andreiko et al. describes a method of acquiring certain shape information of teeth from a plaster model of the teeth. The plaster model is placed on a table and a picture is taken of the teeth using a video camera positioned a known distance away from the model, looking directly down on the model. The image is displayed on an input computer and a positioning grid is placed over the image of the teeth. The operator manually inputs X and Y coordinate information of selected points on the teeth, such as the mesial and distal contact points of the teeth. An alternative embodiment is described in which a laser directs a laser beam onto a model of the teeth and the reflected beam is detected by a sensor. The patent asserts that three-dimensional information as to teeth can be acquired from this technique but does not explain how it would be done. Neither of the techniques of Andreiko have met with widespread commercial success or acceptance in orthodontics. Neither technique achieves in vivo scanning of teeth. Moreover, the video technique does not produce complete three-dimensional information as to the teeth, but rather a limited amount of two-dimensional information, requiring significant manual operator input. Even using this technique, additional equipment is required even to describe the labial surface of a tooth along a single plane.

The art has also lacked a reliable, accurate, low-cost, and easily used scanning system that can quickly and automatically acquire three-dimensional information of an object, without requiring substantial operator input, and in particular one that can be held in the hand and used for in vivo scanning or scanning a model. The present invention meets this need.

SUMMARY OF THE INVENTION

An interactive, orthodontic care system is provided based on scanning of teeth. The system includes a hand-held scanner and associated processing system for capturing images of the dentition of the patient and processing the images to generate a full, virtual, three-dimensional model of the dentition. A data conditioning system processes the virtual, three-dimensional model and responsively generates a set of individual, virtual three-dimensional tooth objects representing teeth in the dentition of the patient A workstation is provided having a user interface for display of the set of individual, virtual three-dimensional tooth objects. Interactive treatment planning software is provided on the workstation permitting a user to manipulate the virtual three-dimensional tooth objects to thereby design a target situation for the patient in three dimensions and parameters for a customized orthodontic appliance for the teeth.

The hand-held scanner and associated processing system, data conditioning system, and workstation may all be installed in an orthodontic clinic. Alternatively, the hand-held scanner and workstation are installed in an orthodontic clinic, and wherein the data conditioning system is installed in a general purpose computer at a remote location from orthodontic clinic. Further, the treatment planning software can be either installed at the clinic, and/or at a remote location, and/or at a precision appliance manufacturing center that manufactures a custom orthodontic appliance. The type of appliance may vary considerably.

The treatment planning apparatus can be considered an interactive, computer-based computer aided design and computer aided manufacturing (CAD/CAM) system for orthodontics. The apparatus is highly interactive, in that it provides the orthodontist with the opportunity to both observe and analyze the current stage of the patient's condition and develop and specify a target or desired stage. A shortest direct path of tooth movement to the target stage can also be determined. Further, the apparatus provides for simulation of tooth movement between current and target stages.

In its broader aspects, the apparatus comprises a workstation having a processing unit and a display, and a memory storing a virtual, complete three-dimensional model representing the dentition of a patient. The virtual three-dimensional model can be obtained from one of several possible sources; in the preferred embodiment it is arrived at from a scanning of the dentition. The apparatus further includes software executable by the processing unit that accesses the model and displays the model on the display of the workstation. The software further includes navigation tools, e.g., typed commands, icons and/or graphical devices superimposed on the displayed model, that enables a user to manipulate the model on the display and simulate the movement of at least one tooth in the model relative to other teeth in the model in three-dimensional space, and quantify the amount of movement precisely. This simulation can be used, for example, to design a particular target situation for the patient.

The development of a unique target situation for the patient has utility in a variety of different orthodontic appliances, including an approach based on off-the-shelf or generic brackets and a custom orthodontic archwire. The scope of the invention is sufficient to encompass other types of appliances, such as an approach based on customized brackets, retainers, or removable aligning devices. In a bracket embodiment, the memory contains a library of virtual, three-dimensional orthodontic brackets. The software permits a user to access the virtual brackets through a suitable screen display, and place the virtual brackets on the virtual model of the dentition of the patient. This bracket bonding position can be customized on a tooth by tooth basis to suit individual patient anatomy. Because the tooth models, brackets and archwire are individual objects, and stored as such in memory, the treatment planning apparatus can simultaneously display the virtual brackets, the archwire and the virtual model of the dentition, or some lesser combination, such as just the brackets, just the dentition, or the brackets and the archwire but not the teeth. The same holds true with other appliance systems.

In a preferred embodiment, the virtual model of teeth comprises a set of virtual, individual three-dimensional tooth objects. A method of obtaining the tooth objects from a scan of teeth, and obtaining other virtual objects of associated anatomical structures, e.g., gums, roots and bone is described. When the teeth are separated from each other and from the gums, they can be individually manipulated. Thus, the individual tooth objects can be individually selected and moved relative to other teeth in the set of virtual tooth objects. This feature permits individual, customized tooth positioning on a tooth by tooth basis. These positioning can be in terms or angular rotation about three axis, or translation in transverse, sagittal or coronal planes. Additionally, various measurement features are provided for quantifying the amount of movement.

One of the primary tools in the treatment planning apparatus is the selection and customization or a desired or target archform. Again, because the teeth are individual tooth objects, they can be moved independently of each other to define an ideal arch. This development of the target archform could be calculated using interpolation or cubic spline algorithms. Alternatively, it can be customized by the user specifying a type of archform (e.g, Roth), and the tooth are moved onto that archform or some modification of that archform. The archform can be shaped to meet the anatomical constraints of the patient. After the initial archform is designed, the user can again position the teeth on the archform as they deem appropriate on a tooth by tooth basis. The treatment planning software thus enables the movement of the virtual tooth objects onto an archform which may represent, at least in part, a proposed treatment objective for the patient.

Numerous other features are possible with the treatment planning software, including movement of the teeth with respect to the other teeth in the archform, changing the position of the virtual brackets and the teeth with respect to each other, or opposing teeth with respect to the selected archform.

Custom archwire bends can be simulated to provide additional corrections. Bonding corrections at the bracket-tooth interface are also possible.

In another aspect of the invention, a method is provided for digital treatment planning for an orthodontic patient on a workstation having a processing unit, a user interface including a display and software executable by the processing unit. The method comprises the steps of obtaining and storing a three-dimensional virtual model of teeth representing the dentition of the patient in a current or observed situation. The virtual model is displayed on the display. The method further includes the step of moving the position of teeth in the virtual model relative to each other so as to place the teeth of the virtual model into a target situation and displaying the virtual model with the teeth moved to the target situation to the user. Parameters for an orthodontic appliance to move the patient's teeth from the current situation to the target situation can be derived from the virtual model and the target situation. For example, if virtual brackets are placed on the teeth, their location in the target situation can dictate the design of an archwire to move the teeth to the target situation.

The scanner system is provided for capturing three-dimensional information of an object. The object can be virtually any object under scrutiny, however the present document will describe an application in which the object is the dentition of a patient suffering from a malocclusion.

The scanning system enables three-dimensional surface information to be obtained with a very high decree of precision. Moreover, the scanning system can be used without requiring precise movement of the scanner, or requiring the object under scrutiny to be fixed in space. Surprisingly, the scanner is able to generate precise three dimensional surface information by simply moving the scanner over the surface of the object, such as by hand, in any manner that is convenient for the user, even if the object moves in any random direction during the scanning within reasonable limits. Thus, the scanner can be used to capture the surface of a patient's dentition in a minute or two, even if the patient moves their head or jaw while the scanning is occurring. Precise knowledge of the spatial relationship between the scanner and the object is not required.

The scanner obtains a set of images, which are processed in a computer to calculate the surface configuration of the object in three dimensions of space automatically, quickly, with high precision, and with essentially no human involvement other than the act of scanning. The precision or accuracy will be dictated largely by the extent to which the object under scrutiny tends to have undercut or shadowed features which are difficult to detect, necessitating a narrow angle between the projection and imaging axes. For teeth, an accuracy of under 20 or 30 microns is possible. This accuracy can be further improved depending on the nature of the surface, such as if the surface does not have a lot of undercut or shadowed features, by increasing the angular separation of the projection axis and the imaging axis.

Each image captured by the scanner is converted to a virtual, three-dimensional point cloud or "frame." The illustrated embodiment has a relatively coarse resolution for any single frame, due to a coarse projection pattern, but a fine resolution is obtained by obtaining multiple images and performing a registration procedure on the frames, as described below. Since each point on the surface of the object is captured in a plurality of images (such as five or six in a typical example of scanning), the registration of frames results in a fine resolution. An even finer resolution can be obtained by scanning slower and capturing more images of the surface of the object from different perspectives and registering the resulting frames to each other.

This surface configuration of the object in three dimensions of space can be represented as a mathematical model, i.e., a virtual model of the object, which can be displayed on any workstation or computer using available software tools. The mathematical model can be viewed in any orientation in space, permitting detailed analysis of the surface. The model can be compared to template objects stored in a computer. Deviations in the object from the template can be quantified and analyzed. Further, the virtual model can be transported from one computer and another computer anywhere in the world essentially instantaneously over communications links such as the Internet. The model can be replicated in a computer and thus shared and used by multiple users simultaneously.

The scanner system is useful for a wide variety of industrial, medical, archeological, forensic, archival, or other purposes. Furthermore, the scanner can be scaled down in size such that it can be hand-held and used to scan small objects, e.g., teeth or small machined parts, or scaled up in size so that it can be used to make mathematical models of larger scale objects such as works of art, sculptures, archeological sites (e.g., the caves at Lascaux, France or the dwellings or kivas in Mesa Verde National Park), rooms or building facades.

In accordance with a preferred embodiment, the scanner system includes a projection system that projects a pattern onto the object along a first optical axis. The pattern may consist of parallel lines, parallel lines separated by shapes or colors, such as colored dots, or other suitable pattern. The projected pattern is used to gather information as to the surface characteristics of the object in accordance with the methods and procedures described in more detail below.

The scanner further includes an electronic imaging device, preferably in the form of a charge-coupled device comprising a two-dimensional array of photo-sensitive pixels. The electronic imaging device is oriented along a second optical axis different from the first optical axis. The electronic imaging device forms an image of the pattern after reflection of the pattern off of the object under scrutiny. The surface configuration of the object will cause the projection pattern to become distorted and changed, and thereby provide information as to the surface configuration. This information as to the surface is captured by the imaging device as two-dimensional images of the reflection pattern. These images are processed in accordance with procedures described herein to derive three-dimensional information as to the surface of the object.

The scanning system, in a preferred embodiment, further includes a memory that stores data representing a three axis (X, Y, Z) calibration relationship for the scanner. The calibration relationship can be in the form of a table or in the form of a mathematical function (e.g., polynomial, spline, or other function). The calibration relationship identifies two properties of the scanner: (1) pixel coordinates for the electronic imaging device for numerous portions of the pattern, said pixel coordinates associated with distance information from the projection system in a Z direction at least two different Z distances, and (2) distance information in X and Y directions, for the numerous portions of said pattern, at the at least two different Z distances. A method of obtaining the calibration relationship is described in detail below. While the simplest form of the relationship is a table, as described in detail below, these calibration relationships could be equivalently represented by one or more mathematical functions as will be apparent to those skilled in art.

The calibration relationship is used to derive three-dimensional coordinates for points on the surface of an object imaged by the imaging device. The generation and use of the preferred calibration table is also explained in further detail below. Other calibration tables or procedures are also possible. The use of the calibration relationship allows the scanner to operate without precise knowledge of the optical and mechanical properties of the scanner, as is required in prior art systems.

The scanning system further includes at least one data processing unit, e.g., the central processing unit of a computer or a digital signal processor, which processes the images of the projection pattern after reflection from the surface of the object. The processing unit compares data from the image (e.g., pixel locations where certain points in the projection pattern are imaged) to the calibration relationship to thereby derive spatial information, in three dimensions, of points on the object reflecting the projected pattern onto the electronic imaging device. Multiple processing units can be used to reduce the amount of time it takes to process the two-dimensional images, calculate three-dimensional coordinates for points in each image, and register frames of three-dimensional coordinates relative to each other to generate a complete virtual model of the object.

The scanning system thus derives three-dimensional information of the object from the images generated by the imaging device and from the calibration relationship stored in memory. Precise knowledge of the optical characteristics of the scanner, the angles between the first and second optical axes, the angle between the optical axis and the point in the imaging device, or the separation distance of the projection device from the imaging device are not necessary. The projection system and the imaging device can be even uncoupled relative to each other. The calibration relationship automatically and completely compensates for these issues, as well as manufacturing variations and tolerances in the scanner optics, in a highly reliable manner. Moreover, knowledge of the distance from the scanner to the object is not required. Additionally, control over the distance between the scanner and the object is not required, within reasonable limits dictated by the depth of focus of the imaging optics. Ideally, during scanning the distance from the scanner to the object is maintained within the limits of the Z distances used during calibration, and that distances is within the combined depth of focus of the projection optics and the imaging optics.

The scanning system can be constructed such that the memory, processing unit, and optical elements are in a single unit. Alternatively, the processing unit and memory can be located at a separate location, such as a scanning workstation or "scanning node", in order to reduce the size of the scanner per se. In such an embodiment, the projection system and the image-recording device can be miniaturized into a hand-held scanner device. A suitable cable connects the scanner device to the workstation to thereby supply the processing unit with scan data, and to receive commands (illumination commands, start/stop commands, etc.) from the workstation.

Preferred appliance manufacturing systems are also described, including bending apparatus that bends medical devices, such as orthodontic appliances like archwires, fixation plates and other devices. Bracket placement trays are also described. As one embodiment, an orthodontic appliance manufacturing system is provided comprising a machine readable memory storing digital data representing a three-dimensional virtual model of a malocclusion of a patient and digital information representing the location of orthodontic brackets to be placed on the malocclusion, said memory further storing digital data representing a three-dimensional virtual model of the patient's teeth and the dentition and location of orthodontic brackets at a target situation in three dimensions. The apparatus further includes a wire bending robot. A rapid prototyping instrument such as SLA (stereolithography) is provided for generating a three-dimensional physical model of the malocclusion with the brackets placed on the malocclusion. A forming device forms a bracket placement tray matching the geometry of the physical model of the malocclusion with the brackets. The bracket placement tray may be removed from the physical model, said tray formed with spaces for placement of brackets and enabling bonding of the brackets to the teeth at a desired location based on the virtual model of the dentition and the placement of orthodontic brackets on the malocclusion.

Numerous other features of the appliance manufacturing apparatus, the treatment planning software, the scanning system and related features will be more apparent from the following detailed description.

BRIEF DESCRIPTION OF THE DRAWINGS

FIG. 7 is a cross-sectional view of the scanner of FIG. 3, showing the optical elements of the projection and imaging aspects of the scanner.

FIG. 8 is a perspective view of a scanner calibration apparatus of station that is used to calibrate the scanner and obtain data for entry in a calibration table stored in the memory of the scanner system.

FIG. 10 illustrates a fundamental principle of the technique that is used for calibration of the scanner and generation of three-dimensional information of an object, which is considered to be an improvement over the calculations required by the method of FIG. 9.

FIG. 24 is an illustration of a first calibration table for the scanner after completion of the Z calibration step;

FIG. 25 is an illustration of a second calibration table for the scanner after completion of the X-Y calibration step. The entries in the second calibration table of FIG. 25 are used to complete the mm entries in the calibration table of FIG. 24.

FIG. 26 is an illustration of the first calibration table for the scanner after the calculations from the table of FIG. 25 have been performed for ray $R_{2,3}$ and the results entered in the first table. It will be understood that a similar calculation from calibration table #2 (FIG. 25) is done for each ray at both distances and the entries in mm for each ray are entered in calibration table #1 (FIG. 24).

FIG. 37D illustrates that the low resolution of the scanner's projection pattern, as indicated by the widely spaced points in FIG. 37C, is compensated by registration of large overlap of frames, as illustrated in FIG. 37C, and results in a high resolution surface.

FIG. 48A-48C are a flow diagram of a cumulative registration process.

FIG. 54 is a screen shot of a workstation computer (either scanning station or back office server workstation), showing the available registration parameters and variables that can be changed by the user when performing either a frame to frame registration or a cumulative registration.

FIG. 60 also shows the various parameters by which the orthodontist can adjust the shape of the arch, the distance between the teeth, the distance between the molars, and other parameters, so as to provide a unique and customized target situation for the patient.

FIG. 76 also shows the various parameters by which the orthodontist can adjust the shape of the arch, the distance between the teeth, the distance between the molars, and other parameters, so as to provide a unique and customized archform for the patient.

in FIG. 89 the gripping tool at the distal end of the arm is omitted for sake of clarity to show the various other aspects of the arm.

FIG. 99 is a simplified illustration of a set of teeth showing the origin of a coordinate system that is used to calculate bracket location for a set of brackets, in three dimensions, for a patient. The bracket location for the teeth in a target situation determines the shape of an orthodontic archwire.

FIG. 100 is an illustration showing the vectors drawn from the origin of the coordinate system to the center of the brackets.

FIG. 101 is a perspective view of an orthodontic bracket.

FIG. 102 is an illustration of a vector drawn from the origin of the coordinate system to the bracket, a normal vector N perpendicular to the slot surface of the bracket, and a tangential vector T extending in the direction of the slot of the bracket.

FIG. 103 shows the normal vector Y for a particular bracket, the tangential vector X, the tangential distance $T_d$ and antitangential distance $AT_d$.

FIG. 104 shows in matrix form the values for an individual bracket which describe the location of the bracket and its orientation, which are used to generate the commands for the robot to form the orthodontic archwire.

FIG. 105 is an illustration of a set of points P1, P2, P3, ... PN which represent a set of bending points associated with individual brackets for a patient in a target situation. The location of the points in the three-dimensional coordinate system is known.

FIG. 106 is an illustration of a section of wire between points P1 and P4 in which a bend is placed between points P2 and P3.

FIG. 112 is an illustration showing the overbending method set forth in FIG. 111.

FIGS. 113A-113E are a series of schematic drawings of the fixed and moveable gripping tools of FIG. 92, showing how they moved relative to each other and grip and release the archwire to place the archwire in position to form a bend between points P2 and P3 of FIG. 105.

FIG. 114 is a schematic illustration showing how the movable gripping tool bends an archwire while maintaining a constant distance from the fixed gripping tool.

FIGS. 115A-15C illustrate how a bend may be formed in a series of steps.

FIGS. 116A-116D are a series of schematic drawings of the fixed and moveable gripping tools of FIG. 92, showing how they move relative to each other to place the archwire in position to form a bend between points P4 and P5.

FIG. 117 is an illustration of the points defining a portion of an archwire, and illustrating a technique for placing bends in wires where a substantial distance exists between the straight wire segments.

FIG. 118 is an illustration of a portion of an archwire showing a bend formed therein to increase the forces applied by the wire when the wire has nearly straightened out, e.g., near the end of treatment.

FIG. 119 shows the wire segment of FIG. 118 installed between two teeth.

FIG. 120 shows a wire with a loop in the wire.

FIGS. 121A-121B illustrate one possible method of forming the loop in the wire of FIG. 120.

DETAILED DESCRIPTION OF PREFERRED EMBODIMENT

Part 1. Overview

Figure 1:
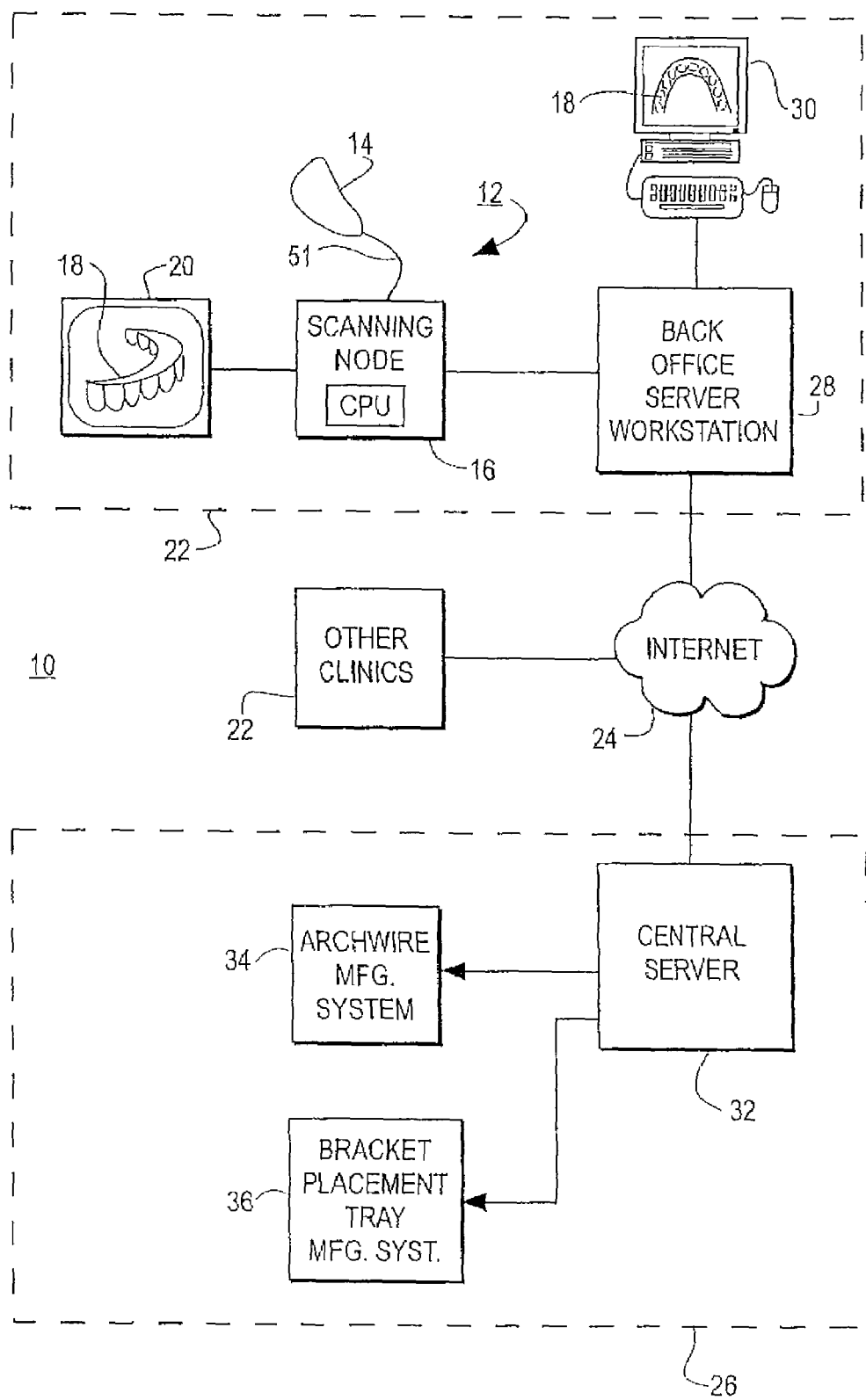
FIG. 1 is an illustration of an orthodontic care system incorporating a hand-held scanner system in accordance with a representative embodiment of the invention. The hand-held scanner is used by the orthodontist or the assistant to acquire three-dimensional information of the dentition and associated anatomical structures of a patient and provide a base of information to diagnose and plan treatment for the patient.

FIG. 1 is an illustration of an orthodontic care system 10 incorporating a scanner system 12 in accordance with a representative embodiment of the invention. The scanner system 12 includes a hand-held scanner 14 that is used by the orthodontist or his assistant to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional computer model 18 of the dentition and provides the orthodontist with a base of information for diagnosis, planning treatment, and monitoring care for the patient. The model 18 is displayed to the user on a monitor 20 connected to the scanning node 16.

As noted above, the scanner system 12 described in detail herein is optimized for in-vivo scanning of teeth, or alternatively, scanning a plaster model of the teeth and/or an impression of the teeth. However, it will be apparent to persons skilled in the art that the scanning system 12 can by readily optimized for a variety of other diagnostic and/or treatment planning and/or monitoring uses in the medical arena. An example is scanning the face or head and planning plastic or orthopedic surgery. It can be readily adapted to virtually limitless number of applications in industrial, manufacturing, forensic, archeological, scientific, archival or other applications.

The orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user interface, including a monitor 30. The back office server 28 executes an orthodontic treatment planning software program. The software obtains the three-dimensional digital data of the patient's teeth from the scanning node 16 and displays the model 18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized archwire for the patient given the selected bracket positions. When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22. The invention is also applicable to other types of appliance systems; brackets and archwires are shown in the illustrated embodiment but other types of appliance systems can benefit from the scanning system described herein, such as removable aligning devices; retainers, Herbst appliances, etc.

As shown in FIG. 1, the precision appliance service center 26 includes a central server 32, an archwire manufacturing system 34 and a bracket placement manufacturing system 36. These details are described later.

Figure 2:
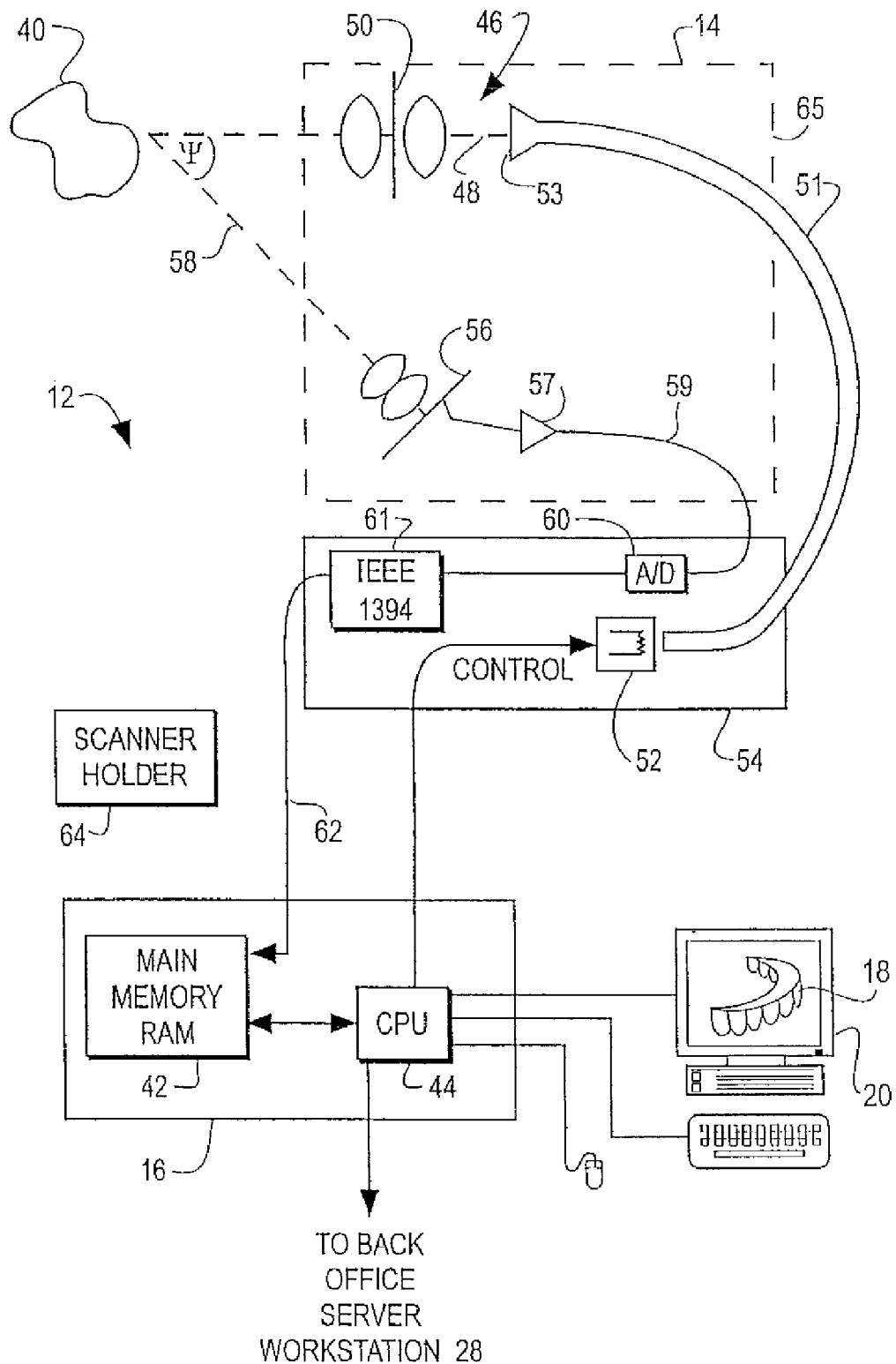
FIG. 2 is a block-diagram of a scanning system, suitable for use in the orthodontic care system of FIG. 1.

FIG. 2 is a more detailed block-diagram of the scanning system 12, suitable for use in the orthodontic care system of FIG. 1. The scanning system 12 is a mechanism for capturing three-dimensional information of an object 40, which in the present example is the dentition and surrounding anatomical structures of a human patient, e.g., gums, bone and/or soft tissue. The scanning system 12 includes a scanner 14 which is used for image capture, and a processing system, which in the illustrated example consists of the main memory 42 and central processing unit 44 of the scanning node or workstation 16.

The scanner 14 includes a projection system 46 that projects a pattern onto the object 40 along a first projection axis 48. The projected pattern is formed on a slide 50 which is placed in front of a light source 53. In the illustrated embodiment, the light source 53 comprises the terminus of a fiber-optic cable 51. The cable 51 carries a high intensity flash generated by a flash lamp 52 located in a base unit 54 for the scanner. A suitable flash lamp is the model FX-1160 flash unit available from Perkin Elmer. The illuminations of the flash lamp 52 cause the pattern contained in the slide 50 to be projected onto the three-dimensional surface of the object. Further details on the types of patterns suitable for the pattern are set forth in the following co-pending patent applications of Rüdger Rubbert et al: Ser. No. 09/254,755 filed Mar. 9, 1999; Ser. No. 09/560,131 filed Apr. 28, 2000, and Ser. No. 09/673,863 filed Nov. 30, 2000 assigned to the assignee of the present invention, the contents of which are incorporated by reference herein. A presently preferred projection pattern is described below. The details on the optics of the projection system 46 are set forth in further detail below.

The scanner 14 further includes an electronic imaging device 56 comprising an array of photo-sensitive pixels. A preferred embodiment is an off-the-shelf, color-sensitive, charged-coupled device (CCD) of a size of 1,028×1,028 pixels arranged in an array of rows and columns. The Sony ICX205AK CCD chip is a suitable electronic imaging device. The electronic imaging device 56 is oriented perpendicular to a second imaging axis 58, which is off-set from the projection axis 48. The angle $\Psi$ between the projection and imaging axes need not be known in a preferred embodiment of the invention. However, if the 3D calculations are made in accordance with the parameters of FIG. 9, then the angle and the separation distance between the center of the imaging device 56 and the center of the light source 53 need to be known.

The angle $\Psi$ will be optimized during design and manufacture of the scanner depending on the desired resolution required by the scanner. This, in turn, is dependent on the degree to which the surface under scrutiny has undercuts and shadowing features which would result in the failure of the imaging device to detect the projection pattern. The greater the angle $\Psi$, the greater the accuracy of the scanner. However, as angle $\Psi$ increases, the presence of undercuts and shadowing features will block the reflected pattern and prevent capture of the pattern and subsequent three-dimensional analysis of those portions of the surface. Angle $\Psi$ is shown somewhat exaggerated in FIG. 2, and will generally range between 10 and 30 degrees for most applications.

The electronic imaging device 56 forms an image of the projection pattern after reflection of the pattern off of the surface of the object 40. The reflected patterns imaged by the imaging device contain three-dimensional information as to the surface of the object, and this information needs to be extracted from the images. The scanning system therefore includes a processing subsystem which is used to extract this information and construct a three-dimensional virtual model of the object 40. In the preferred embodiment, this processing subsystem consists of a memory 42 storing calibration information for the scanner, and at least one processing unit, such as the central processing unit 44 of the scanning workstation 16. The location of the memory and the processing unit is not important. They can be incorporated into the scanner 14 per se. Alternatively, all processing of the images can take place in the back office server 28 or in another computer. Alternatively, two or more processing units could share the processing in order to reduce the amount of time required to generate the three-dimensional information.

The memory 42 stores a calibration relationship for the scanner 14. The calibration relationship, which can be in the form of a table or one more mathematical functions, comprises information used to compute three-dimensional coordinates of points on the object that reflected the projection pattern onto the imaging device. The information for the table is obtained during a calibration step, performed at the time of manufacture of the scanner 14. The calibration table includes an array of data storage locations that contain two pieces of information. Firstly, the calibration table stores pixel coordinates in X and Y directions for numerous portions of the projection pattern that are imaged by the electronic imaging device 56, when the pattern is projected onto a calibration surface at two different distances during a calibration procedure. Secondly, the table stores distance information, (e.g., in units of tenths of millimeters), in X and Y directions, for the portions of the projection pattern imaged at the two different distances. A preferred method for generation and use of the calibration table is explained in further detail below.

The scanning system requires at least one processing unit to perform image processing, three-dimensional calculations for each image, and registration of frames to each other. The processing unit 44 in the illustrated embodiment is the central processing unit (CPU) of the scanning work station 16. The CPU 44 processes the image of the pattern after reflection of the pattern off the surface of the object 40 and compares data from the image to the entries in the calibration table. From that comparison (or, more precisely, interpolation relative to the entries in the table, as explained below), the processing unit 44 derives spatial information, in three dimensions, of points on the object that reflect the projected pattern onto the electronic imaging device.

Basically, during operation of the scanner to scan an object of unknown surface configuration, hundreds or thousands of images are generated of the projection pattern as reflected off of the object in rapid succession as the scanner and object are moved relative to each other. For each image, pixel locations for specific portions, i.e., points, of the reflected pattern are compared to entries in the calibration table. X, Y and Z coordinates (i.e., three dimensional coordinates) are obtained for each of these specific portions of the reflected pattern. For each picture, the sum total of all of these X, Y and Z coordinates for specific points in the reflected pattern comprise a three-dimensional "frame" or virtual model of the object. When hundreds or thousands of images of the object are obtained from different perspectives, as the scanner is moved relative to the object, the system generates hundreds or thousands of these frames. These frames are then registered to each other to thereby generate a complete and highly accurate three-dimensional model of the object 40.

Stray data points are preferably canceled out in generating the calibration table or using the calibration table to calculate three-dimensional coordinates. For example, a smoothing function such as a spline can be calculated when generating the entries for the calibration table, and the spline used to cancel or ignore data points that deviate significantly from the spline.

FIG. 2 also shows a few other features of the presently preferred scanning system 12. After the CCD imaging device 56 captures a single image, the analog voltage signals from the device 56 are amplified in an amplifier 57 and fed along a conductor 59 to an analog to digital converter 60. The digital signal is converted into a bitmap stream of digital image data. The data is formatted by a module 61 into an IEEE 1394 "firewire" format for transmission over a second conductor 62 to the main memory 42 of the scanner work station 16. The scanning system includes an optical scanner holder 64 for the user to place the scanner after the scanning of the dentition is complete. These details are not particularly important and can vary considerably from the illustrated embodiment. As noted earlier, preferably the scanning system is constructed to provide a minimum of equipment and clutter at the chair side.

Hence, the scanning work station 16 is preferably located some distance away from the chair where the patient sits. The cable leading from the scanner 14 to the base station and/or workstation 16 could be suspended from the ceiling to further eliminate chairside clutter.

The scanning work station 16 also includes the monitor 20 for displaying the scanning results as a three-dimensional model 18 of the dentition in real time as the scanning is occurring. The user interface also includes a keyboard and mouse for manipulating the virtual model of the object, and for entering or changing parameters for the scanning, identifying sections or segments of scans that have been obtained, and other features. The scanning station may also include a foot switch, not shown, for sending a signal to the CPU 44 indicating that scanning is commencing and scanning has been completed. The base station may alternatively include a voice recognition module that is trained to recognize a small set of voice commands such as START, STOP, AGAIN, REPEAT, SEGMENT, ONE, TWO, THREE, FOUR, etc., thereby eliminating the need for the foot switch. Scanner start and stop commands from the CPU 44, in the form of control signals, are sent to the light source 52, thereby controlling the illumination of the lamp 52 during scanning.

The light source 52 operates at a suitable frequency, preferably at least greater than one flash per second, such as six flashes per second, and the frame rate of the CCD imaging device 56 is synchronized with the flash rate. With a frame rate of 6 frames per second, and a scanning motion of say 1-2 centimeters per second, a large of overlap between images is obtained. The size of the mirror at the tip 68 of the scanner influences the speed at which scanning is possible. The illustrated embodiment of the mirror at the tip 68 is 18 mm square. A larger mirror reflects more surface of the object and enables faster scanning. A smaller mirror requires slower scanning. The larger the mirror, the more difficult in-vivo scanning becomes, so some trade-off between size and utility for in-vivo scanning exists.

This overlap between images generated by the scanner 14, and resulting three dimensional frames, allows a smooth and accurate registration of frames relative to each other. The frame rate and permissible rate of scanner motion will depend on many factors and can of course vary within the scope of the invention. Flashing a high intensity flash lamp for a brief period of time is a preferred embodiment since it is desirable to reduce the exposure time of the CCD imaging device 56 to reduce blurring since relative motion exists between the scanner and the object. A high intensity lamp is desirable to achieve sufficient signal strength from the imaging device. A preferred embodiment uses 5 μsec flash times with similar exposure periods. An alternative embodiment would use a constant illumination source of high intensity, and control exposure of the imaging device using a shutter, either a physical shutter or using electronic shutter techniques, such as draining charge accumulating in the pixels prior to generating an image. Scanning using longer exposures would be possible without image blur, using electronic image motion compensation techniques described in Lareau, et al., U.S. Pat. No. 5,155,597.

Figure 3:
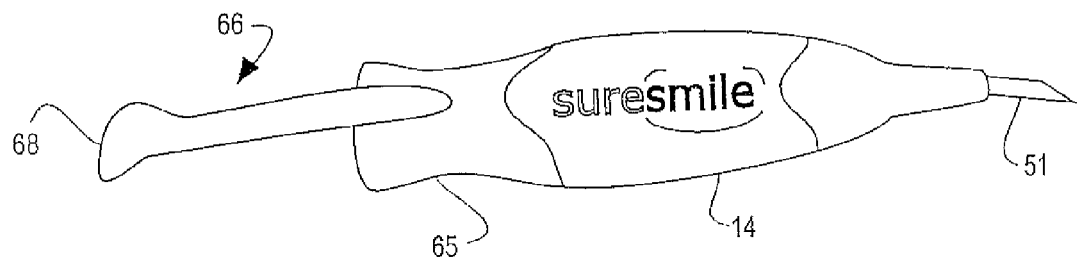
FIG. 3 is a perspective view of a hand-held scanner used to acquire information of an object under scrutiny, suitable for use in the orthodontic care system of FIG. 1.

FIG. 3 is a perspective view of a hand-held scanner 14 used to acquire information of an object under scrutiny, suitable for use in the orthodontic care system of FIG. 1. The projection system 46 and the electronic imaging device 56 of FIG. 2 are contained in the housing 65 for the scanner. The housing 65 is sized and shaped to be held in a human hand. The scanner 14 includes an elongate distal portion 66 having a tip 68. The tip 68 is sized and shaped such that it can be inserted into and moved within an oral cavity of a human so as to enable scanning of anatomical structures inside the oral cavity. A heating mirror (not shown) is placed on the underside of the tip 68 to direct the projection pattern from the optics of the scanner onto the object and to direct the reflected pattern from the object towards the imaging optics 108 of FIG. 7 associated with the electronic imaging device 56. The mirror housing has A/C conductive heating coil that heats the mirror. The mirror is heated to approximately 40 degrees to prevent fogging of the mirror while the scanner is used in-vivo.

Figure 4:
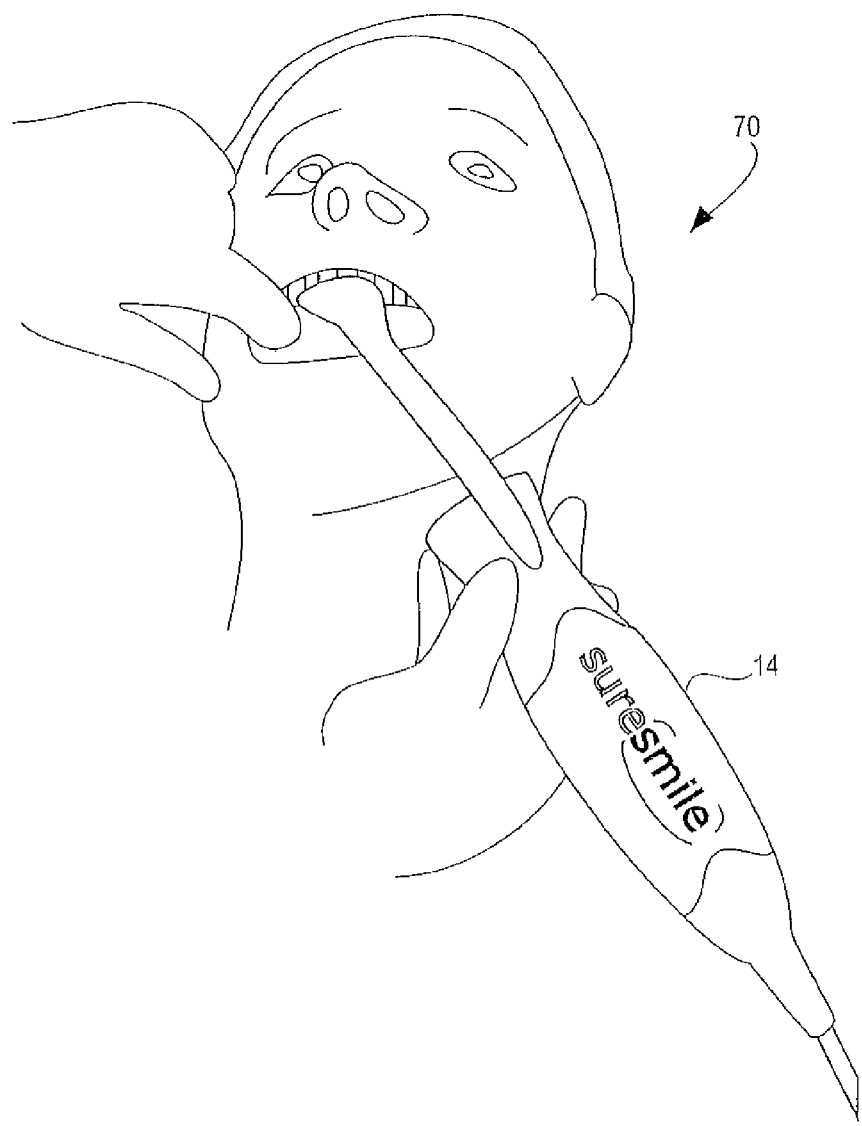
FIG. 4 is an illustration of a patient being scanned with the hand-held scanner of FIG. 3.

FIG. 4 is an illustration of a patient 70 being scanned with the hand-held scanner 14 of FIG. 3. The checks and lips are retracted from the teeth and the tip 68 of the scanner is moved over all the surfaces of the teeth in a sweeping motion at a velocity of perhaps 1-2 centimeters per second. The entire upper or lower jaw may need to be scanned in a series of scans, one for the left side, one for the right side, and one for the front. These individual scans are registered to each other as described below. Voice commands or activation of the foot switch (not shown) indicates when each scanning segment is initiated and terminated. The entire process takes just a few minutes. Depending on the color and translucency of the object and the illumination intensity and frequency of the light source in the scanner, it may be necessary to apply a very thin coating of a bright reflective substance such as Titanium Dioxide to the object.

While FIG. 4 illustrates in-vivo scanning of a human patient, the scanner can of course be used to scan a plaster model of the dentition if that is preferred, or an impression taken from the patient. When scanning an impression or a plaster model, the scanning may be formed in a single pass, without the need for registering scan segments to each other. It is also possible that a scan of a patient may be partially taken in vivo and the remainder from a model or an impression.

Figure 5:
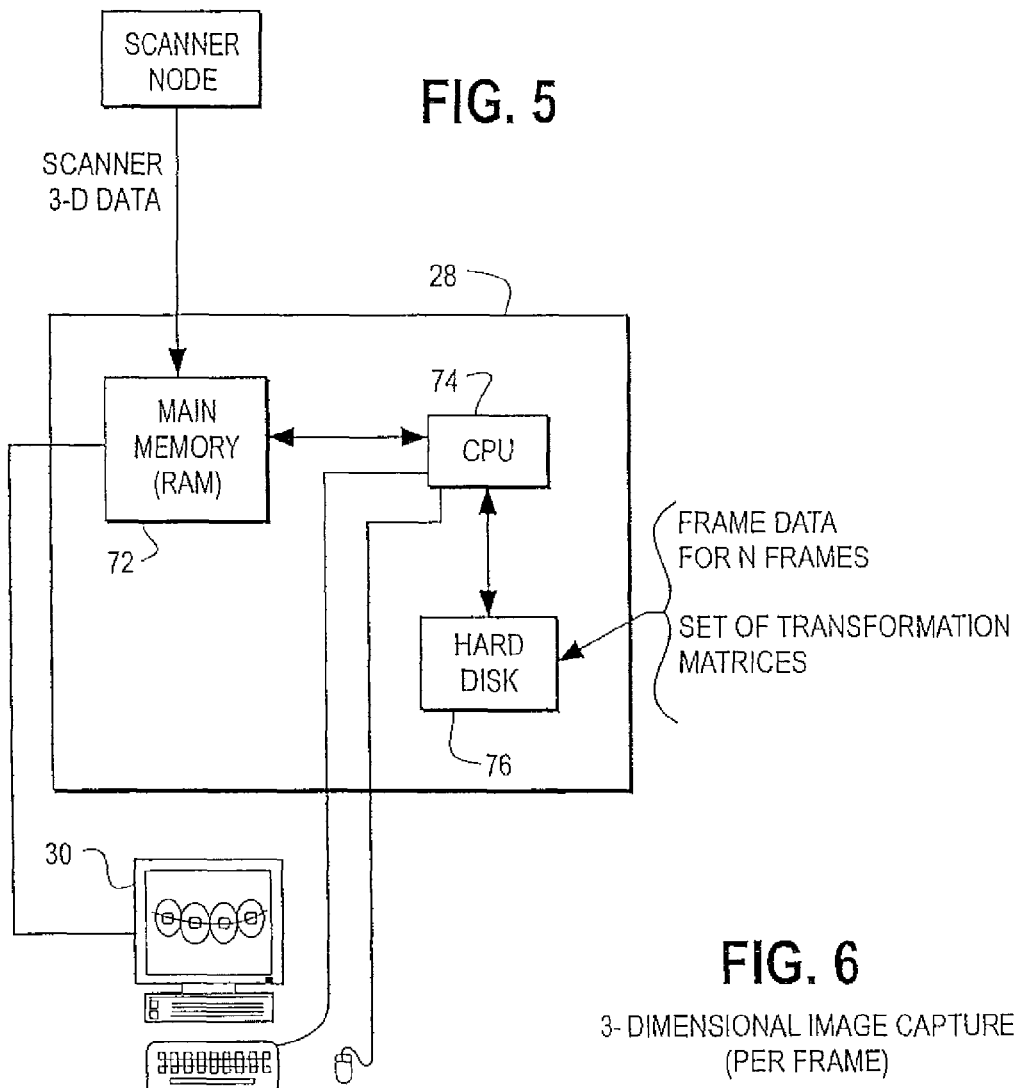
FIG. 5 is a block diagram of the back office server of FIG. 1 showing the elements used to calculate the digital model of the patient's dentition and display the digital model on a screen display of the server.

FIG. 5 is a block diagram of the back office server of FIG. 1 showing the elements used to calculate the digital model of the patient's dentition. After the scanning workstation has processed all the images captured by the scanner and generated a set of three dimensional frames, the frame data is transmitted to the back office server 28. The back office server 28 performs a cumulative registration process for the frames and ultimately generates and displays the digital model on a screen display 30. The raw scanner data in the form of three-dimensional frames is stored in the main computer memory 72. The frame data for N captured images, i=1 ... N from the scanner is stored in the hard disk 74. The hard disk also stores a set of (N−1) transformation matrices $[T]_i$, for i=2−N. The transformation matrices basically contain information as to how each frame of three-dimensional points needs to be translated and rotated in a three-axis Cartesian coordinate system in order to be registered with the other frames in a best-fit manner. One of the frames, such as the first frame in the series, is a starting point for registration and no transformation matrix is obtained for that frame. The generation of the transformation matrices, and use of the matrices with the frame data to generate the three dimensional model, is described in further detail below.

Part 2. Three-Dimensional Image Generation

Figure 6:
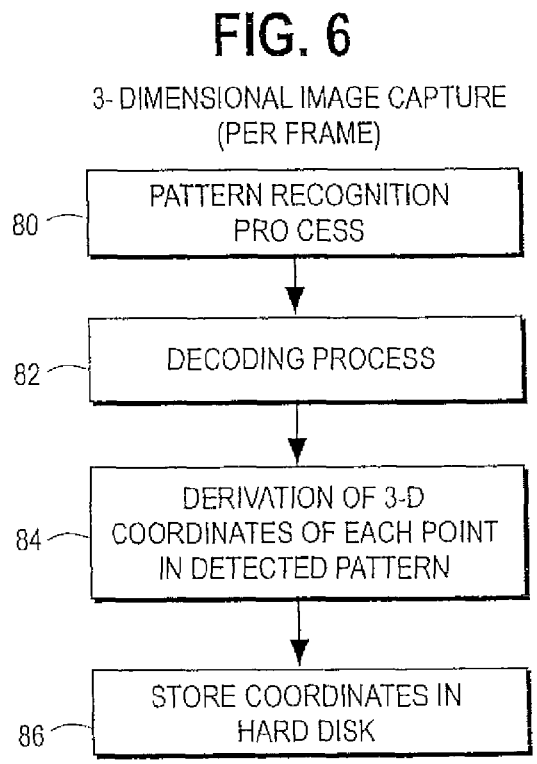
FIG. 6 is a flow diagram illustrating the sequence of steps used by the processing unit in the scanning station to calculate three-dimensional information of an object from images captured by the scanner.

With the above general introduction and overview in mind, a presently preferred process of capturing two dimensional images with the scanner and generation of a three-dimensional model for each image will now be described in detail in this section. FIG. 6 is a flow diagram illustrating the sequence of steps used by the processing unit 44 in the scanning station 16 (FIG. 2) to calculate three-dimensional information of an object for a single image captured by the scanner 14. This process shown in FIG. 6 is performed for each image.

This process can be executed in one processor, or may be performed or shared by multiple DSP processors sharing access to a memory storing the captured two-dimensional bitmap images from the scanner, e.g., memory 42 of FIG. 2. The type of processor is of course not important. The goal of distributed processing is to reduce the time required for processing the scanned image. For example, one processor could perform the cross-correlation process described below, another perform the pattern recognition, another decoding, and another 3-D calculation. These processes could be performed independently, each process associated with independent files shared on a disk memory. The processor assigned to one or more of the processes of FIG. 6 accesses the files as needed. For example, the output file from the decoding process is written on a disk or memory available to the other processing units. The processing units are on a network in this example. The processor assigned to 3-D calculation access the decoding output file and writes the result, a set of coordinates for N frames and N−1 transformation matrices, onto the disk or memory. Any one of the processors assigned to perform registration could then access the N frame data and the N−1 transformation matrices and perform the registration procedures described below.

The process of FIG. 6 consists of four principal steps: a pattern recognition process 80, a decoding process 82, a process 84 of derivation or calculation of three-dimensional coordinates for each point in the detected and decoded pattern, and finally a step 86 of storing the three dimensional coordinates in a memory, such as the memory 42 of the scanning work station 16. Again, this process is performed for each captured image during the scanning process. In a typical scanning scenario, hundreds or even thousands of images may be captured, hence this process of FIG. 6 may be performed hundreds of times. The result of the process is the storage of a large number of sets of three-dimensional coordinates, each set or "frame" associated with a single captured image. The registration of these frames relative to each other to generate a complete virtual model of the object is described in Part 3 of this document.

As the scanner is moved over the dentition, the imaging device acquires a series of bitmap images. The acquired bitmaps are analyzed using pattern recognition. Pattern recognition detects the median lines of the projected lines, endpoints of the lines and the centers of the colored dots. Other types of patterns are of course possible, such as using triangles, squares, or other coding features. The coding is in the vertical direction (in the direction of the parallel lines), since the distortion of the projection pattern provided by the surface of the object is in this direction, as explained more fully in the Rubbert et al. patent application Ser. No. 09/560,131 filed Apr. 28, 2000, incorporated by reference herein.

The pattern recognition process uses sub-pixel-precision. The color of every dot is analyzed as well. Based on the knowledge of the pattern structure and using the colored dots, the origin in the pattern for every recognized line is determined. This is necessary, as significant portions of the projected pattern may not be visible to the imaging optics due to shadowing, undercuts and un-sharp areas. A two-dimensional to three-dimensional conversion algorithm uses the knowledge of the origin of each imaged line with respect to the pattern to compute three-dimensional coordinates of the points in the object. As the lines are often captured only as fragments, the decoding algorithm does not always have sufficient information on each line to unequivocally assign that line to the pattern. The algorithm therefore examine several scenarios of possible affiliations and looks for conflicts. In this way the inconsistent scenarios are filtered out. The lines in the projection pattern do not change their order in the image. For example, if the lines in the projection pattern are sequentially numbered 1-80, and line 43 is to the left of line 44, in the captured image line 43 will be always be to the left of line 44 and never to the right of line 44. Inconsistent scenarios are indicated where the order of lines is violated. The correct order of the lines can be deduced by a suitable algorithm that examines the scenarios based on line order and eliminates all those where conflicts or inconsistent line numberings exists. A unique solution will be found.

While the preferred embodiment of the three-dimensional conversion algorithm is based on a sophisticated calibration process and does not make use of any knowledge of the optical parameters, an alternative embodiment could use general principle of analytical triangulation assuming that we do have such knowledge. Analytical triangulation will be explained with reference to FIG. 9. The projecting device projects a pattern of distinguishable elements onto a surface. This projected pattern is imaged. For each captured element, is must be possible to tell its origin at the pattern. This allows us to determine the angle $\alpha$ between the optical axis of the projection device and the one ray that has projected that element. The location of the pixel at the CCD chip that has captured that element allows us to determine the angle $\beta$ between the optical axis of the imaging system and the one ray that leads from the projected element at the surface to the CCD pixel. Knowing those two angles, the angles of the two optical axes with respect to the baseline and the length of the baseline, allows us to calculate the spatial position of the element relatively to the scanning device. This calculation can be done for every detected element within one captured image and leads to a plurality of three-dimensional points. It is important to understand that as a result from this calculation we receive an undistorted, true to scale representation of the surface. While every two dimensional image shows distortions due to parallax effects, the triangulation process eliminates this effect.

The analytical triangulation method requires precise knowledge of optical parameters. The preferred embodiment using a calibration table for the scanner does not require this knowledge.

A. Scanner Manufacture and Calibration

Before describing the details of the process steps shown in FIG. 6, an illustrative embodiment of the scanner 14 itself and its manner of calibration will be described first.

FIG. 7 is a cross-sectional view of a portion of the handheld scanner 14 of FIG. 3, showing the optical elements of the projection and imaging aspects of the scanner. The scanner includes the fiber-optic cable 51 carrying flashes from a flash lamp in the base station 54 of FIG. 2 to a condenser system consisting of a group of lenses 53A. Light from the light source 53 illuminates a pattern formed in a slide 50. Wide variation is possible in the choice of the pattern. A presently preferred embodiment is described subsequently in conjunction with FIG. 11. The pattern is directed by a projection lens system 102 out of the scanner to the mirror housed at the tip 68 of the scanner (FIG. 3) and towards the object under investigation. The scanner further includes a several LED light sources 106 (e.g., 2 or 6), which are used to provide general illumination of the object during scanning to assist the user in scanning the dentition. A prism 104 surrounds the LED light sources. The axis of the projection system is shown as axis 48.

The projection pattern is reflected off of the object, reflected by the mirror in the tip 68 and received by an imaging lens system 108 centered about an imaging axis 58. The received pattern is reflected off a mirror 110 onto the CCD electronic imaging device 56. The CCD 56 produces a voltage signal for each pixel in the device. The level of the signal is an indication of the level of light impinging on that pixel, allowing an image to be produced from the CCD. The signals are read out of the CCD using known circuitry and amplified. The amplified analog signal is collected and transmitted along conductors 59 to the base unit for conversion to digital form. The signal from the CCD is converted into a colored bitmap image in the illustrated embodiment. Color is used in the projection pattern in the illustrated embodiment, therefore a CCD chip is selected which can detect colors. A black and white system is of course also possible.

In the illustrated embodiment, the separation distance between the light source and the projection pattern is not known or needed, nor is the angle between the axes 48 and 58. However, some non-zero angle between the axes is required in order to obtain depth information. The angle selected will depend on the type of surface or object the scanner will be used for. These types of implementation details will vary considerably depending on the application. Furthermore, it is possible to make the two axes 48 and 58 completely independent of each other by locating the projection and imaging in separate, independently moveable devices. This is described in more detail in the patent application of Rüdger Rubbert et al, Ser. No. 09/254,843, the contents of which are incorporated by reference herein. The calibration procedures described herein are of particular advantage when the projection device and the imaging device are in two separate, independently moveable units.

FIG. 8 is a perspective view of a presently preferred scanner calibration station 120 that is used to calibrate the scanner 14 at the time of manufacture. The purpose of the station 120 is to obtain data for a calibration relationship for the scanner, such as a calibration table, which is stored in the memory of the scanner system. Some variation in the design of the calibration station is possible; the principle of operation of the calibration station is that the scanner is calibrated by projecting the pattern onto a reference object of precisely known geometry at two known distances (in the Z direction) and known spatial extent (X and Y directions). A planar reference object is preferred, but it is theoretically possible to use any object of known geometry, but more computationally complex to use such objects. The goal of the calibration procedure is to compile a set of information (e.g., in the form of a table) that completely calibrates the scanner and places it in condition for use to scan objects of unknown surface geometry, without the need for precise knowledge of the mechanical or optical properties of the scanner. While the present embodiment describes a calibration table as the result of the calibration process, the information may be in other equivalent forms, such as mathematical relationships or formulae between pixel address and distance, which are operated on to derive distance information at the time of use.

Before discussing the presently preferred calibration device and calibration relationship, a discussion of the principles of the calibration invention will be set forth for ease of understanding.

Figure 9:
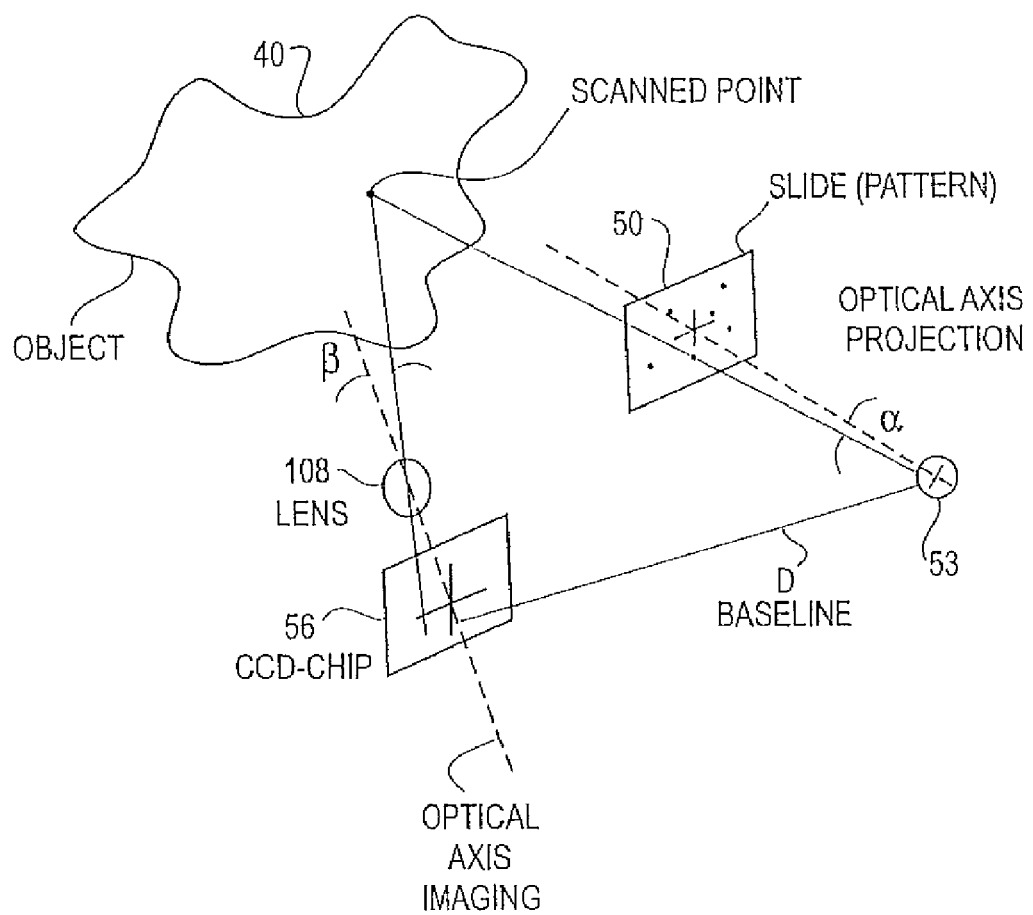
FIG. 9 is an illustration of the relevant parameters that can be used to calculate surface configuration of the object in accordance with a known fashion.
Figure 9A:
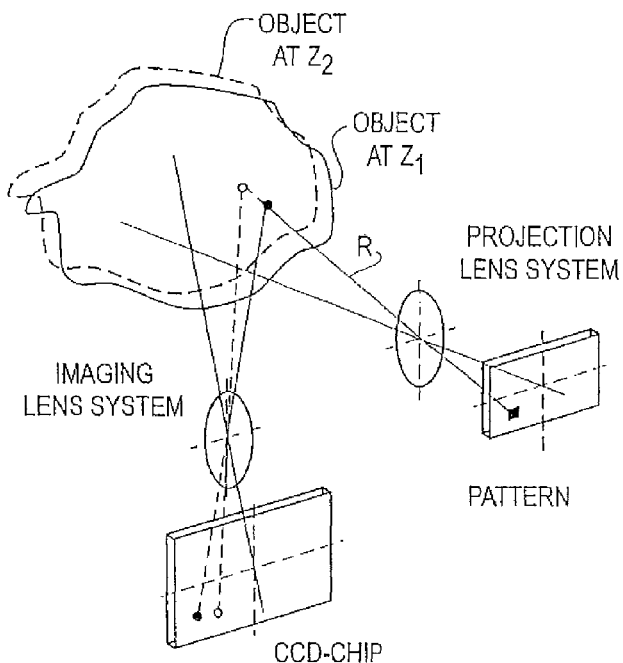
FIG. 9A is an illustration of an electronic imaging device of a scanner, associated imaging lens system, and an object reflecting a projection pattern onto the imaging device at two different distances.

A 3D imaging device as disclosed in this application does initially not deliver 3D information, but only 2D information as the CCD chip is a 2D imaging device. Information on the $3^{rd}$ dimension therefore has to be determined in an extra processing step. The additional information that we can use to perform such a 3D calculation is the spatial arrangement of the optical components, such as shown in FIG. 9A. FIG. 9A shows a schematic arrangement of components. One portion of the pattern is indicated with a small square, and the ray along which this portion would be projected is also displayed. The point, where this ray would intersect with the surface of the object, is displayed as a circle. At the center of this circle, the portion of the pattern would be projected onto the surface of the object. One of the reflected rays will run through the imaging lens system and such be projected onto the surface of the CCD chip, which will cause a corresponding signal. In this figure, only the center rays are displayed, e.g. the rays that run through the center of the lens systems.

Assuming that there is precise knowledge of the geometrical arrangement of the components, it would be possible to precisely calculate the spatial coordinates of the part of the surface of the object that reflects the considered portion of the pattern. This calculation is only possible under three preconditions:

(i) The geometric arrangement of all components of the scanning system must be precisely known,
(ii) The exact characteristics of all components must be known (true x/y-coordinates of all CCD pixels, including precise knowledge of the dimensions of the pattern; and
(iii) The lens systems must be 'ideal' which means that the center ray must be an ideal straight line.

In mass production scenario for a scanner, it will be almost impossible to guarantee these preconditions. One possible approach would be to calibrate the individual devices, which means that the deviations of the characteristics from the ideal configuration are determined and noted ("compensative calibration"). The 3D calculation will then base on algorithms like described before, but will additionally take into account known deviations to compensate for individual characteristics of each device. However, this compensational calculation has to be set up very carefully, and errors in terms of plus/minus signs will not easily be detected especially when the deviations are minor.

Another challenge is presented by scanning devices like disclosed in PCT/DE97/01797 by Rubbert, where imaging device and projection device are not physically connected to each other, and therefore the geometrical relationship may be completely unknown.

The calibration procedure that is described herein does not require any pre-knowledge of any dimensions of the optical and mechanical components, and thus can be termed "independent calibration". Furthermore, even any knowledge of the angle formed by the two optical axes (angle of triangulation) is not required.

Figure 9B:
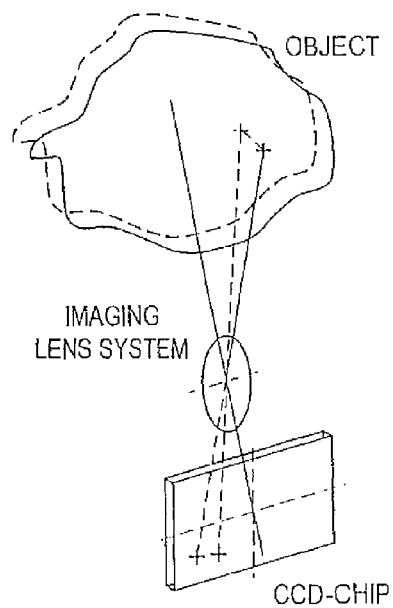
FIG. 9B is an illustration of how the different position of the object reflecting a given ray causes the ray to impinge on a different location of the imaging device (CCD chip).

The background of this procedure can be described best by again just looking at one specific portion of the pattern that is being projected along a ray onto the surface to be measured like indicated in FIG. 9B. It is important to understand that this portion of the pattern will always be projected along this specific ray R, which is defined by the optical characteristics of the lens system and the arrangement of the pattern and the lens system with respect to each other. If this portion of the pattern is being reflected from any surface sitting in the field of view, we can be absolutely sure that this point of the surface will be located somewhere along this ray R. However, we do not know at which position along this ray the point is located. To be able to determine this, the "independent calibration" method basically takes samples. The first sample will be a surface that is located at a certain distance $Z_1$ from the projection device. The reflected portion of the pattern will show up at a specific pixel at the CCD chip (or perhaps over several pixels depending on the size of the portion of the pattern). It is important to understand that every surface that is ever being hit by this ray at this Z-distance will always cause a reflection of this ray R directed to this pixel (we are dealing with diffuse reflection, so every point being reflected will send rays into many directions, regardless of the angle between ray and surface). This implies that every time when this portion of the pattern is being reflected onto the pixel, we know exactly that this point of the surface is located at distance $Z_1$.

Knowledge of the distance between $Z_1$ and the scanner is not required as long as the scanner will not be used as an absolute measuring system. If we want to use the scanning system as an absolute measuring system, which means that we want to measure the location of points relative to the scanner and not only relative to each other, we would then need to use the Z-values with respect to the origin of the coordinate system of the scanner. The illustrated embodiment is not an absolute measuring system, but nevertheless generates accurate virtual models of the object true to scale.

During the calibration process, we will acquire a plurality of such "samples" for different portions of the pattern reflected off a calibration surface at different Z-distances, where the relative Z-distances of these levels with respect to each other must be known. It will be discussed further below, how many samples will typically be required to receive a complete calibration. The result of this sampling process is the first calibration relationship that is derived for the scanner: (1) pixel coordinates for the electronic imaging device for numerous portions of the pattern, said pixel coordinates associated with distance information from the projection system in a Z direction at least two different Z distances.

Having this first part of the calibration procedure done, we can determine the Z-component of every part of the measured surface that is reflecting the pattern onto the CCD chip. However, we do not have knowledge of the X- and Y-coordinates. To get this information, we need to perform the second part of the calibration.

Figure 9C:
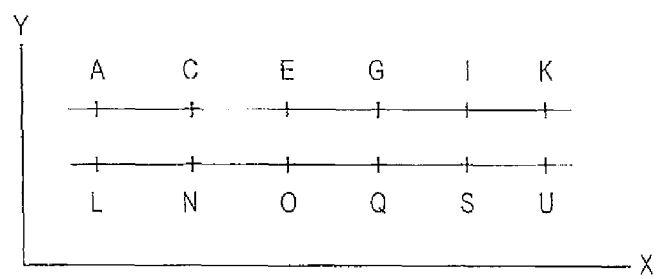
FIG. 9C is an illustration of pixel coordinates in X and Y directions for portions of the pattern (crosses A, L, C, E, G, etc.) at a certain Z distances, with a best fit line or mathematical function connecting the portions together.

Again, we will take "samples", but this time we will not make use of the pattern that is being projected onto the object during normal use of the scanner (the projection unit will be switched off). Rather, images are obtained of a reference object in the field of view that is equipped with features of a known geometry, i.e., known X-Y spatial relationship. The simplest implementation would be a point. In FIG. 9C, such a feature is a plurality of cross-hairs. The feature being projected onto the CCD chip will show up at a specific pixel (or several pixels depending on the size of the feature). The X/Y-coordinates of the pixel at the CCD chip are then assigned to the X/Y-value of the location of the feature (and assigned to a certain Z-distance).

It is obvious that if the feature is being moved in Z-direction, the location of the projection of the reference object at the CCD chip will change. We therefore have a dependence on the Z coordinate, which signifies that the Z-location of the feature must have a known reference to the Z-location(s) of the surfaces that have been used in the first part of the calibration. For instance, such a feature could be located at $Z_1$; other features might be located with a known reference to $Z_1$.

The first feature being captured in this manner would serve as a reference. A certain X- and Y-value (in mm or inches) would be assigned to the location of this feature. If such a feature would be placed close to the optical axis of the imaging system, it would be preferable to assign X=0 mm and Y=0 mm to this location. If we want to use the scanning system as an absolute measuring system, which means that we want to measure the location of points relative to the scanner and not only relative to each other, we would then need to use the X/Y/Z-values of this feature with respect to the origin of the coordinate system of the scanner.

During the calibration process, we will again acquire a plurality of such "samples" at different X-Y- and Z-locations, where the relative X-, Y- and Z-values of the locations of these features with respect to each other and with respect to the Z-values of the first part of the calibration must be known. It will be discussed further below, how many samples will typically be required to receive a complete calibration.

It is important to understand that the determined relationship between the X- and Y-coordinates of any feature being captured and specific pixel coordinates at the CCD chip exists only with respect to the Z-coordinate of the feature. A movement in Z will change the X/Y-value. Therefore, during normal operation of the scanner, when the calibration results are being used to calculate 3D coordinates, we first have to calculate the Z-coordinate of any point on a surface using the calibration values acquired in part 1, and basing on these results we can then perform the X/Y calculation, using the calibration results of part 2 of the calibration process.

There are several options with regard to the number of "samples" to take during calibration and the way how the results may be stored. The most straightforward approach would be to collect pixel coordinates for at least two Z-levels of the projected pattern. The number of pixel coordinates will depend on the resolution of the pattern. The Z-levels will preferably be defined within the depth of focus of the scanner projection lens systems and imaging lens systems, but close to the boundaries of this depth. Having collected pixel coordinates for at least two levels, would allow for interpolation of all other Z-levels. Part 2 of the calibration procedure could also comprise features (points) distributed evenly across the field of view, and those features could again be placed at two different Z-levels, which would allow for an easy interpolation of X- and Y-values. The pixel coordinates acquired in both parts of the calibration process could in the simplest embodiment be stored in a table.

However, this straightforward approach has certain disadvantages. First of all, an apparatus is required. Otherwise it would not be possible, to place the surfaces required for part 1 in a controllable manner with respect to each other, and the features being captured in part 2 also need to be precisely placed with respect to each other and to the calibration surface used in part 1. Usage of such a calibration apparatus is not a problem within an industrial production environment. But if scanners need to be calibrated for instance in an orthodontic office, it is not recommendable to always ship such a device to the location.

But there is no need to calibrate each portion of the pattern in various Z-levels. If a device is used, that comprises surfaces at different Z-levels, portions of the pattern will be projected onto levels that are closer to the scanner, and portions will be projected onto levels that are further away. It is well possible, to interpolate also the pixel coordinates that are not acquired during calibration.

Assuming that portions A and C of the pattern will be projected onto level $Z_1$, while portions C and D will be projected onto level $Z_2$, we will receive pixel coordinates for portion A and C assigned to Level $Z_1$ ($x_{A1}$ and $y_{A1}$ for A, $x_{C1}$ and $y_{C1}$ for C) and pixel coordinates for portion B and D assigned to Level $Z_2$ ($x_{B2}$ and $y_{B2}$ for B, $x_{D2}$ and $y_{D2}$ for D). It is well possible to linearly interpolate for instance $x_{A2}$ (which has not been acquired) from $y_{B2}$ and $y_{D2}$. In the same manner $y_{B1}$ could be interpolated from $y_{A1}$ and $y_{C1}$. Another way to receive calibration values that have not been acquired directly would be to draw the acquired pixel coordinates for a certain Z-level onto a sheet of paper and then to construct a best-fit line (either straight or curved) through those points. If the mathematical function of this best-fit line is stored, the pixel coordinates can be calculated using that function instead of storing them separately. The operation of determining a best-fit line can of course also be done directly in the computer. The best fit line concept is illustrated in FIG. 9C.

This procedure would work as well for part 2 of the calibration procedure where pixel coordinates are being acquired for specific features assigned to X-, Y- and Z-values. Again only a subset of features has to be captured at each Z-level, and the remaining values can be interpolated in the way described above. It would therefore also be possible to use just one calibration device that provides surfaces at least two Z-levels to perform part 1 of the calibration and comprises features at those surfaces that allow for part 2. The density of portions of the pattern, i.e., features to be captured, depends on the optical quality of the components of the scanner. We should capture at least four portions of the pattern, preferably close to the corners of the CCD imaging device 56 to provide a reliable interpolation.

The advantage of this calibration process is that it requires absolutely no pre-knowledge of the mechanical and optical characteristics of the scanner and automatically compensates for irregularities of the optical components, this including the CCD chip and the pattern. It is therefore useful to calibrate scanners that are made from cheap parts, and in can be used on scanners that have no known relationship between the imaging and the projection device.

With the foregoing discussion of the principles of the invention in mind, a representative embodiment of a scanner calibration device and method will be described with particularity with reference to FIG. 8. The presently preferred scanner calibration system includes mount or holder 122 for holding the scanner fixed in position during calibration. The holder is affixed to the top of a table 124. A calibration apparatus is positioned directly in front of the scanner 14. The calibration apparatus consists of a Z-direction carrier 126 having one portion 128 fixedly mounted to the table and a second portion 130 which can move back and forth in the Z direction between two different positions Z1 and Z2. An X-direction carrier 131 is mounted to the moveable portion 130 of the Z-direction carrier. The X-direction carrier consists a first portion 132 which is mounted to the moveable portion 130, and a second portion 134 which is moveable in the X direction relative to the first portion 132, as indicated.

The X-direction carrier 131 has mounted to its upper surface 136 two calibration devices: (1) a smooth, planar calibration surface 138 used for calibration of the scanner in the Z-direction, and (2) an X-Y calibration surface 140 used for calibration of the scanner in the X and Y direction. The X-direction carrier also contains a light 142 for providing back illumination of the X-Y calibration surface 140.

To calibrate the scanner 14, carriers 126 and 131 are moved such that the Z-direction calibration surface 138 is positioned in front of the scanner 14. An image is taken of the projection pattern reflecting off the surface with the surface 138 at some arbitrary distance Z1 from the scanner. Then the carrier 130 is moved a distance away ($\Delta Z$) to a new position Z2, and a second image is taken. Pixel addresses where the specific locations of the pattern are imaged in the electronic imaging device are determined and stored in a calibration table in a memory. The distance $\Delta Z$ is also known precisely and stored in the scanner memory or in the computer that performs the scanner calibration.

Then, the carriers 126 and 131 are moved such that the X-Y calibration grid 140 is placed at the distance Z1 and an image is taken. The image is generated by activating the source 142, with light from the source 142 passing through numerous tiny apertures 143 in the calibration surface 140 and impinging on the electronic imaging device 56. (The pattern illumination source is not used in this part of the calibration). The carrier portion 130 is moved to the position Z2, and another image is generated. Using the known separation distance between points in the X-Y calibration grid 140, X and Y distance information for points in the pattern imaged in the first part of the calibration procedure is computed. The results are stored in the calibration table. This process is described in further detail below. When the scanner calibration is finished, the scanner serial number and scanner calibration table (or other representation of the calibration relationship, such as a set of mathematical equations) are stored in memory in the scanner or in a computer associated with the scanner that processes the scanned images.

Figure 8A:
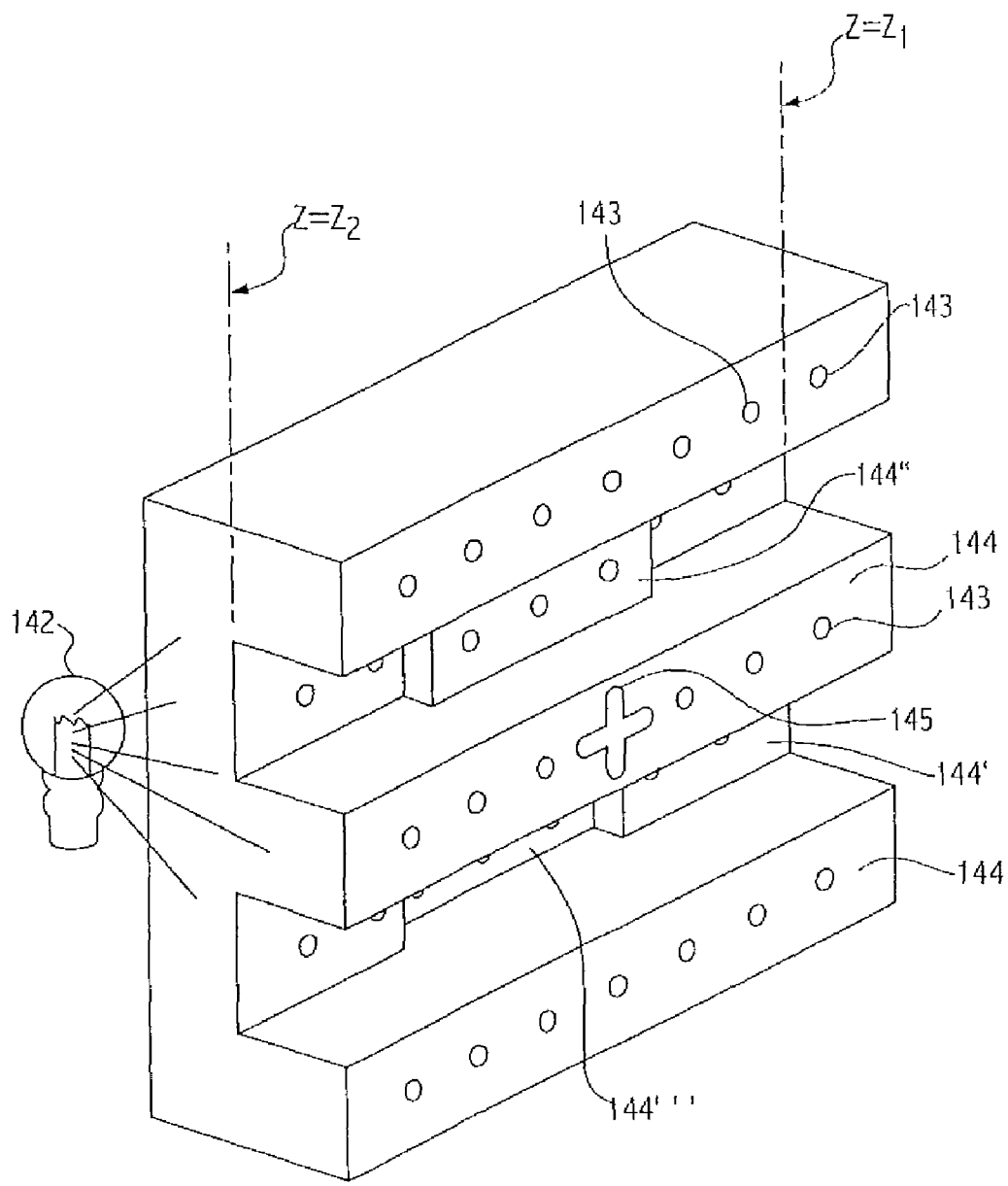
FIG. 8A is a perspective view of an alternative embodiment of a calibration device for the scanner in which the Z direction and X-Y calibration surfaces of FIG. 8 are combined into a single surface.

An alternative configuration of the calibration surfaces is shown in FIG. 8A. The calibration device consists of a set of reflective, planar, parallel planes 144, 144', 144" and 144''', of known distance from each other and from the scanner, with apertures 143 spaced at known distances along the surfaces of the planes and at known distances from adjacent planar surfaces. A cross feature 145 at the center forms the origin of the calibration surface, and is used as explained below. Two of the surfaces 144, 144', 144" and 144''' are used for the Z calibration surface. For X and Y calibration, the backlighting illumination source 142 is activated and light passes through the apertures 143 onto the electronic imaging device. The entire two-dimensional focal plane of the electronic imaging device is calibrated from an interpolation of known points in the surfaces 144, 144', 144" and 144''', in accordance with teachings described in detail herein. The embodiment of FIG. 8A is considered more cumbersome than the embodiment of FIG. 8, but is offered to illustrate that other configurations for a calibration surface are possible. In fact, curved surfaces or sloping surfaces could even be used, but the simplest surface is a planar surface oriented directly at the electronic imaging device.

Thus, in one possible alternative embodiment of the invention a calibration device is provided for a scanner projecting a pattern onto an object and receiving a reflection of the pattern off the object. The calibration devices comprise a calibration surface 144 receiving said projected pattern comprising two or more parallel surfaces (e.g., 144 and 144") of known separation distance and spatial extent and a plurality of point sources of light 143 provided in the two or more parallel surfaces. As described herein the point sources of light are apertures which allow light to pass through the surfaces 144 from the light source 142, but other configurations are possible. For example, the point sources of light could be light emitting diodes arranged in an array in the surface 144. The apertures 143 are formed in a precise and known spatial relationship relative to each other, such as by forming the holes with a precision high powered laser on a sheet of metal. Alternatively, instead of apertures 143, black dots could be formed on paper using a highly accurate printing process, and the black dots imaged by the CCD 56.

The calibration procedure described herein represents an alternative, and more preferred way of computing three-dimensional information for images as compared to prior art methods. FIG. 9 is an illustration of the relevant parameters that can be used to calculate surface configuration of the object in accordance with a known fashion. The method of FIG. 9 requires knowledge of the separation distance D or baseline between the detector and the light source, the angle between the axes 48 and 58, and the angles $\alpha$ and $\beta$ shown in the Figure. The present calibration method and method of calculation of three-dimensional information does not require any of this information. The calibration procedure compensates for imperfections in the optics in the optical paths, and therefore eliminates the need for high precision optics. Further, there is no need for precise knowledge of the placement of the scanner relative to the calibration planes. There is no need to know the angle between the axes 48 and 58, the separation distance between the scanner and the object being scanned, or any absolute value of the location of the object in any global coordinate system. The scanner allows for truly reference independent scanning, yet it gives very precise description of the three-dimensional surface.

The calibration will typically be performed once during manufacturing, which should be enough to last the life of the scanner. However the scanner can simply and quickly re-calibrated if the need arises.

Figure 10:
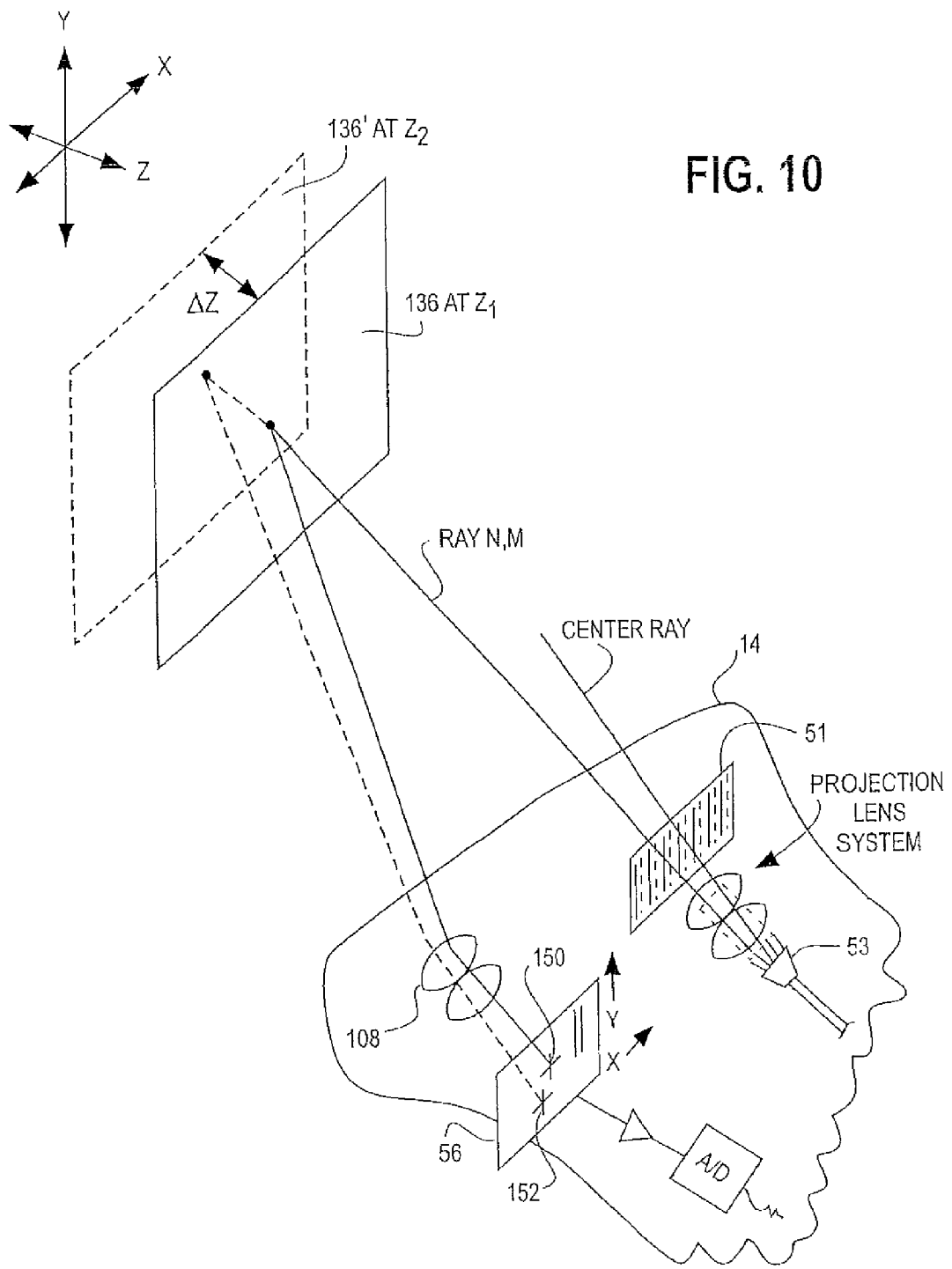
FIG. 10 is a illustration of an arbitrary ray $R_{n,m}$ which is projected from the projection system onto a calibration surface and captured by the electronic imaging device, with the calibration surface positioned at two different distances from the scanner, Z1 and Z2 and separated by a distance ΔZ.

A representative example of the calibration of the scanner will be better understood from FIG. 10 and the following discussion. FIG. 10 is a illustration of an arbitrary, unique ray $R_{n,m}$ which is projected from the projection system of the scanner onto the smooth, planar calibration surface 138 of FIG. 8 during the first part of the calibration procedure. The ray $R_{n,m}$ is captured by the electronic imaging device 56, with the calibration plane positioned at two different distances from the scanner, Z1 and Z2. The distance between the two locations is $\Delta Z$. Distance Z1 need not be known, however the separation distance $\Delta Z$ is known. The separation distance $\Delta Z$ will vary depending on the depth of focus of the imaging optics 108 in the scanner 14.

FIG. 10 illustrates a fundamental principle of the technique that is used for calibration of the scanner and generation of three-dimensional information of an object, which is considered to be an improvement over the calculations required by the method of FIG. 9. FIG. 10 illustrates that when the plane 136 is at a distance Z1, the ray $R_{n,m}$ impinges on the imaging device at the location 150. When the calibration surface 136 is moved to position Z2, the ray $R_{n,m}$ impinges on the detector at point 152. The pixel coordinates for ray $R_{n,m}$ at both positions is stored in a calibration table. In actuality, the pixel coordinates for a large number of rays from the projection pattern are stored for Z1 and Z2. These pixel coordinates, along with X and Y dimension measurements from a second part of the calibration procedure, give all the information needed to create a calibration table necessary to compute three-dimensional coordinates for an object that has been scanned with the projection pattern.

Ray $R_{n,m}$ corresponds to a single point in the projection pattern. Knowledge of where in the projection pattern ray $R_{n,m}$ originated from is required. Hence, some pattern recognition and decoding of the detected pattern is needed to identify the specific portions of the pattern that are being imaged by the various portions of the CCD electronic imaging device. To understand the pattern recognition process, the reader is directed to FIGS. 11, 12, 17, 18 and 19 and the following discussion.

Pattern Recognition

Figure 11:
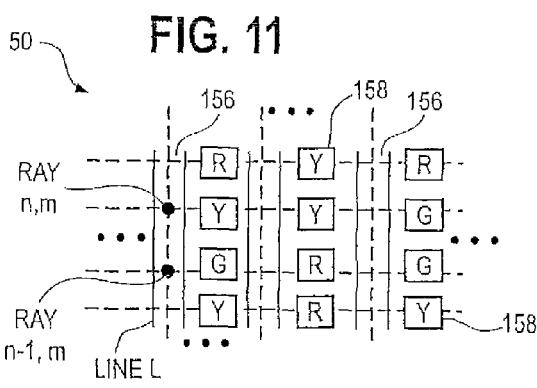
FIG. 11 is an illustration of a portion of a pattern that is projected from the scanner of FIG. 3 onto an object, the projection pattern comprising an array of parallel lines separated from each other by colored dots, it being understood that other types of projection patterns are possible.
Figure 12:
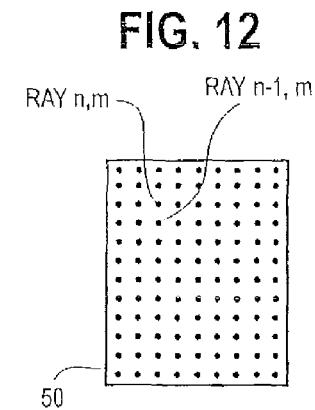
FIG. 12 is an illustration showing that the various rays of the projection system through the pattern of FIG. 11 can be represented by an array of N×M points.

FIG. 11 is an illustration of a portion of a pattern that is projected from the scanner of FIG. 3 onto an object (including the calibration surface 138). The projection pattern comprises an array of parallel lines 156 separated from each other by red, green and yellow colored dots 158, it being understood that other types of projection patterns are possible. The sequence of the colored dots 158 vary along the length of the lines 156, and in the direction perpendicular to the lines. This technique is used such that using pattern recognition and decoding processes, described herein, every region in the projection pattern can be decoded from the pixel data from the imaging device. FIG. 11 illustrates that $Ray_{n,m}$ can be taken to have originated at the intersection on one particular line and one particular colored dot, and this location can be determined precisely form the pattern recognition and decoding process. Similarly, the ray along the line L one row below ray $R_{n,m}$ can also be identified. In the present example, the pattern is constructed such that there are N columns or lines, and M rows of colored dots. FIG. 12 illustrates showing that the various rays of light passing through the pattern of FIG. 11 can be represented by an array of N×M points.

Figure 14:
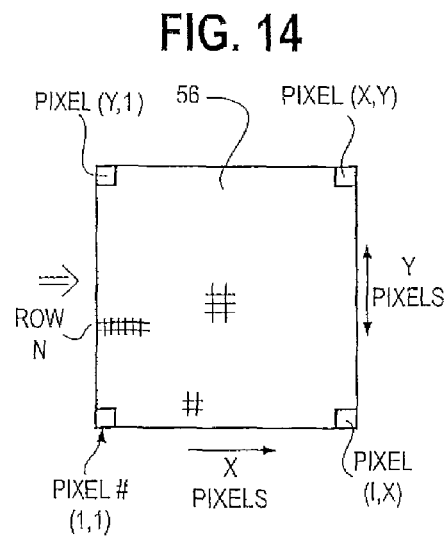
FIG. 14 is an illustration of the electronic imaging device, comprising an array of pixels arranged in X columns and Y rows.

This array of points representing the projection pattern of FIG. 11 is imaged by an electronic imaging device or CCD 56 arranged in an array of row and columns, as shown in FIG. 14. There are X columns of pixels in the X direction and Y rows of pixels in the Y direction. In the illustrated embodiment there are 1,028 pixels in each direction.

Figure 17:
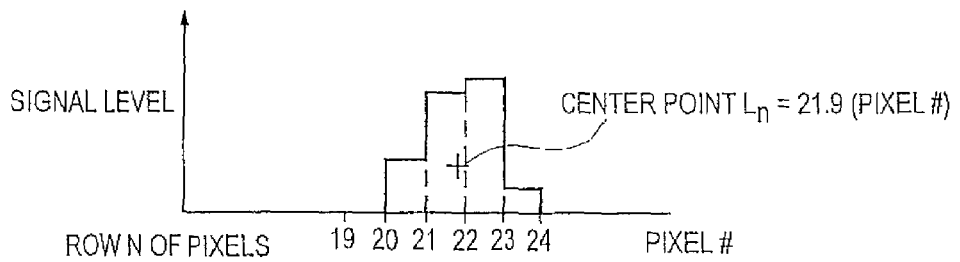
FIGS. 17, 18 and 19 illustrate the pattern recognition process for captured two dimensional images, as a first step in deriving three-dimensional information as to the object.
Figure 18:
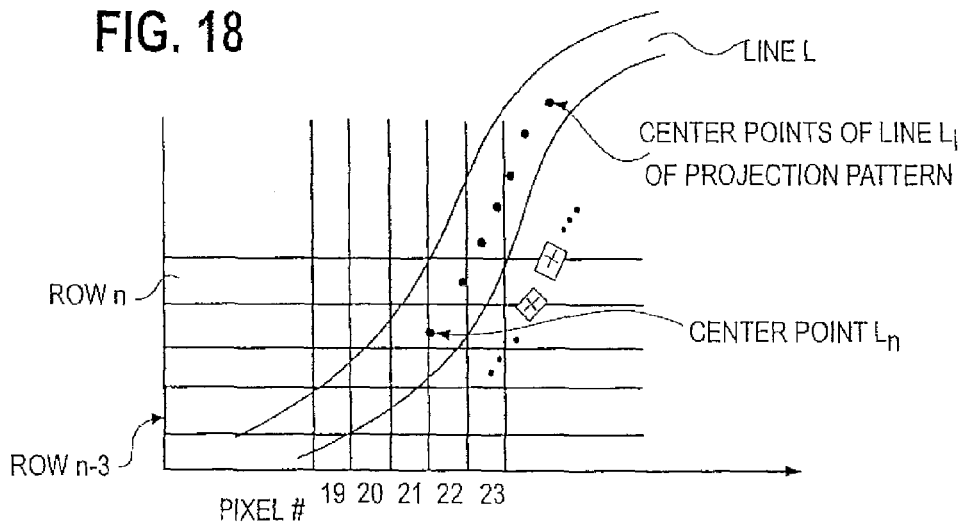
Figure 19:
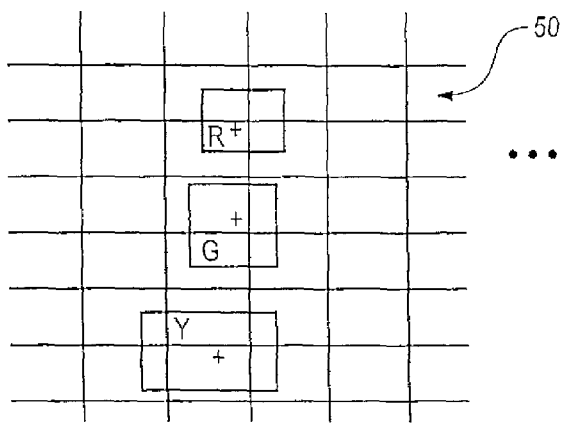

FIGS. 17, 18 and 19 illustrate the pattern recognition process for captured two-dimensional images. FIG. 17 shows the signal level from one row of pixels in the electronic imaging device. The signal indicates that line L of the projection pattern is imaged at pixels 20-23 of a particular row of the pixels. Averaging of the pixel values over the four pixels allows the center point of the line relative to pixel 21 to be calculated, with sub-pixel resolution. FIG. 18 shows how the line L and adjacent colored dots are imaged on the surface of the imaging device in this example. Note that the line is not necessarily centered over any column of pixels and hence the averaging must be performed to determine the center point in the line. A similar pattern recognition process is performed for the colored dots, as indicated in FIG. 19. The center of each colored dot is located, as is the center points of the lines for every line and colored dot imaged by the imaging device.

The pattern recognition process thus takes the output signals of the imaging device (in the form of a colored bitmap image) and returns a set of pixel locations for centers of lines and centers of particular colored dots. The next step in the process is correlating these pixel locations for lines and colored dots to particular lines and colored dots in the projection pattern. This process is referred to as decoding (process 82 in FIG. 6), and is described in detail below. Decoding is not normally needed during the calibration procedure described in conjunction with FIG. 8, since the Z calibration surface is planar and the arrangement of the projection pattern on the CCD 56 is preserved. Decoding is used however during use of the scanner to scan an object of unknown surface configuration.

Decoding

The decoding process is the process of converting a set of pixel addresses for lines imaged by the imaging device, and a set of pixel addresses for particular colored dots imaged by the imaging device, to particular lines and colored dots in the projection pattern. Decoding is not absolutely required during calibration (particularly where the Z calibration surface is a planar surface). It is used, however, during processing of images on an object having undercuts, shadow features, or other irregularities. It may be possible to decode only a portion of the received pattern, since ordering of lines in the projection pattern is preserved. For example, if lines 13 and 16 are decoded, lines 14 and 15 are also decoded since their spatial relationship relative to lines 13 and 16 are preserved.

The imaging analysis process needs to know that a particular pixel is imaging a particular line or a particular colored dot. The projection pattern or screen 50 (FIG. 2) varies continuously in both directions, due to the unique and continually varying sequence of the colored dots. The decoding process simply examines where the red, yellow and green dots are being imaged in the imaging device, and compares these results with the known sequence of red, yellow and green dots in the projection pattern, and thereby locates or identifies each ray with reference to the projection pattern. For example, the process knows that, for example, pixel 21 in row N of the imaging device is imaging the center of line 13, row 55, in the projection pattern.

Referring again to the calibration set-up of FIGS. 8 and 10, the scanner takes two images of the Z-calibration surface 138, one at distance Z1 and the other at distance Z2. The pixel addresses where each ray $R_{n,m}$ in the projection pattern is imaged by the array is stored in a calibration table referred to herein as calibration table #1, shown in FIG. 24. At this point, we know how the imaging of the projection pattern varies as the calibration surface is moved in the Z direction relative to some imaginary plane Z1 in front of the scanner. However, the X and Y relationship is not yet known. Therefore, the scanner must be calibrated in the X and Y direction using a pattern of known geometry. This is explained in conjunction with FIGS. 8 and 13-16.

Figure 13:
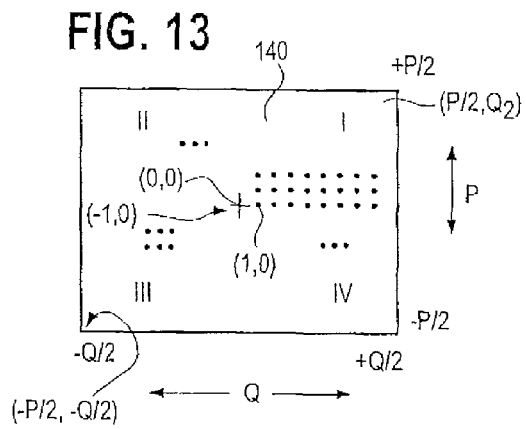
FIG. 13 is a illustration of the X-Y calibration surface of FIG. 8, showing the array of Q×P points in the calibration surface being organized into a coordinate system having an origin at the center of the surface and breaking the surface up into four quadrants I-IV.
Figure 23:
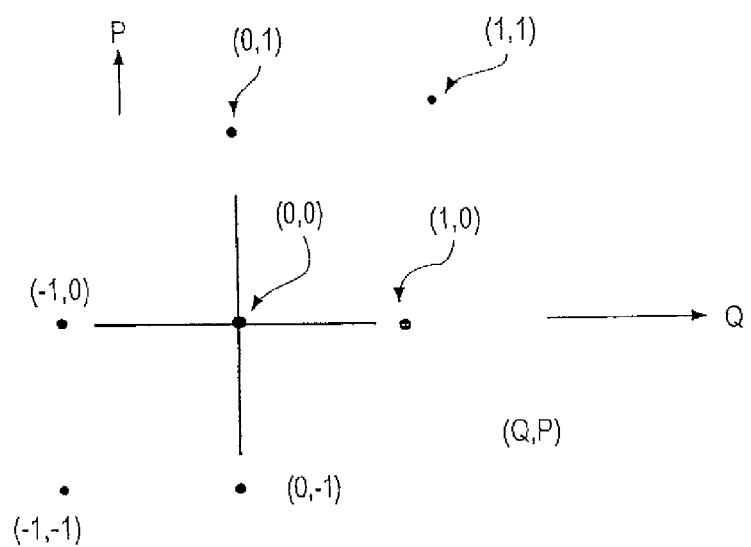
FIG. 23 is an illustration showing the coordinate system that used for the X-Y calibration surface in generating the entries for the calibration tables for the scanner.

FIG. 13 is a illustration of the X-Y calibration surface 140 of FIG. 8, showing the array of Q×P points (tiny apertures 143) in the calibration surface 140 being organized into a coordinate system having an origin at the center of the surface 140, in the shape of a cross 145. The calibration surface 140 is conceptualized as consisting of four quadrants I-IV. FIG. 23 shows one possible numbering convention of the points in the surface at the origin. In the illustrated embodiment, the points of the X-Y calibration surface 140 are actually tiny apertures spaced from each other a known distance (e.g., 1 mm). The apertures act as a plurality of point sources of light when the light source 142 positioned behind the surface 140 is activated. These points of light are imaged by the electronic imaging device 56 during the second part of the calibration step. By counting pixel signals (indicating the imaging of a point source in the surface 140) over from the origin in the X and Y directions, it is possible to determine which point in the surface 140 is being imaged by which pixel, again with sub-pixel resolution. Since we know the address of the pixels which illuminate the specific portions of the projection pattern, and we can know the distance from the origin of the surface 140 that this pixel is imaging, it is therefore possible to calibrate the pixels in the X and Y directions. A second calibration table, shown in FIG. 25, is used as an interim step to generate the distance values in the X and Y directions for the principal calibration table #1 in FIG. 24.

Figure 15:
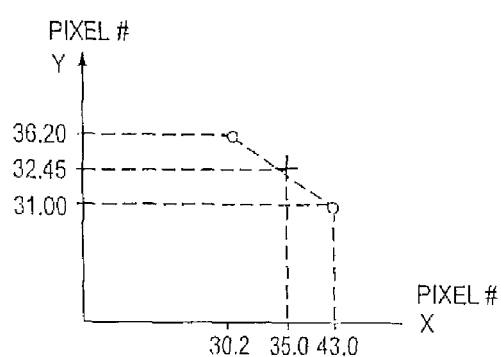
FIG. 15 is an illustration showing the interpolation of pixel addresses in X and Y directions for given ray $R_{2,3}$ from a scanned object from two points of the X-Y calibration plane previously imaged by the electronic imaging device during calibration.
Figure 21:
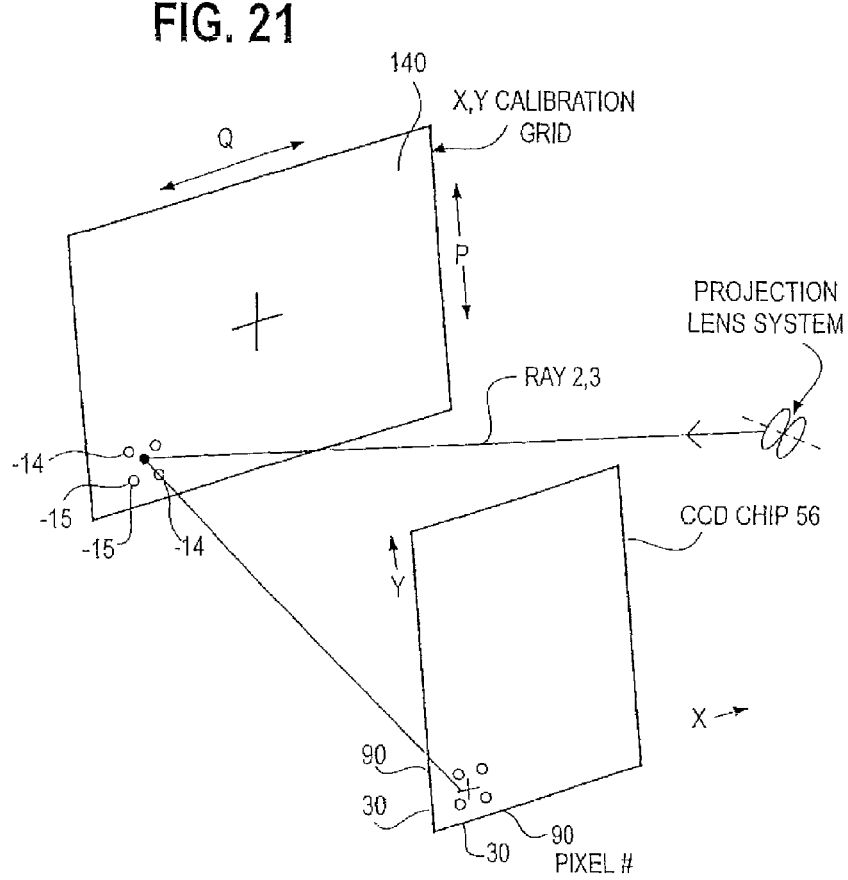
FIG. 21 illustrates the relationship between the projection of ray $R_{2,3}$ from the projection system and the X-Y calibration surface of the calibration station.

This process will be explained by example. FIG. 15 is an illustration showing the interpolation of pixel addresses in X and Y directions for a given ray $R_{2,3}$ from a scanned object from two points of the X-Y calibration plane previously imaged by the electronic imaging device during calibration. FIG. 15 indicates that a given point in the projection pattern, ray $R_{2,3}$, is imaged by some pixel that is located between the pixels that imaged points in surface 140 that are in quadrant III, between 14 and 15 points to the left of the origin and between 14 and 15 points below the origin. This is suggested by FIG. 21, which shows where ray $R_{2,3}$ is imaged on the CCD chip. FIG. 21 also indicates where the corresponding points on the X-Y calibration surface 140 are imaged by the pixels in the electronic imaging device. As is shown in FIG. 21, in the present example the pixel values are between 30 and 90 in the X and Y directions.

FIG. 25 shows the X-Y calibration table #2 that is used for generating distance entries in X and Y directions in the calibration table No. 1 shown in FIG. 24. FIG. 25 illustrates that for each point in the X-Y calibration surface 140, corresponding pixel addresses for pixels imaging those points are identified and stored in the table. This is done for all points in the four quadrants of the X-Y calibration surface 140. These values are obtained when the X-Y calibration surface is positioned at both distances Z1 and Z2, and an image is generated at both positions. The entries in the table are pixel addresses in X and Y directions, expressed in sub-pixel resolution. Representative entries for Quadrant I are shown, it being understood that entries are made for all the points in the X-Y calibration surface.

Now, if we know that ray $R_{2,3}$ of the projection pattern from the Z-calibration procedure (using the calibration surface 138) is being imaged at a particular location, we can use the calibration table #2 of FIG. 25 to compute an entry in mm for table #1. Again, using the present example, assume ray $R_{2,3}$ (corresponding to line 2, row 3 in the projection pattern) is imaged by pixel having an address of 30.2 in the X direction and 36.2 in the Y direction, at Z=Z1. The distance in mm can be calculated from an interpolation of the entries in calibration table 2 of FIG. 25. This is indicated for the entries in line 2, row 3. At the Z=Z1 distance, this point is imaged at pixels 30.2 in the X direction and 36.2 in the Y direction, which corresponds to a distance of −14.6 mm in the X direction from the origin and −14.4 mm in the Y direction. Similarly, at Z=Z2, this point is imaged by pixels 43.0 in the X direction and 31 in the Y direction, which corresponds to a distance of −14.8 mm in the X direction and −15.8 mm in the Y direction. This information is entered into table #1, as shown in FIG. 26.

Figure 22:
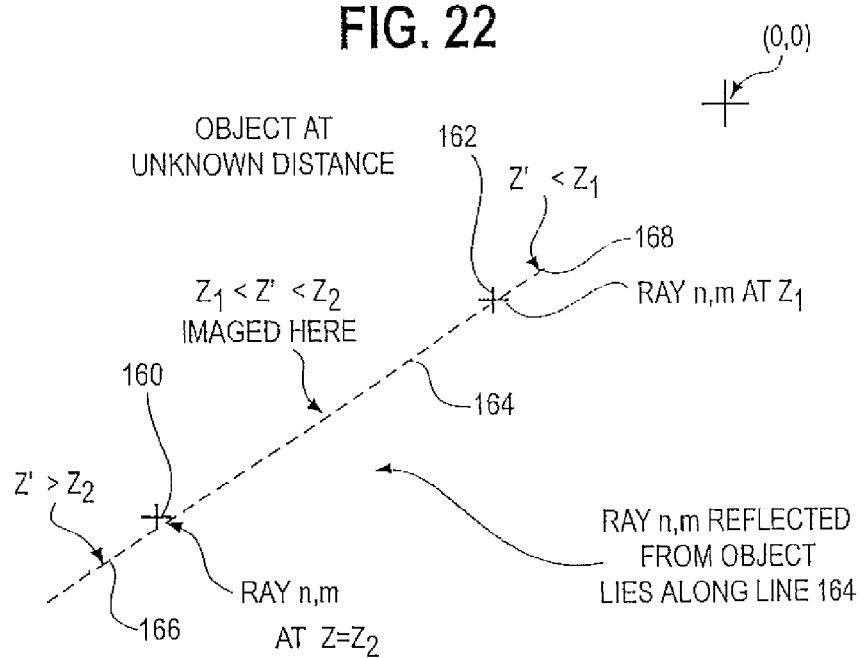
FIG. 22 is an illustration showing the relationship between the unknown distance Z' of the object from the scanning device and the locations where ray $R_{n,m}$ is imaged by the electronic imaging device at distances $Z_1$ and $Z_2$.

This interpolation takes advantage of a linear relationship that exists between pixel address and distance for objects at an unknown distance Z' from the scanner. This can be best appreciated from FIG. 22. Since we know that ray $R_{n,m}$ is imaged at one point 160 in the imaging device at Z=Z1, and that it is imaged at another point 162 at distance Z=Z2, the ray must fall along the dotted line 164 where Z' is between Z1 and Z2. Similarly, if Z'>Z2 it lies along the line indicated at 166. If Z'<Z1, it lies along line 168. This linear relationship between distance and pixel address is the key to obtaining Z information as to ray $R_{n,m}$ and X and Y distance in mm. Furthermore, since ΔZ is known exactly during the calibration (e.g., 7 mm in the illustrated embodiment), and a linear relationship exists between pixel address and distance, the location of exactly where ray $R_{n,m}$ lies along the line 164, 166 or 168 tells us with precision the position of the unknown object in the Z direction, relative to virtual plane Z1. This location of where ray $R_{n,m}$ is being imaged by the electronic imaging device is arrived at by the pattern recognition and decoding processes described herein.

Figure 16:
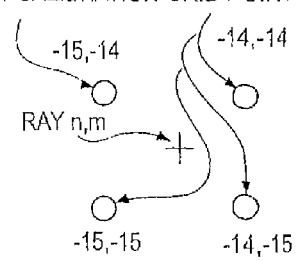
FIG. 16 is a more detailed illustration of the location of the ray $R_{2,3}$ from the scanned object relative to the points of the X-Y calibration plane.

Referring again to the example of FIGS. 16 and 17, we know ray $R_{n,m}$ is imaged at some region of the CCD, and this is stored in table 1 (FIG. 25). From calibration table 2 (FIG. 26) we know the X and Y coordinates of neighboring points in the X-Y calibration grid in the region of ray $R_{n,m}$. By interpolation of the X and Y coordinates, we can calculate the distance in mm from the origin since the points in the X-Y calibration grid are separated from each other a known distance. This is done for all N×M portions of the projection pattern.

For example, calibration table 1 of FIG. 24 tells us that ray $R_{2,3}$ is imaged at pixel addresses X=30.3 and Y=36.2 for Z=Z1, and at pixel address X=43 and Y=31 at Z=Z2. We then look to the table 2 entries (FIG. 25) to find the closest X and Y points in the X-Y calibration grid by looking at the pixel addresses in table 2. This is shown in FIG. 16. An interpolation of the pixel addresses in table 2 to the known pixel address from table 1 results in an X, Y address in mm. In the present example, X in mm=−14.6, Y in mm=−14.4. The results are now added to table 1, see FIG. 26. The same is done for the distance Z=Z2. The same is of course performed for all the N×M rays in the projection pattern, resulting in a completely filled calibration table 1. Table #1 in FIG. 26 only shows the entries for ray $R_{2,3}$, but the process is done for all rays for Z=Z1 and Z=Z2.

Figure 20:
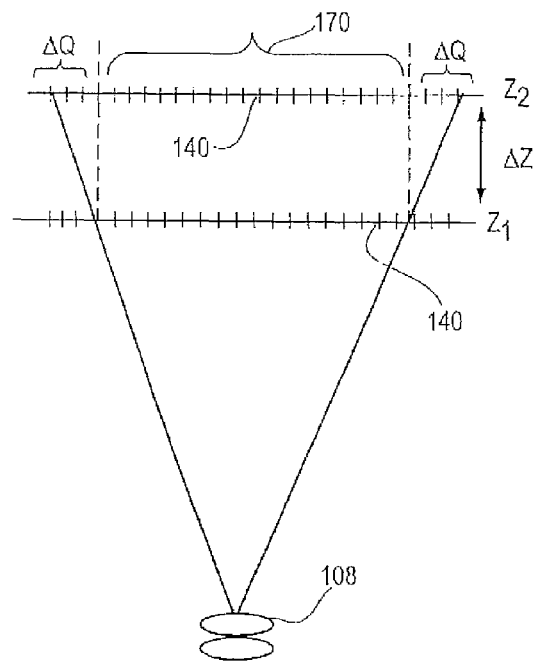
FIG. 20 illustrates the points of the X-Y calibration plane from the calibration station of FIG. 7 at two positions relative to the optical elements of the electronic imaging device.

FIG. 20 illustrates the points of the X-Y calibration plane from the calibration station of FIG. 7 at two positions Z1 ands Z2, relative to the optical elements of the electronic imaging device. It will be apparent that when the Z=Z1, some points in the X-Y calibration plane will not be imaged, but will be when Z=Z2. These points, indicated by ΔQ in the Q direction, exist also in the P direction. The calibration table 2 takes these into account. Some points in all four quadrants may not be imaged at Z=Z1, but will be imaged at Z=Z2 during X-Y calibration. Points indicated at 170 are imaged at both values of Z.

From the above, in one aspect of the present invention, a machine-readable memory is provided for a scanner used to calculate three dimensional information of an object scanned by the scanner. The memory may be in the scanning unit itself, in a separate work station for the scanner, or in any computing device such as a remote computer that processes acquired image data and generates a three-dimensional model of the object. The memory comprises an array of data storage locations containing a calibration relationship for the scanner, such as a table. The calibration relationship identifies pixel coordinates for numerous portions of a pattern projected onto a calibration surface located at two different distances from the scanner, and distance information in X and Y directions for the portions of the pattern for the two different distances. The calibration entries stored in memory allow the scanning system to compute three-dimensional coordinates for points on an object reflecting the projection pattern onto the electronic imaging device.

Now that the scanner has been completely calibrated, it is ready to scan objects at some unknown distance and having some unknown surface configuration. The derivation of X, Y and Z coordinates for the surface will be explained in the next section.

Derivation of 3-D Point Cloud Per Image (Step 84, FIG. 6)

With reference to FIGS. 6 and 26, we now explain the derivation of spatial coordinates in three dimensions for a single captured image. With the entries in Table 1 completely filled out during calibration, the scanner is now able to derive X, Y and Z coordinates for any object at an unknown distance. The scanner has the most accuracy when the distance is between the values Z1 and Z2, such that the captured images are in focus, but distances outside of this range may still be able to be imaged and decoded.

First, the electronic imaging device 56 captures an image and the image is subject to the pattern recognition and decoding, steps 80 and 82 in FIG. 6, described in detail above. This process results in a set of pixel coordinates stored in memory for all the lines and colored dots of the pattern that are projected onto the object and imaged by the pixels of the CCD. Comparison of the pixel addresses of the captured image with the entries in Table 1 in FIG. 26 (when completely filled out during calibration) yields the coordinates of every point in the captured imaged, in three dimensions.

The process is as follows:

First, compute the Z value of every portion in the projection pattern found in the captured image using table 1, given the known line and row number of the portion of the pattern, and the associated pixel number. The unknown distance, Z', for any point, measured from the virtual plane Z1 is as follows $$Z' \text{ (in mm)} = \Delta Z \times \frac{\text{measured pixel \#} - \text{pixel \# for line and row of pattern at Z1}}{\text{pixel \# for line and row of pattern at Z2} - \text{pixel \# for line and row of pattern at Z1}}$$

where $\Delta Z$ is the distance from Z1 to Z2 in the calibration set up described above.

Using ray $R_{2,3}$ as an example, if this ray is imaged at pixel #35 in the X direction, from table 1 the calculation is as follows $$Z' \text{ (in mm)} = 7.0 \text{ mm} \times \frac{35 - 30.2}{43 - 30.2} \text{ where } \Delta Z \text{ is } 7 \text{ mm.}$$

$$= \Delta Z \times \sigma$$

Here, $\sigma = 0.375$, a linear scaling factor.

Therefore Z'=0.375×7 mm or 2.625 mm. The point on the object reflecting ray $R_{2,3}$ is 2.625 mm from the virtual plane Z1. The Z value for all other points in the object are also measured relative to a virtual plane Z1.

Now, Table 1 (FIG. 26) is referred to determine the mm values in the X and Y direction for this point in space and another interpolation is performed to the mm entries in table 1. The calculation is as follows:

Since we know we have line 2, row 3 in the pattern (from the pattern recognition and decoding process), we need to interpolate the mm entries in table 1.

X value is between −14.6 and −14.8 ΔX=0.2 mm

Y value is between −14.4 and −15.8 ΔY=1.4 mm

The true value of $X = X_{at\ Z1} - (\sigma \times \Delta X)$, similarly the true value of $Y = Y_{at\ Z1} - (\sigma \times \Delta Y)$.

Therefore:

The true value of X for ray $R_{2,3}$=−14.6−(0.375×0.2)=−14.675 mm

The true value of Y for ray $R_{2,3}$=−14.4−(0.375×1.4)=−14.925 mm

Summarizing, the X, Y and Z coordinates for the point in the object reflecting ray $R_{2,3}$ is X=−14.675 mm Y=−14.925 mm Z=−2.625 mm These points are stored in memory 42 of the scanning work station 16, step 86 of FIG. 6. This process is performed for every ray $R_{n,m}$ in the projection pattern that is recorded in the captured image. The result is a set of three-dimensional coordinates in space, referred to herein as a "frame", for each captured image. This set of points can be calculated in a small fraction of a second with a general-purpose computer.

The pattern recognition, decoding and 3-C coordinate calculation process will now be explained with reference to two-dimensional bitmap images of teeth. The process described below is the same for any object being scanned.

Part 3. Generation of Digital Impression

A complete three-dimensional model of the patient's dentition can be generated from the scanning system of the present invention. The process requires an operator moving the scanner 14 (FIG. 3) over the dentition, preferably in-vivo, and generating a series of frames of images. The frames are obtained at a rate of at least one frame per second as the scanner is moved over the teeth. The scanning of an entire jaw may require three separate scanning operations or "segments" due to maneuverability constraints and a break in the capturing of images. While the scanning is occurring, the four steps of FIG. 6 are performed for the stream of captured images. The end result is the storage of a set of frames in the main memory of the scanning work station 16. The frames can be registered to each other using one or more of a using a variety of frame registration techniques described in detail below. Once all the frames have been registered to each other, a complete three-dimensional virtual model of the patient's dentition is displayed for the orthodontist. This computer model provides a base of information for diagnosis and planning treatment. An introduction to the treatment planning aspects of the overall orthodontic care system is set forth in Part 4.

Figure 27:
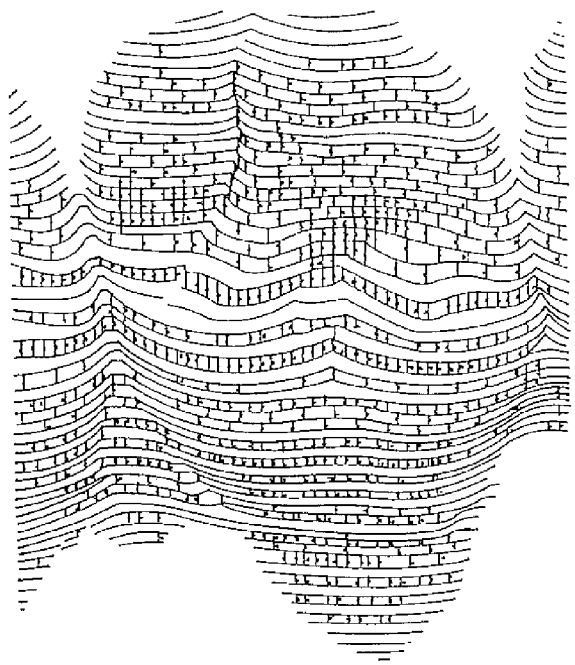
FIG. 27 is an illustration of a two-dimensional bitmap image of a tooth and associated anatomical structures captured by the electronic imaging device of the scanner of FIGS. 1, 2, 3 and 4, prior to any signal processing in the scanning node or workstation.

FIG. 27 is an illustration of a two-dimensional bitmap image of a tooth and associated anatomical structures captured by the electronic imaging device 56 of the scanner of FIGS. 1, 2, 3 and 4, prior to any signal processing in the scanning work station 16. An inspection of FIG. 27 indicates that the image includes various lines and colored dots of the projection pattern, as it is reflected off of the tooth and associated anatomical structures. The location of where these lines and colored dots are imaged on the imaging device 56 contains information as to the three-dimensional shape of the tooth and associated anatomical structure.

Figure 28:
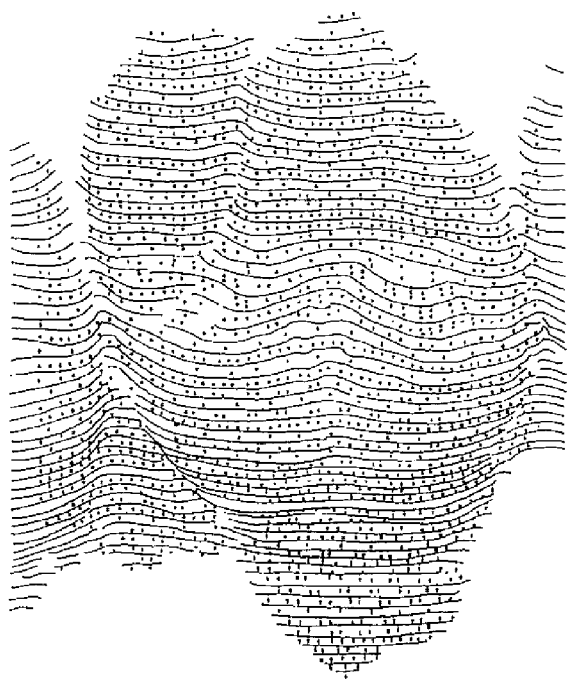
FIG. 28 is an illustration of the image of FIG. 27 after pattern recognition and filtering operations have been performed.

Referring back to FIG. 6, the first step is a pattern recognition process on the captured image. FIG. 28 is an illustration of the image of FIG. 27 after pattern recognition and filtering operations have been performed. The filtering operation basically returns a zero pixel value for those pixels where the pattern recognition process cannot detect the lines and the colored dots, for example due to the surface being out of focus (i.e., out of range of the scanner optics).

After the decoding operation is done on the image of FIG. 28, the result is a set of pixel locations where the decoded rays $R_{n,m}$ of the projection pattern were imaged in the imaging device 56. Step 84 is performed for all such rays, using calibration table #1 of FIG. 26 stored in memory for the scanner. The result, step 86 of FIG. 6, is a set of three dimensional coordinates for all the points in the image, a point cloud comprising a "frame." FIG. 29 is an illustration of a single "frame" of data, that is, a three-dimensional point cloud of a scanned object which has been calculated from a single two dimensional image by the pattern recognition, decoding, and 3-D calculations described herein.

Figure 29:
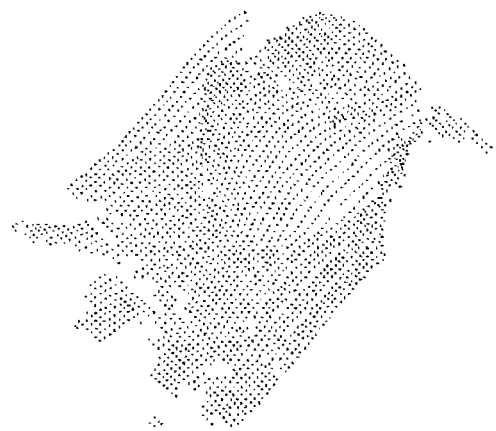
FIG. 29 is an illustration of a single "frame" of data, that is, a three-dimensional point cloud of a scanned object which has been calculated from a single two dimensional image by the pattern recognition, decoding, and 3-D calculations described herein.
Figure 30:
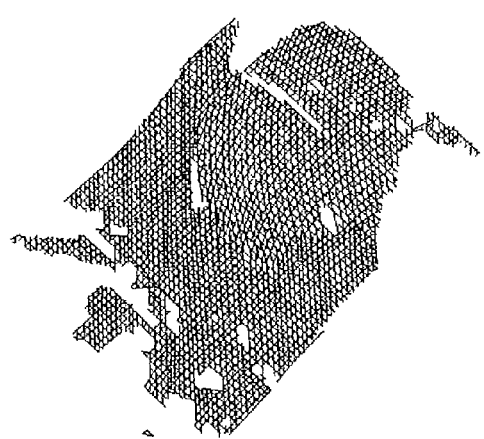
FIG. 30 is an illustration of the points of the cloud of FIG. 29 in which three adjacent points of the cloud are joined together to form triangle surfaces.
Figure 31:
FIG. 31 is a view of the three-dimensional surface formed from the triangle surfaces shown in FIG. 30.
Figure 32:
FIG. 32 is a view of the surface of FIG. 31, smoothed by a smoothing algorithm to give a smoother representation of the surface of the object.

FIG. 30 is an illustration of the points of the cloud of FIG. 29, in which three adjacent points of the cloud are joined together to form triangle surfaces. The usage of the triangle surfaces in a registration process is described below. FIG. 31 is another view of the three-dimensional surface formed from the triangle surfaces shown in FIG. 30. FIG. 32 is a view of the surface of FIG. 31, smoothed by a smoothing algorithm to give a smoother representation of the surface of the object. Commercially available off-the-shelf software exists for taking a set of three dimensional coordinates and displaying them on a computer monitor, and such software is used to display the three dimensional surfaces (if desired by the user).

Figure 33:
FIG. 33 is another example of a bitmap image obtained by the electronic imaging device of the scanner.
Figure 34:
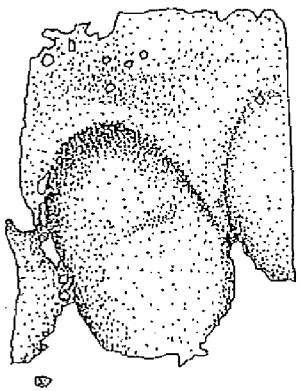
FIG. 34 is a plan view of the three-dimensional surface obtained from the two-dimensional bitmap image of FIG. 33.
Figure 35:
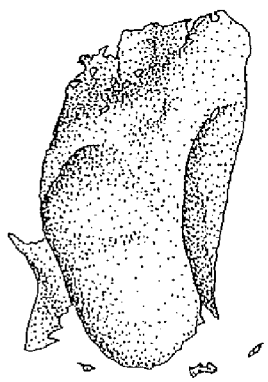
FIG. 35 is a perspective view of the three-dimensional surface shown in FIG. 34.

FIG. 33 is another example of a bitmap image obtained by the electronic imaging device of the scanner. FIG. 34 is a plan view of the three-dimensional surface obtained from the two-dimensional bitmap image of FIG. 33, after the steps of FIG. 6 have been performed. FIG. 35 is a perspective view of the three-dimensional surface shown in FIG. 34. The software programs enable the surface to be rotated in any degree of freedom, allowing for complete inspection and visual analysis of the surface.

Since the scanner and scanned object move relative to each other during capture of the scanned images, the three dimensional coordinates for a large number of frames will not agree with each other. In other words, the X, Y and Z coordinates for a given point on the object will change from frame to frame since the point was imaged from a different spatial orientation for each image. Hence, the frames have to be registered to each other to generate a complete overall digital model of the object. The present invention provides for various registration procedures to be performed on the frames, to find a best-fit solution for coordinates of the object in one frame vis-à-vis coordinates of the object in other frames. These registration procedures are described in the following section.

Figure 36:
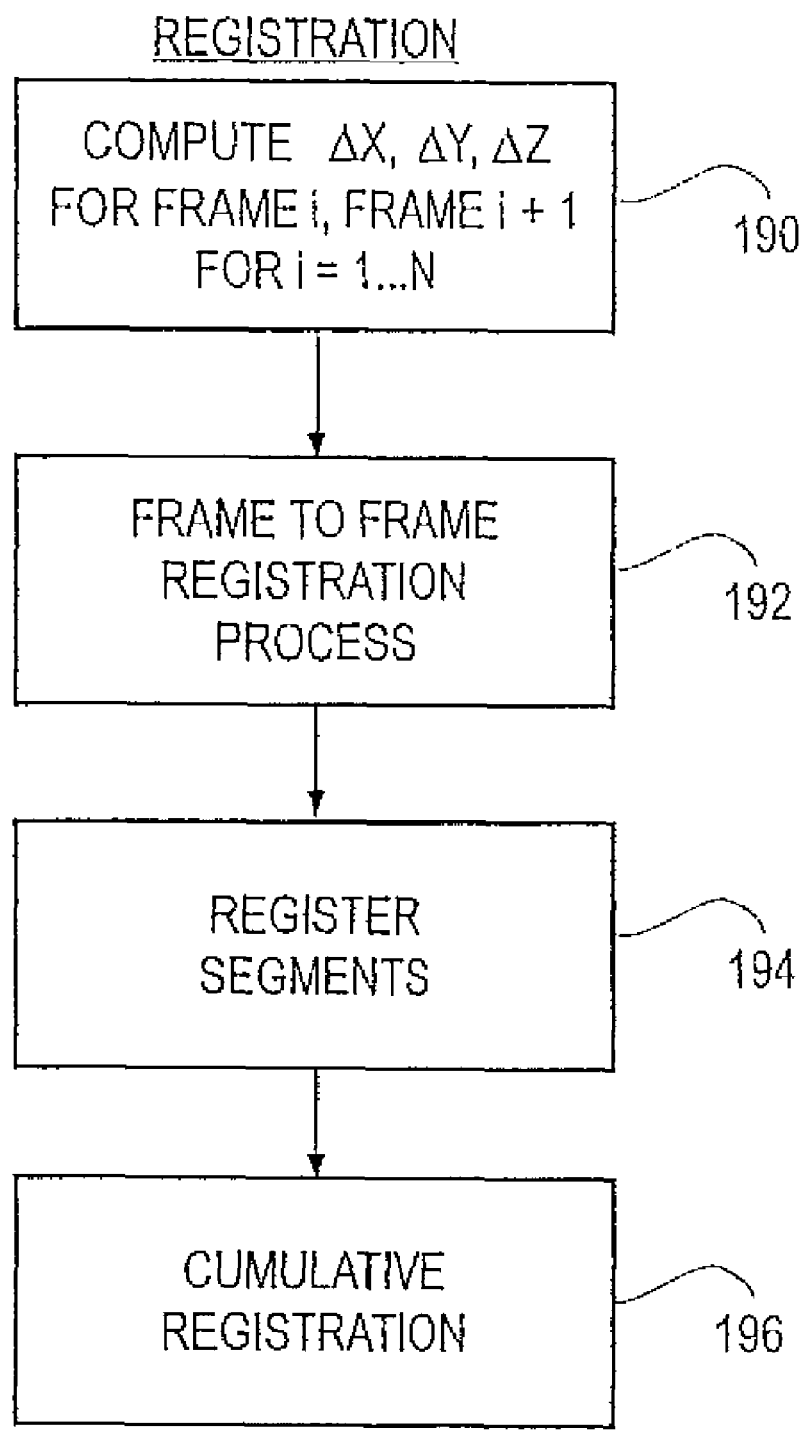
FIG. 36 is a flow chart shown illustrating the steps performed to generate a complete three-dimensional model of the dentition of a patient from a series of scans of the upper and lower jaws.

FIG. 36 is a flow chart illustrating the steps performed to generate a complete three-dimensional model of the dentition of a patient from a series of scans of the upper and lower jaws. The steps include an initial step 190 of determining an entry point into a registration process, a frame to frame registration process 192 of registering one frame to another, a segment registration process 194 to register segments (i.e., portions of a scan where the scan was interrupted for some reason) to one another, and finally a cumulative registration procedure 196 in which the frames are registered to all other frames to obtain a slightly more accurate model of the object than that obtained by frame to frame registration. It will be understood that depending on the application, the step 194 may not be required, a frame to frame registration may only be needed, or the user may only desire a cumulative registration and steps 192 or 194 are not performed at all.

Figure 37A:
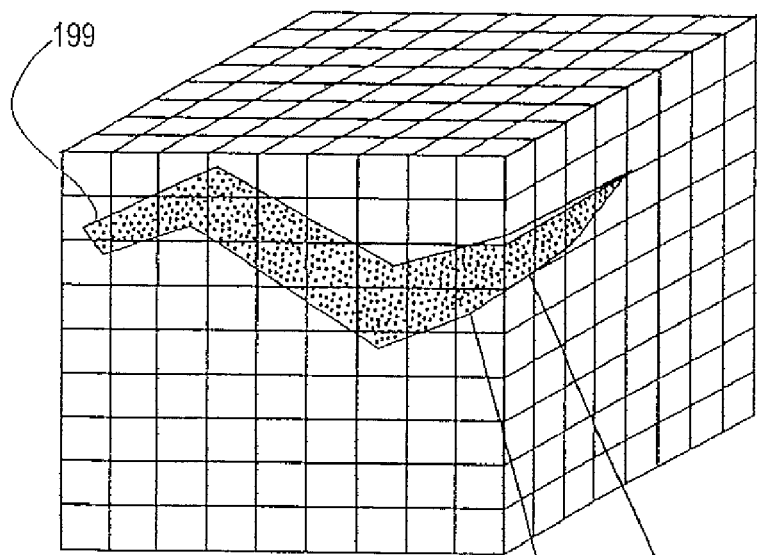
FIG. 37A is an illustration of a mathematical model of a surface of an object after generation of several frames of data and registration of such frames relative to each other to generate a complete model of the surface of the object.
Figure 37B:
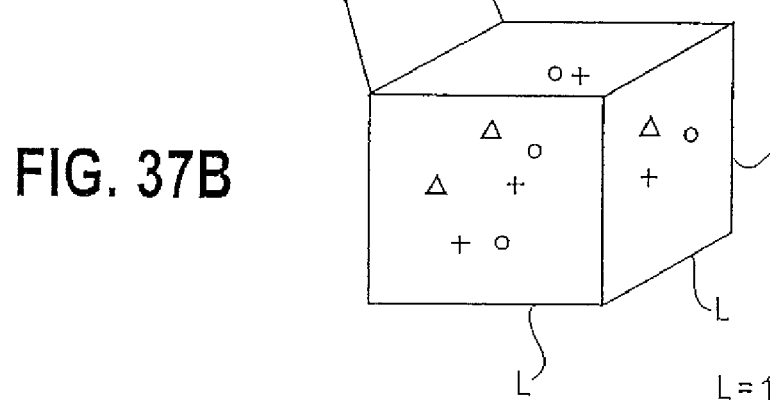
FIG. 37B is a illustration of one small three-dimensional section of the model of FIG. 38A, showing points from three different frames that are located in approximately the same position in three dimensional space after the registration of these frames has been completed.

The result of registration is a three-dimensional model containing all the points from the frames captured by the scanner. An example of such a model is shown in FIG. 37A, where surface 199 indicates the sum total of points of all the frames in three-dimensional space. FIG. 37B illustrates one small section of the surface, showing for example the points in three-dimensional space from three frames.

Figure 37C:
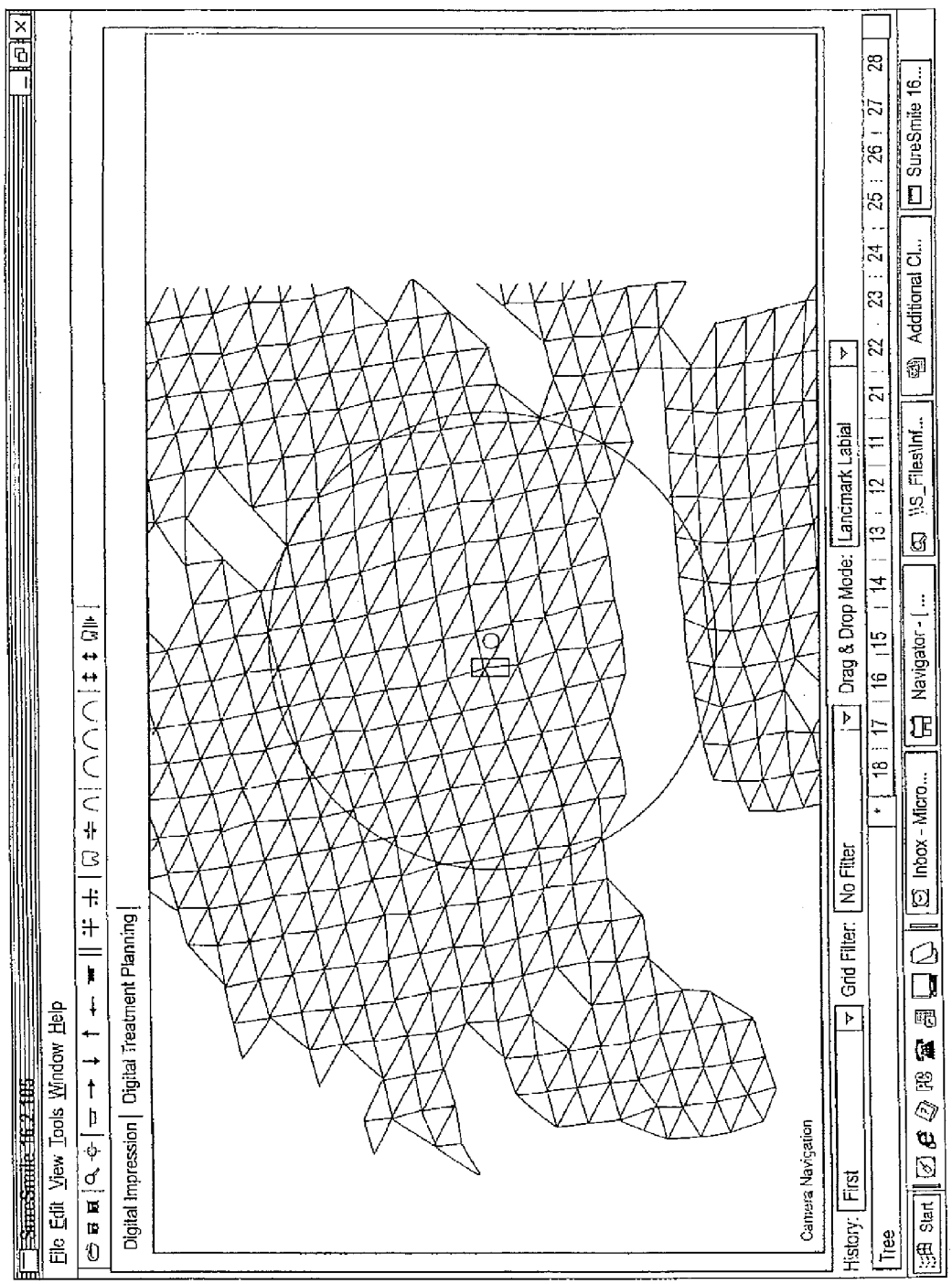
FIG. 37C is a screen shot on the user interface of a back office work station of FIG. 1, showing triangle surfaces for points comprising one frame obtained from scanning a tooth.
Figure 37D:
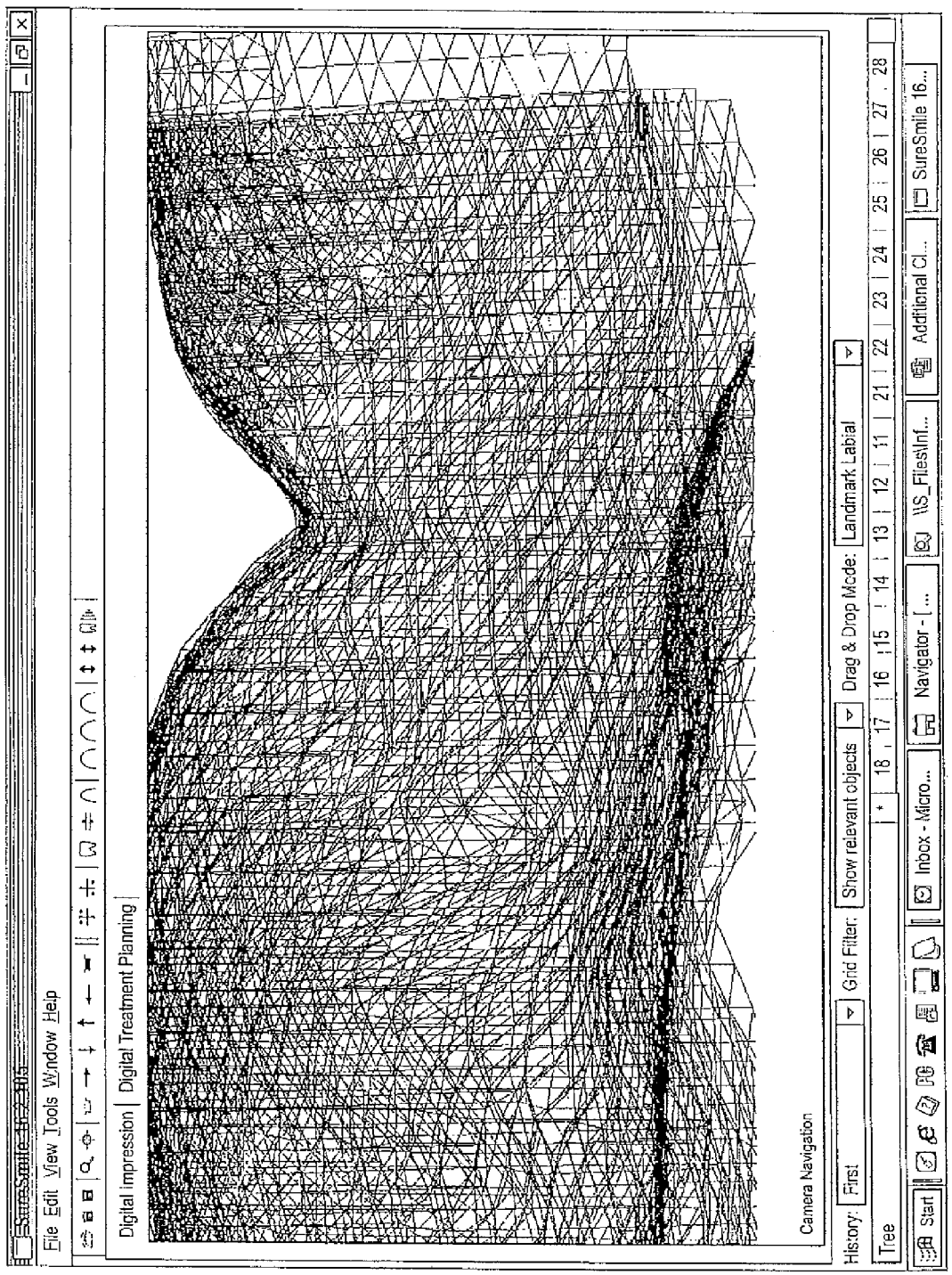
FIG. 37D is a screen shot showing a registration of a large number of overlapping frames on the tooth, of which the frame of FIG. 37C is one frame.

A preferred registration technique involves registering a set of points (three-dimensional coordinates) comprising a frame to a surface formed by a previous frame (or group of frames), rather than registration of one set of points to another set of points. This is due to a relatively coarse projection pattern used in the illustrated embodiment; the points can be low in density as compared to the curvature of the object. FIG. 37C shows one frame from a scan of a tooth, with the points in the frame connected by lines to form a set of triangle surfaces. The coarseness of the projection pattern (and widely spaced points in the point cloud) is compensated by the fact that a given portion of the surface is captured by overlapping frames, and the registration occurs from the points in one frame to the surface in the previous frame or a surface defined by more than one previously registered frames. The registration process described herein ultimately permits a fine resolution in the three-dimensional model. This is indicated by FIG. 37D, showing all the frames for the tooth scan registered to each other to create a very fine and high resolution virtual model of the tooth.

A. Entry Point into Registration (Step 190, FIG. 36)

Registration processes require a starting point for fitting one frame, frame i to another frame, frame i+1. The starting point, in the illustrated embodiment, is rough calculation of the offset between overlapping points in the frames in X, Y and Z directions. Whereas prior art systems have good pre-knowledge of the spatial relationship due to the known physical arrangement of the scanner and the object, the present system does not. The starting point is the initial assumption of spatial relationship between one frame and the previous frame (and one frame and a set of previous frames).

Figure 38A:
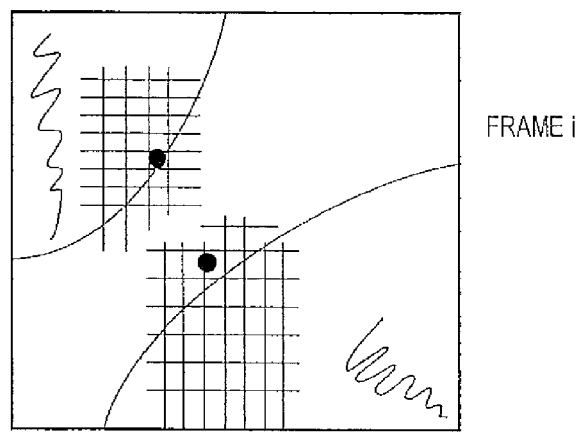
FIGS. 38A-38C are an illustration of a two-dimensional cross-correlation procedure in the X and Y directions. The procedure, along with the procedure in FIGS. 37A and 37B, is used to find an initial entry point into a registration algorithm between successive frames of data.
Figure 38B:
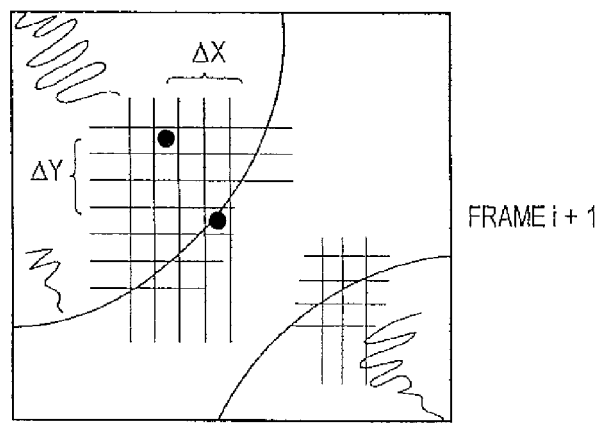
Figure 38C:
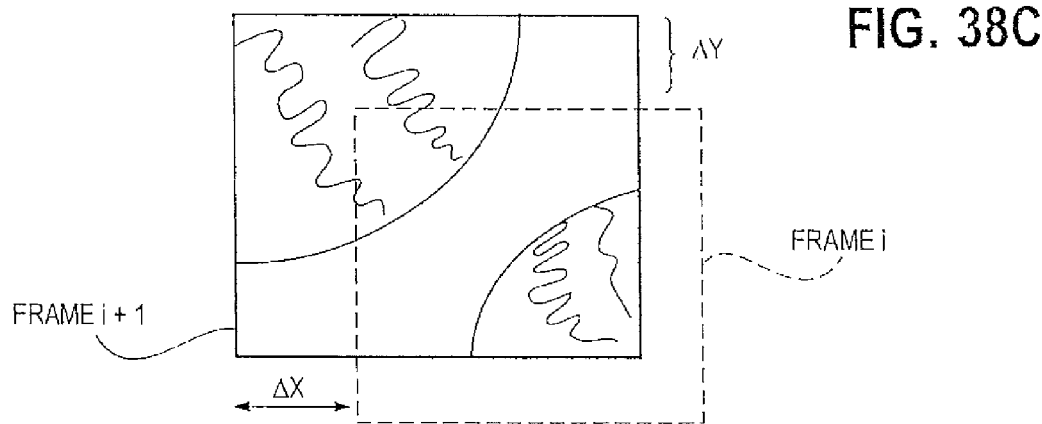
Figure 39A:
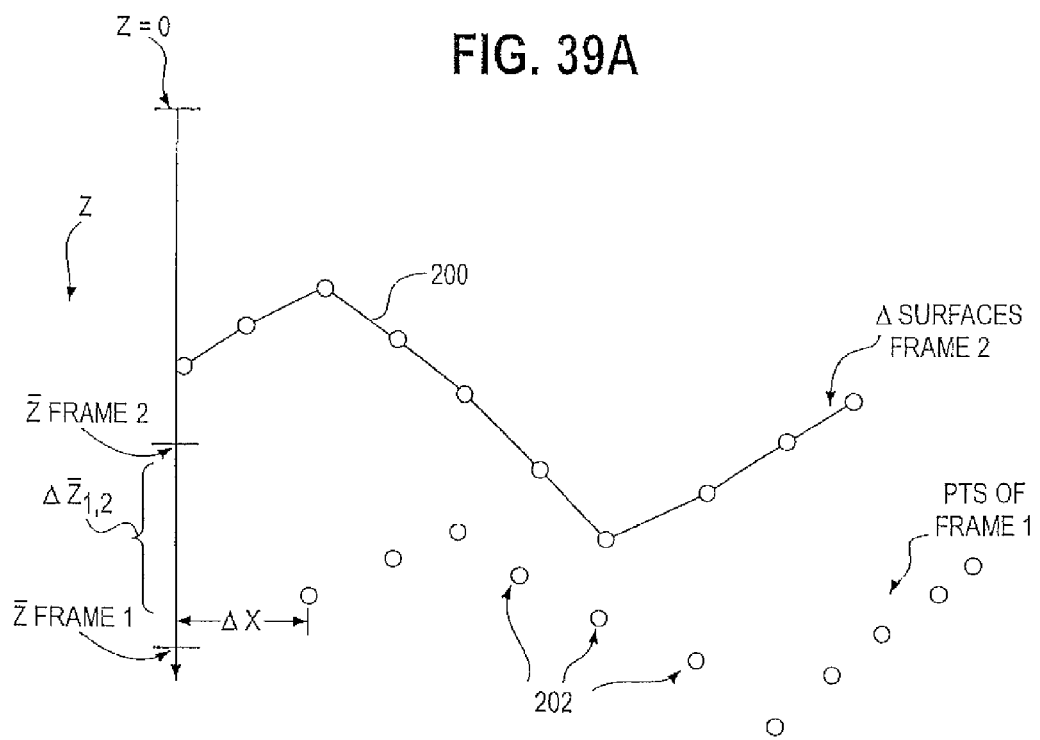
FIGS. 39A and 39B are an illustration of a one-dimensional correlation procedure in the Z direction for two successive frames.
Figure 39B:
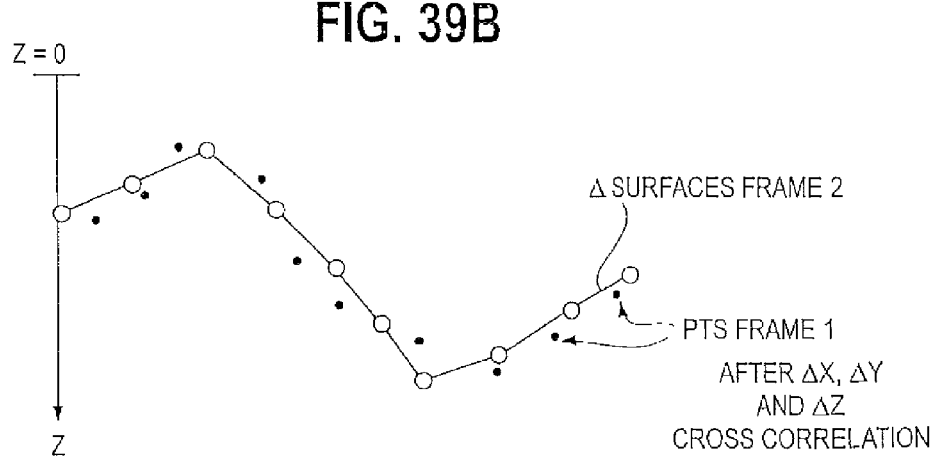

The method of calculation of the offset in X and Y directions is illustrated in FIG. 38A-C. FIGS. 38A-38C are an illustration of a two-dimensional cross-correlation procedure in the X and Y directions. The procedure, along with the procedure in FIGS. 39A and 39B, is used to find an initial entry point into a registration algorithm between successive frames of data.

It can be seen from FIGS. 38A and 38B that frame i+1 is moved in the X and Y directions from frame i. To obtain the amount of movement, $\Delta X$ and $\Delta Y$, the images are projected to both X and Y axes by adding all pixel values of every row, acquiring a one dimensional Y-vector, and adding all the pixel values of every column, acquiring a one-dimensional X-vector. This is performed for both frames, resulting in $X_{frame\ i}$ and $X_{frame\ i+1}$ and $Y_{frame\ i}$ and $Y_{frame\ i+1}$. The vectors are smoothed to suppress the influence of the projected pattern.

To compute $\Delta X$, the absolute value of the difference between each value of the X-vector of frame i (frame i–$X_{frame\ i}$) and the X vector of frame i+1 (frame i+1–$X_{frame\ i+1}$) is calculated with a varying position shift within a range of –xa<k<+xe. The sum of these values represents the resemblance of $X_{frame\ i}$ and $X_{frame\ i+1}$ shifted by a certain amount k.

The minimum value of k is determined. This result gives the shift or movement in the $\Delta X$ direction.

The same process is also performed the Y direction. As can be seen in FIG. 38C, if frame i is moved by an amount $\Delta X$ and $\Delta Y$, the overlapping points in both frames will have the same values and the sum of the difference in pixel value will be approximately zero.

FIGS. 39A and 39B are an illustration of a one-dimensional correlation procedure in the Z direction for two successive frames, in the present example frame 1 and frame 2. Line 200 represents a three-dimensional surface of the second frame, formed by connecting three adjacent points in the point cloud. The set of points 202 represents the points of the point cloud representing frame 1. To compute the Z offset, $\Delta Z$, the sum is taken of all the Z values of Frame 2, and the result divided by the number of points, resulting in an average Z value of Frame 2. The same is done for Frame 1. The difference between the average Z value of Frame 2 and the average Z value of Frame 1 is the Z offset, $\Delta Z$. FIG. 37B illustrates the result after translation of Frame 1 by the amount $\Delta X$, $\Delta Y$ and $\Delta Z$. The result is that the points of frame 1 are quite close to the triangle surfaces of Frame 2. The values of $\Delta X$, $\Delta Y$ and $\Delta Z$ are stored for Frame 1 and used as an entry point to a registration procedure.

B. Frame to Frame Registration

Frame to frame registration is a process for registering one frame with another frame, that is, finding a best-fit in terms of translation and rotation make overlapping points in the frames agree with each other. If the frames are generated in sequential order, frame to frame registration refers to registration of the second frame to the first frame, the third frame to the second frame, from the fourth frame to the third frame, etc. Frame to frame registration can be performed very quickly. It can be performed in a manner such that the operator of the scanning system sees the results of frame to frame registration on the monitor of the scanning work station while they are still scanning the patient. What they see is an accurate three-dimensional representation of the dentition on the monitor, for those portions of the dentition that have been scanned thus far. As additional frames are obtained, they are registered to the previous frame and added to the computer model. When scanning is complete, the computer model can be rotated around on the monitor and inspected to see that all relevant portions of the teeth and anatomical structures have been scanned. The user thus gets immediate feedback on the results of the scanning using frame to frame registration.

FIGS. 40A-40D is a flow chart of a frame to frame registration process for a set of frames, each frame consisting of a three-dimensional point cloud of a scanned object. Each frame is typically generated from a different spatial orientation of the scanner relative to the object due to movement of the scanner during image capture, hence the frames overlap to at least some extent. The registration process is used to find a best fit between the frames relative to each other, and thereby provide a complete three-dimensional virtual model of the surface of the object from all of the frames. The end result of the frame to frame registration is a substantially exact three dimensional model of the scanned object. This object is represented by a large set of point coordinates in computer memory. The result is also represented as a set of transformation matrices providing information as to how each frame of points should be translated and rotated in three dimensions in order to fit to the previous frame.

The frame to frame registration process is also an iterative process. At the end of each iteration, a comparison is made as to how "close" the two frames are to each other in three dimensions. If they are not close enough (with "closeness" determined in absolute terms by a quality index, say in microns), another iteration is done, using the results of the first iteration. The frame to frame process may continue for tens or even hundreds of iterations, depending on how fine or precise the user wants the registration to be. The process stops when a best fit between two frames has been reached or a maximum number of iterations has occurred.

Referring now to FIG. 40A-40D in conjunction with FIGS. 39 and 41-43, an initial step 209 is performed as an entry point into the registration procedure. In this step, the processes of FIG. 39A and described previously is performed to make a Z-coordinate transformation of frame i–1 and frame i. Basically, this transformation is performed by summing the Z coordinate values of both frames individually, finding a median Z value for each frame, finding the difference or $\Delta Z$ value from these median values, and shifting one frame (frame i) by this amount to bring the Z coordinates of all the points in that frame closer to the points of frame i–1. The rationale of step 209 is as follows. The Z axis measurements of a surface represent a degree of freedom of the scanner movement. Scanner movements in the Z direction do not provide significant new information on the object being scanned. However, because of the focus optics of the electronic imaging device (108 in FIG. 7), the visible surface of the object becomes slightly smaller or larger depending on how much the scanner is moved in the Z direction relative to the surface, while the center of the surface (or, loosely speaking, the "center of gravity") of the visible area basically remains nearly the same with Z direction movement. The Z coordinate transformation step 209 eliminates this effect by normalizing the Z surface coordinates. This process also makes possible the exclusion criteria of step 2 described below, by which non-overlapping points and stray data points are excluded from the registration process.

Figure 40A:
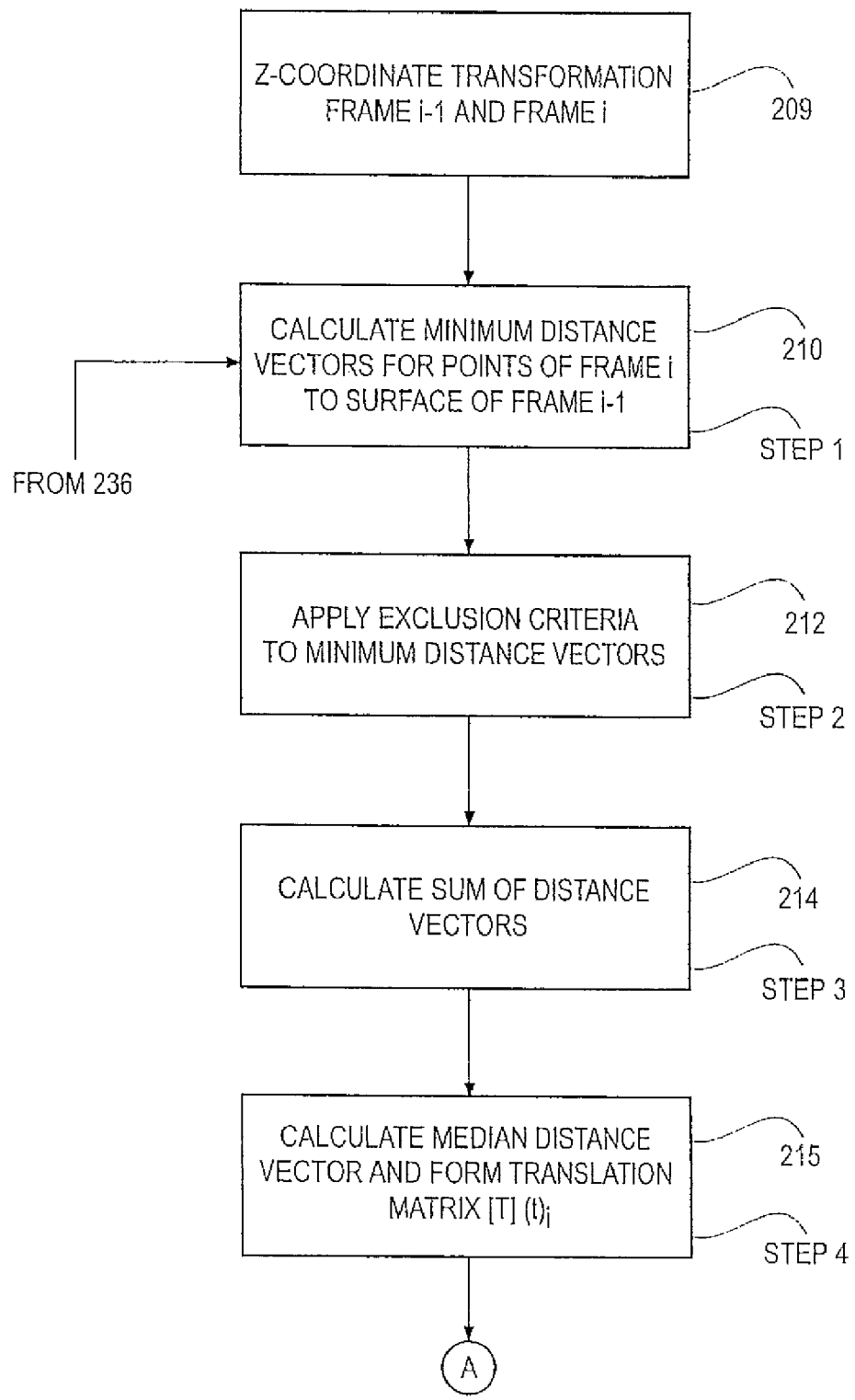
FIGS. 40A-40D are an illustration of a frame to frame registration process for a set of frames, each frame consisting of a three-dimensional point cloud of a scanned object. Each frame is typically generated from a different spatial orientation of the scanner relative to the object due to movement of the scanner during image capture, hence the frames overlap to at least some extent. The registration process is used to find a best fit between the frames relative to each other, and thereby provide a complete three-dimensional virtual model of the surface of the object from all of the frames.
Figure 41:
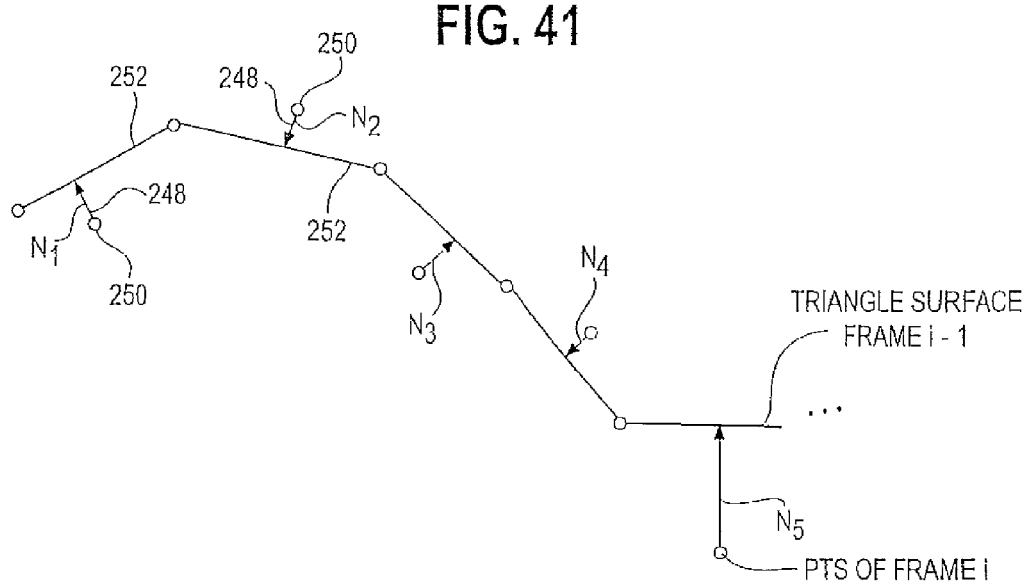
FIG. 41 illustrates the normal vectors used in the process of FIG. 40.

The registration procedure itself starts with step 1, 209 in FIG. 40A. At this step, minimum distance vectors 248 (N1, N2, ...) are calculated from every point in Frame i to the surface of frame i–1. The surface of a frame can be obtained easily by connecting neighborhood points to together with a triangle or other polygon. The minimum distance vector, for each point in Frame i, is defined as the distance vector having a magnitude which is the minimum of the following three vectors: 1) the shortest vector from the point intersecting a triangle surface in frame i–1 normal to the triangle surface; 2) the shortest vector from the point orthogonal to the edge of a triangle surface in frame i–1, and 3) the shortest vector from the point to the nearest point in frame i–1. Most often, but not always, this will be a normal vector, type 1) above. In the example of FIG. 41, minimum distance vectors 248 are computed from the points 250 in frame i to the triangle surfaces 252 of frame i–1, with the vectors 248 normal to the surfaces 252.

At step 2 (212 in FIG. 40A), three exclusion criteria are applied to the minimum distance vectors of step 1, in order to eliminate non-overlapping data points between the two frames and to eliminate stray data points. First, all minimum distance vectors that relate to a boundary element (edge or point) in frame 1 are excluded. Second, all remaining minimum distance vectors with an amount exceeding a certain predefined value R, likely indicating stray data points, are excluded. Thirdly, only triangle surfaces are taken into consideration which form the outside surface with respect to the scanner viewing direction. Every surface has by definition two sides. We regard the "outside" surface as the surface of the object that is oriented towards the scanner.

Figure 42:
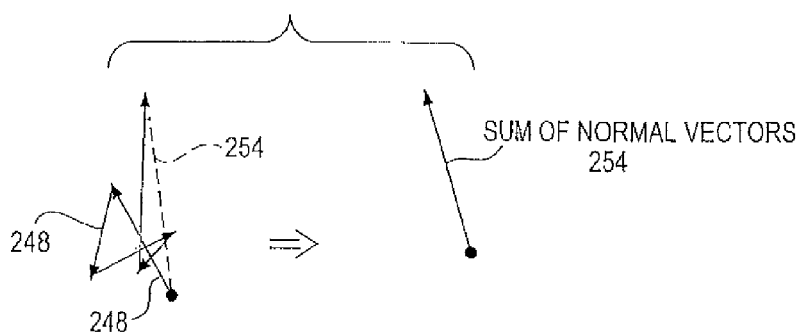
FIG. 42 illustrates the summation of the normal vectors from frame 1 to reach a net normal vector $N_{net}$.

At step 3 (214) the vector sum of all the minimum distance vectors $N_1 \ldots N_N$ is computed. This is shown in FIG. 42, with vector 254 representing the vector sum.

At step 4 (215), the median minimal distance vector (t) is computed by multiplying the vector sum 254 by the scalar 1/N. The median minimal distance vector basically constitutes a measure of how frame i should be translated in X Y and Z directions in order to better fit to frame i−1. Now, the registration process needs to compute a rotation factor, which is explained by steps 5-8, to indicate how frame i needs to be rotated in order to better fit frame i−1.

At step 5 (216), the X, Y and Z components of the median minimal distance vector is subtracted from every point in frame i. This is performed by making a copy of the frame i coordinates and operating on the copy as an interim step in the procedure, the underlying data from frame i is unchanged. At the same step the "center of mass" of the points of frame i which are not excluded by step 2 is calculated. The "center of mass" is defined as the vector sum of position vectors of all mentions points scaled by the inverse of the number of points.

Figure 43:
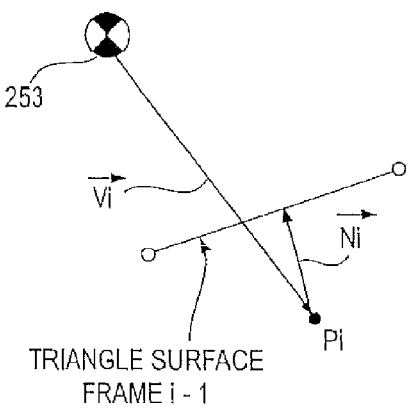
FIG. 43 illustrates the vectors Vi and Ni from the process of FIG. 40.
Figure 44:
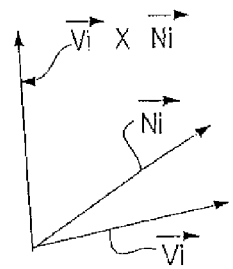
FIG. 44 illustrates the cross product of vectors Vi and Ni.

At step 6 (218) a calculation is made of the cross product of two vectors for every point in frame i. With reference to FIG. 43, the two vectors are as follows: 1) a position vector Vi extending from the origin 253 of the global coordinate system to the points in frame i, subtracted by the vector of the center of mass of the remaining points of frame i as calculated in step 5, and 2) the identified minimum distance vector Ni for that point.

At step 7 (220), a calculation is made of the vector sum of the cross vectors calculated in step 6, that is the net cross vector $$\sum_j (v_j \times n_j)$$

for all i points in the frame i, where x is the cross product operator.

At step 8 (222), the vector sum of step 7 is weighted against the inverse of the sum of all squares of the position vectors (Vi) of the points in frame i, to arrive at a rotation vector U. U is interpreted as follows: The direction of U gives us the rotation axis and the magnitude of U is the angle or amount of rotation. In particular, if we consider Vi to be the position vectors from the origin of the coordinate system to the vertex of every point, and Ni being the minimal distance vectors defined above, then the weighting is as follows:

$$U = \frac{\sum_j (v_j \times n_j)}{\sum_j v_j^2}$$

The reasoning behind this weighting is as follows. If you imagine the distance vectors as the realization of linear spring elements, the vector sum of the cross products represents the aggregate moment, or rotational discrepancy, generated between both frames. In the case of small deviations between the position of frame i and its final position, it can be assumed that the rotational moment also determined the direction of the necessary adjustment. The scaling with the help of the inverse of the sum of the squares of the position vectors considers the global extension of frame i. That is, the larger the distances of the points from the center, the larger is the ratio of rotational moment and angle between the present position and the target position. In a global sense, the mentioned factor (inverse of the sum of squares of position vectors) describes this ratio.

The derivation of the proper scaling factor is by no means an exact calculation. It has, however, turned out that using this factor in all empirical cases, the iteration of defining overlapping areas and execution of transformations converges.

At step 9, the result of step 8 is scaled with an empirical "acceleration factor" f. The factor f serves to possibly accelerate this convergence. A value of f of greater than 1 is appropriate for relatively large rotational displacements, but in any event has to be determined empirically.

At step 10 (226), the result of step 9 is interpreted as an axis of rotation, the magnitude of which indicates the amount by which frame i has to be rotated in order to make the local overlapping areas of both frames lie within each other. The magnitude of the rotation vector is interpreted as the angle around which frame i has to be rotated.

A rotation transformation matrix [T](R) is calculated for frame i. This formula shows how to convert the rotation vector resulting from step 9, where β is the original length of the net cross vector which equals the angle of rotation that is required to fit the overlapping areas of frame i to frame i−1 and u is the unit vector of U, $$u = \frac{U}{|U|}$$

with components $u_x, u_y, u_z$.

$$[T](R) = \begin{pmatrix} (1-\cos\beta)u_x^2 + \cos\beta & (1-\cos\beta)u_x u_y - u_z\sin\beta & (1-\cos\beta)u_x u_z + u_y\sin\beta \\ (1-\cos\beta)u_y u_x + u_z\sin\beta & (1-\cos\beta)u_y^2 + \cos\beta & (1-\cos\beta)u_y u_z - u_x\sin\beta \\ (1-\cos\beta)u_z u_x - u_y\sin\beta & (1-\cos\beta)u_z u_y + u_x\sin\beta & (1-\cos\beta)u_z^2 + \cos\beta \end{pmatrix}$$

To obtain a unique transformation operator for calculating the translation and the rotation transformation in a closed manner a 4×4 matrix representation is used. The relation between the 4×4 representation and the three dimensional rotation represented by 3×3 Matrix [T](R) is as follows $$[T_4](R) = \begin{pmatrix} [T](R) & 0 \\ 0 & 1 \end{pmatrix}$$

and between the 4×4 representation and the three dimensional translation, represented by vector (t)

$$[T_4](t) = \begin{pmatrix} 1 & 0 & 0 & t_x \\ 0 & 1 & 0 & t_y \\ 0 & 0 & 1 & t_z \\ 0 & 0 & 0 & 1 \end{pmatrix}$$

To apply this 4×4 matrices on the three dimensional vectors the following convention is made: A three dimensional vector is transformed into the 4 dimensional vector space by identifying the first three components of the 4 vector with the components of the three dimensional vector but the fourth component is always unique. $(x,y,z)^T \rightarrow (x,y,z,1)^T$ At step 11 (228 in FIG. 40 C), a transformation matrix for frame i, $[T4](i)$, is calculated by multiplying the rotation matrix $[T4](R)$ (from right) by the translation matrix $[T4](t)$ from step 4 $[T_4](i)=[T_4](R)[T_4](t)$.

Alternatively, the point cloud of frame i can be separately and independently operated on by the rotation matrix and the translation vector.

At step 12 (230), a calculation is made of the square root of the sum of the squares of the minimum distance vectors calculated in step 1 (210) of FIG. 40A, which indicates the closeness factor quality of the registration in this iteration, value MA below. At step 12 (232) the closeness factor MA is compared to a quality index or threshold indicative of a successful registration (e.g., 50 microns). If the value MA is greater than the quality index, the registration process is repeated another iteration. All of the points in the ith frame are updated by operation of the transformation matrix $[T4]_i$, as indicated at step 234. The process goes back to step 1 as indicated at 236, and another iteration is performed of steps 1-13.

Figure 40B:
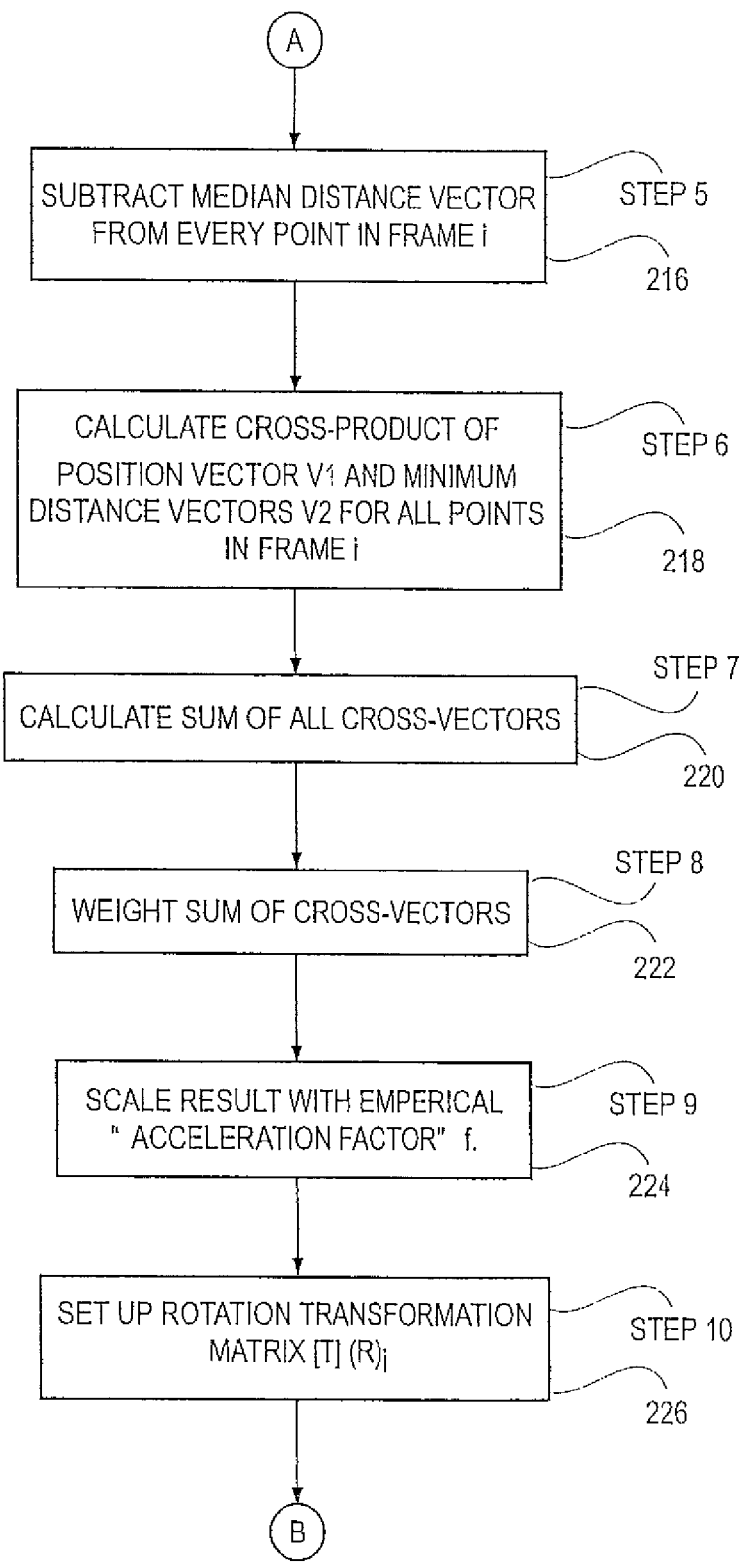
Figure 40C:
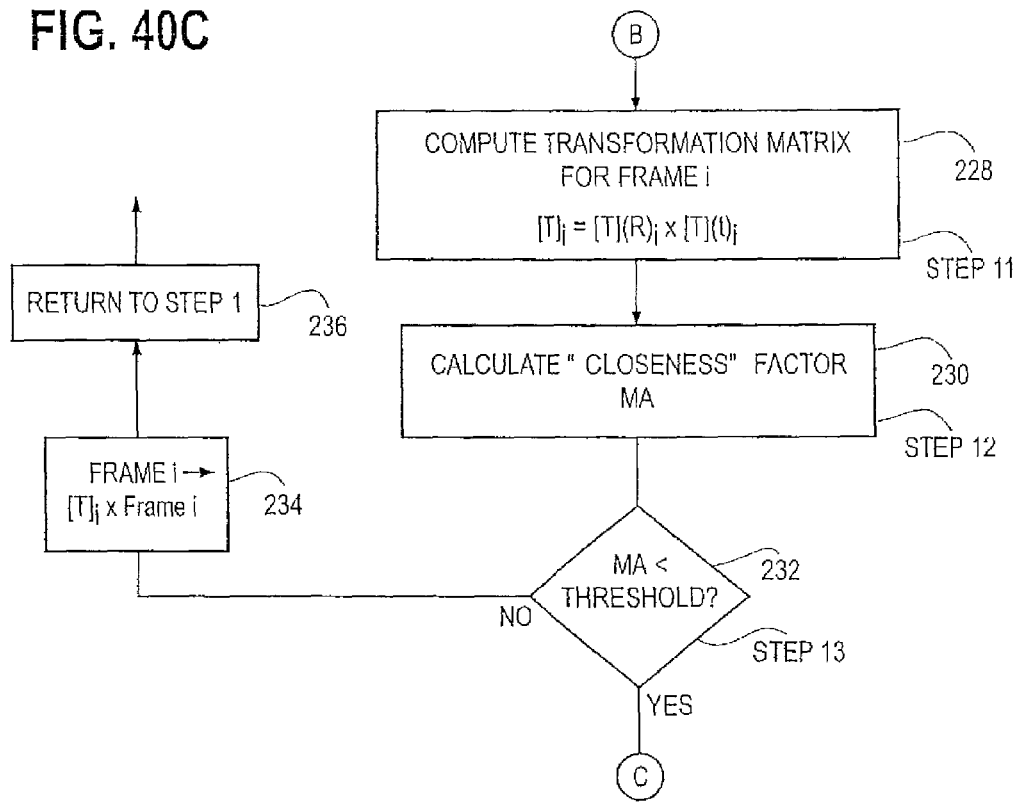
Figure 40D:
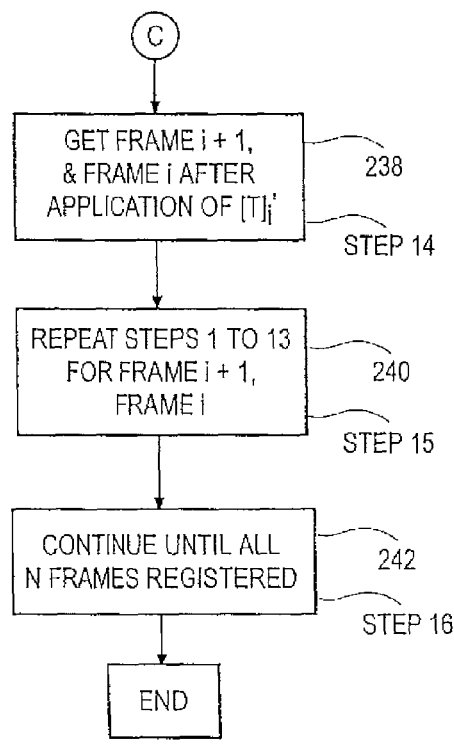

If the closeness factor MA is less than the quality index, the registration process proceeds for the next frame. As shown in FIG. 40D, at step 14 the process retrieves the next frame (frame i+1) and frame i after application of the transformation matrix $[T4]i$. At step 15 (240), the iterative process of steps 1-14 is repeated for frame i and frame i+1. This process continues until all the N frames have been registered, as indicated at step 16 (242). At the end of the process, the result is a set of points comprising the three-dimensional model, and a set of transformation matrices $[T4]_2$ to $[T4]_N$ for each of the frames (other than the first frame, frame 1), which are used to generate the three dimensional model. One frame, such as frame 1, the first one generated, is chosen as the starting frame for the registration and there is no transformation matrix for that frame.

Figure 45:
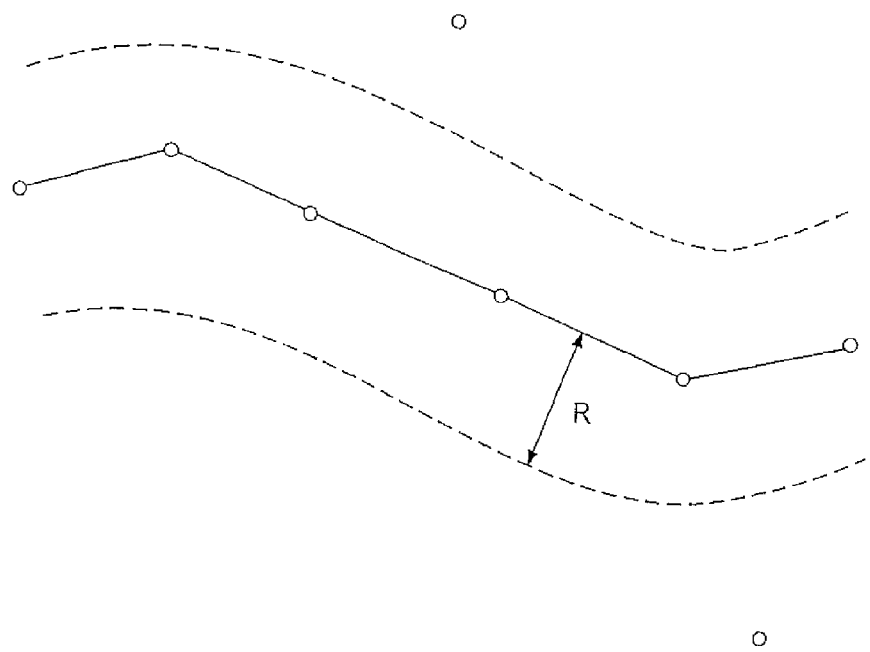
FIG. 45 illustrates the parameter R, which is used in the frame registration process to discard or filter out points which are greater than a distance R from the triangle surfaces.

FIG. 45 illustrates that a range variable R can be used to filter or limit the number of points in a frame that are used when calculating net normal vectors, triangle surface, cross vectors, etc. The purpose of the range variable R is to screen out stray data points far from the triangle surface of the previous frame. The stray data has the effect of skewing the entries of the transformation matrix and increasing the number of iterations until the quality index is met. R can be for example 1 mm, or much less such as 1/50 mm.

Figure 46:
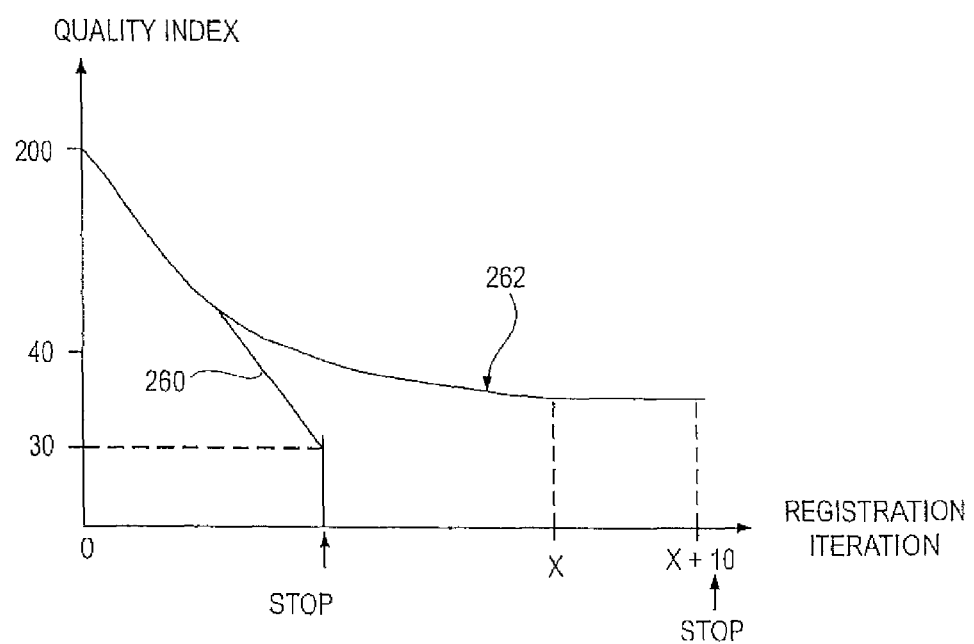
FIG. 46 is an illustration of the closeness factor or quality index, measured as the magnitude of the net normal vector $N_{net}$, as a function of iterations of the process of FIG. 40, showing how the quality index improves with successive iterations of the registration process.

FIG. 46 illustrates two ways in which the frame to frame registration process may terminate. As shown by line 260, the process may terminate when the closeness factor goes below the threshold, here 30 microns. Alternatively, the closeness factor may level off at some value above the quality index, despite further iterations of steps 1-13 of FIG. 40. This is indicated by line 262. When the closeness factor MA does not improve by at least some amount per iteration (say 1 percent) after 10 iterations, the process is deemed complete. Here, the designation x indicates the iteration in which the amount of improvement in the quality index from the previous iteration to that iteration was first less than a threshold, e.g., 1 percent.

C. Cumulative Registration of Entire Jaw

As noted above, cumulative registration is an alternative or improvement to a frame to frame registration. The difference between the two is that frame to frame registration only registers one frame to one other frame, whereas cumulative registration is a registration of a frame to more than one other frame, such as where one frame is registered to all previously registered frames. There are numerous types of cumulative registrations that can be performed, and a few examples will be given here. An advantage of cumulative registration is more accuracy in the resulting three-dimensional model. The disadvantage is that cumulative registration can be significantly more computationally intensive, and therefore require more time to be performed using currently available low cost microprocessors or computers.

Figure 47A:
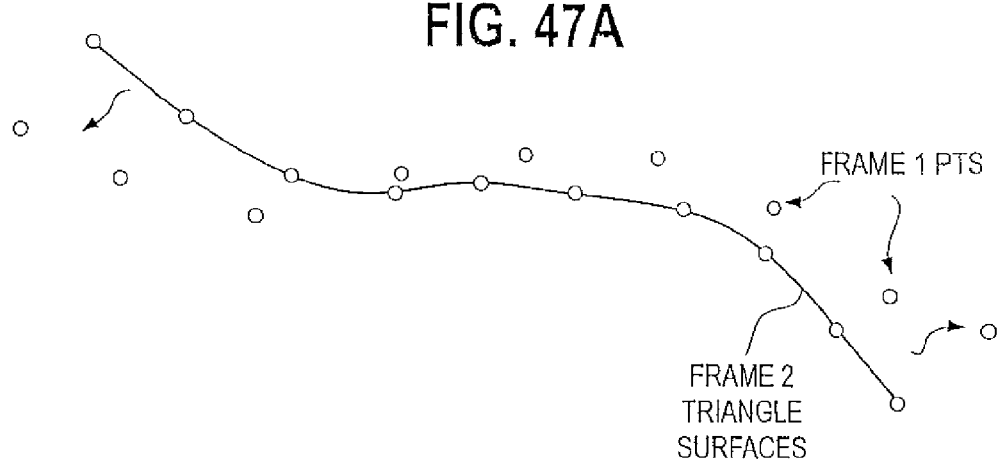
FIGS. 47A and 47B are an illustration of a cumulative registration procedure, which is an alternative to the frame to frame registration procedure of FIG. 40.
Figure 47B:
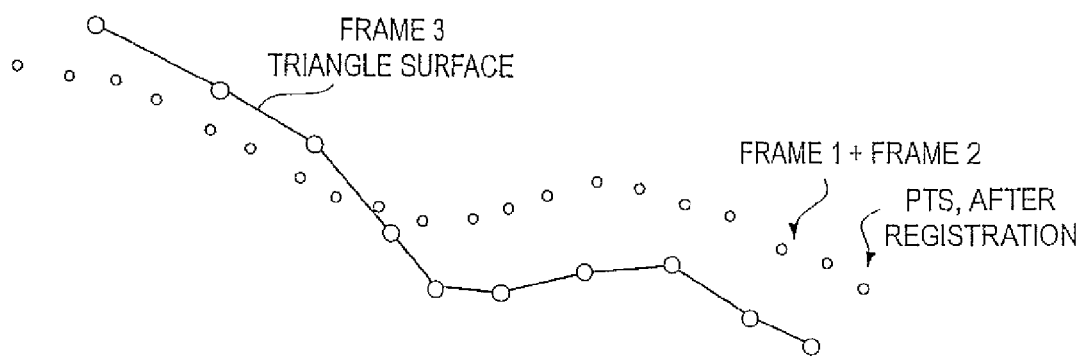

FIGS. 47A and 47B are a simplified illustration of one possible cumulative registration procedure. FIG. 47 A shows triangle surfaces of frame 2 and points of frame 1. The points and surfaces represented in FIG. 47A actually are in three dimensions. After registration of frame 2 to frame 1, we are ready for frame 3. Unlike frame to frame registration, frame 3 is registered to both frame 1 and frame 2. In other words, triangle surfaces are formed on the points of frame 3 and minimal distance vectors are calculated for each of the points in frame 1 and frame 2 (after registration to frame 1), and the other steps of FIG. 40 are performed. As each new frame is retrieved, it is registered to the total sum of points from all the previous frames, after the previous registration.

Figure 48B:
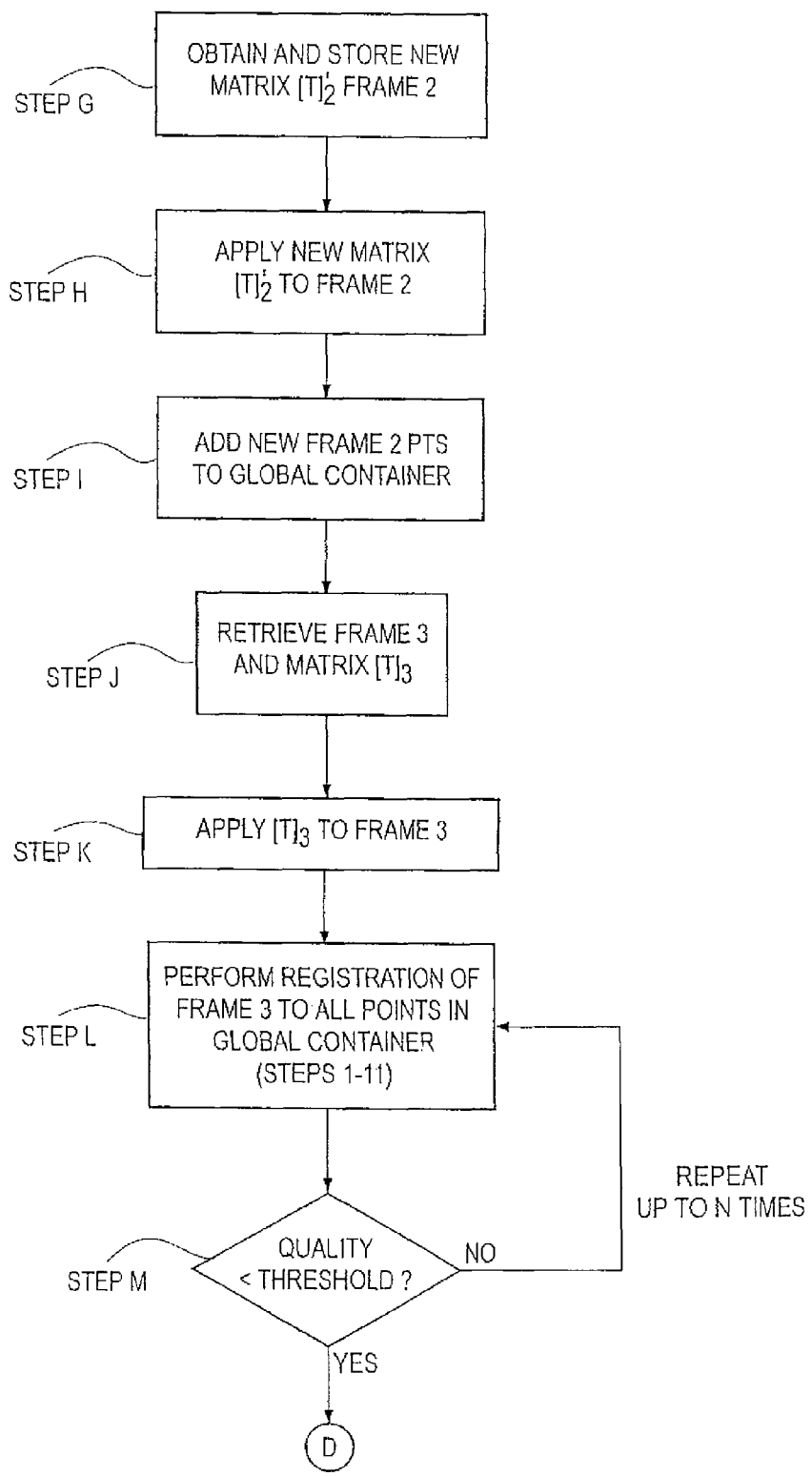
Figure 48C:
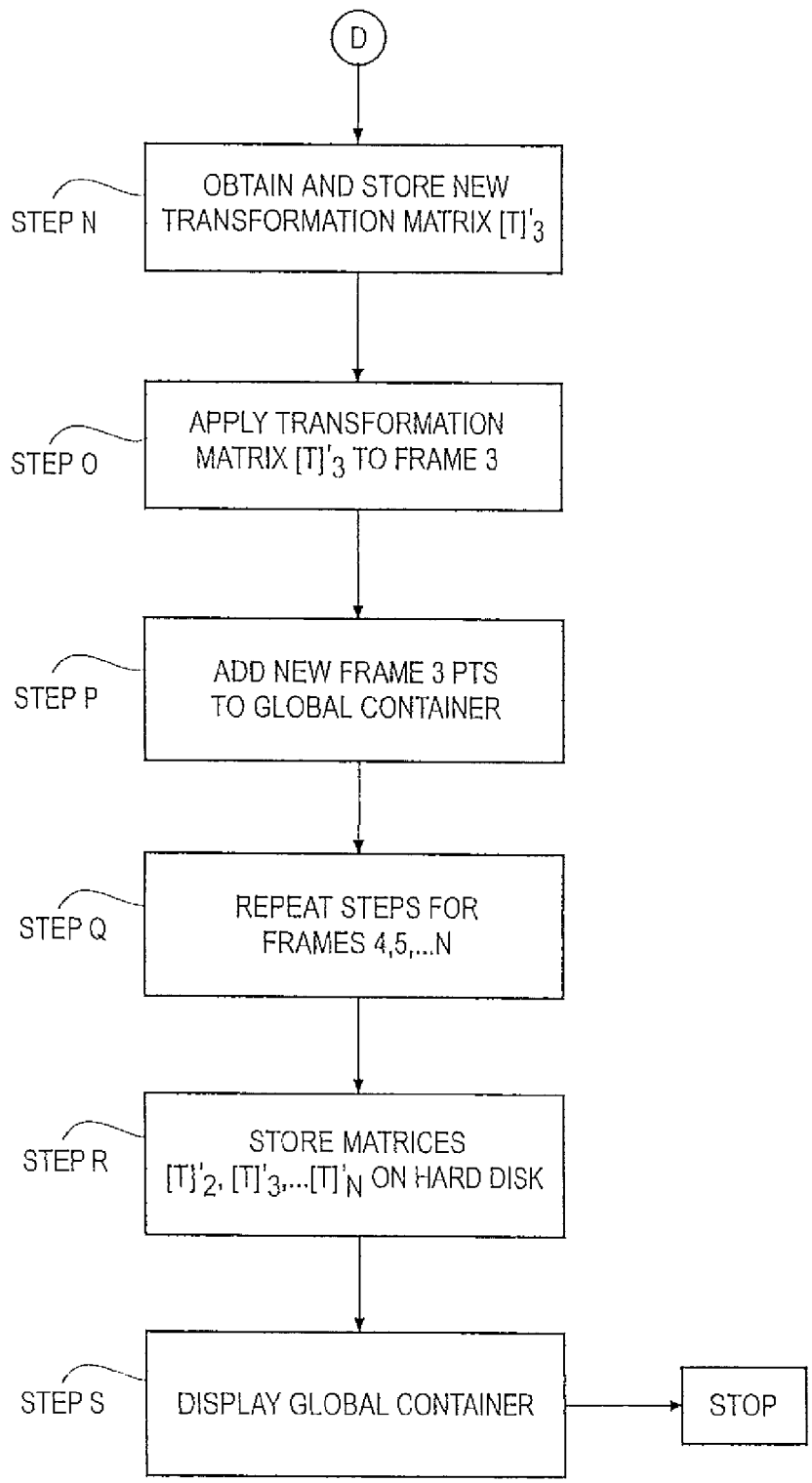

FIG. 48A-48C are a flow diagram of one possible cumulative registration process. At step A (270), the points of the first frame are retrieved from memory.

At step B, the points of the second frame are retrieved from memory.

At step C, the transformation matrix $[T]_2$ is retrieved for frame 2. This process assumes that the transformation matrix for each frame has already been generated, such as after a frame to frame registration process has been performed.

At step D, the transformation matrix $[T]_2$ is applied to frame 2.

At step E, a registration is performed of the points of frame 1 to the points of frame 2, after the transformation matrix $[T]_2$ has been applied to frame 2. Basically, the steps 1-11 of FIG. 40A-40B are performed.

At step F, a check is made as to whether the quality of the registration is less than a threshold. If not, the registration is performed again (with the points of frame 2 updated by a new transformation matrix). Steps 278 and 280 are performed over and over again until either the quality threshold is met or a maximum number of iterations has occurred.

If the index is met or the maximum number of iterations has been reached, the process proceeds to step G (282). The new transformation matrix for frame 2, designated $[T]_2'$ is obtained and stored.

At step H, the new transformation matrix $[T]_2'$ is applied to the points of frame 2.

At step I, the new transformed points of frame 2 are added to a "global container". The global container is merely memory locations containing the points from frame 1 and the points of frame 2 as transformed.

At step J, frame 3 and its transformation matrix $[T]_3$ is obtained from memory.

At step K, the transformation matrix $[T]_3$ is applied to the points of frame 3.

At step L, a registration is performed of frame 3, as transformed, to all the points in the global container. Steps 1-11 of FIG. 40 are performed.

At step M, a check is made to see if the quality index is below the threshold. If not, another iteration of the registration process is performed. This repeats until the quality index is below the threshold or a maximum number of iterations is reached.

If the threshold is met (or the maximum number of iterations is reached), the process proceeds to step N. The new transformation matrix $[T]_3'$ is obtained and stored in memory.

At step O, this new transformation matrix is applied to the points of frame 3.

At step P, the points in frame 3 after the transformation operation is performed are added to the global container.

At step Q, the process of steps A-P of FIG. 48 are performed for the rest of the N frames.

At step R, all the transformation matrices $[T]_2'$. $[T]_N'$ are stored on the hard disk of the back office server. These transformation matrices are used whenever the finished global container (complete three-dimensional model) needs to be generated again at a later date (or on another workstation). The model is generated by simply applying $[T]_2' \ldots [T]_N'$ to the raw frame data comprising frames 2 . . . N.

At step S, the global container is displayed to the user. This can be on the monitor of the back office server 28 or on the monitor 20 of the scanning station 16 (FIG. 1). Since the global container is a digital representation of the object, it can be transported across a computer network and displayed and shared by another terminal. For example, where the back office server has a connection to the Internet, the model can be transported over the Internet to the precision appliance service center 26 and displayed there. It can also, for examples be shared among various orthodontic, periodontal or dental specialists so that they can collectively study the patient remotely and cooperatively plan care.

Figures 49, 50:
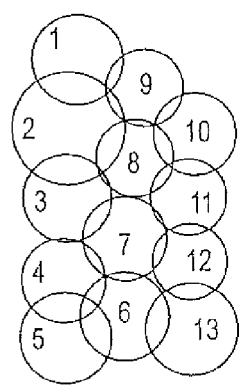
FIG. 49 is an illustration of a set of frames illustrating a different order for frame registration than frame to frame registration, with the order based on the location on the surface of the object for a given frame relative to the location on the surface for other frames.
FIG. 50 is a simplified illustration of a set of frames, showing the order in which the frames were obtained, with the neighborliness of the frames relative to other frames being the basis for the registration order shown in FIG. 49.

FIG. 49 is an illustration of a set of frames, illustrating a variation from the cumulative registration set forth in FIG. 48. In FIG. 49, a different order of frame registration is performed from that of frame to frame registration. In particular, frame to frame registration and cumulative registration of FIG. 48 are performed in the order in which the frames are obtained. This need not be the case. In fact, a more accurate registration may be obtained by registration of frames in an order based on "neighborliness", that is, based on the concept that all frames imaging a particular portion of an object should be registered together (or in sequence such they are registered one after the other). The order of registration is indicated by the left hand column of numbers. The right hand side of FIG. 49 merely illustrates that each frame consists of X, Y and Z coordinates for a set of points. The frames need not and usually will not have the same number of points.

In FIG. 49, the registration order is based on the location on the surface of the object for a given frame relative to the location on the surface for other frames. FIG. 50 is a simplified illustration of a set of frames, showing the order in which the frames were obtained, with the neighborliness of the frames relative to other frames being the basis for the registration order shown in FIG. 49. Frame 7 (F7) is the chosen starting frame. So, the frames surrounding frame F7 are registered next. This is shown by the order of registration being F7, F3, F4, F11, F12, F6, . . . as indicated.

Figure 51:
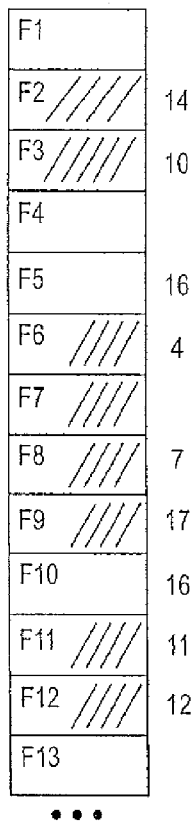
FIG. 51 is another illustration of a set of frames, with registration of frames performed in accordance with the method of FIG. 49, with the marking in frames 2, 3 6 and 7 etc. indicating that that frame has been registered. The marking is just a way of illustrating that the computer keeps track of which frames have not been registered, as a check to insure that no frames are omitted during the registration procedure of FIG. 49.

FIG. 51 is another illustration of a set of frames, with registration of frames performed in accordance with the method of FIG. 49. The order of registration is indicated by the column of numbers to the right of the frames. The marking in frames 2, 3, 6 and 7 etc. indicates that those frames have been registered. The marking is just a way of illustrating that the computer keeps track of which frames have been registered, as a check to insure that no frames are omitted during the registration procedure of FIGS. 49 and 50. The manner of selecting the other frames, e.g., frame 4 and 5, can be based on a number of criteria, such as the order of obtaining the frame, the neighborliness to other frames already registered, and so forth.

Figure 52:
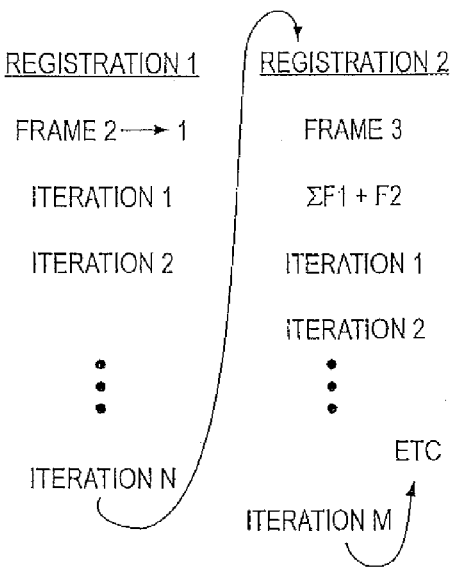
FIG. 52 is an illustration of cumulative registration based on the first captured frame (F1) as being the base line for all successive registrations.
Figure 53:
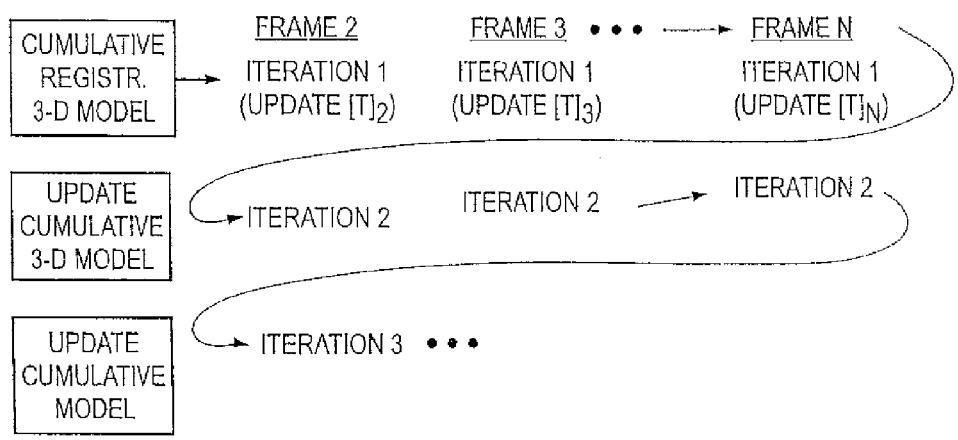
FIG. 53 illustrates an alternative registration procedure in which each frame in the set of frames is registered to a cumulative registration 3-dimensional model of the object, in sequential order, with one iteration of the frame registration process. This is followed by an updating of the cumulative 3-dimensional model and a repeat of the registration process with updated values for the transformation matrix [T] for each frame.

FIG. 52 is an illustration of cumulative registration based on the first captured frame (F1) as being the base line for all successive registrations. This is essentially the technique of FIG. 48. FIG. 53 illustrates an alternative registration procedure in which each frame in the set of frames is registered to a cumulative registration 3-dimensional model of the object, in sequential order, with one iteration of the frame registration process. This is followed by an updating of the cumulative 3-dimensional model and a repeat of the registration process with updated values for the transformation matrix [T] for each frame. The process continues until the quality values are within acceptable limits, or after a predetermined number of iterations have been performed. Still other possibilities for cumulative registration exist. The choice of which one to use will depend on the available computing resources, the amount of time required to perform the cumulative registration for the technique, and the desired accuracy.

Figure 54:
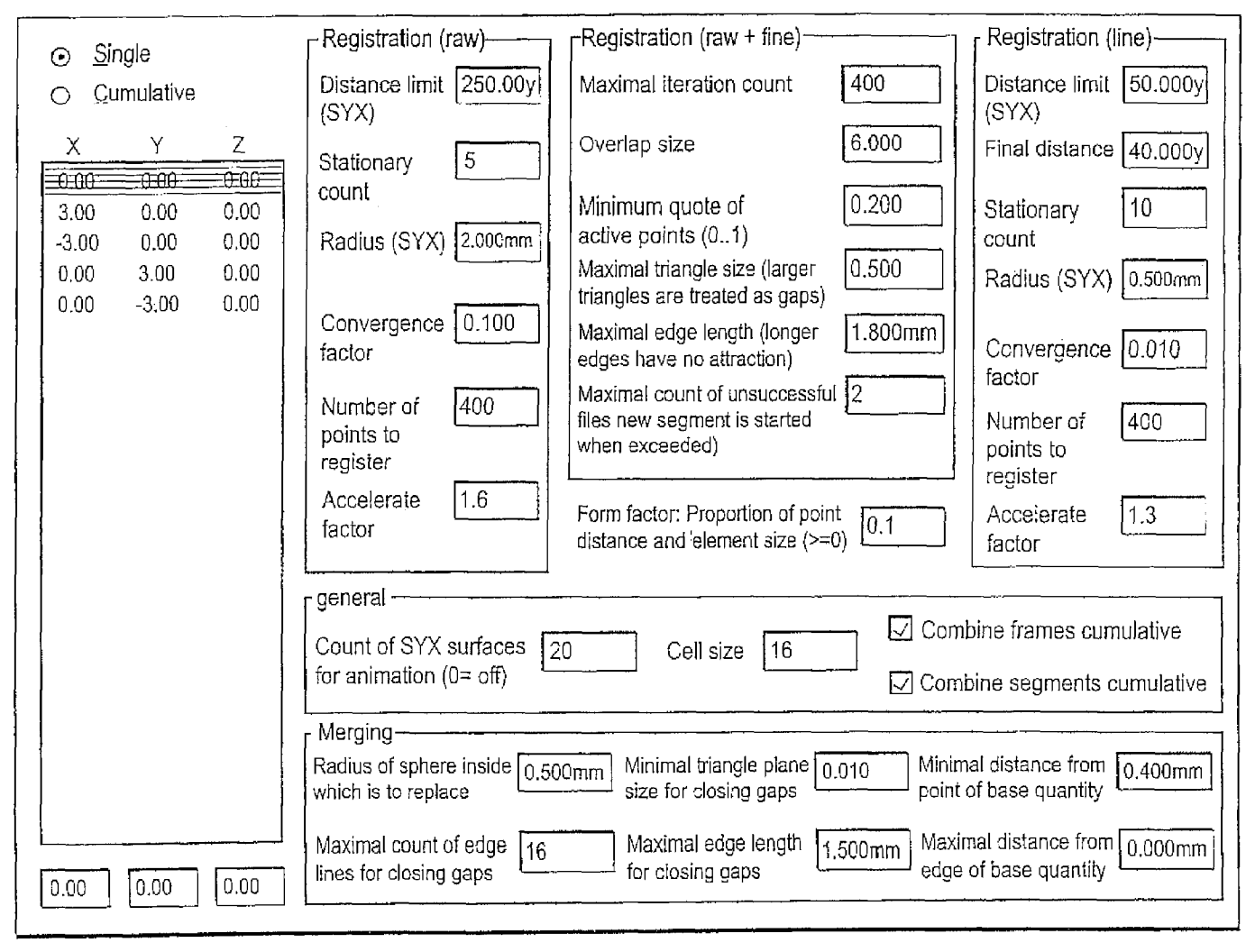

FIG. 54 is a screen shot of a workstation computer (e.g., either a scanning station or back office server workstation), showing the available registration parameters and variables that can be changed to optimize the registration when performing either a frame to frame registration or a cumulative registration. The parameters may vary widely depending on the type of object being scanned, the amount of time needed to obtain a result from registration, the speed at which the scanner is moved relative to the object and the amount of overlap, etc. FIG. 54 illustrates that the user is able to select and modify the registration procedure parameters as they see fit. Two different types of registration are indicate here, a "raw" registration, in which the quality index ("distance limit") is 250 microns, and a fine registration, wherein the quality index is reduced to 50 microns. The distance limit is computed as the square root of the sum of the squares of the normal vectors divided by the number of points in the frame. The term "stationary count" indicates the number of iterations to continue of little or no improvement in the quality index is seen. The Radius value refers the filter R shown in FIG. 45. The convergence factor 0.10 refers to the minimum amount of improvement needed between successive frames before a stationary count commences. The convergence factor is computed by taking the difference of the squares in the quality index of the ith iteration and the i−1th iteration and dividing by the square of the quality index of the ith iteration.

The number of points to register indicates the minimum amount of overlap in points (within boundary R) needed to attempt a registration. An "accelerate" factor is shown, with a value of 1.6. This means that the points are moved in the X, Y and Z directions in the transformation matrix by an amount of the net normal vector multiplied by the accelerate factor. The use of an accelerate factor has been found to reduce the number of iterations required to meet the quality index.

The maximum iteration count value is a stop value to keep the process from running into an endless loop. The overlap size value is a limit, in terms of $mm^2$, of the size where registration is performed. This serves to screen out stray points from the registration algorithm. The minimum quota of active points is a minimum amount of overlap between two frames before registration will be attempted, expressed as a fraction of 1. The maximum triangle size is a filter to filter out triangle sizes where the size of the triangle is too large, indicating a stray data point. The maximal edge length is simply the maximum permissible length of one side of one of the triangle surfaces. The Maximal count of unsuccessful files is the number of unsuccessful sequential registrations before a failure of the registration process will be declared.

Figure 55:
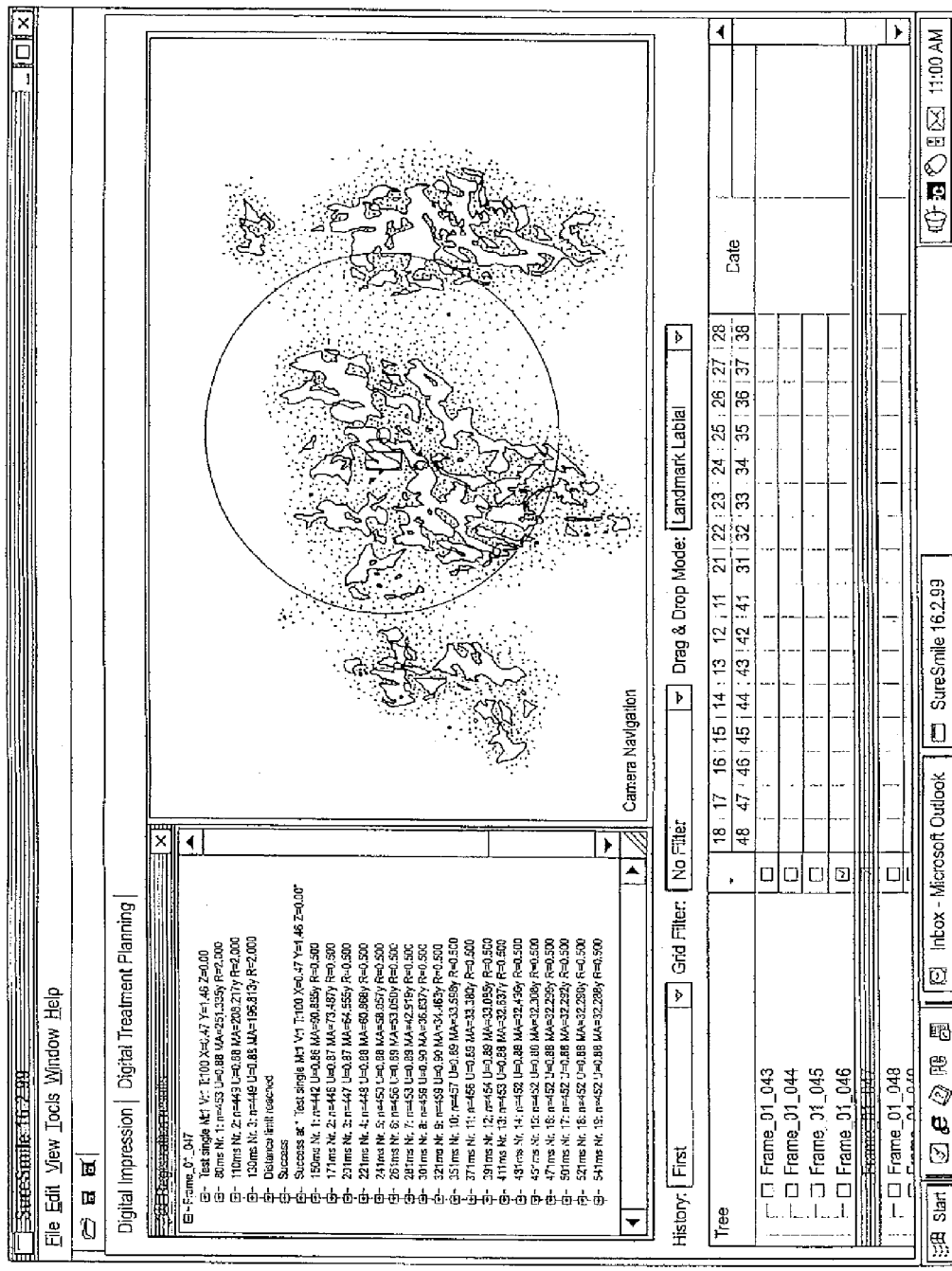
FIG. 55 is a screen shot from a workstation computer showing a frame to frame registration in accordance with FIG. 40 for two frames in a set of frames.

FIG. 55 is a screen shot from a workstation computer showing a frame to frame registration in accordance with FIG. 40 for two frames in a set of frames. The various parameters shown in FIG. 54 are selected and used in the frame to frame iteration. In this instance, frame 47 is being registered to frame 46. The surface of frame 46 is shown in white, frame 47 is shown in dark tones. The left hand side of FIG. 55 shows the results of each iteration, including the running time, the number of the iteration, the number of overlapping points, the overlap between frames (U), expressed as a fraction of 1, the quality index MA, and the value of the filter R. After 3 iterations, the quality index for coarse registration was met. The process continued with the fine registration. A series of fine registration iterations were performed. Note that the quality index MA improves with each registration iteration.

Figure 56:
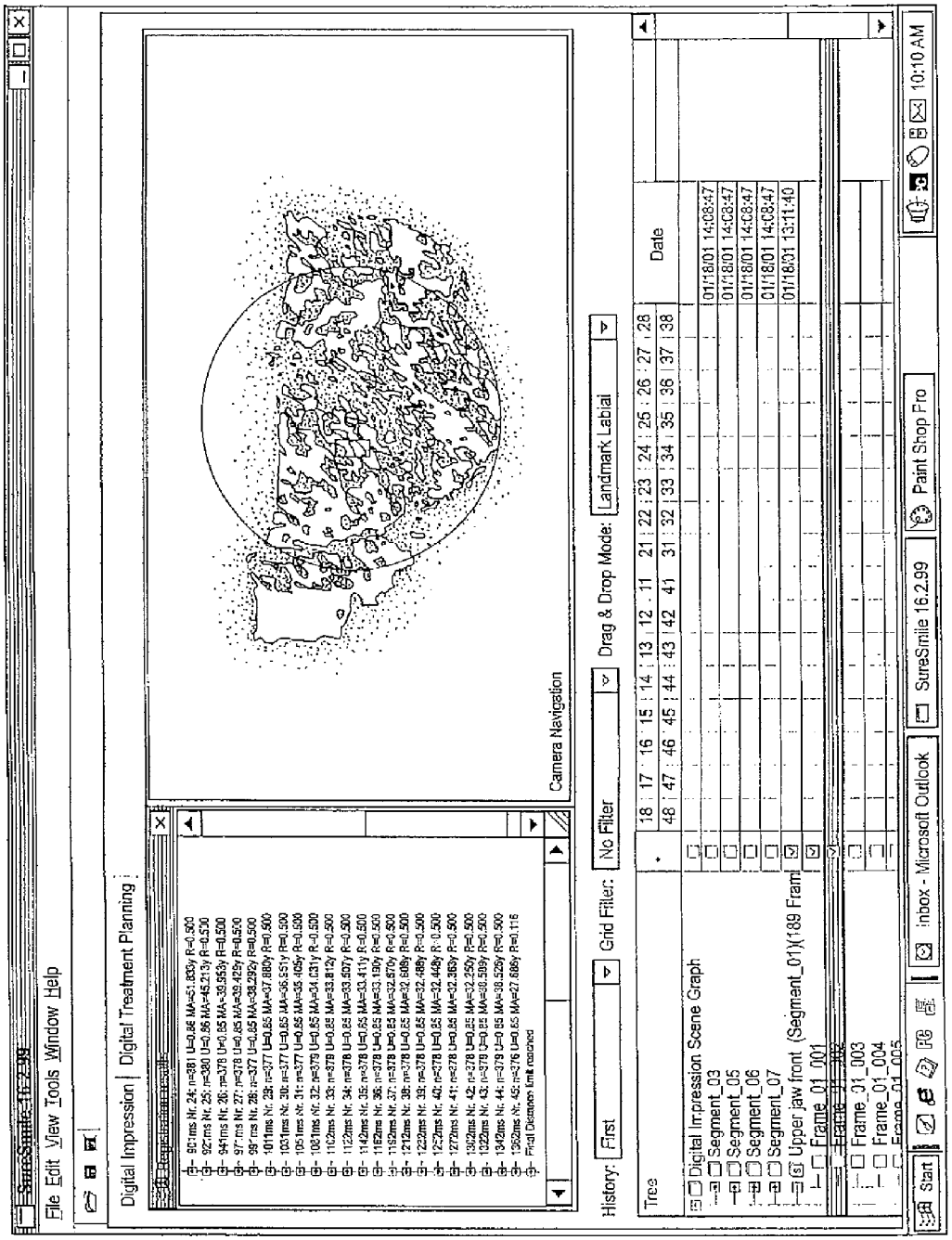
FIG. 56 is a screen shot showing the results after forty five iterations of the frame to frame registration process of FIG. 40, and with the right hand side of the screen shot showing the two frames superimposed on each other.

The data from the last twenty iterations, and the final result, of a registration of frame 2 to frame 1 in a typical scan of teeth are shown in FIG. 56. After 45 iterations, the distance limit of 30 microns was met (MA=27.686 microns). Note that the graphical representation of frame 1 (white) and frame 2 (darker tones) is such that there is essentially an equal amount of frame 1 and frame 2 in the picture. This indicates that a "best fit" between frames 1 and 2 has been achieved.

D. Segment Registration

When scanning any object, such as teeth, the situation may arise in which the operator of the scanning cannot capture all the surfaces of the object in one scanning pass. The interruption may be due to the need to physically move the scanner to a location that is impossible to reach from one location, the need for the patient to take a break from the scanning, or some other reason. When scanning teeth of a single jaw, the scanning is typically performed in two or three different segments. First, one side of the jaw is scanned, then the front of the jaw, and then the other side of the jaw. In this situation, there are three different segments of the object. All the frames of each segment are registered to each other, typically using a frame to frame registration. Then the segments are registered to each other. After this has been done, a cumulative registration is performed of the entire jaw.

To perform the segment registration, there must be some way of indicating where at least one point in one segment is common to another segment. Segment registration thus requires some overlap between segments. The scanning workstation provides a mechanism to indicate at least one point where two different segments overlap. In the case of the scanning of teeth, the operator of the scanner will typically include the canine teeth in scans of both sides of the jaw, and in the scan of the front of the teeth. The operator can also be instructed to scan these teeth in the side and front segments. Therefore, the segment registration proceeds by the user selecting or indicating a point on the canine teeth to use for performing segment registration. A procedure referred to herein as "landmarking" is used to select the point used to register segments. It will be understood that a similar process will be performed when scanning other types of objects where more than one segment was used to completely scan the object.

E. Landmarking

Figure 57:
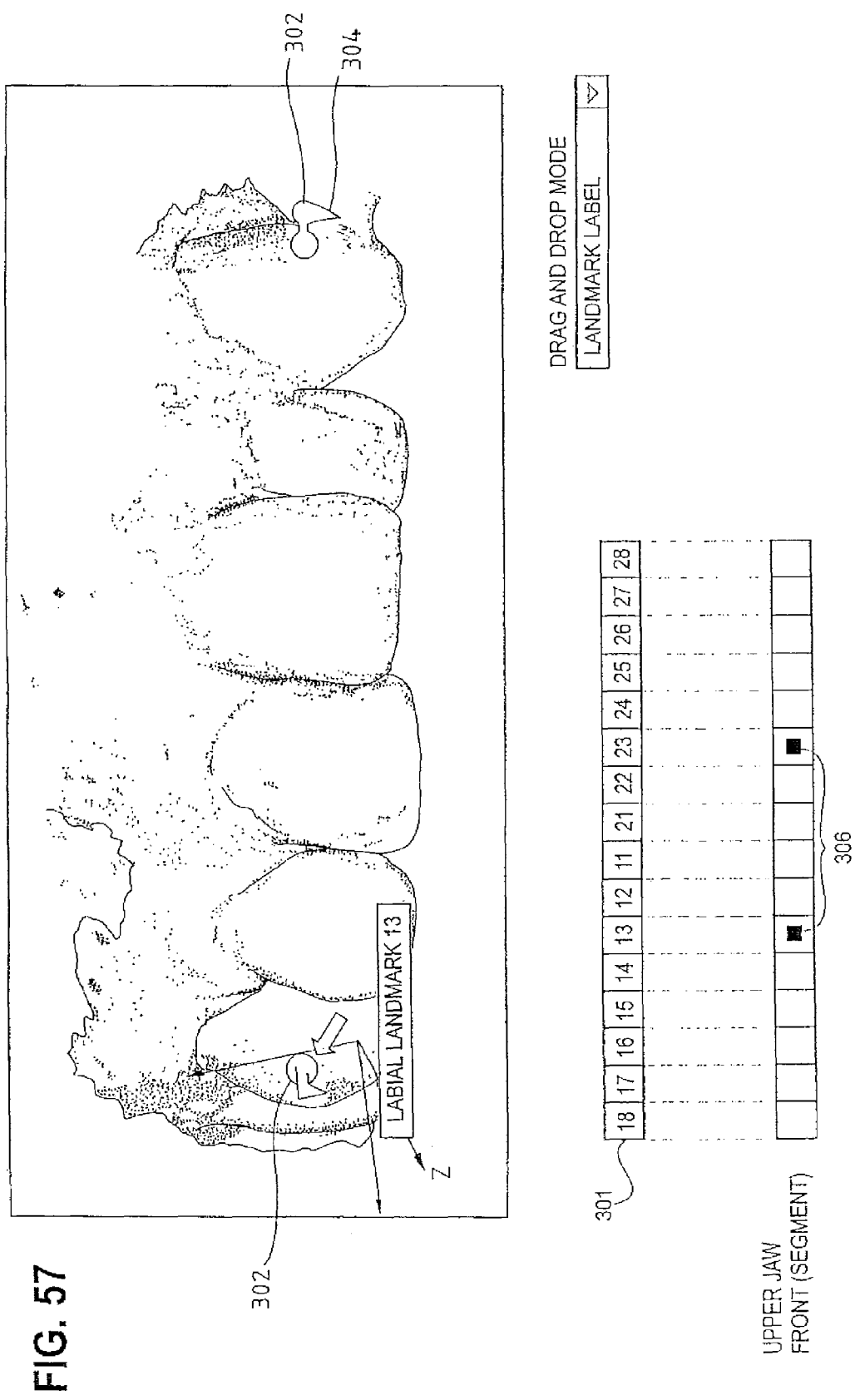
FIG. 57 is a screen shot showing a graphical representation of a three-dimensional model of a patient's upper front teeth after a frame to frame registration. The user is applying landmarks to the teeth as a preliminary step in treatment planning, and as a step in registering overlapping segments of a scanned upper jaw relative to each other to calculate a complete model of the upper jaw and associated dentition.

FIG. 57 is a screen shot showing a graphical representation of a three-dimensional model of a patient's upper front teeth (segment 1) after a frame to frame registration of this segment. The user is applying landmarks to the canine teeth as a preliminary step in treatment planning, and as a step in registering overlapping segments of a scanned upper jaw relative to each other to calculate a complete model of the upper jaw and associated dentition.

The purpose of the landmarking shown in FIG. 57 is to select a point on the canine teeth which is common to the front scan and the two side scans. The landmarking is also done at a point on the labial surface of the teeth that would be a suitable location for placement of an orthodontic bracket as part of an appliance to correct a malocclusion. The landmarks are characterized by both a point location and an orientation. To place the landmarks, the user clicks on a tooth number, indicated by the row of numbers 301, and drags the cursor with a mouse to the surface on the canine teeth where they wish to place the landmark. They then release the cursor, and the landmark 302 appears on the tooth. The landmark has an arrow 304 which must point to the incisal edge of the tooth. The user can rotate the landmark to place the arrow in the proper orientation by simply clicking on the landmark and turning the mouse one way or the other. As each landmark is placed, a box below the tooth number is highlighted as indicated at 306.

The tooth numbering convention shown in FIG. 57 is as follows: the first number indicates the quadrant of the patient's dentition, with 1 being upper right, 2 being upper left, 3 being lower left, 4 being lower right. The second number is the tooth number with 1 being the incisor. Thus, the landmarks are placed at teeth 13 and 23, the upper canines.

Since these canines overlap their respective side scan, and since the X, Y and Z coordinates of the point on the labial surface of the tooth where the landmark is placed is assigned in the computer, it is now possible to register the front segment shown in FIG. 57 to the two side segments. This segment registration is now performed. The overlapping frames between each segment can be registered to each other, or to the entire other segment.

After segment registration is performed, a cumulative registration of the entire jaw is performed in accordance with the procedure of FIG. 48. After the cumulative registration is performed, the virtual three-dimensional model of the entire jaw is presented to the orthodontist on the monitor in the back office server workstation 28.

Note that if the scanning is done in one pass, e.g., where it is performed on a plaster model, there is no need for segment registration. The landmarking step can be eliminated in that event, although it may nevertheless be performed as a step in placing virtual brackets on the teeth objects of the virtual model.

In planning treatment for the patient, the orthodontist conceptualizes teeth as individual teeth objects that can be moved independently of each other to correct the patient's malocclusion. Furthermore, orthodontists are trained to make physical models of the patient's dentition from an impression, cut the teeth from the model, and then individually move the teeth relative to each other to provide a target situation which corrects for the malocclusion. Therefore the back office server workstation 28 includes interactive treatment planning software which enables the orthodontist to do this with the virtual three-dimensional model of the patient's dentition. In order to do this treatment planning, it is highly desirable therefore to process the three dimensional model resulting from a cumulative registration by separating the teeth from the gums and other anatomical structure, and presenting the just crowns of the teeth to the orthodontist. This allows virtual individual teeth objects to be moved independently in three dimensions on the computer. This process of separation of the teeth from the cumulative registration into individual teeth objects will be described next.

The separation process described below has one further advantage, namely requiring less memory to represent an individual tooth. Cumulative registration may result in an extremely large number of points from a large number of frames to represent any given tooth. The separation process, as described below, reduces this data set to a single set of points that describe a single surface representing the surface of the tooth. Much less memory is required. Consequently, the treatment planning software can process treatment planning steps for the teeth more quickly.

F. Separation of Teeth into Individual Tooth Objects (Tooth Modeling)

FIG. 58A-58F are a series of illustrations showing the generation of an individual tooth model from a scanned tooth. The process will now be explained in detail.

Figure 58A:
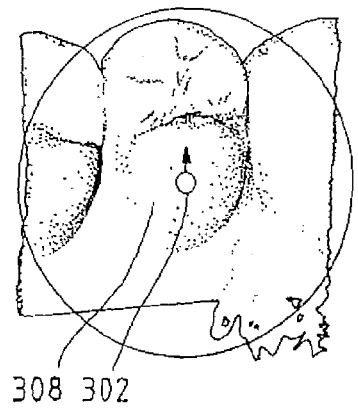
FIG. 58A-58F are a series of illustrations showing the generation of an individual tooth model from a scanned tooth, shown in FIG. 58A, and a template tooth, shown in FIG. 58B. A library of template teeth similar to FIG. 58A are stored as three-dimensional computer models in computer memory. The individual tooth model is a three-dimensional tooth object having a single set of points defining the boundaries of the tooth. The individual tooth model reduces the amount of data required to represent the tooth, as compared to the data representing the tooth after a cumulative registration of a large number of frames. Individual tooth models are also invaluable in interactive orthodontic treatment planning since they can be independently moved relative to each other in simulation of treatment scenarios.
Figure 58B:
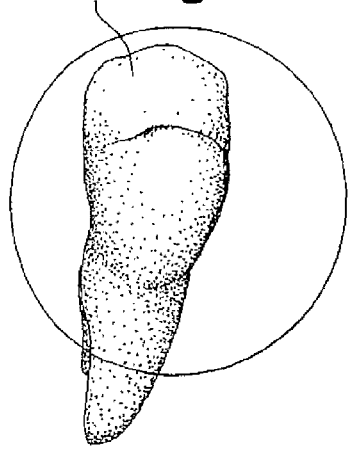
Figure 58C:
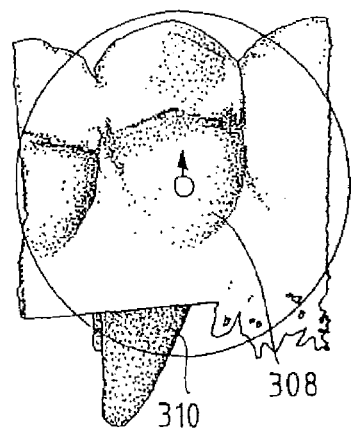

FIG. 58A shows the scanned dentition and associated anatomical structure surrounding the tooth 308. This tooth is tooth number 14 in the numbering convention shown in FIG. 57. The back office server workstation stores a three-dimensional virtual template tooth object for each tooth in the maxilla and the mandible. The template tooth 310 for tooth number 14 is shown in FIG. 58B. The template tooth object 310 is a three-dimensional tooth object having a single set of points defining the boundaries of the tooth. As shown in FIG. 58C, the template tooth 310 is positioned approximately in the same location in space as the tooth 308. The landmark 302 assists in providing the proper axial rotation of the template tooth to have it fit properly with respect to the tooth 308. The template tooth is placed at the point cloud of the dentition according to the labial landmark 302. The template tooth can be scaled larger or smaller or positioned arbitrarily by the user, in order to get a close a position as possible to the point cloud of the dentition.

Figure 58D:
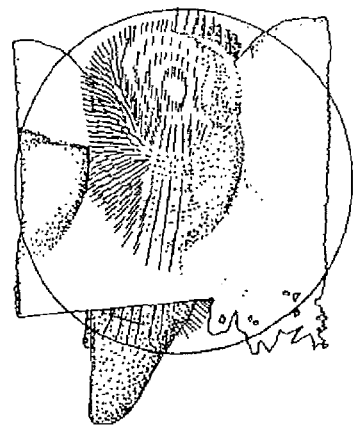
Figure 58E:
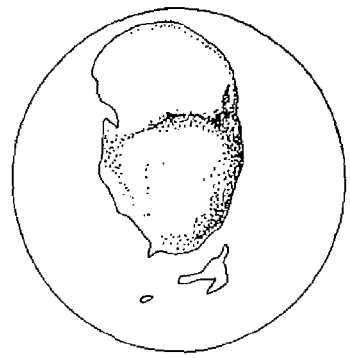
Figure 58F:
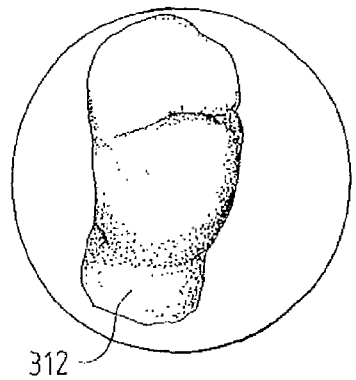

As shown in FIG. 58D, vectors are drawn from the points on the template tooth to the scanned point cloud of the tooth 308. Every ray intersects several surfaces, depending on how often the respective part of the surface has been covered during scanning. For each vector, a surface is selected. Preferably, the smallest triangle surface is selected, since this surface corresponds to an image taken by the scanner when the scanner was positioned in a more perpendicular orientation to the dentition surface, resulting in more accuracy in the determination of the coordinates of that portion of the surface. As another possibility, the outermost surface is selected, using a filter to insure that no extraneous surfaces are used. These points of the surfaces intersected by all the vectors are combined as newly generated triangle surfaces and therefore form one consistent surface shown in FIG. 58E. Then, finally, missing parts of the tooth are completed from the template tooth. The result is shown in FIG. 58F. In a second pass, this generated object is then used as a template tooth, and the steps indicated by FIG. 58C-58F are repeated in an iterative fashion. This is done to make sure that the algorithm works even if there are significant differences between the original template tooth and the scanned point cloud, e.g, a gap in scan data, different geometry in the tooth. The goal is to provide an algorithm that does not required a closely fitting template tooth object.

Figure 59:
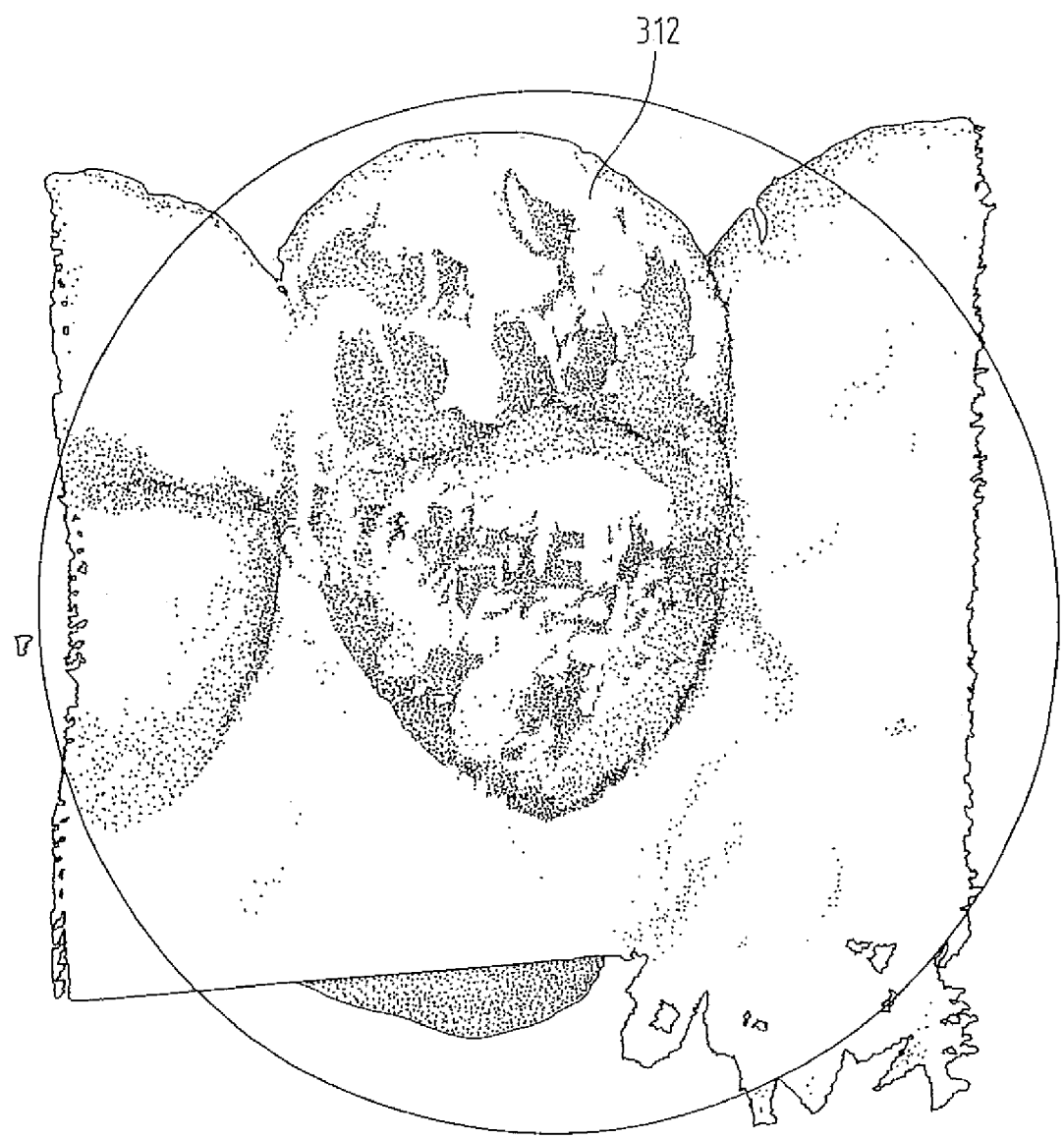
FIG. 59 is an illustration of the tooth model of FIG. 58D positioned in the computer model of the patient's dentition, surrounded by other anatomical structures.

The final result, an individual three-dimensional virtual tooth object 312, is then displayed to the user, as shown in FIG. 59. The result may be displayed on the workstation user interface as a three-dimensional superposition of the original data (white) and the separated model of the tooth (darker tones or contrasting color). These tones allow the user to ascertain whether there is an even distribution of white and dark tones, indicating good fit between the scanned tooth 308 and the individual tooth object 312. This step may be automated by an algorithm detecting the difference (or the sum of the differences), and repeating the process if the difference is too great.

This process is of course performed for all the teeth. The result is a set of individual tooth objects for all the teeth in the patient's dentition. The teeth can be displayed either alone, or in conjunction with the surrounding anatomical structures such as shown in FIG. 59.

Some human interaction is used in the embodiment described above in context of FIG. 58. While the process could be performed for all the teeth in both arches on the workstation at the orthodontic clinic, that is not necessary. In particular, since the virtual model of the dentition and the template teeth exist as digital data in memory, they can be transported to a remote location and the task of separation of the dentition into virtual teeth objects could be performed at another location. This has the advantage of not tying up the back office workstation or server 28 in the clinic unduly, and requiring less labor at the clinic. We therefore contemplate that the function could be performed as a service of the precision appliance service center 26 of FIG. 1, or perhaps even by some other entity or service provider equipped with the necessary computer hardware and software. Once the virtual tooth objects are obtained for all the teeth in the dentition, the set of virtual tooth objects could be sent over the Internet back to the clinic for treatment planning and other purposes. It would also be possible for the entity performing the separation of tooth objects to also present an initial proposed treatment to the orthodontist (such as a target situation, location of brackets, and design of orthodontic archwire), and let the orthodontist take the process from there or simply indicate her approval.

Separation of teeth from the virtual model of the dentition could also be performed automatically using algorithms to detect incisal edges of the teeth, grooves between teeth, and grooves indicating the intersection of the gums and the teeth.

Two types of errors can occur when separation of teeth objects from other structure (e.g., other teeth and gums): 1) the data is selected for a tooth that does not in actuality belong to the tooth, such as gums and adjacent teeth, and 2) data that does belong to the tooth is ignored.

We address the first problem by providing an erase mode on the workstation software that is performing the modeling process. In this mode, the user is provided with a tool that erases triangle surfaces from the 3-D data, e.g., by highlighting unwanted areas with a mouse and clicking an erase icon or other similar technique. As each tooth is modeled individually, parts of the data that represent the unwanted data, e.g., data belonging to other teeth or gingival tissue, are eliminated from the tooth. This is only a temporary process; it is used only to model that tooth and underlying scanned data is preserved. When modeling the adjacent tooth, that data is used again. The erasing process can be performed directly on the original scan data. However, this can be inconvenient since the original scan data can consist of a huge overlay of data.

As an alternative, and more preferred approach, the user works on a tooth model that has already been created and consists of one shell of triangles. Thus, the erasing mode would be used for example after one iteration of the process of FIG. 58A-F. The selection and erasing process is much faster. The modeling algorithm calculates the surfaces to be deleted from the model in a single pass. The remainder of the iterations of the process of FIG. 58 can typically be performed without any further erasing.

Figure 64A:
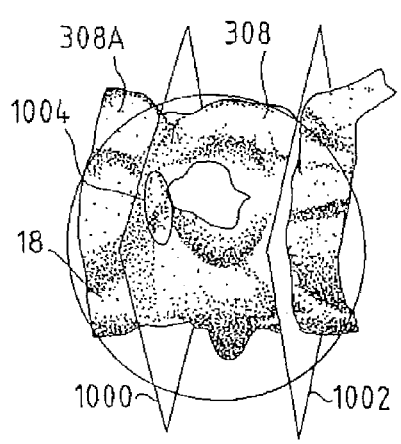
FIGS. 64A-64D are four views of a virtual model of a portion of the dentition generated by the scanning system of FIG. 1, illustrating alternative methods for separating teeth from associated anatomical structure, e.g., other teeth and gingival tissue, as a part of the process described in conjunction with FIG. 58A-58F.

As another alternative for elimination of unwanted data, cutter plane tools can be provided on the workstation software to assist the user in selection of correct tooth scan data. The activation of this feature is shown in FIG. 64A. In this technique, two planes 1000 and 1002 are superimposed on the scanned virtual model 18 of the dentition. The user is able to translate or rotate the planes 1000 and 1002 in any orientation in space using suitable navigation tools on the workstation 28 user interface. The planes may be in different colors. The planes serve as boundaries for the selection of tooth scan data as an individual virtual tooth object, or as part of the iterative procedure of FIG. 58. All 3-D data that is outside of the planes 1000 and 1002 is ignored. The intention of the planes of FIG.

64A is to simulate the physical process of cutting a physical model of teeth into discrete tooth objects.

FIG. 64A indicates that the two planes may not work perfectly since teeth are curved or crooked at the contact area between adjacent teeth, and the plane 1000 may in fact intersect two different teeth. In FIG. 64A, the area in region 1004 indicates where some triangle surfaces from the adjacent tooth 308A are included in the region between the two planes 1000 and 1002. These parts of tooth 308A can be manually erased by the erase mode feature described above.

Figure 64B:
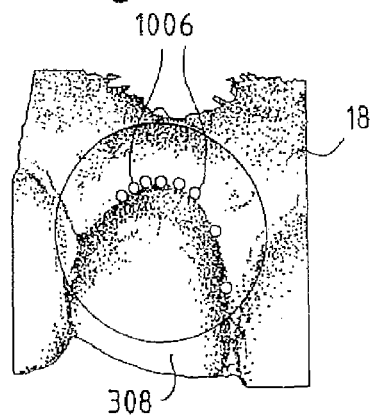
Figure 64C:
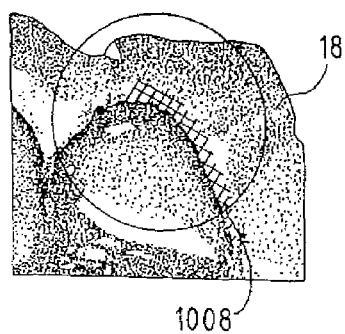
Figure 64D:
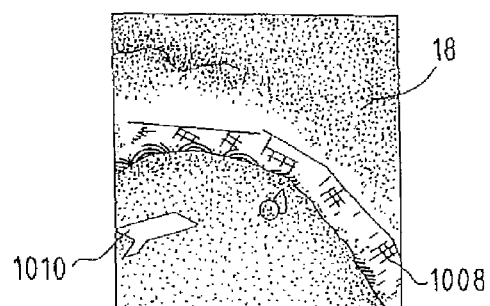

Another possible method for separation of the teeth, without including extraneous anatomical structures, involves allowing the user to click with a mouse multiple points on the surface of the tooth where the tooth intersects adjacent anatomical structures. In FIG. 64B, the user has highlighted areas 1006 on the tooth 308 where the tooth intersects gingival tissue. As each area is highlighted and selected (e.g., by a click of the mouse), the software records the coordinates of points associated with these areas 1006. Then, a series of planes are constructed which connect these points (or surfaces) together. These planes 1008 are indicated by the hatched area of FIGS. 64C and 64D. The planes 1008 serve the same functions as the cutter planes 1000 and 1002 of FIG. 64A; i.e., they define a boundary separating the tooth from associated non-tooth anatomical structures, such as gums and other teeth. Depending on the anatomy of the patient, it may be necessary to highlight closely-spaced areas, as shown in FIG. 64B, so that the planes 1008 match the contours of the gum and tooth.

Referring now to the second problem, the tooth separation process of FIG. 58A-F can be forced to use proper data that would otherwise be ignored. Specifically, the user clicks certain areas where original scan data has been wrongfully ignored. Clicking on the area forces the modeling algorithm to pick original data points from the scan including the selected areas. For example, region 1010 in FIG. 64D has scan data associated with it, but such data was ignored in a frame to frame registration process. The user highlights this area and points for those areas are filled in from the original scan data for pertinent frames covering this area.

To allow for a safe operation of this user interaction, the modeling algorithm will internally mark or classify each generated point in the virtual tooth model as being based on scan data (true points), or if it has been constructed by the algorithm due to the lack of data (artificial points, supplied by the template tooth 310 in FIG. 58B). A lack of data will always occur in the spaces between teeth since the scanner cannot usually capture images of the gaps between teeth effectively. A lack of data can also occur due to improper scanning. The lack of data can be cured to a certain extent by the modeling algorithm of FIG. 58, with the lack of data supplied by the template tooth, e.g., in the gaps between teeth, and adapting this template tooth to the scanned dentition as described above. Artificial points can be marked as such and displayed in a different color or using lighter or darker tones. The manipulations of the user described above for wrongfully ignored data will have effect only on the artificial surfaces.

Figure 65:
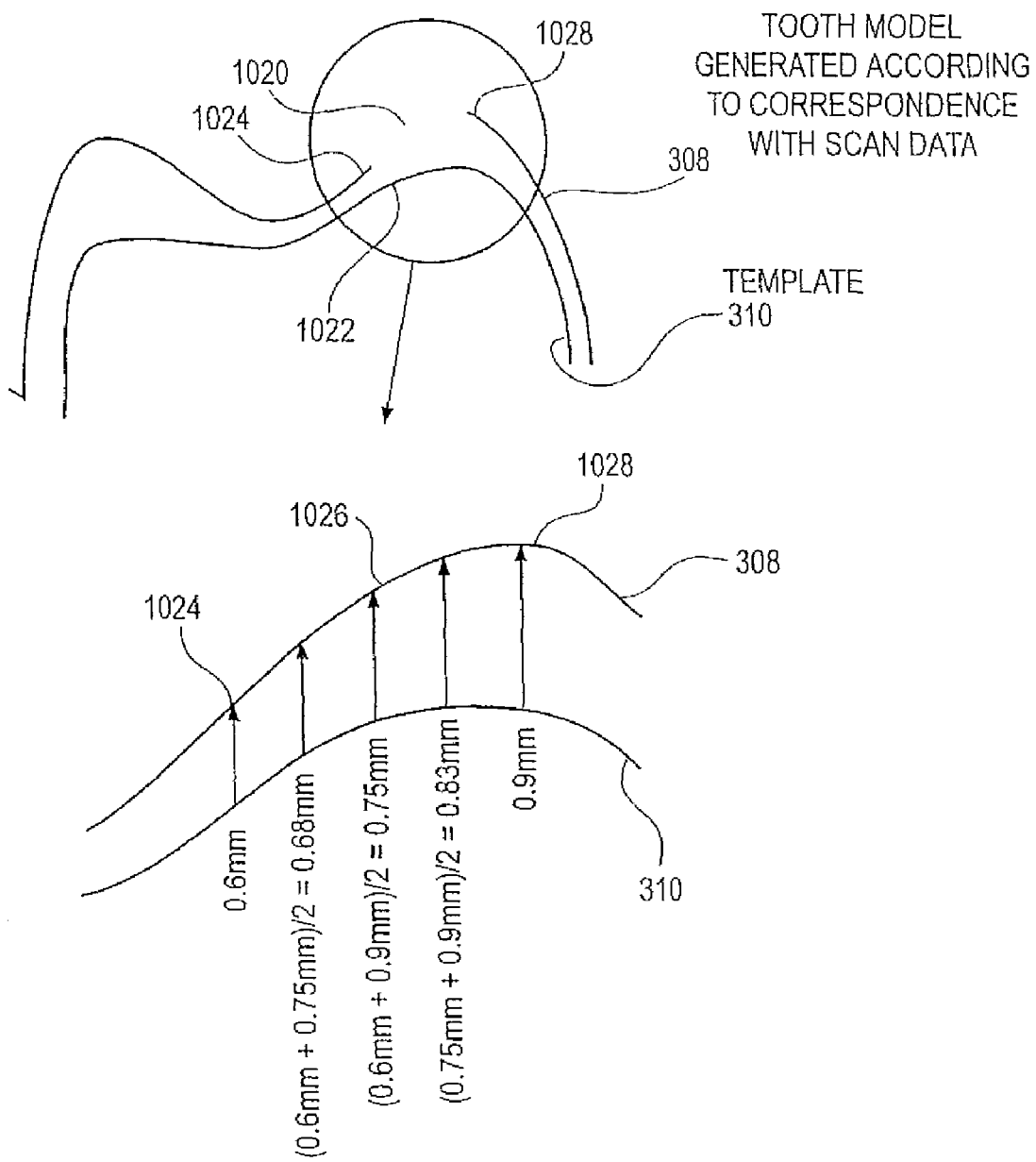
FIG. 65 is an illustration of an interpolation procedure that can be used in the process described in conjunction with FIGS. 58A-58F to fill in holes in scan data from a template object.

Missing data or gaps from the tooth scan can also be filled from the template tooth using a simple interpolation procedure, such as shown in FIG. 65. The example of FIG. 65 will be given in one dimension (Z); a similar process occurs in the other dimensions X and Y. As shown, the scan data for the tooth 308 includes a gap indicated at 1020. The template tooth includes a surface 1022 that corresponds to this gap. To fill in the surface, the distance in mm is determined between the point at the left hand edge of the gap 1024 and the template surface 310 in the Z direction (0.6 mm). The same is done for the right hand edge 1028 (0.9 mm). A mid point is chosen 1026 and the values are averaged to arrive at the distance for point 1026 (0.75 mm) This process is repeated for intermediate points as indicated. After a suitable number of interpolations, the points in the template tooth 310 are moved in the Z direction by the measured or calculated amounts, here 0.6 mm, 0.68 mm. 0.75 mm. 0.83 mm. 0.9 mm. These points are now connected by lines to form triangle surfaces to complete the surface of the tooth 308.

The tooth model, once created, can be modified to simulate various treatments that may be made on the tooth, such as interproximal reduction, or grinding portions of the tooth away, by using the erase mode, clipping planes similar to the planes 1000 and 1002 of FIG. 64A, or some other convenient means.

The library of standardized template teeth described above is based on standard tooth models for each teeth in one possible embodiment. The library described above could be augmented to include a library of teeth based on the ethnicity, sex, age, or other factors. For example, the library could consist of one library of template teeth for Hispanics, another library of template teeth for Orientals, a third library of template teeth for Caucasians, etc. These libraries could be supplied with the treatment planning software, obtained from a third party, or even created from patient scans. For example, after each scan using the present system, the software cuts the teeth into individual tooth objects using the process described above and stores the teeth in memory, along with identifying indicia such as the race, sex and age of the patient. Over time, a large collection of virtual tooth objects for various types of patients will be obtained. These virtual teeth can be registered to each other for a given ethnic type, on a tooth by tooth basis, to result in a new library of template teeth for a given ethic group, which are stored in memory. The user can thereafter identify for the software which library of template teeth to use for a new patient based on the relevant criteria such as ethnicity.

Alternatively, in some situations it may be desirable to use a contralateral tooth as the template tooth, and not a template tooth from the library of template teeth. In this situation, a tooth object of one of the contralateral teeth is obtained from a template tooth in a library and the cumulative registration scan. Then, the tooth object of the contralateral tooth is obtained by using the contralateral tooth as the template tooth and the cumulative registration scan as explained above.

In some situations, the template tooth may need to be modified. A few example of such situations are a partially erupted molar, a tooth that has been chipped, or a tooth that has been the subject of extensive previous dental work. Since the template tooth exists as a mathematical model, it can be displayed on the user interface and modified. The modification can be made using suitable navigation software and a clipping or erasing feature to delete part of the model. One way is providing a clipping plane feature, by which a plane intersects the template tooth in a orientation and location defined by the user using suitable navigation tools. The portion of the template tooth on one side of the plane is deleted. The user positions the plane at the desired location on the template tooth to roughly match the anatomical structure of the tooth in question. This process will result in a smooth execution of the tooth separation algorithm and result in a virtual tooth model that substantially exactly matches the structure of the patient's tooth.

The virtual tooth model may be extended beyond merely the crowns of the teeth. For example, a library of standardized virtual root templates for each of the teeth may be stored in the memory of the workstation. As individual virtual models of each tooth are created, the standardized root for that tooth are matched up with the virtual tooth model to thereby created an individual virtual tooth model of the entire tooth.

This process can be extended to templates of virtual gum tissue. On one hand, after separation of the individual virtual tooth models from the gum tissue the remaining portion of the scan data depicts the gum tissue (or at least a portion of the gum tissue, depending on the tissue scanned). This gum tissue may be substantially incomplete. The incomplete portions can be supplied by a template of virtual gum tissue, e.g., gums for an entire arch. The template of virtual gum tissue can be scaled up or down or modified as may be necessary to fit the anatomical structure of the patient. A registration of the template gum to the scanned gingival tissue enables a complete three-dimensional virtual model of the gums to be created.

This process can be extended to template bones, both mandible and maxilla. The goal here is to create a three-dimensional virtual model of the patient's mandible or maxilla. A virtual three-dimensional model of the mandible and maxilla can be obtained from a variety of sources, including CAT scan data, or skeletal specimens. The models are stored in the memory of the workstation. The virtual template mandible and maxilla are then expanded, contracted, or otherwise modified to fix to the patient's anatomy. X-rays of the patient may assist in the process. When the modified virtual template mandible and maxilla are created, the virtual teeth, gums and or roots can be displayed together with the maxilla or mandible, either alone or together with the orthodontic appliance.

The concept of template virtual objects can be extended to virtual template crowns, and the scanning features and user interface on the workstation extended to simulation of virtual crowns and adaptation of virtual crowns to virtual prepared teeth. For example, a prepared tooth is scanned as described herein and represented as a virtual three-dimensional model. A template virtual three-dimensional crown for the tooth (and typically for all 32 teeth) is stored in memory on the workstation or accessed from a database. The shape of the virtual template crown is reduced or adapted to form fit the prepared tooth where crown and prepared tooth surfaces meet. The shape of the cusps of the crown can be obtained from the surface configuration of the opposing tooth and adjacent teeth, or from the surface configuration of a contralateral tooth that is also scanned and represented a virtual tooth object.

Once the crown shape has been arrived at on the workstation, it can be exported as a 3-D crown object file to a remote location such as a lab for manufacture of the crown. For example, the 3-D crown object file is fed to a stereolithography machine and a physical model of the crown is made. A mold is made from the physical model. The crown is formed in the mold from gold or porcelain made using the lost wax technique. Alternatively, the 3D crown object file can be supplied to a CNC milling machine for machining a crown. Such crowns could be made from any suitable ceramic or metallic material, including stainless steel. This process represents a substantial savings of time and labor in manufacturing crowns. The typical crown preparation process is a manual process.

The concept of virtual template tooth objects and user manipulation of tooth objects on a computer can also be used in the field of dentures. Traditionally, an impression is taken of the gums and associated bony alveolar structures and these anatomical structures are cast in plastic or wax. Pre-formed teeth are set into the wax in a desired occlusion. The dentures are cast in acrylic using the lost wax technique. This process can be automated using the scanning methods described herein and using virtual three-dimensional template teeth.

First, the gums and associated anatomical structures are scanned and represented as a three-dimensional virtual model on the workstation. Then, virtual template teeth are retrieved from memory. The template teeth are sized up or down as necessary to conform to the archform represented by the virtual model of the gums. The virtual template teeth are then placed on the archform. At this point, a three-dimensional virtual model of the teeth, gums and associated anatomical structures is represented in the workstation memory as a three-dimensional virtual object. This digital object can be exported anywhere, such as to a remote location where dentures are manufactured. From this object, a denture can be manufactured from a variety of techniques, including milling and casting. For example, a stereolithographic physical model of the dentition and/or gums can be made and a denture cast in a mold obtained from the physical model using the lost wax technique.

The virtual template teeth can also be used in forensic dentistry, i.e., reconstruction of the identity of a victim from teeth. As an example, a jaw containing some teeth can be scanned as described above and represented as a three-dimensional virtual object. Missing teeth can be reconstructed by importing virtual template teeth and placing them on the virtual object. The virtual template teeth may be based on age or ethnicity if such information is known. Contra-lateral teeth can be constructed by using existing scanned teeth as the template tooth and placing the scanned tooth in the contralateral position. Eventually, a complete virtual representation of the dentition can be obtained and viewed on the workstation. The shape of the face of the victim can be reconstructed by adding template virtual objects comprising soft tissue, gums, lips, cheeks, skin, hair, etc., and modifying the template objects using navigational tools based on the three-dimensional object or other information known about the victim.

Another example of using template teeth is for purposes of diagnosis and detection of tooth wearing, e.g., due to bruxism. In this example, the original scan taken of the patient is converted into a three-dimensional virtual model. The individual teeth are optically separated into virtual three-dimensional tooth objects as described above. Either this original virtual model of the entire dentition or the set of virtual three-dimensional tooth objects can be considered as a template. Over the course of time, the dentition is scanned again periodically and converted into a three-dimensional virtual model as described above. The individual teeth (or the dentition as a whole) is compared to the template to identify differences due to wearing of teeth. This can be performed by overlaying the two models, each in a different color or tones, and visually detecting where tooth surfaces were present initially but are not present in the current virtual model. Alternatively, measuring tools can be provided on the user interface to measure the height of the tooth or other distances that may be indicative of wear, and numerical values immediately presented to the user on the user interface. These measurements can be compared with measurements made of the template. Now, tooth wear can be quantified precisely.

As yet another possibility, individual tooth objects are obtained from the original scan of the patient. These tooth objects are stored in the memory. In the case of a loss of the patient's tooth due to an accident or due to an extraction, the virtual tooth objects provide a precise template for manufacture of a replacement tooth. The replacement tooth could be manufactured for example using the stereolithograpy and lost wax techniques referred to above.

The creation of virtual tooth models allows virtual brackets to be virtually bonded to individual virtual teeth. The virtual brackets are obtained from a 3D CAD model of the bracket obtained from the manufacturer of the bracket. Alternatively, the brackets could be scanned and virtual bracket models obtained from registration of the scan frames into a virtual three dimensional model of the bracket. In either event, the virtual brackets are stored in memory and later accessed from the user interface of the orthodontic workstation. For example, the virtual brackets are placed on the teeth at the location of the landmarks and then moved by the user accessing suitable navigational tools provided by the user interface.

The virtual bonding of the brackets is merely a superposition of the virtual bracket onto the virtual surface of the tooth. Since both the bracket and the tooth are separate and independent virtual objects, they can be moved freely relative to each other, for example to optimize the position of the bracket. Preferably, the treatment planning software allows the user to interactively position the brackets along any combination of X, Y and Z directions, as wells as rotation about three orthogonal rotational axes. In one possible embodiment, the bracket placement correction is made by the user performing the following steps:

1) navigating through the treatment planning software until the virtual model of the dentition and the virtual brackets are displayed (this can be either the target situation or the malocclusion);
2) selecting a bracket for movement by either clicking on the bracket or selecting a bracket number from a drop-down menu;
3) accessing navigational controls for the bracket, such as by clicking on an icon that displays navigational controls for moving virtual objects such as brackets;
4) allowing the user to select either move the teeth with the bracket or move the bracket freely in three dimensions; and
5) using the navigational controls to move the brackets in three dimensions as desired.

If the bracket is moved independent of the tooth model, when the user is finished with the movement of the bracket the virtual tooth is moved to the location of the bracket. Bonding corrections for bonding the bracket to the tooth are updated. The bracket is then virtually bonded to the tooth. This process can be performed for each tooth. The result is that the orthodontist customized the placement of virtual brackets to the teeth. The archwire, which passes through the bracket slots, will have the required bends to move the teeth to the desired target situation regardless of the positioning of the brackets on the teeth.

The combination of the displayed set of virtual orthodontic brackets, together with the virtual orthodontic archwire, thus presents to the user a customized virtual orthodontic appliance. The virtue of the customized virtual orthodontic appliance is that it can be studied, modified, shared between two computers, and transported electronically over a communications medium for fabrication of the orthodontic appliance. The treatment planning software is essentially a specialized CAD/CAM system that allows the design of virtually any configuration of tooth objects, bracket objects, wire objects and other appliances and objects. Because these objects exist as independent mathematical objects, they can be selectively displayed together or alone. For example, the treatment planning software displays an icon or button on the user interface that allows the user to select or deselect the teeth, wires, brackets or virtual objects or appliances, as desired. For example, the teeth and archwire can be displayed together with the brackets deleted from the user interface. The orthodontist can then select an individual tooth object, move it in three dimensions, and the movement of the tooth carried over to a repositioning of the bracket in three dimensions and a changing of the shape of the archwire.

Furthermore, while the above process of creation of tooth models has been described in conjunction with the scan data from the hand-held scanner, this is not required. The separation of tooth objects can be performed with any three-dimensional model of the teeth, regardless of how the three-dimensional model is obtained. The three-dimensional model could be acquired from a CT scan, a laser scan from a plaster impression, or otherwise.

Part 4. Treatment Planning

Introduction

Treatment planning software is provided on the workstation of the orthodontic clinic, and possibly at other remote locations such as the precision appliance center of FIG. 1. The treatment planning software can be considered an interactive, computer-based computer aided design and computer aided manufacturing (CAD/CAM) system for orthodontics. The apparatus is highly interactive, in that it provides the orthodontist with the opportunity to both observe and analyze the current stage of the patient's condition and develop and specify a target or desired stage. A shortest direct path of tooth movement to the target stage can also be determined. Further, the apparatus provides for simulation of tooth movement between current and target stages.

In its broader aspects, the apparatus comprises a workstation having a processing unit and a display, and a memory storing a virtual, complete three-dimensional model representing the dentition of a patient. The virtual three-dimensional model can be obtained from one of several possible sources; in the preferred embodiment it is arrived at from a scanning of the dentition. The apparatus further includes software executable by the processing unit that accesses the model and displays the model on the display of the workstation. The software further includes navigation tools, e.g., typed commands, icons and/or graphical devices superimposed on the displayed model, that enables a user to manipulate the model on the display and simulate the movement of at least one tooth in the model relative to other teeth in the model in three-dimensional space, and quantify the amount of movement precisely. This simulation can be used, for example, to design a particular target situation for the patient.

The development of a unique target situation for the patient has utility in a variety of different orthodontic appliances, including an approach based on off-the-shelf or generic brackets and a custom orthodontic archwire. The scope of the invention is sufficient to encompass other types of appliances, such as an approach based on customized brackets, retainers, or the removable aligning devices mentioned earlier. In a bracket embodiment, the memory contains a library of virtual, three-dimensional orthodontic brackets. The software permits a user to access the virtual brackets through a suitable screen display, and place the virtual brackets on the virtual model of the dentition of the patient. This bracket bonding position can be customized on a tooth by tooth basis to suit individual patient anatomy. Because the tooth models, brackets and archwire are individual objects, and stored as such in memory, the treatment planning apparatus can simultaneously display the virtual brackets, the archwire and the virtual model of the dentition, or some lesser combination, such as just the brackets, just the dentition, or the brackets and the archwire but not the teeth. The same holds true with other appliance systems.

In a preferred embodiment, the virtual model of teeth comprises a set of virtual, individual three-dimensional tooth objects. A method of obtaining the tooth objects from a scan of teeth, and obtaining other virtual objects of associated anatomical structures, e.g., gums, roots and bone is described. When the teeth are separated from each other and from the gums, they can be individually manipulated. Thus, the individual tooth objects can be individually selected and moved relative to other teeth in the set of virtual tooth objects. This feature permits individual, customized tooth positioning on a tooth by tooth basis. These positioning can be in terms or angular rotation about three axis, or translation in transverse, sagittal or coronal planes. Additionally, various measurement features are provided for quantifying the amount of movement.

One of the primary tools in the treatment planning apparatus is the selection and customization or a desired or target archform. Again, because the teeth are individual tooth objects, they can be moved independently of each other to define an ideal arch. This development of the target archform could be calculated using interpolation or cubic spline algorithms. Alternatively, it can be customized by the user specifying a type of archform (e.g, Roth), and the tooth are moved onto that archform or some modification of that archform. The archform can be shaped to meet the anatomical constraints of the patient. After the initial archform is designed, the user can again position the teeth on the archform as they deem appropriate on a tooth by tooth basis. The treatment planning software thus enables the movement of the virtual tooth objects onto an archform which may represent, at least in part, a proposed treatment objective for the patient.

Numerous other features are possible with the treatment planning software, including movement of the teeth with respect to the other teeth in the archform, changing the position of the virtual brackets and the teeth with respect to each other, or opposing teeth with respect to the selected archform. Custom archwire bends can be simulated to provide additional corrections. Bonding corrections at the bracket-tooth interface are also possible.

In another aspect of the invention, a method is provided for digital treatment planning for an orthodontic patient on a workstation having a processing unit, a user interface including a display and software executable by the processing unit. The method comprises the steps of obtaining and storing a three-dimensional virtual model of teeth representing the dentition of the patient in a current or observed situation. The virtual model is displayed on the display. The method further includes the step of moving the position of teeth in the virtual model relative to each other so as to place the teeth of the virtual model into a target situation and displaying the virtual model with the teeth moved to the target situation to the user. Parameters for an orthodontic appliance to move the patient's teeth from the current situation to the target situation can be derived from the virtual model and the target situation. For example, if virtual brackets are placed on the teeth, their location in the target situation can dictate the design of an archwire to move the teeth to the target situation.

In a preferred embodiment, the method includes the step of providing screen displays on the display enabling a user of the workstation to operate the user interface so as to place virtual three-dimensional objects representing orthodontic appliances, e.g., brackets, onto the surface of teeth in the virtual model. A library of the virtual brackets can be stored in memory and a landmarking procedure used to place the brackets on the teeth at the desired location. Anatomical considerations may dictate movement of the brackets from their originally selected position to a new position. Accordingly, the software provides navigational tools enabling a user to change the position of the brackets relative to the teeth.

The treatment planning system is based on individual tooth objects which can be moved to any position in three dimensional space. They can be moved in several ways—by direct user specified movement, and by adding an object comprising an orthodontic appliance and changing the configuration of the appliance to cause the teeth to move. For example brackets can be virtually bonded to the teeth and the position of the brackets changed in three dimensions to move the teeth. Alternatively, an archwire shape can be defined which fits into the slots in the brackets. Movement of the archwire can be simulated, resulting in a simulation of tooth movement.

The treatment planning software includes features enabling more accurate diagnosis. For one thing, the virtual model of the dentition can be manipulated in three dimensions at will, resulting in complete visual assessment of the model. Measurement tools are also provided by which the orthodontist can determine the distance between any two points on the model. This allows the user to quantify the patient's morphology both at initial and at target stages. Thus, treatment progress, proposed changes in appliance design, or tooth movement can be quantified precisely. By measuring the differences and changes in morphology during the care cycle, the orthodontist can quickly and accurately assess patient treatment. Changes in treatment can be made early on. The result is shorter treatment times (and the ability for the orthodontist to service more patients per year).

The treatment planning system incorporates virtual objects comprising orthodontic appliances that may be used to treat the patient. The invention provides for design of complete appliance systems and simulation of various treatment scenarios prior to initiation of treatment A bite registration scan is obtained from the patient to spatially correlate the scans of the upper and lower jaws when the dentition is clenched. This scan is used to provide a registration of the upper and lower jaw to determine the correct relative position. This bite registration scan is usually needed at the beginning of treatment to set the relation between the upper and lower jaws.

Landmarks such as shown in FIG. 57 are then placed on the labial surfaces of all the teeth. The illustrated embodiment places landmarks manually, but this process could be automated. The landmarks are placed initially on the molars and the front teeth, and an estimated position for the landmarks on the other teeth can be made, such as in the same plane, based on the relative position of the landmark with respect to the gingival tissue and incisal edge of the tooth, or other factors.

The landmarks are placed at the location where the orthodontist expects to place an orthodontic bracket to correct the malocclusion. The bracket shape is shown on the monitor 30 (FIG. 1). Three-dimensional templates for a variety of commercially available brackets are stored in memory and the software asks the orthodontist to select a particular manufacturer and style of bracket to use with the patient. Thus, as the landmarks are placed, virtual brackets appear in the computer model on the labial surfaces of the teeth where the orthodontist desires to place the brackets. The orthodontist can move the bracket position depending on the type of forces the orthodontist wishes to create on teeth to correct the malocclusion.

Figure 60:
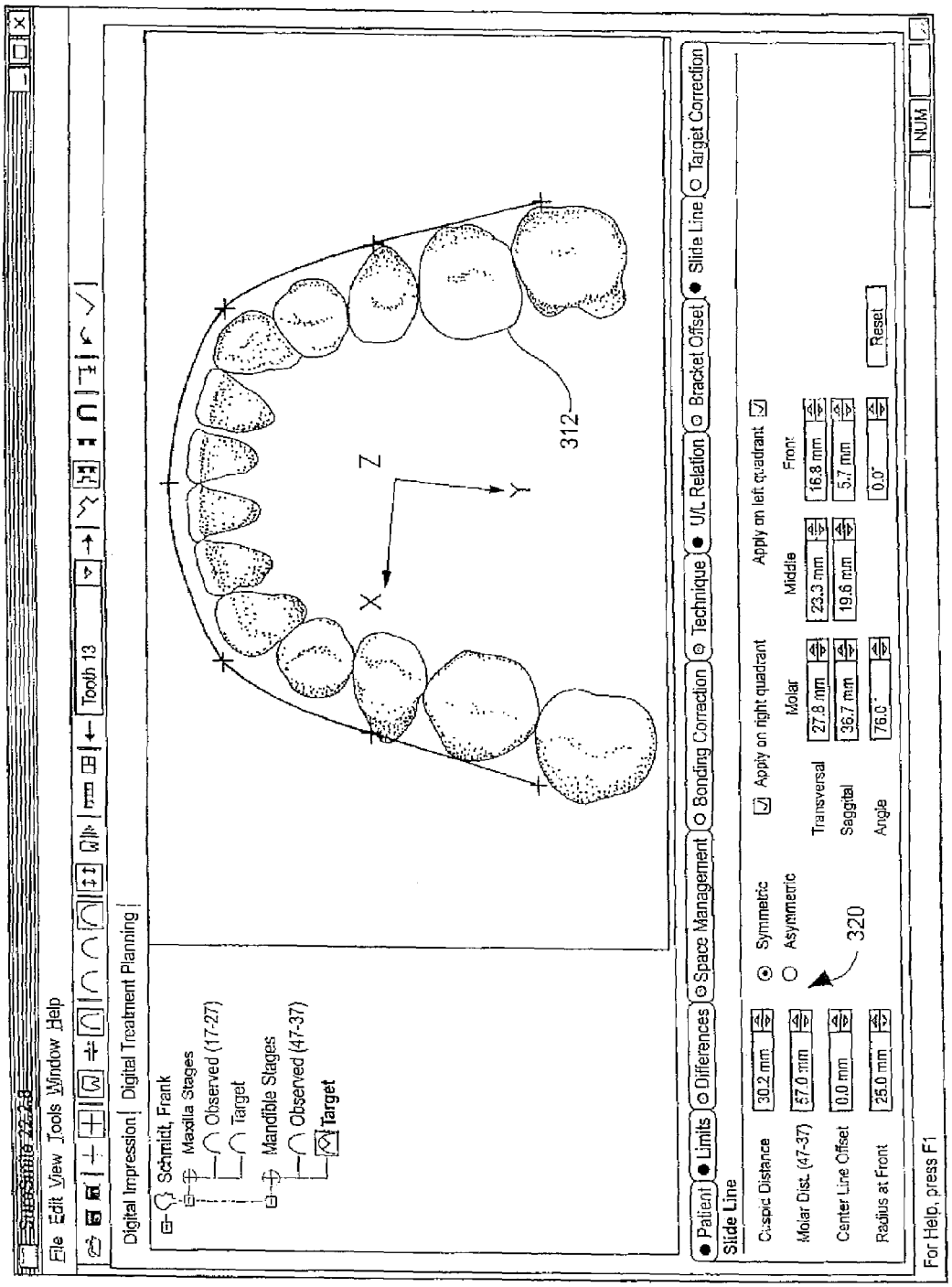
FIG. 60 is a screen shot from an orthodontic workstation showing the computer model of the patient's teeth positioned in a target or desired condition, as a result of the user selecting an archform for the patient and the computer placing the teeth along the arch selected by the user.
Figure 61:
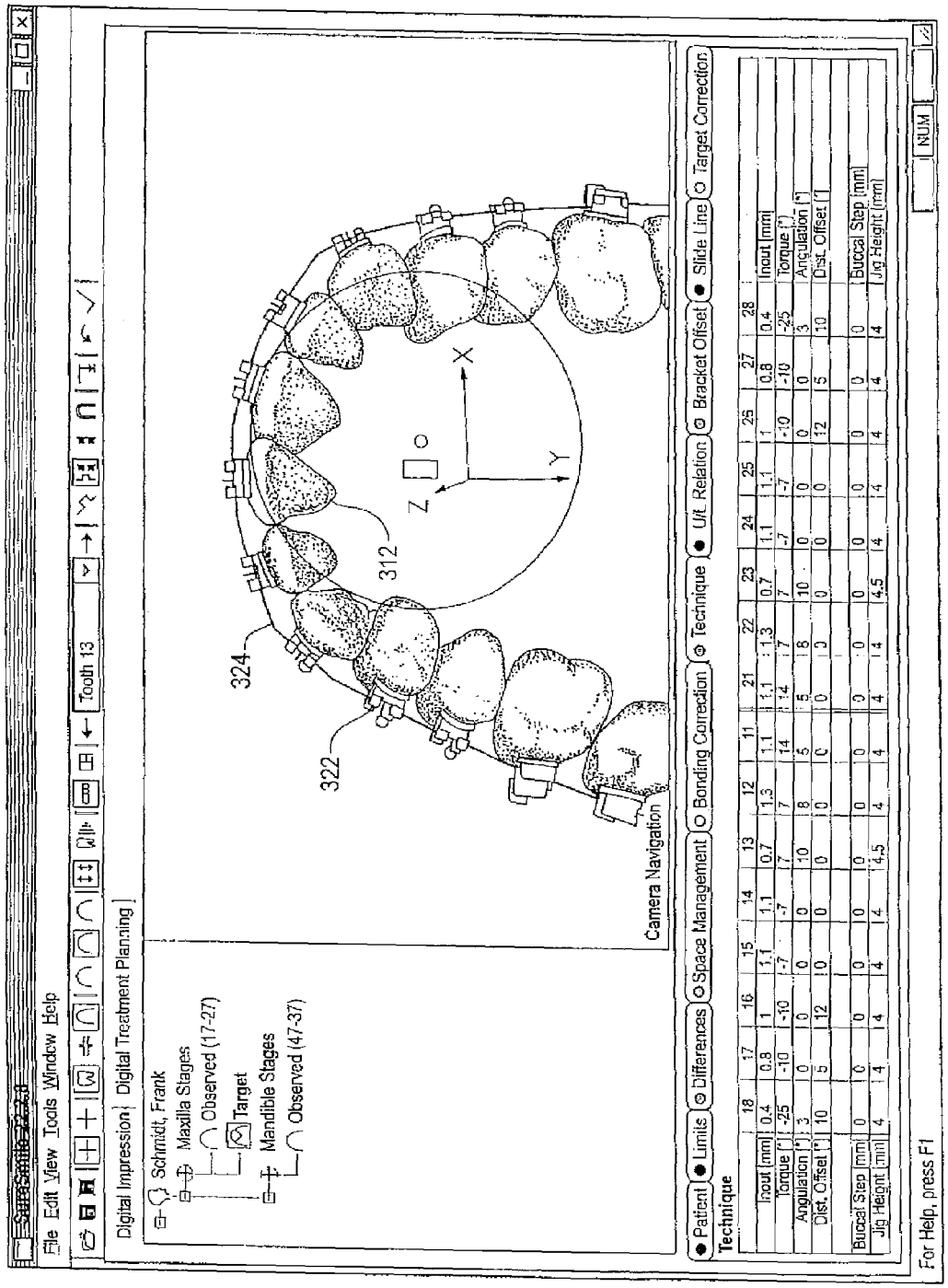
FIG. 61 is another screen shot showing the computer model of the patient's teeth in a target situation, also showing the numerous parameters available to the orthodontist to customize the tooth position, orientation, angulation, torque, and other parameters on a tooth by tooth basis for the target archform.

FIG. 60 is a screen shot from an orthodontic workstation showing the computer model of the patient's teeth objects 312 positioned in a target or desired condition. The illustration is the result of the user selecting an archform for the patient from a known type of archform (e.g., Roth), and the computer placing the teeth along the arch selected by the user. This is executed by placing the virtual brackets the orthodontist placed on the teeth along the curve selected by the orthodontist. The brackets are omitted from FIG. 60, but are shown in FIG. 61. The software allows the orthodontist to change many variables in the target situation, simply by entering new values in the slide line area 320 of the screen display, by mouse operation of up and down arrows to scroll through available values, or by mouse operation of a bar to change the values, or other similar technique. FIG. 60 shows some of the parameters by which the orthodontist can adjust the shape of the arch, the distance between the teeth, the distance between the molars, and other parameters, so as to provide a unique and customized target situation for the patient.

FIG. 61 is another screen shot showing the computer model of the patient's teeth in a target situation, also showing the numerous parameters available to the orthodontist to customize the tooth position, orientation, angulation, torque, and other parameters on a tooth by tooth basis for the target archform. Virtual brackets 322 are positioned on the tooth objects 312 at the location where the user placed the landmarks. A virtual archwire 324 passes through the slots in each virtual bracket.

Figure 62:
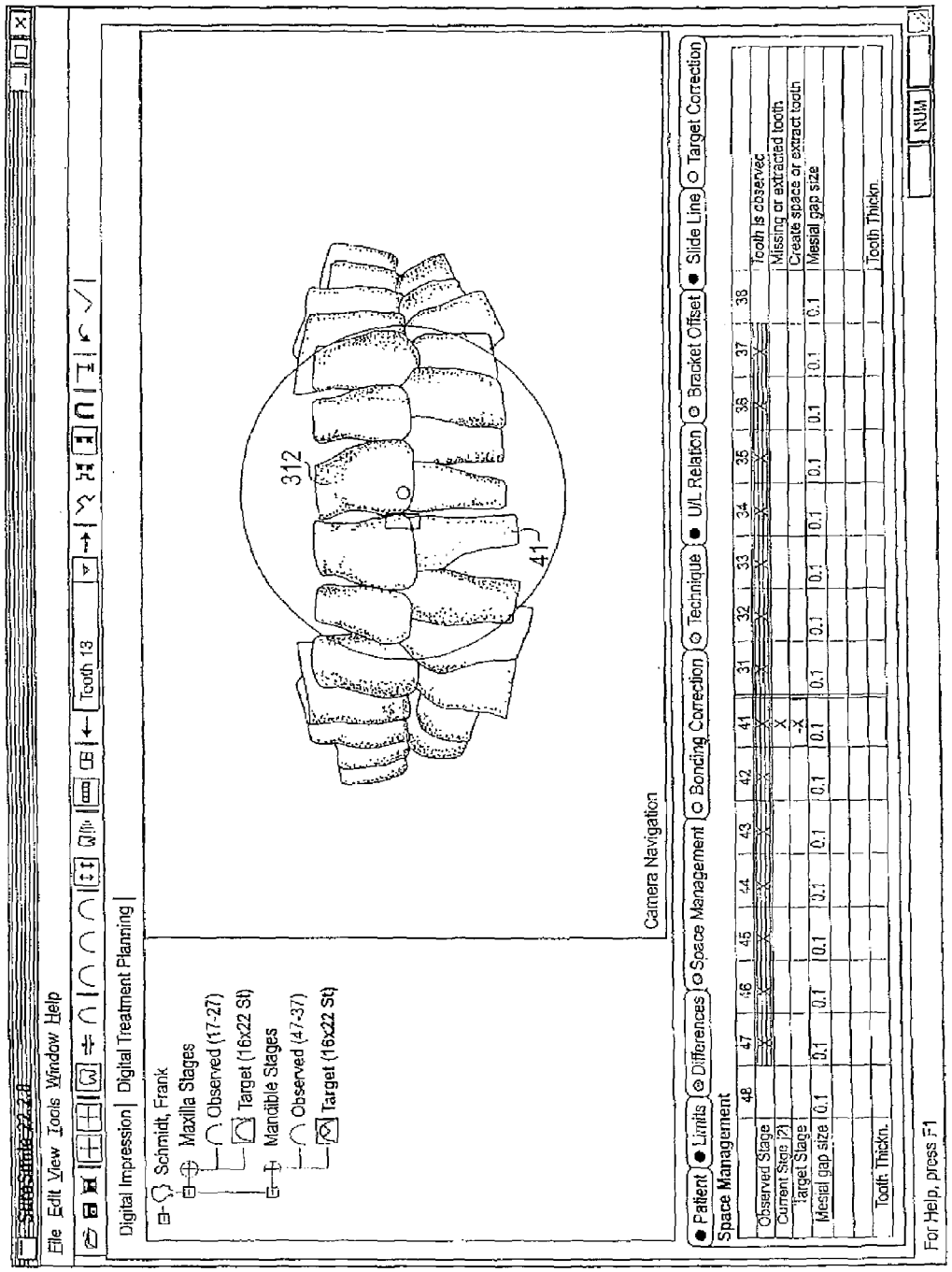
FIG. 62 is another screen shot showing a front view of the target situation and additional parameters available to the orthodontist for moving teeth relative to each other in planning treatment for the patient.

FIG. 62 is another screen shot showing a front view of the target situation and additional parameters available to the orthodontist for simulating the movement and positioning of teeth relative to each other in planning treatment for the patient. For example, in FIG. 62, the cursor is moved onto the virtual tooth 41 (in the tooth numbering convention) and the mouse is clicked. Tooth 41 is then highlighted. If the orthodontist wants to extract that tooth, they then click on the box 22 to extract the tooth in the simulation. Alternatively, tooth 41 could be rotated about any of three axis of rotation, moved in the X, Y or Z direction, or a larger or smaller gap could be created between teeth.

Figure 63:
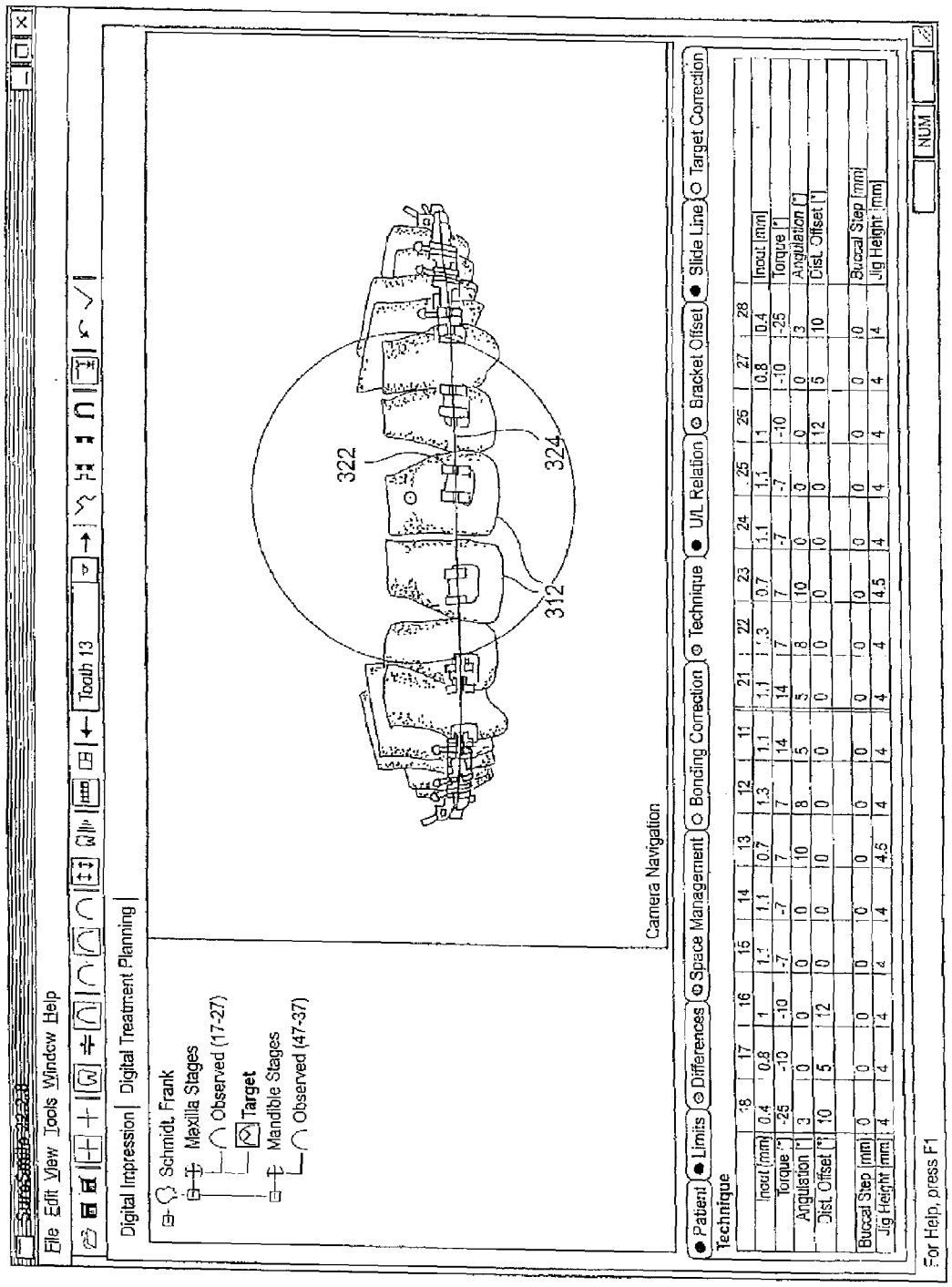
FIG. 63 is a screen shot of a target situation for the patient showing the virtual tooth in a target position, a set of virtual brackets placed on the teeth, and a virtual archwire.

FIG. 63 shows the target situation for the upper arch, with the virtual brackets 322 in place. The orthodontist can adjust the bracket 322 position, archwire shape 324, or tooth 312 position, on a tooth by tooth basis to thereby optimize treatment planning for the patient.

The result of the treatment planning is the generation of a set of bracket placement positions and the display on the monitor of the shape of a customized orthodontic archwire to treat the malocclusion. Information as to the location of the brackets, the three-dimensional model of the malocclusion, the three dimensional model of the target situation, and the type of archwire to use are sent to the precision appliance center 26 of FIG. 1. A customized orthodontic archwire is manufactured in accordance with the bracket location and type and the target situation for the patient. Additionally, a transfer tray is manufactured to assist the orthodontist to place the brackets at the proper location. The transfer tray, brackets and archwire are shipped to the orthodontist's clinic 22. The orthodontic appliance is then applied to the patient and treatment commences.

Because the hand-held scanner allows for scans of the dentition in a matter of minutes, the scanner becomes an important tool in monitoring treatment. As the treatment progresses, the movement and position of the teeth during treatment can be quantified with a high degree of precision. The orthodontist can discern during treatment that corrections in the wire need to be made, for example due to biological influences affecting tooth movement. The treatment planning software on the workstation displays the current situation, and also the target situation. A new customized archwire is designed on the computer. The relevant information for making the new archwire is sent to the precision appliance service center and a new archwire is manufactured and shipped to the clinic.

Monitoring scans are taken during treatment to measure and quantify progress and detect deviations from the expected treatment. Since each of the tooth objects is already stored, the monitoring scan need not be of the entire dentition, but rather needs to only be of one surface, such as the occlusal surface, or the lingual surface, or some combination of the two. A bite scan with the teeth in a clenched condition is also taken to get the current upper and lower relation. The position of the rest of the teeth is obtained from the virtual tooth objects 312 of the patient's teeth (FIG. 58F). After the monitoring scans are performed, a registration is performed of the scanned data relative to the tooth models to complete the teeth and derive a current virtual model of the patient at that point in treatment. Study of this virtual model and comparison to the target virtual model of the teeth and the virtual model at the beginning of treatment can indicate whether progress is as anticipated or if additional correction to the orthodontic appliance need to be made. These corrections will typically be carried out as wire changes in an archwire orthodontic treatment regime, in which new bends are placed in the orthodontic archwire.

Initial Virtual Bracket Placement

With the individual teeth now cut from the three-dimensional model of the dentition and represented as tooth objects, they can be moved relative to each other in three dimensions. Since orthodontics assumes that a bracket is fixedly bonded to a tooth, by moving the bracket one moves the tooth. The next step in the process is thus selecting an initial location to bond the brackets to the tooth. As noted below, this initial location can be adjusted by the treatment planning software. The spatial location of the surfaces of the bracket and the surfaces of the corresponding tooth are known. Collision avoidance algorithms are used to keep the bracket positioned on the surface of the tooth and prevent the virtual bracket from entering the tooth itself, a clinically undesirable result. The user is able to move the bracket independently of the tooth by activating an icon (such as one shaped like a magnet to signify the mating of the bracket to the tooth). When the bracket is moved to the new location, the tooth matches up to the surface of the bracket.

The brackets are represented in the software as virtual three-dimensional objects, and the surface of all the brackets and the teeth are known in three dimensional spatial coordinates. Accordingly, collision detection algorithms are employed to detect when simulated tooth or bracket movement would result in a collision between brackets and teeth. Similar collision algorithms are provided to prevent the adhesion surface of the bracket from migrating into the body of the virtual tooth object and to keep the brackets located on the surface of the teeth. IF the user wishes to move the location of the brackets, the movement of the teeth follows the movement of the bracket. Also, again since the bracket is a three-dimensional virtual object with known spatial coordinates, the user is provided with a tool (such as an icon) which when activated allows the user to move the bracket about one plane or axis, and freeze the movement in the other directions.

Initial virtual bracket placement is done as follows. Landmarks 302 such as shown in FIG. 57 are placed on the labial surfaces of all the teeth. The landmarks are placed at the location where the orthodontist expects to place an orthodontic bracket to correct the malocclusion. The bracket shape is shown on the monitor. Three-dimensional templates for a variety of commercially available brackets are stored in memory and the software asks the orthodontist to select a particular manufacturer and style of bracket to use with the patient. Thus, as the landmarks 302 are placed, virtual brackets appear in the computer model on the labial surfaces of the teeth where the orthodontist desires to place the brackets. The orthodontist can move the bracket position depending on the type of forces the orthodontist wishes to create on teeth to correct the malocclusion. Because the brackets are individual objects and stored in memory, when they are placed on the surface of virtual teeth complete position information is known in three dimensions. As such, the brackets can be displayed either alone, or in conjunction with teeth, or hidden from view, by means of appropriate user specified commands on the user interface. For example, the screen display showing the target or current stage can have an icon indicating hide brackets, or display brackets, and activating the icon causes the brackets to be hid or displayed. The same is true for other virtual objects that exist independently of other objects, such as tooth models and the archwire.

With the teeth now separated into individual tooth objects, and the orthodontist can now view the current target stage, custom design a target situation for the patient, and design the appliance to treat the malocclusion. These aspects will now be described in further detail.

Viewing the Observed (Current) Stage

Figure 69:
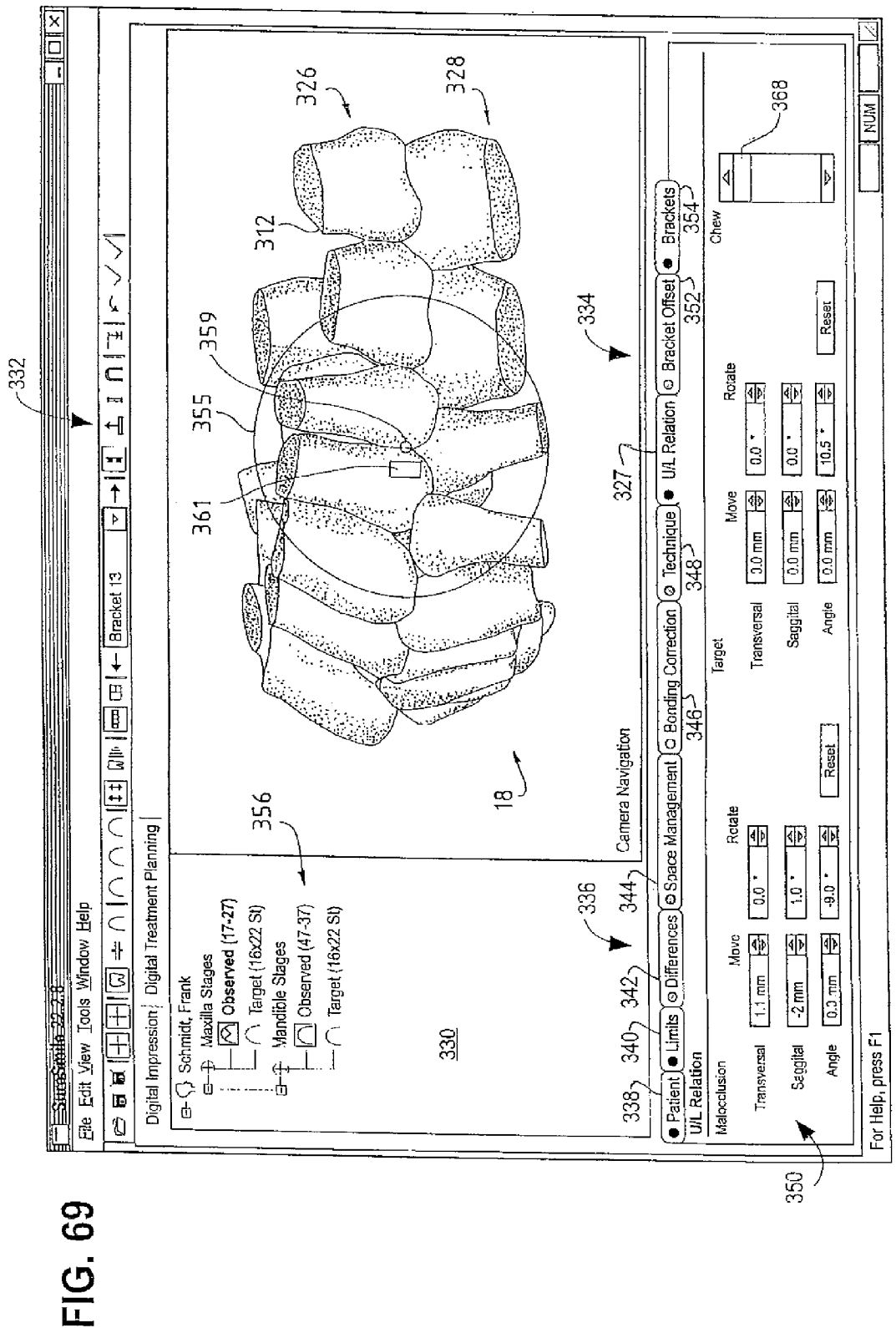
FIG. 69 is a screen shot from the treatment planning software showing a set of individual tooth objects representing the observed stage of a patient suffering from a malocclusion.

FIG. 69 is a screen shot showing a three-dimensional model 18 of a malocclusion, showing the teeth 312 in both the upper and lower arches 326 and 328, respectively. The screen 330 includes a row of icons 332 across the upper portion of the display, which are associated with various tools available to the user to view the dentition, virtual brackets, and current and target archforms. The lower portion 334 of the screen includes a set of tabs 336 that are accessed in various aspects of treatment planning. These tabs 336 include a patient tab 338, which accesses the screen of FIG. 66. A limits tab 340 allows a user to breakdown the tooth movement between observed and target stages into stages, such as 30 percent, 50 percent and 75 percent, and display the tooth positions for both arches at these positions. A differences tab 342 quantifies the differences (in terms of translation and rotation) between the observed and target stages for each tooth. The space management tab 344 permits the user to simulate extraction of one or more teeth and adjust the spacing between teeth in either arch. A bonding correction tab 346 allows for adjustment of tooth position to be realized via bonding corrections. The technique tab 348 allows the user to select a bracket prescription and default settings for bracket height (distance from bracket slot to incisal edge of tooth). The tab also displays the parameters for the bracket prescription chosen by the user. The upper/lower (U/L) relations tab 327, selected in the screen shot of FIG. 69, allows the user to modify the relation of the upper and lower jaws, by both translation in three axes (transversal, sagittal and vertical directions) and by rotation about these axes. The user manually enters values in the field 350 to change any parameter, and the change is immediately reflected in the view of the model of the dentition.

The tabs also include a bracket offset tab 352 that allows a user to reposition the bracket on a tooth and specifies numerical values for each bracket placement modification. A brackets tab 354 allows a user to enter information as to the type or manufacturer of brackets for each tooth in the both arches.

A further "morphing" tab could be provided which would animate the movement of the teeth from malocclusion to target situations based on treatment steps or limits defined by the user (explained in further detail below).

The screen shot of FIG. 69 also includes a region 356 that allows the user to navigate between views of the observed stage and views of the target stage. Here, the user has highlighted or selected both arches in the observed stage, so the screen display shows the model of the dentition in the current or observed stage.

Figure 67:
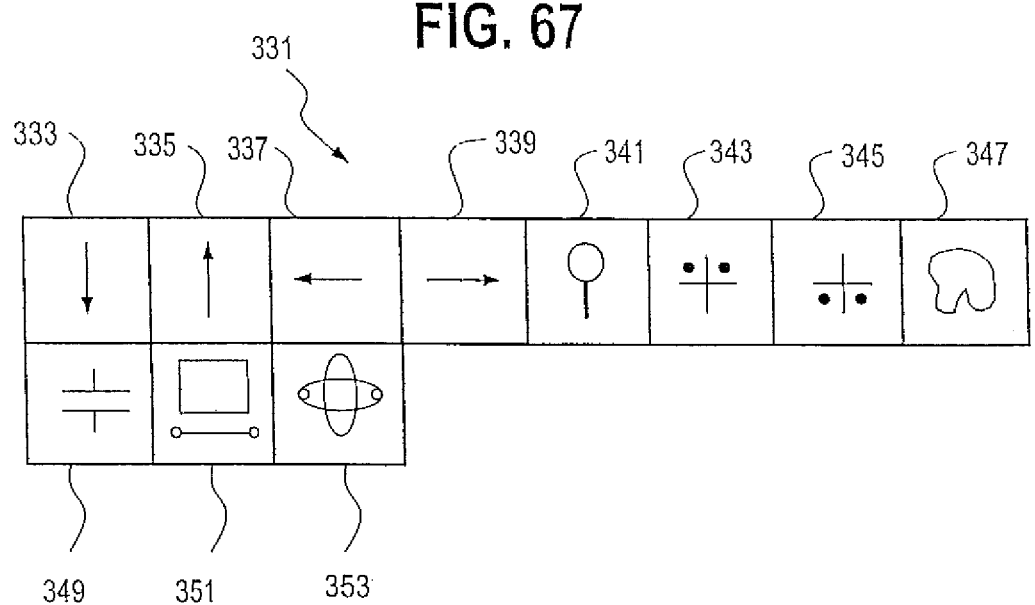
FIG. 67 is an illustration of a series of icons that appear on a screen display that provide some tools for viewing the three-dimensional model of the patient's dentition.

Referring to FIG. 67, the treatment planning software preferably displays a plurality of icons 331, not all of which are shown in FIG. 69, to enable the user to quickly and easily view the three dimensional model in various standard perspectives. For example, the icons 331 of FIG. 67 include icons 333, 335, 337 and 339 for viewing the dentition in top, bottom, right hand side and left hand side views, respectively. An icon 341 is provided which zooms in or out. Icons 343 and 345 allow the user to select for viewing just the upper or lower arches, respectively, including virtual teeth, virtual brackets and virtual archwire. The icon 347 allows the user to show or hide the virtual dentition, excluding brackets and archwires. An icon 349 allows the user to select or deselect the virtual brackets. A marker icon 341 is used for measurement functions (described below) and an object navigation icon 353 is used for manipulating any of the virtual objects on the screen.

Figure 70:
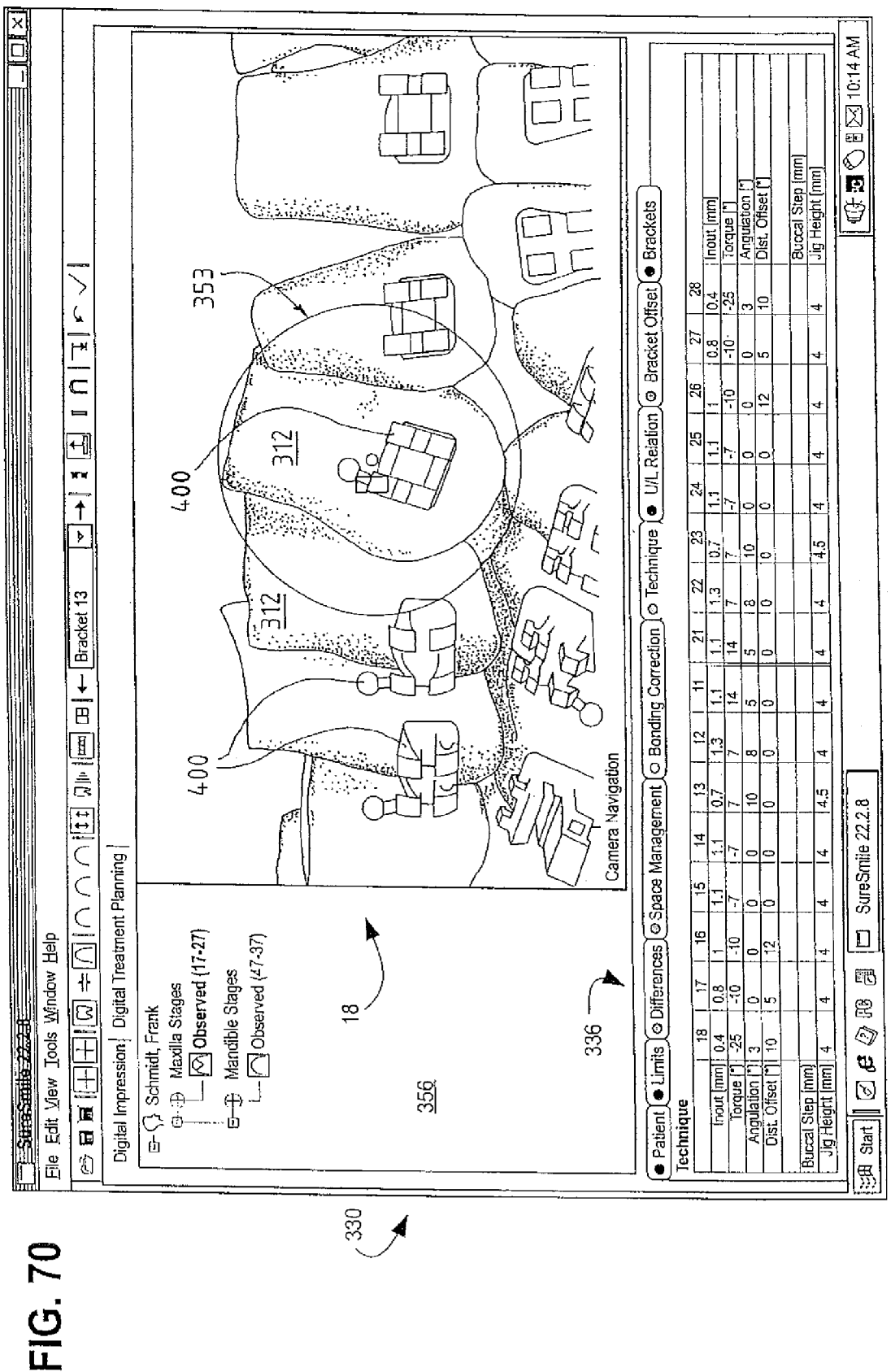
FIG. 70 is another screen shot from the treatment planning software, showing the observed stage and the placement of virtual three-dimensional brackets on the surfaces of the teeth.

When positioning multiple objects in the three-dimensional view, such as shown in FIG. 69, the camera navigation icons of FIG. 67 move all the elements together. As shown in FIG. 70, the initial placement of the virtual brackets 400 can be displayed along with the teeth. Further, the camera navigational tools allow the user to zoom in an zoom out in any desired degree. However, the virtual teeth 312 and virtual brackets 400 are individual three-dimensional objects which can be selected and moved independently. One way of moving objects is by entering new positional values (e.g, in terms of mm of displacement or angle of rotation, as described later). Another method provided by the software is using object navigational controls, activated by clicking the icon 353 or by accessing the function via a tools menu. The object navigation controls allow the user to move the object based on orthodontic judgment and visual feedback. The amount of movement is stored and can be displayed using numerical position information. As will be discussed in further detail below, the bracket position can be individually adjusted on a tooth by tooth basis. Furthermore. the camera navigation icons permit navigation of the archforms (i.e., the teeth placed on some selected archform), navigation of the brackets, or navigation of the archwire.

The object navigation tools first require an object (e.g., tooth, bracket, archwire, etc.) to be selected. To select and deselect any object displayed on the screen, the user places the cursor over the object and double clicks the mouse. The selected object is highlighted in a separate color. Additional objects are selected by pressing and holding down the <CTRL> button while double clicking additional objects. To magnify the object, the object is selected as described above and the icon 341 is clicked.

Figure 68:
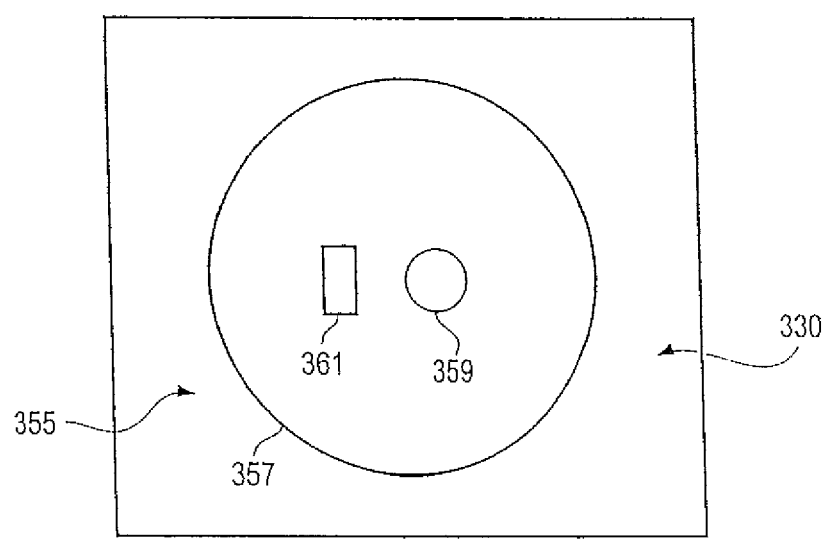
FIG. 68 is an illustration of a set of icons which are part of the screen displays which act as a navigational tool and allow the user to manipulate the three-dimensional models of teeth and brackets on the display.

To move the selected objects, the software provides an object navigation icon 353. When the icon 353 is selected, object navigational tools appear on the screen 330. These navigational tools 355 are shown in FIG. 68 and FIG. 69. The object navigational tools 355 comprise a large circle 357, a small circle 359 and a small rectangle 361. First, the object is selected as described above. Then, the object navigation icon 353 is clicked, activating the tools 355 such that they are displayed. The user then positions the mouse pointer relative to the tools 355 and presses and drags as described below to position the object. When the mouse pointer is outside the large circle 357, when they start dragging the object is turned either clockwise or counterclockwise depending on the direction of dragging. When the mouse pointer is positioned within the large circle 357, when they start dragging they rotate the object in any direction. When they start dragging from inside the small circle 359, the object is moved in one plane. When they start dragging from inside the rectangle 361, by dragging down the object is moved closer, by dragging upward the object is moved farther away.

Measuring Objects

Referring again to FIG. 67, the icon 351 allows the user to establish a measurement marker on any portion of the virtual model of the dentition. The user uses the icon 351 to place markers at any two points on the dentition and the distance between the markers is displayed on the screen.

To use the icon 351, the user clicks on the icon, and then clicks anywhere in the 3-D view of the dentition to place markers. A straight line is drawn between two markers. The distance between the markers appears on the screen, e.g., at the upper left hand corner of the windowpane of the 3-D view. A tool in the Tools menu in includes a DELETE ALL MARKERS function to delete the markers.

The measurement function allows the user to measure tooth size, inter-molar width, inter-canine width, the arch length, curve of spee, and other important orthodontic and diagnostic parameters. The measurement aspect of the invention is particularly significant in that it permits precise quantification of simulated tooth movement, both in terms of establishing initial treatment plan as well as monitoring treatment.

Viewing Cross-Sections of Model

Figure 73:
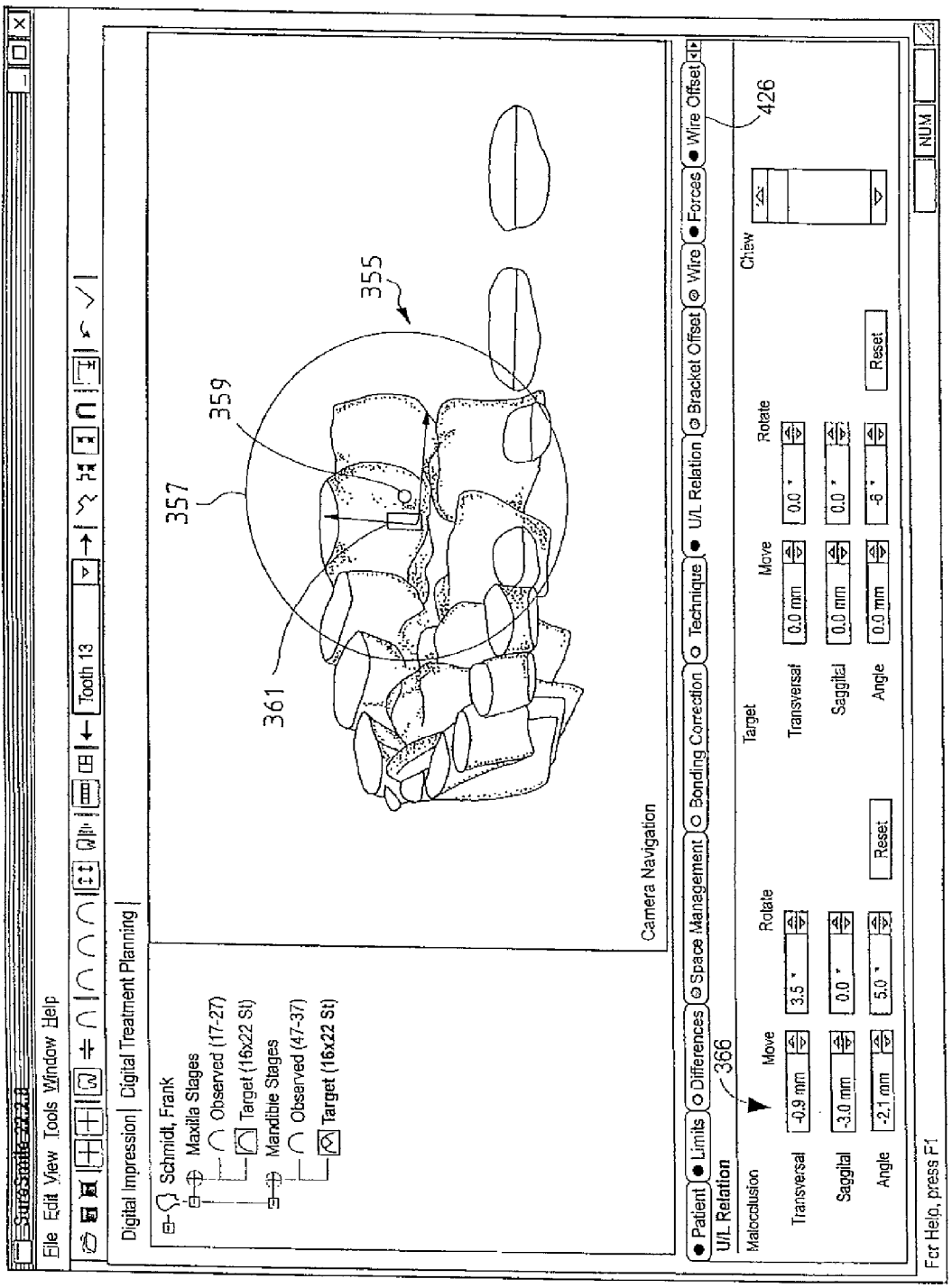
FIG. 73 is a screen show showing a cross-section or "clipping plane" view through the upper arch in a target situation.
Figure 74:
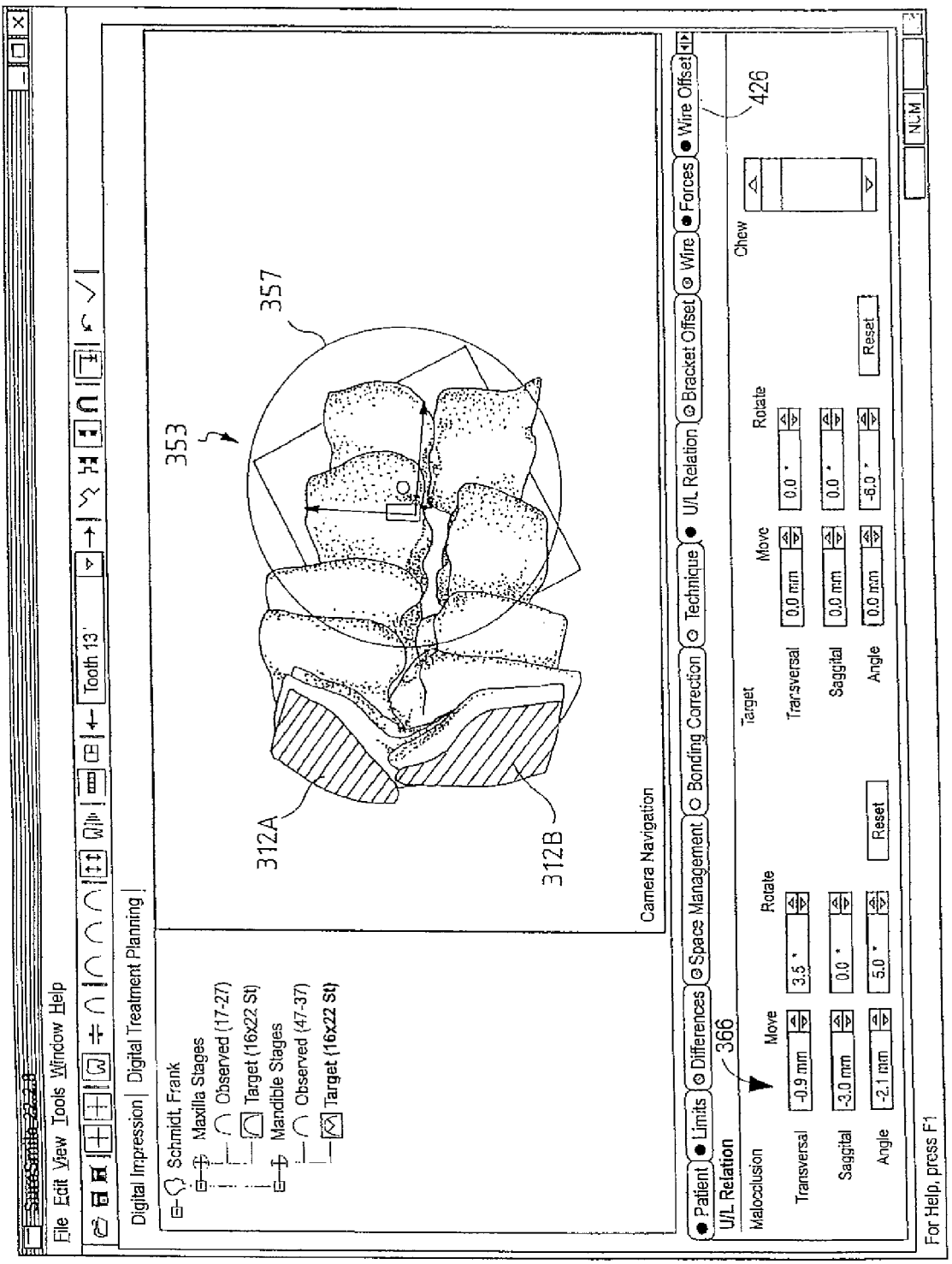
FIG. 74 is a screen shot illustrating of a portion of a target arch, showing a vertical cross-section or clipping plane taken through the teeth. This view is helpful in adjusting the relation between the upper and lower jaw.

The viewing options also include a clipping plane feature by which cross-sections of the teeth through any desired plane are possible. As shown in FIG. 73, the clipping plane is shown through the upper jaw, but the user at can move this plane in three-dimensional space at will. If the teeth are magnified, this clipping plane feature is very useful for inspecting contact points between the upper and lower jaw, viewing and adjusting the upper and lower jaws in the initial bite registration, and adjusting the location of the occlusal plane. For example, in FIG. 74 the clipping plane is shown through the upper and lower incisors 312A and 312B.

The clipping plane is manipulated like an object with the object navigational tools shown in FIG. 68. The plane is accessed using a tools menu and the user highlights or selects SHOW CLIPPING PLANE. A plane appears on the screen. The user then clicks on the object navigation icon 353 (FIG. 67). The object navigational controls 355 of FIG. 68 then are displayed. The user then positions the mouse pointer over the navigational controls 353 to adjust the position of the clipping plane. When they start dragging in the region outside the large circle 357 (FIG. 68, FIG. 73), the plane is turned clockwise or counterclockwise. Then they start dragging inside the large circle 357, the plane is rotated in the direction indicated by the dragging. When they start dragging from inside the small circle 359, the clipping plane is moved in the direction of the dragging. When they start from inside the rectangle 361, if they drag up they cut less into the model, by dragging down they cut further into the model.

Viewing and Adjusting Initial Bite Registration

The first step in typical treatment planning is deciding where to place the teeth in three-dimensional space. This will ordinarily involve a definition or fixation of the vertical level of the teeth relative to the bones, and defining an occlusal plane, and adjusting the occlusal plane sagittally and transversely. This, in turn, will ordinarily involves an assessment of structural relationship between the teeth and the maxilla and mandible. The orthodontist performs this by accessing and studying X-ray, CAT scan, photographs or other two dimensional data stored in the patient records portion of the treatment planning software, and of course the three-dimensional model of the malocclusion, with the teeth either represented as individual tooth objects or in context with the surrounding anatomical tissue. The mid-sagittal profile of the incisors and molars is set up by superimposing the mid-sagittal plane of the teeth over the X-ray.

Figure 66:
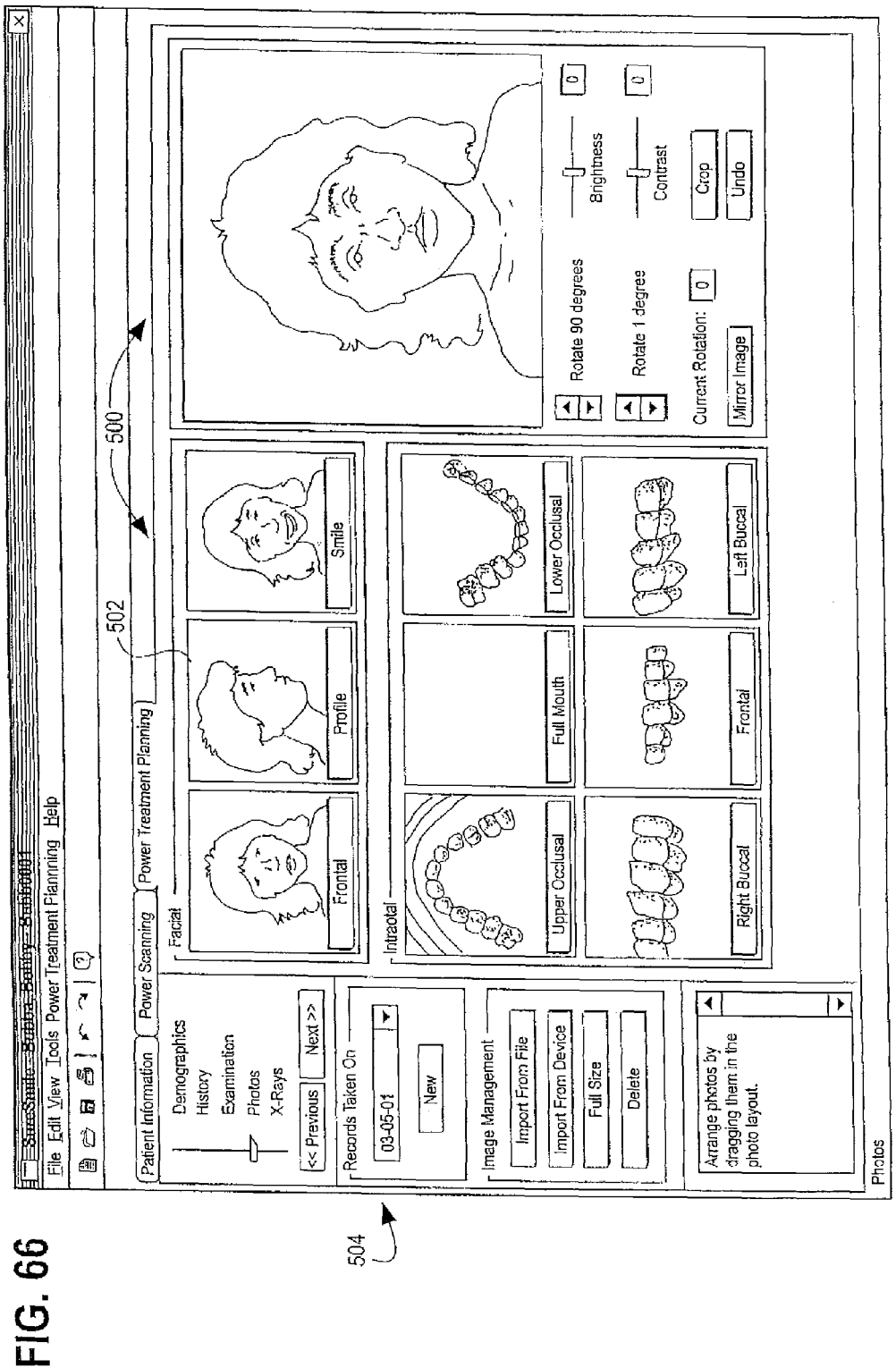
FIG. 66 is a screen shot of a workstation user interface display showing a patient records screen which the user access various information regarding the patient, including dental history, X-ray photographs, medical history, photographs of the face, teeth and head and the three-dimensional model of the malocclusion.

FIG. 66 is a screen shot from the workstation running the treatment planning software showing a patient information screen. The screen includes a region 500 for storing various photographs 502 of the patient's head and face, and various views of the patients dentition. The photographs are taken with a digital camera and loaded into the workstation, and accessed from the treatment planning software. The patient information section of the software also includes separate screens for entering and displaying other pertinent information for the patient, accessed through a menu 504. These additional screens (not shown) include the patient demographics, patient medical, dental and orthodontic history, examination notes, and X-rays.

To assist this process, the treatment planning software provides the ability to view and adjust the initial bite registration. The initial bite registration between the upper and lower arches can be modified using the U/L relation tab 327 of FIG. 69. The user can move or rotate the lower jaw relative to the upper jaw by entering values in the field 366. The user can also simulate a chewing motion of the upper and lower jaws by moving the slide bar 368 down. During this simulation the lower jaw moves from side to side and up and down to simulate a chewing motion.

Figure 71:
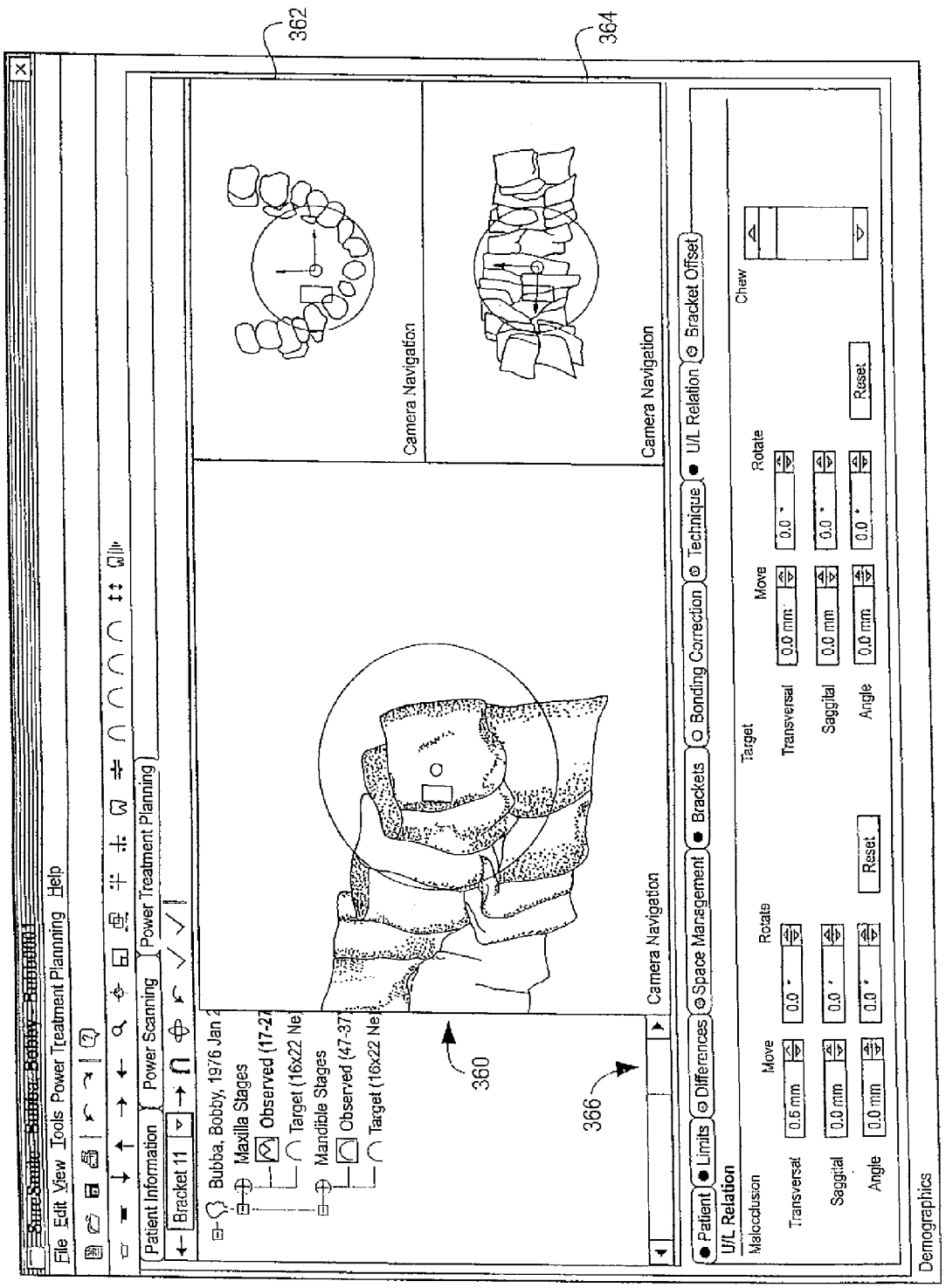
FIG. 71 is another screen shot from the treatment planning software, showing several views of the observed stage and the fields by which an orthodontist can enter values to alter the relation of the upper jaw to the lower jaw as an initial step of planning treatment.

FIG. 71 shows how the three-dimensional viewing area on the screen on the workstation can be broken up into separate screens using known windowpane techniques. Here, in windowpane 360, the area of the molar in the observed stage is displayed, with the orthodontist able to assess the upper and lower relation and change values for the upper and lower relation in three planes of space. Simultaneously, windowpane 362 shows the upper and lower jaws as seen from above. Windowpane 364 shows the dentition looking from the molars out towards the incisors, a view the orthodontist would otherwise not be able to access without the three-dimensional virtual model. These various views, plus the clipping plane tool, and the X-Ray and patient photograph data in the patient records portion of the software, provide a complete suite of tools for effective orthodontic diagnosis, treatment planning, and appliance design, including initial bite registration.

Figure 72:
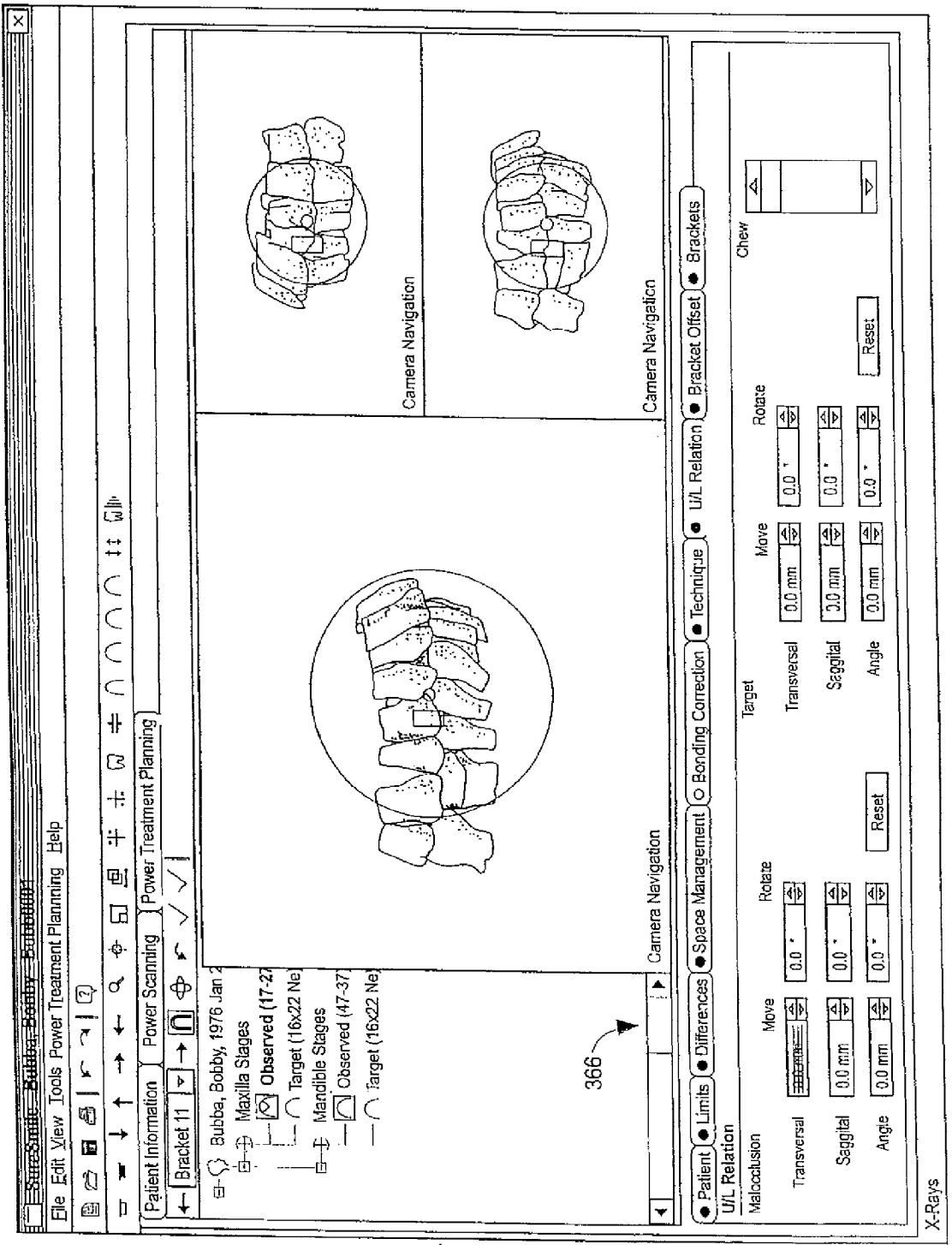
FIG. 72 is another screen shot showing several views of the malocclusion displayed simultaneously, similar to FIG. 71.

FIG. 72 is another screen shot showing the three-dimensional model of the dentition in the observed stage. No values have been entered in the malocclusion field 366 in the U/L Relations tab. By inspection of the upper and lower jaws (using magnification or clipping plane features if needed), the user can set numerical values in field 366 and immediately simulate the corresponding tooth movement to arrive at a desired upper and lower initial bite registration.

Design of Target Archform

Figure 75:
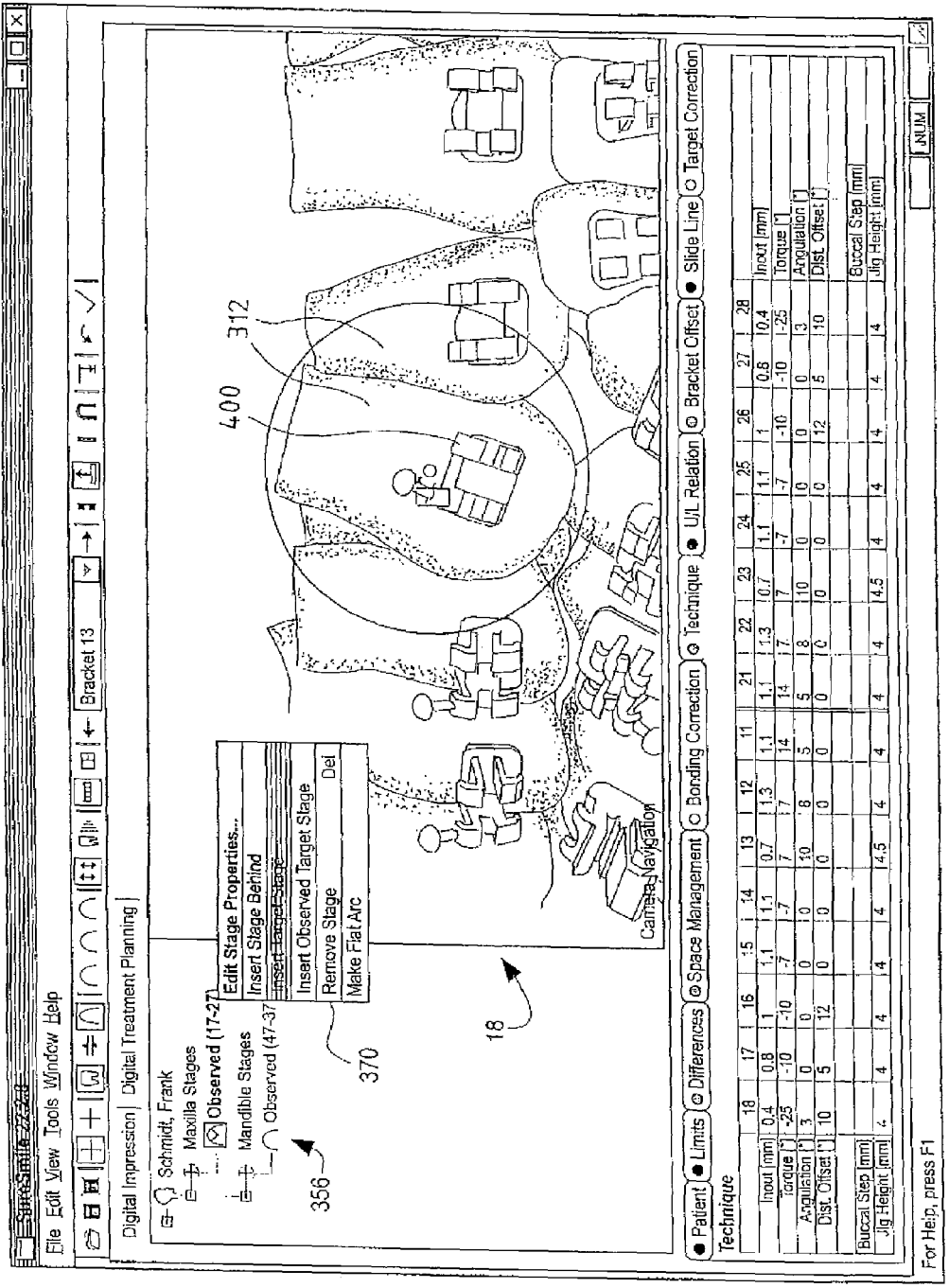
FIG. 75 is a screen shot showing the placement of the virtual brackets on the teeth at the malocclusion, showing the user clicking on an icon to establish an initial archform for the upper arch.

Referring to FIG. 75, after the user has set the initial level of the occlusal plane and inspected the initial observed situation, the next step is selection of a desired or target archform for the patient and the midline. The orthodontist will have previously selected or indicated a general type of archform for the patient, e.g, Roth. The treatment planning software allows the user to generate a target arch based on this archform for the individual patient. The user highlights the observed stage in region 356 and then right clicks the mouse. The pop-up menu 370 appears and the user selects INSERT TARGET STAGE. The target stage is arrived at by creating a flat virtual wire that runs through the virtual bracket slots to create a virtual arch line. The arch shape is based on the user's selected preference for the arch shape, based on the patient's facial anatomy, bone structure, malocclusion, and other parameters using the orthodontist's judgment. The wire target shape has a best fit through the malocclusion bracket slot positions. In one embodiment this wire is flat. It is also possible to design the wire to adapt to the malocclusion in the vertical direction to create a Curve of Spee if desired. The geometry in the transverse direction can also be changed, such as the transverse curve of Monson establishing an inclination of the teeth in the coronal plane.

Figure 76:
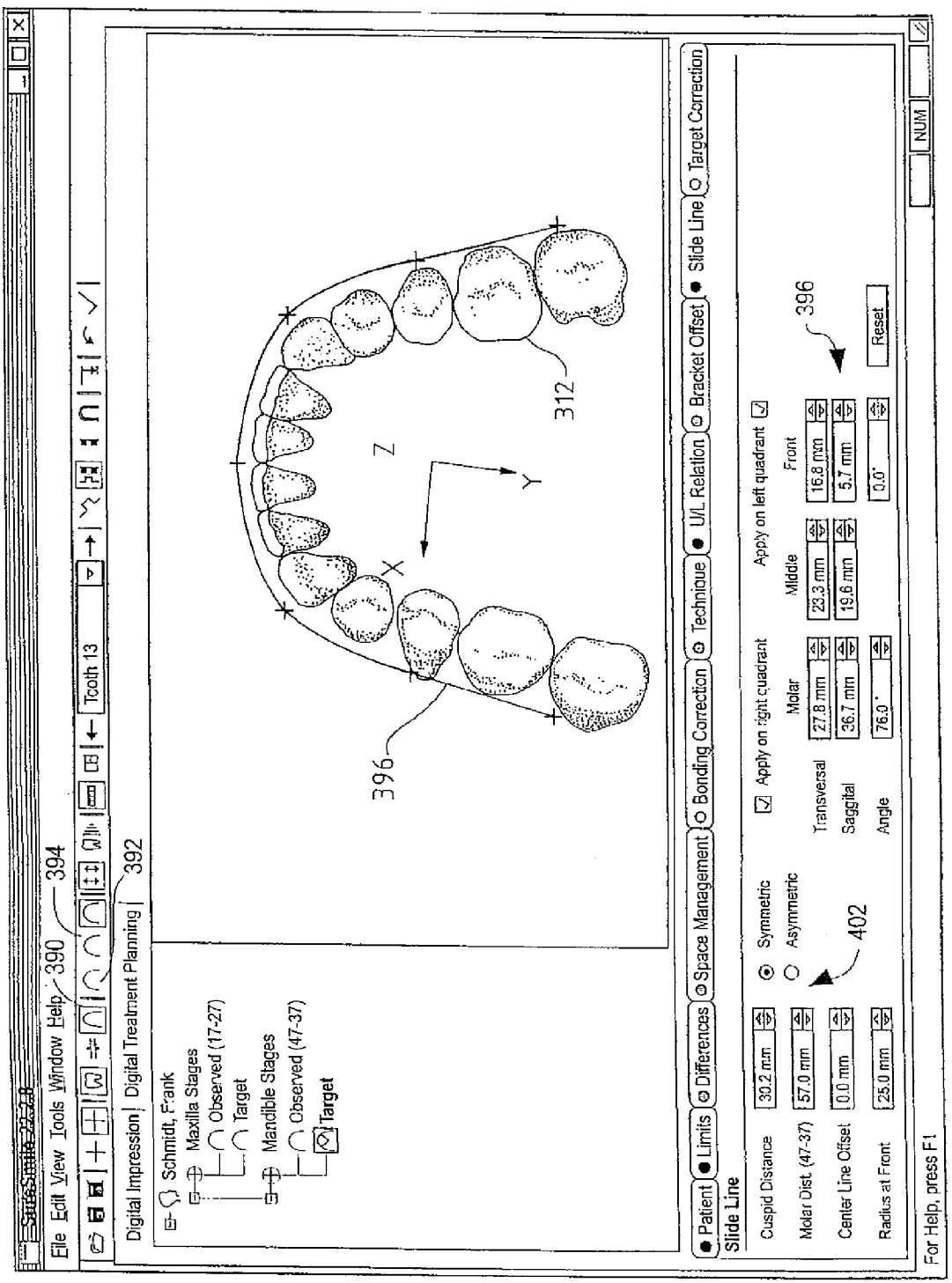
FIG. 76 is a screen shot showing the computer model of the patient's teeth positioned in a target or desired stage, as a result of the user selecting an archform for the patient and the computer placing the teeth along the arch selected by the user.
Figure 77:
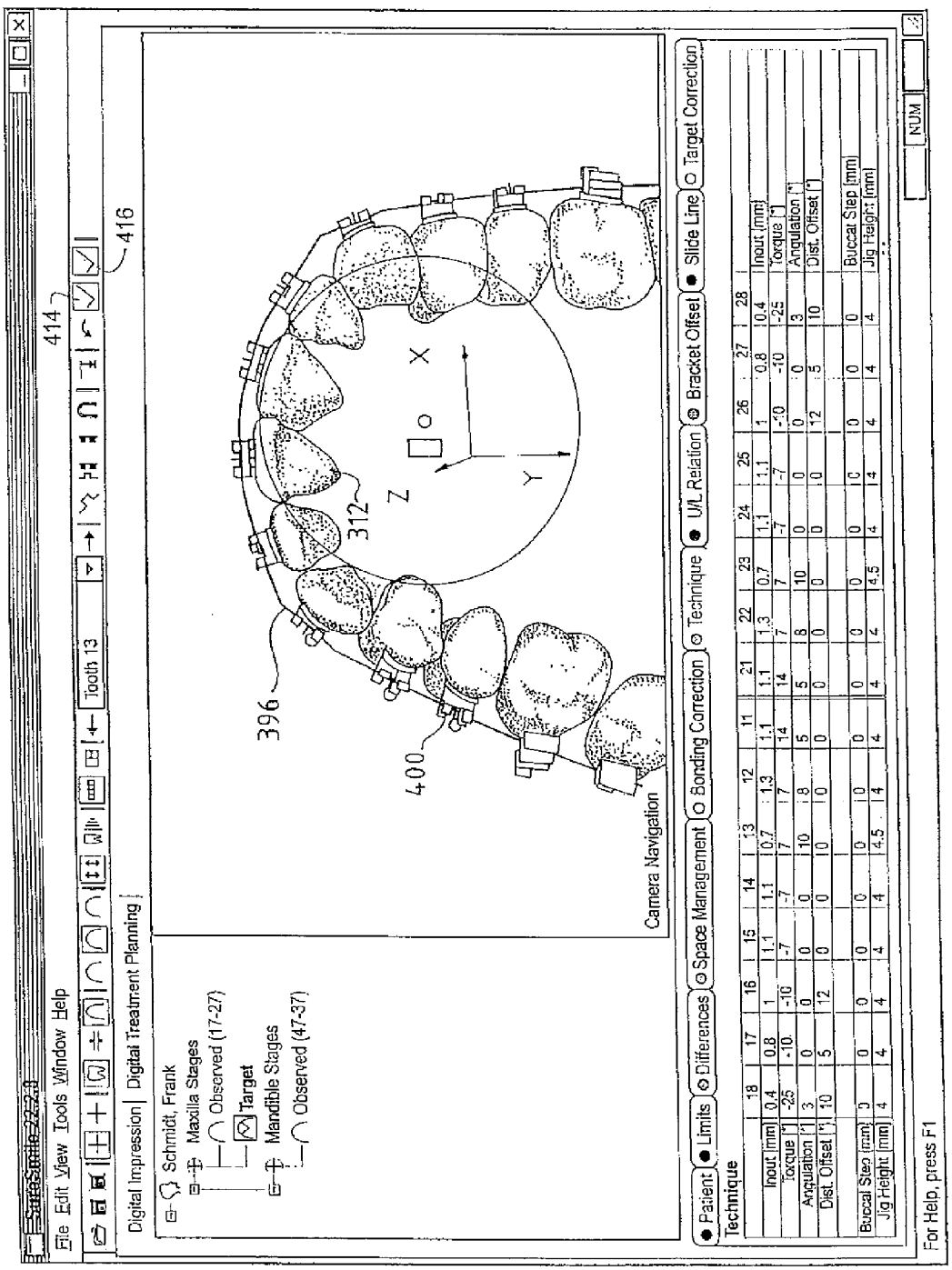
FIG. 77 is another screen shot showing the computer model of the patient's teeth in a target stage, also the brackets and the orthodontic archwire, and showing the numerous parameters available to the orthodontist to customize the tooth position, orientation, angulation, torque, and other parameters on a tooth by tooth basis for the target archform.

FIG. 76 is a screen shot from an orthodontic workstation showing the computer model of the patient's teeth objects 312 positioned in a target or desired condition. The illustration is the result of the user selecting an archform for the patient from a known type of archform and the computer placing the virtual brackets along the arch selected by the user. This is executed by placing or threading the virtual brackets along the archform or curve selected by the orthodontist. The brackets are omitted from FIG. 76, but are shown in FIG. 77. When the initial target archform is created, the slide line tab shown in FIG. 67 is activated.

The initial target archform presented to the user in FIG. 76 is only an initial archform. The treatment planning software allows the orthodontist to change many variables in the target situation, simply by entering new values in the slide line area 402 of the screen display. FIG. 19 shows some of the parameters by which the orthodontist can adjust the shape of the arch, including the distance between the cuspids, the distance between the rear-most molars, the center line offset, and the radius of curvature at the front of the teeth. Slide line area also permits the user to select a symmetrical archform or an asymmetrical archform, and apply corrections on the right and left quadrants as indicated. As values are entered in area 402, the shape of the archform is instantaneously modified on the screen display, allowing the user to simulate various potential archform configurations for the patient.

In generating the archforms shown in FIGS. 76 and 77, the user will ordinarily set up the lower arch first. The upper arch is automatically derived from the lower arch. The user can view the arch forms in several ways using three arch icons 390, 392 and 394. The arch icon 390 is for the malocclusion arch, which causes a blue line to appear on the screen which exhibits the curvature of the observed arch or malocclusion. The line passes through the slots on the virtual brackets, as placed on the teeth. The arch icon 392 is for the target arch, which represents a custom archwire passing through the bracket slots of the teeth in the target situation. The line 396 in FIG. 76 represents this arch. The arch icon 394 if for an ideal spline or curve generated by the software to represent an optimal shape. The arch retains a parabolic shape as the user manipulates the target arch using the entries in the slide line. The numerical values in region 398 of the slide line tab represent checkpoints and boundary conditions on the ideal spline associated with the icon 394. These values can be edited as indicated.

Since the software allows for generation and display of a malocclusion archform and a planned archform, the difference between the two archforms indicates the space needed to control arch length inadequacy; i.e., to identify the need for interproximal reduction, extraction, or control of gap size. Interproximal reduction can be achieved by the clipping plane feature, and the simulation of shaping of individual tooth objects in three planes of space. The simulation of extractions and control of gap is provided for as explained next.

Space Management—Management of Extractions and Gaps Between Teeth

Figure 82:
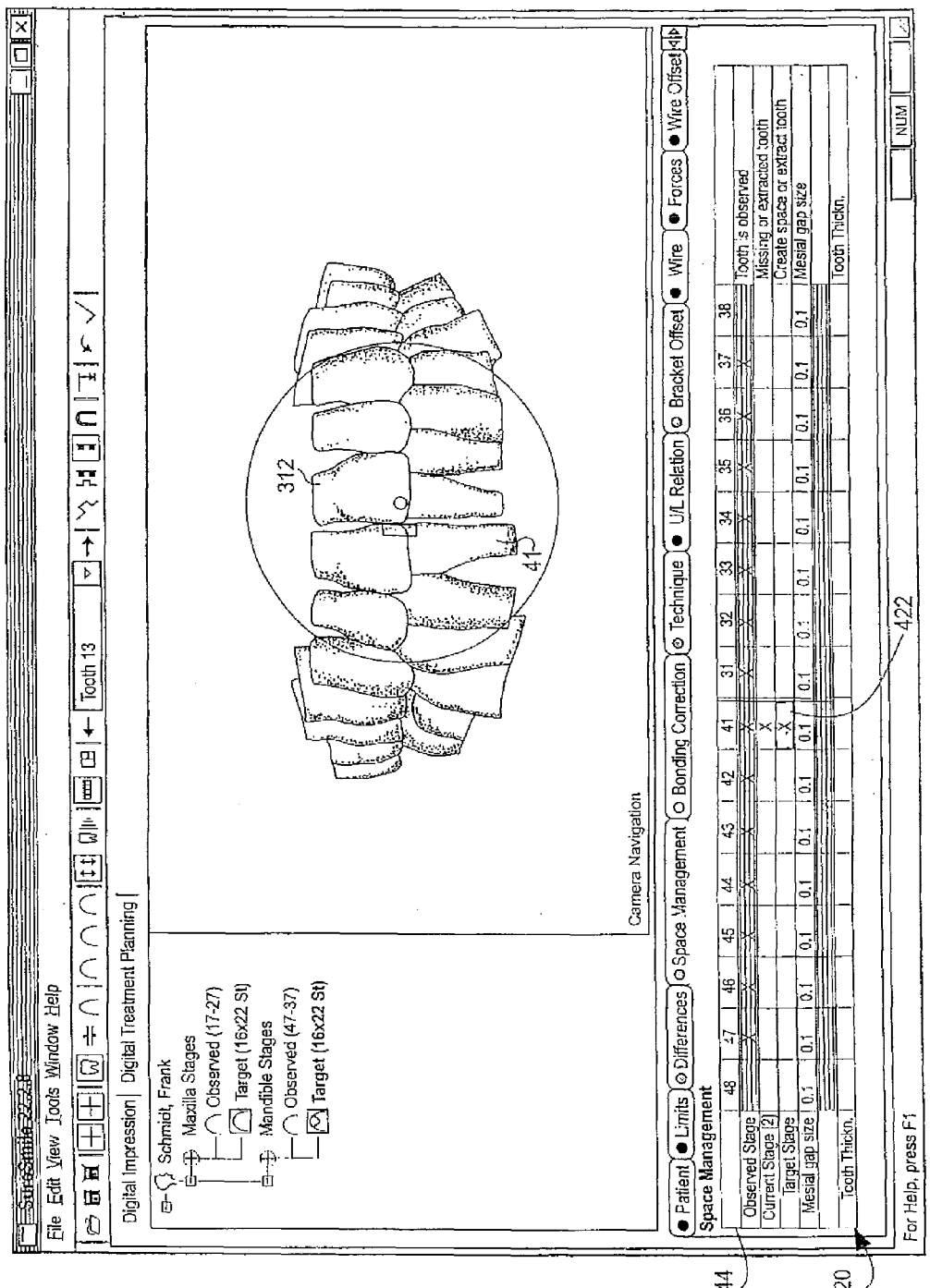
FIG. 82 is another screen shot showing a space management feature by which the target situation can be adjusted by specifying spaces between teeth or by extraction of teeth.
Figure 83:
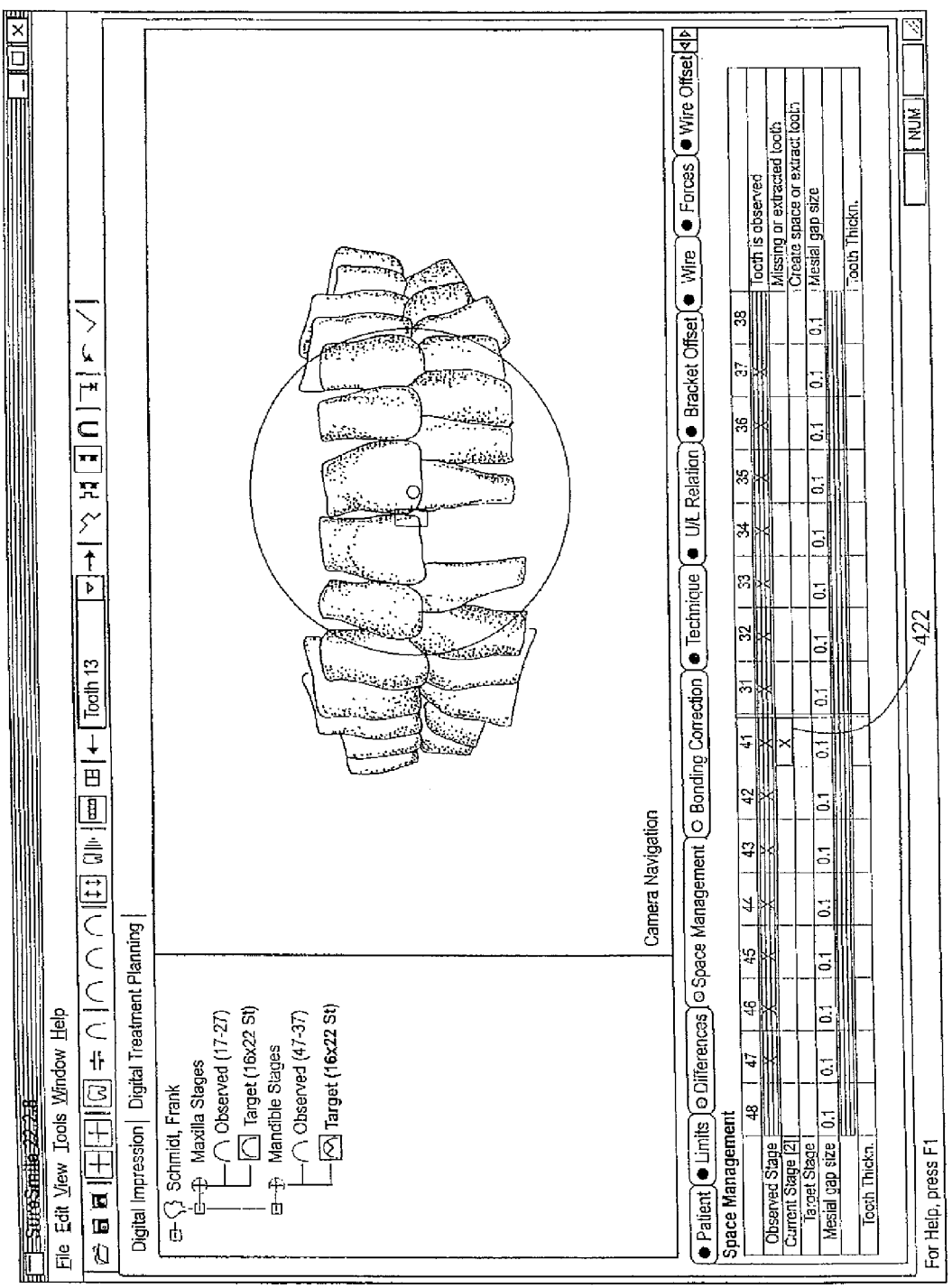
FIG. 83 is a screen shot illustrating the simulation of an extraction of a tooth number 41.
Figure 84:
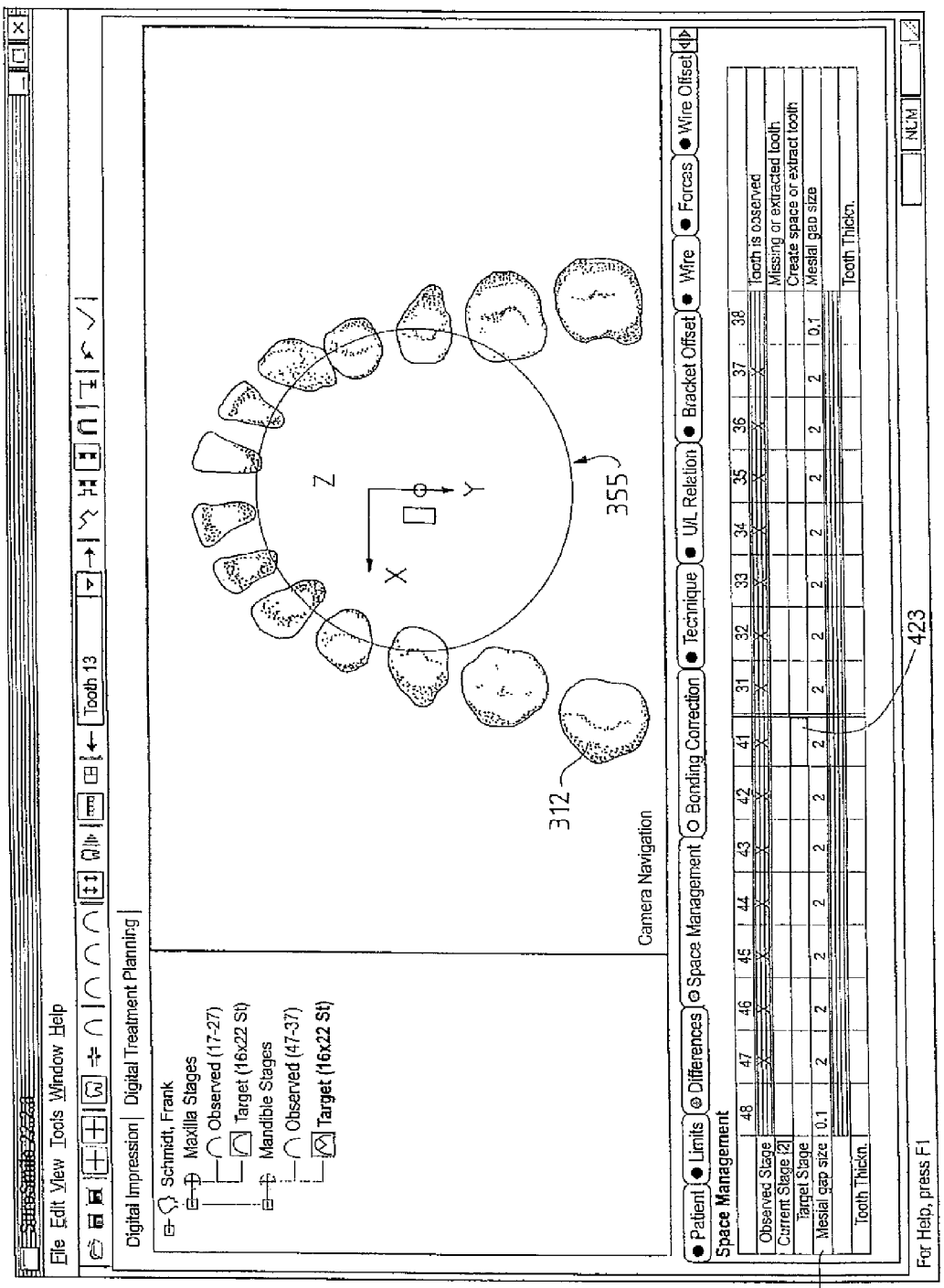
FIG. 84 is a screen shot showing the user modifying the mesial gap between the teeth and showing how the user-specified mesial gap is instantaneously represented on the screen.

The treatment planning software provides a space management tab 344 that is used for managing space between teeth, including tooth extraction. FIG. 82 is a screen shot showing the target situation of both the upper and lower jaws. The user clicks on the space management tab 344, and the region 420 of the tab appears. The region 420 allows the user to simulate the extraction of a tooth in either the current or target stage. Here the user is simulating the extraction of tooth number 41 by clicking on the appropriate cell for that tooth in the rows for current and target stages. The result is shown in FIG. 83. The extraction of tooth 41 is simulated. The region 422 also allows the user to enter values for the mesial gap size between teeth. A default value of 0.1 mm is provided. However, the user can change these values. For example, the user can enter any values in the row of cells for mesial gap size as shown in FIG. 84 (in this example 2 mm). Note also in FIG. 84 that the simulation of the extraction of tooth 41 is not being performed since the cell 423 is not checked. The tooth moves distally if a positive number is typed in the cell for that tooth in the mesial gap size row 424. If a negative number is typed into the cell, the tooth moves mesially.

Adjusting Virtual Bracket Position

After the upper and lower archforms have been optimized, the user may wish to adjust the position of the virtual brackets 400 on the teeth. The step of adjusting the virtual bracket position can also be performed prior to the design of the archform.

The vertical position of the virtual brackets relative to the incisal edge of the virtual teeth is one adjustment that can be made. This distance can be measured using the measurement tool described earlier. Bracket manufacturers have recommendations for this distance. If the initial landmarking has placed the brackets outside of the recommended distance, this distance can be adjusted by using the object navigational tools. Alternatively, the user can select preferred values for the archform and the bracket set (bracket manufacture, bracket technique and wire type, e.g., straight) and the landmarks and virtual brackets will be placed on the teeth at the recommended distance.

The bracket placement can also be performed interactively by the user. The user looks at every tooth 312 one by one (using a screen such as the screen shot of FIG. 75) to see if they are basically satisfied with the bracket 400 position, e.g., angulation, side to side position, and its relation to teeth in the opposing jaw. The user may be performing this step while viewing the malocclusion, or the target stage. To improve the position of the virtual bracket 400, the user selects the bracket, zooms in if necessary, and adjusts the position of the bracket on the tooth surface using the navigational tools as described earlier.

Correction of Individual Tooth Position in Target Archform

Figure 78:
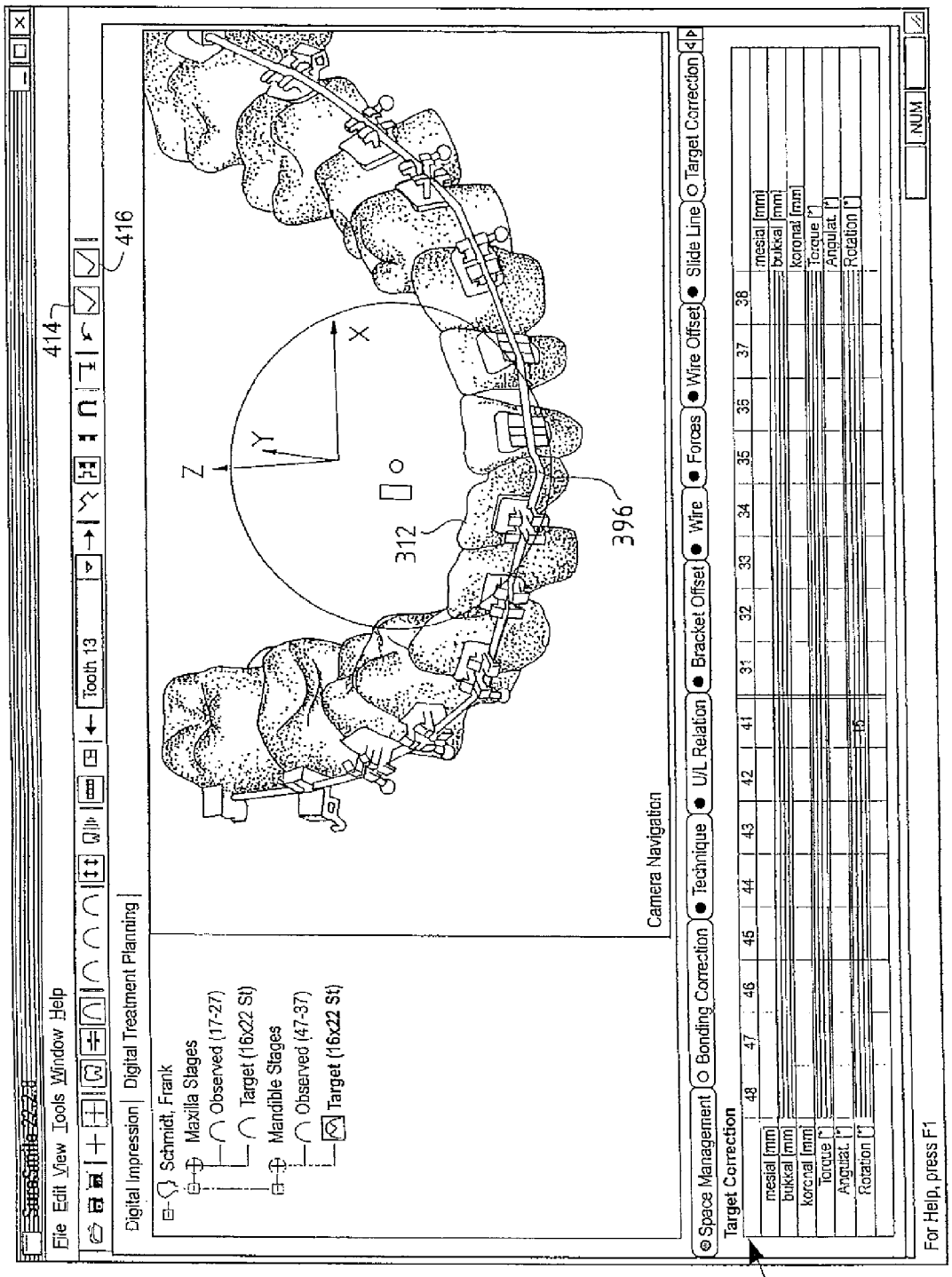
FIG. 78 is another screen shot showing a view of the target situation, with brackets and archwire, showing fields allowing the orthodontist to moving the teeth objects relative to each other in planning treatment for the patient.
Figure 81:
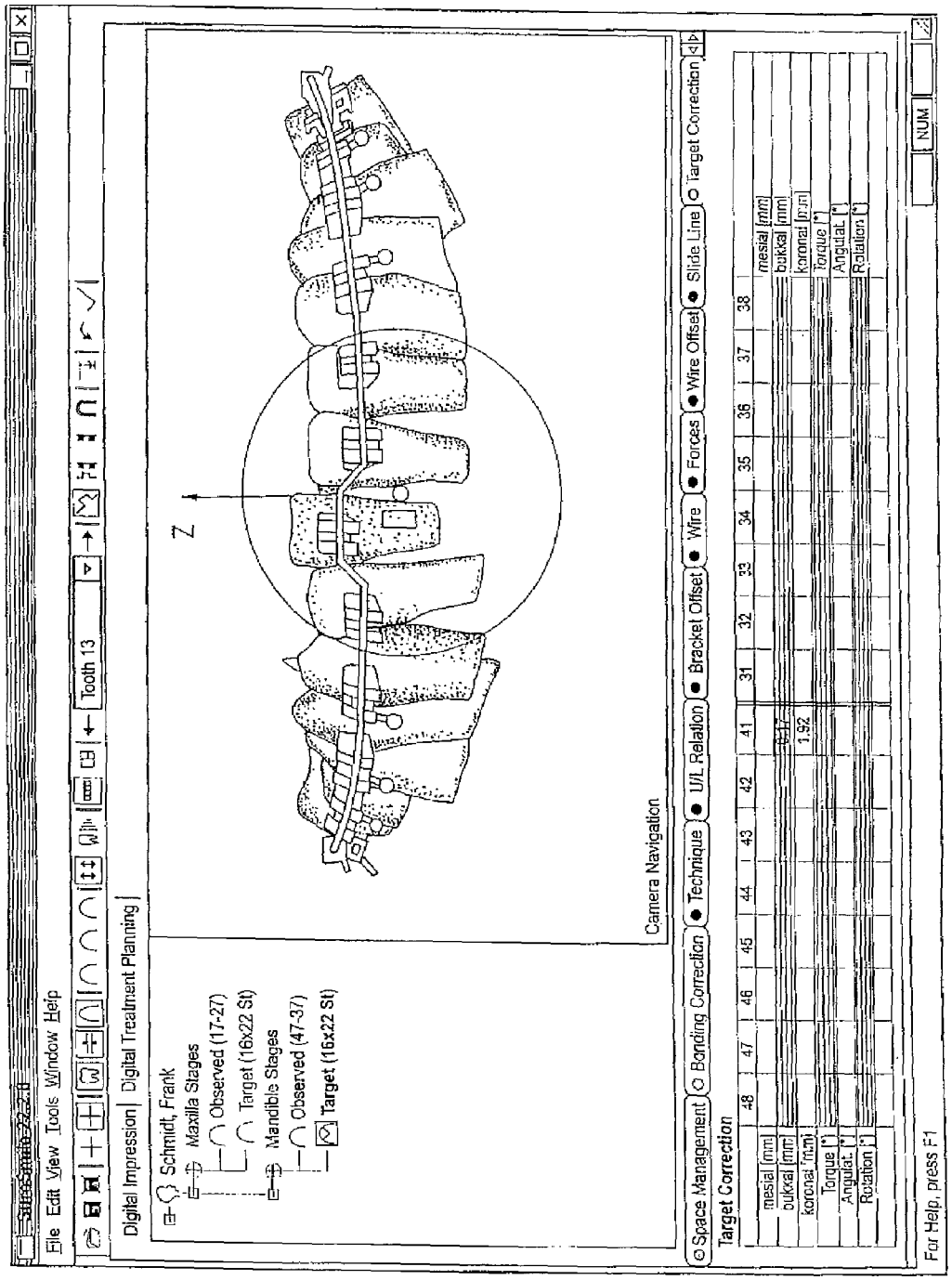
FIG. 81 is another screen show showing the target stage, with the brackets and archwire, showing a tooth moved in the buccal and coronal directions by an amount indicated by the orthodontist, and the correction incorporated into the archwire.

After the archform has been designed and the bracket placement optimized, the user can adjust the individual tooth position on a tooth by tooth basis in the target arch. There are three ways this can be performed. First, the user can use the tables in the Target Correction tab. See, for example, FIG. 78, in which the user has entered a value of −15 degrees for rotation of tooth number 41, and the tooth is rotated by that amount. The correction is realized by a bend in the archwire 396. The bracket position on the tooth does not change in this example. The target corrections tab 410 permits any values to be entered for mesial, buccal and coronal translation in three planes of space, and torque, angulation and rotation movements about three orthogonal axis. Thus, independent tooth position corrections are available in 6 degrees of freedom for every tooth, merely by entering values in the tables in the target corrections tab 410. Another example is shown in FIG. 81, in which a new target position is shown for tooth number 41.

Figure 85:
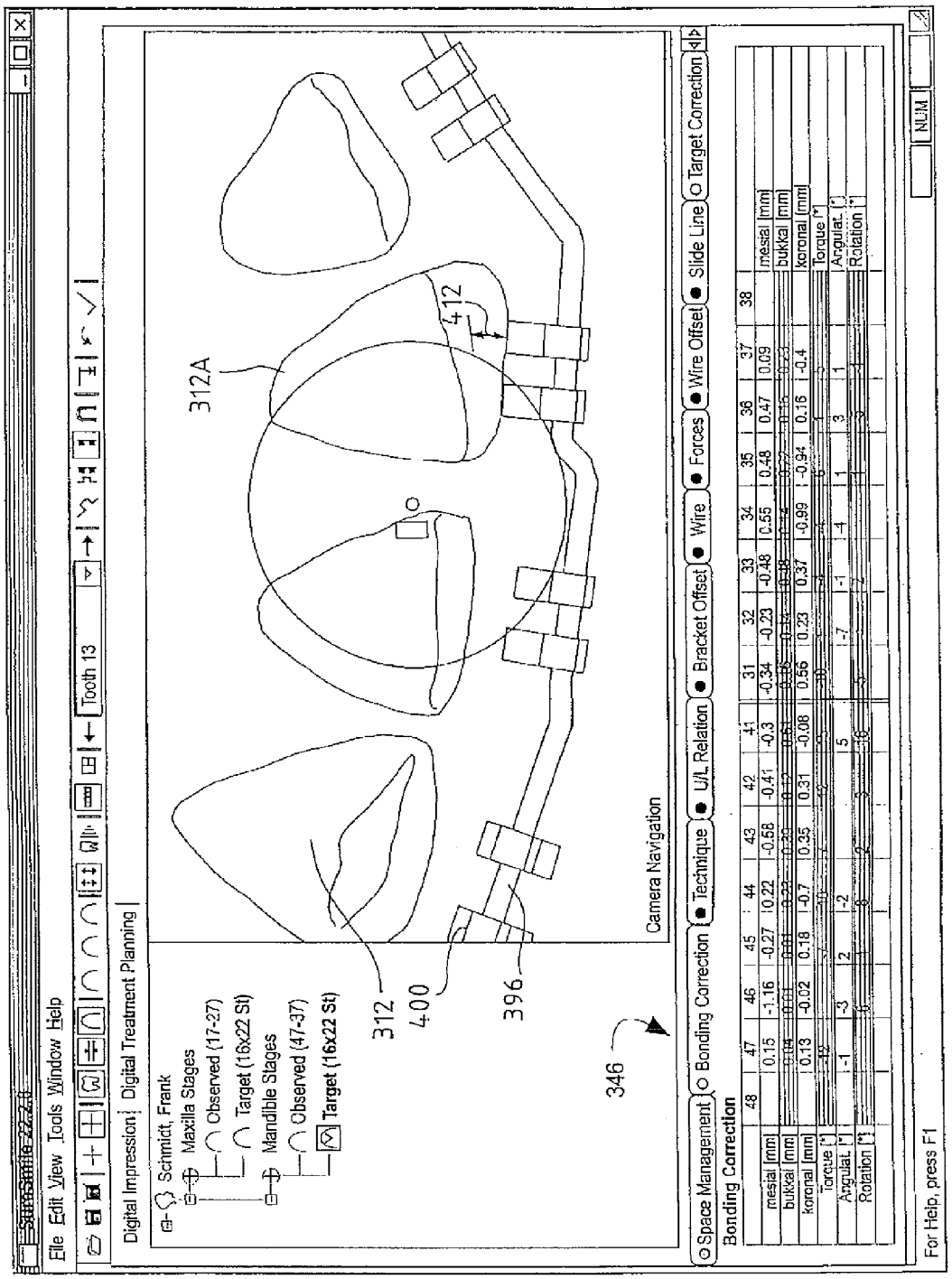
FIG. 85 is a screen shot showing the user modifying tooth position in a target stage on a tooth by tooth basis using a bonding correction feature.

Secondly, the user can move teeth using the Bonding Corrections tab 346 of FIG. 69. An example is shown in FIG. 85. The bonding corrections tab 346 allow the user to enter new values for tooth position for any tooth in the arch by merely entering values in the appropriate cell. The selected tooth 312A (tooth number 41) is moved as indicated (here, a new rotation value of −15 degrees is entered). The virtual bracket remains in the same location in space and the gap 412 between the pad of the bracket and the surface of the tooth is taken up by a bonding adhesive when the bracket is bonded to the tooth.

Examples of common tooth movements that can be simulated using the bonding corrections tab or the target corrections tab are moving the lower incisors buccally or lingually, inclining the incisors axially, and leveling the incisors.

Thirdly, the user can simulate tooth position corrections interactively using the navigational tools. The user displays a target stage as needed. A tooth object is selected as explained above. The user clicks on the zoom icon 341 of FIG. 67 to zoom in or out as needed. The user then clicks on the object navigation icon 353 to display the object navigation controls. The user then uses the navigation controls to move the tooth as desired. The movement of the tooth is recorded as new values in the bonding correction and target correction tables, in case the user wants to quantify the movement or use those tables for further modification of the tooth position. After the user has moved the tooth to the new position, they click one of two check mark icons 414, 416 (FIG. 77, 78) that are highlighted on the screen. The blue check mark 414 realized the new tooth position via a bonding correction. The red check mark 416 realizes the new tooth position via a wire correction.

Figure 79:
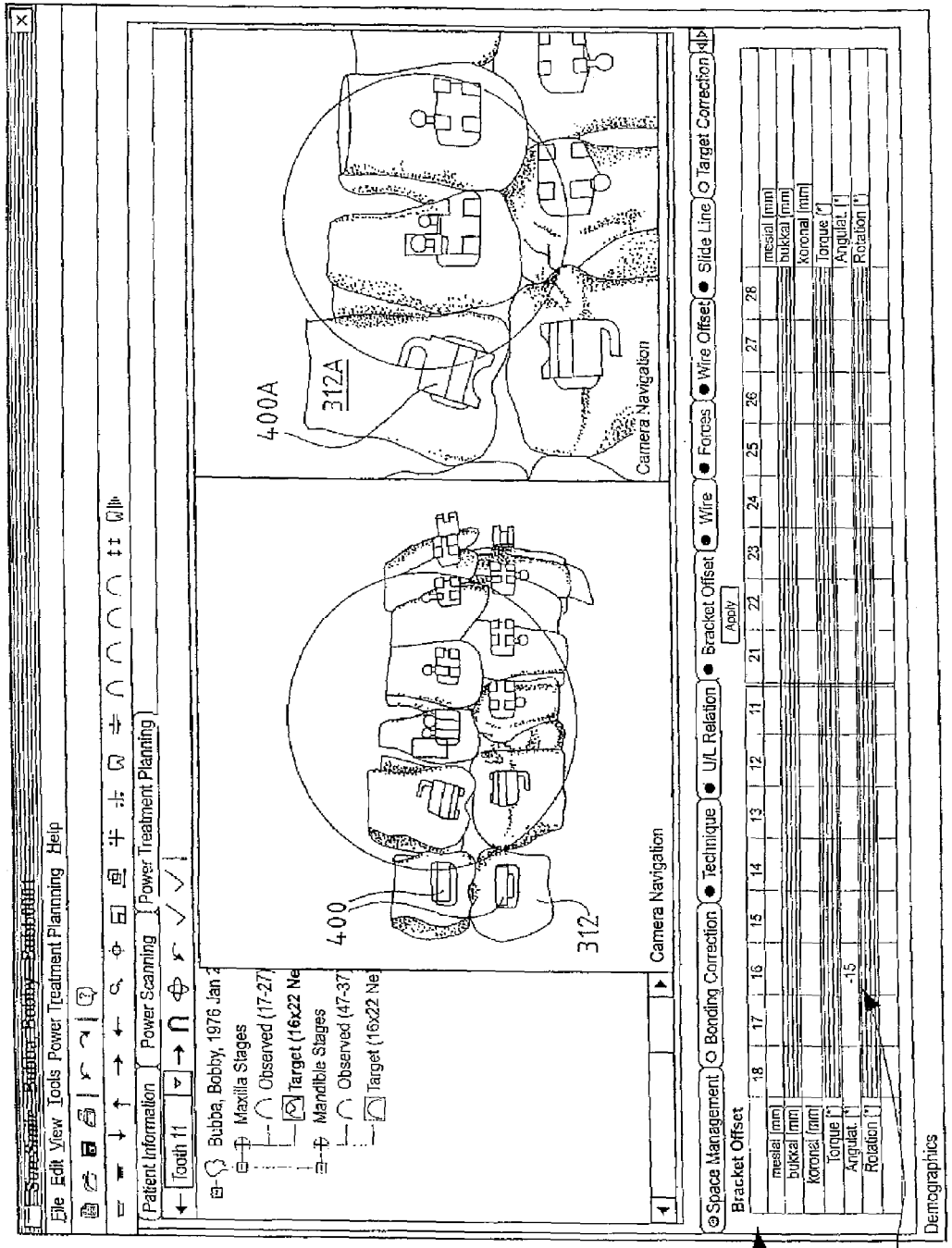
FIG. 79 is a screen show showing a bracket offset correction being entered to move tooth number 16 into an improved occlusal relationship with the opposing jaw.
Figure 80:
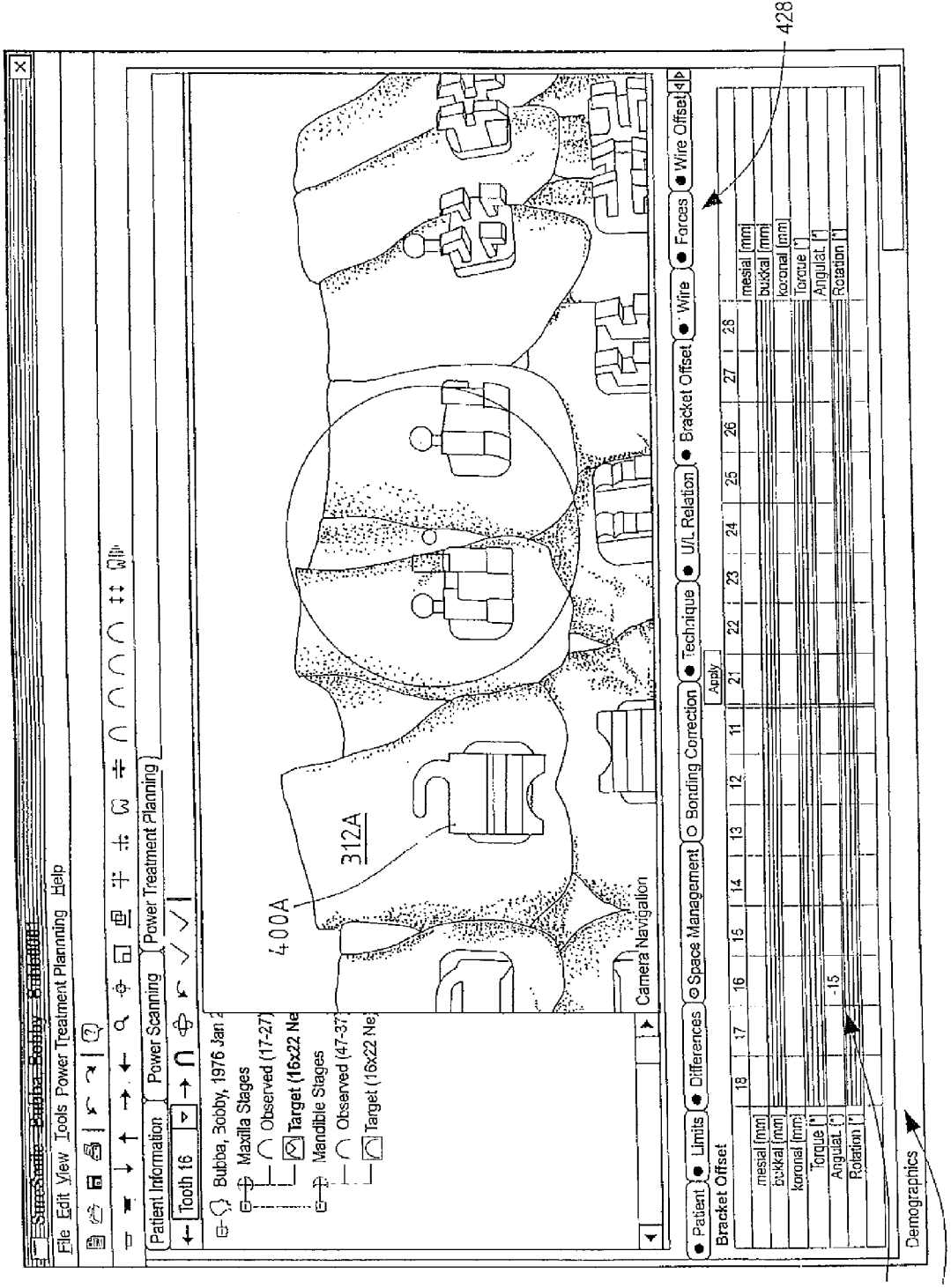
FIG. 80 is a screen shot showing the tooth movement that occurs with tooth number 16 when the bracket offset correction is made.

Another example of correction of individual tooth position is shown in FIGS. 79 and 80. In FIG. 80, the target situation is shown, both with the virtual tooth objects 312 and the virtual brackets 400. Note that with tooth 16 (312A), there is a gap between the rearmost cusp of the tooth and the opposing tooth. The orthodontist can correct this gap by building in a bracket offset, basically repositioning the location of the bracket 400 on the tooth 312A by entering an amount in the table 450 in the angulation cell for tooth number 16 (here −15 degrees). The result is shown in FIG. 80. The change in the angulation value causes tooth number 16 to rotate back into a more desirable occlusion with the opposing tooth.

Wire Tab

Figure 86:
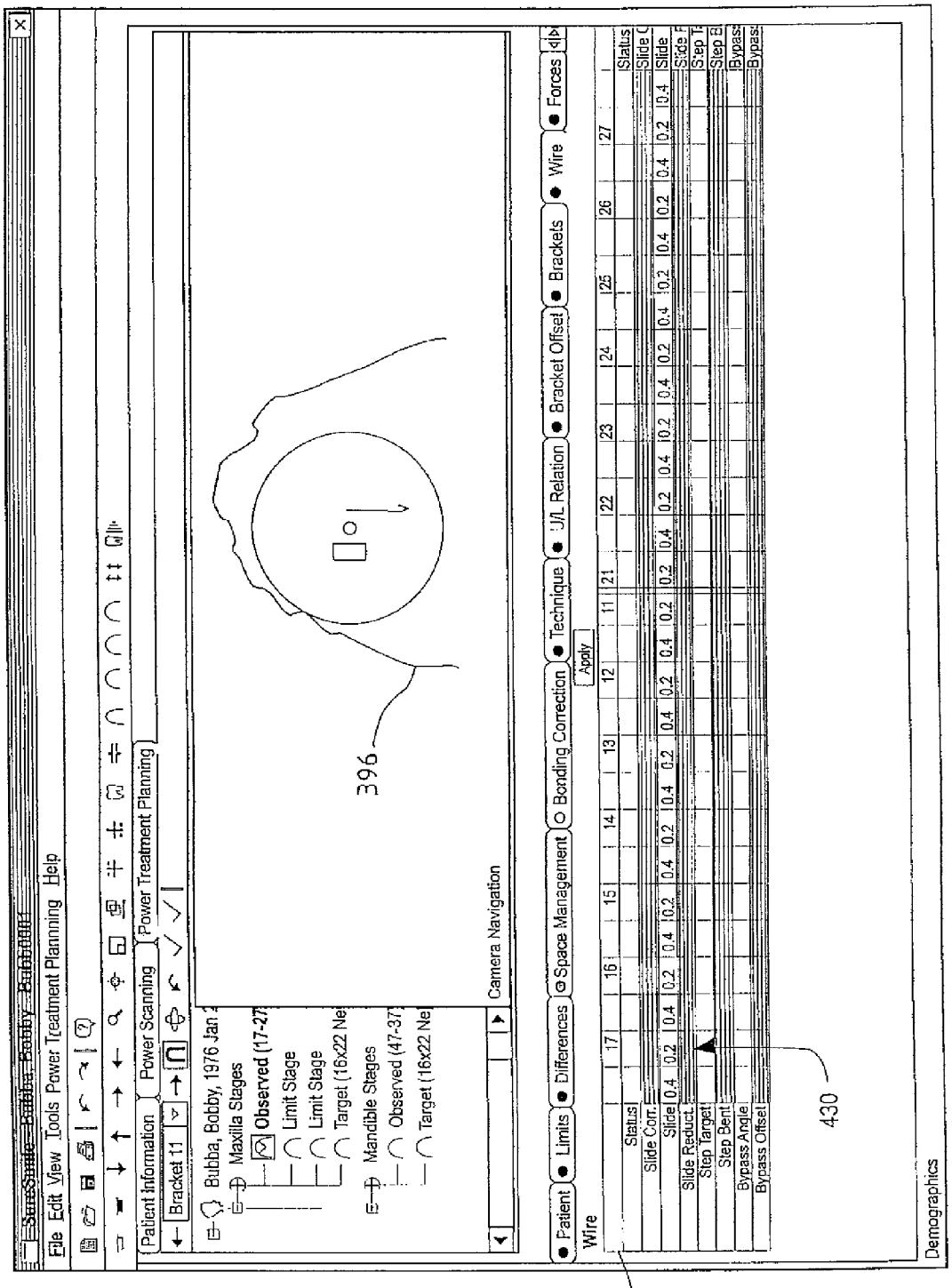
FIG. 86 is a screen shot showing a wire tab, which allows the user to make changes in the shape of an archwire without changing bracket position.

The wire tab 432 of FIG. 86 allows the user to make wire configuration changes, while not changing bracket position. Note that in FIG. 86, the virtual wire 396 is shown isolated from the teeth and brackets. The virtual wire can be scaled to actual size and printed out and provide a template for a manual bending of a wire if the orthodontist chooses not to obtain a wire from the precision appliance manufacturing center. The tab includes a section 430 where the user can view the distance in mm in which the wire will slide relative to the brackets, on a tooth by tooth basis, when the teeth are moved from the current situation to the target situation. Note that a collision is detected for tooth 22 in movement of the tooth from the current situation to the target situation. This can be resolved in several possible ways in accordance with the teachings of U.S. Pat. No. 6,250,918 to Sachdeva et al., Ser. No. 09/451,609 allowed Dec. 7, 2000, the contents of which are incorporated by reference herein.

Additional Wire Bending Corrections

Figure 87:
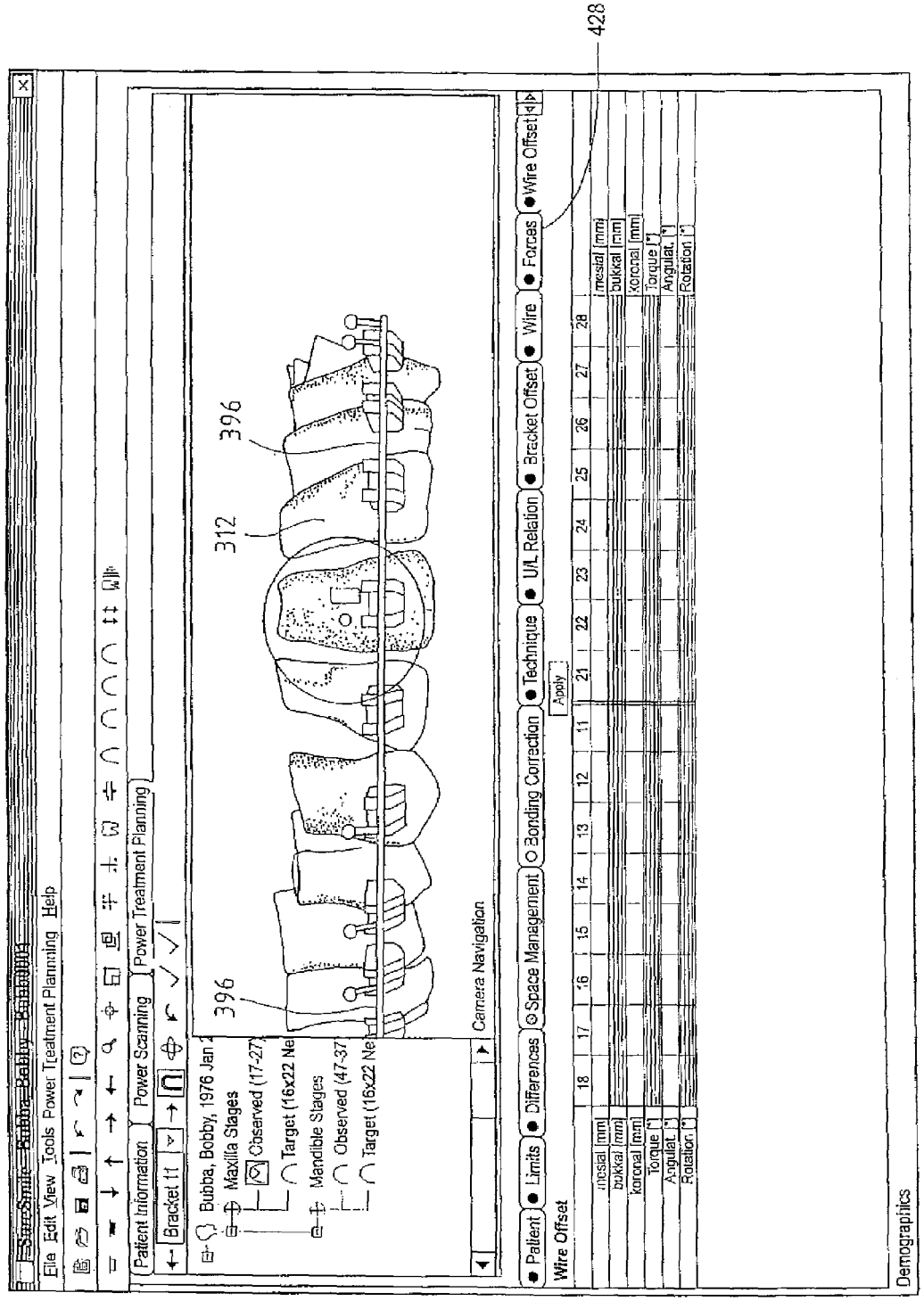
FIG. 87 is a screen shot showing a wire offset tab, which allows the user to change the bend size, location, etc., in the wire.

The wire offsets tab 426 (see FIG. 73 and FIG. 87) allows the user to simulate bending a wire 396 to the corrected tooth position while simultaneously retaining the original bracket position. Note that in FIG. 87 the wire 396 is flat with no corrections indicated. The user highlights one of the teeth in the virtual model and enters new values for tooth position. The change is reflected in a new shape for the wire 396. The tab also allows the user to build in over/under compensation into the archwire. These settings do not affect the bracket position. The characteristics of the wire bends, such as the radius of curvature, can be controlled by accessing a slidings tab (not shown). Another tab, forces 428, displays approximations of the forces the wire applies to each tooth to displace it from its initial position to the target position.

Treatment Stages

Since the difference between the current situation and the target situation is quantifiable in terms of millimeters of movement or degrees of rotation about three axes, the treatment for the patient can be broken up into segments or stages with each stage defined arbitrarily. For example, the orthodontist can specify a first treatment stage as the movement of the teeth from the initial position half-way to the final position. The software includes a screen that permits the user to view the position of the teeth when moved to the half-way position. Basically, the simulation simply multiplies the differences in tooth position between initial and target stages by 0.5 and the resulting tooth positions are displayed on the workstation. Additionally, the user can specify further intermediate positions, such as one fourth or three fourths. With this feature, the orthodontist can monitor treatment and compare the progress of the treatment with the limits or stages that have been set. When the patient comes in for a visit during treatment, the patient's dentition is scanned. The three-dimensional model of the now current situation is compared with the defined stages and perhaps with the target situation. Difference between actual progress and the planned treatment can be quantified. Changes to the archwire can be designed using the treatment planning software to move the teeth in the desired direction to account for unexpected biological influences that may be observed.

The above description of treatment planning has been predicated on the use of a three-dimensional model of the dentition from the scanner, obtained as described above. However, it is possible to perform digital treatment planning by importing into the software three-dimensional software from other sources. Is it known today that three-dimensional models can be exchanged with different software programs in different file formats, similar to the translation programs that convert text documents from one type of file (e.g., Microsoft Word to WordPerfect). Most three-dimensional applications have several import filters for different 3D formats.

However, there are generally two different ways to describe three-dimensional objects: by surface representations and by solid representations. A 3D file that holds 3D data in a surface description consists typically of triangles that form the surface of the object. The STL format is one of the oldest and therefore most common formats that uses triangles. It is used to feed information to stereolithography machines. A more detailed description of STL can be found at http://www.mmsonline.com/artciles.019704.html, the contents of which are incorporated by reference herein.

Treatment Monitoring

Interactive, computer-based treatment monitoring is a significant advantage provided the treatment planning and appliance design aspects of the system described herein. Typically, when the patient comes into to the office during treatment, they will be scanned and a new digital model of the dentition is acquired. From this new model, differences can be monitored between the current situation and the original malocclusion, and differences between the current situation and the target situation or pre-defined limits or treatment stages as defined earlier. These differences can be quantified with precision. For example, a point on the tooth in the current model is selected, and the model of the tooth at the original malocclusion is overlaid on the screen. The superposition of the two teeth allows the user to view the change in position that has occurred. The measurement marker features described earlier allow the user to quantify precisely the amount of movement.

Any deviations between the therapeutic result that is observed and the expected result can be captured precisely and at an early stage in treatment using the scanning and treatment planning features described herein, and corrected for. For example, the orthodontist may need to place additional bends in the archwire. Such additional bends can be performed by simulating the wire shape on the screen, displaying the wire only on the screen, and printing out the screen and using it as a template for bending the wire. The current situation could also be forwarded to the precision appliance center for manufacture of a new appliance. Of course, these monitoring and treatment corrections are applicable to any type of appliance selected for the patient.

Part 5. Appliance Manufacturing

The appliance that is manufactured in accordance with the treatment planned for the patient can vary within the scope of the invention and will depend on the application, including the type of appliance desired by the orthodontist and the patient. Obviously, the treatment planning and simulation features described above can be used in wide variety of treatment regimes, including flat wires and brackets, finishing wires, retainers, Herbst devices, expansion devices, and removable, transparent aligning devices such as those furnished by Align Technologies. For example, the movement of the teeth from the current or observed stage to the target or treatment stage can be broken into a series of movement steps. For each step in the process, the position of the teeth in that stage is known by virtue of the manipulation of the individual tooth models in the treatment planning software. These tooth positions can be used to manufacture the aligning devices.

In a representative embodiment, the results of the treatment planning software are used to generate a customized orthodontic archwire and a bracket placement tray for precise placement of off-the-shelf brackets onto the patient's teeth. When the treatment planning features have been executed to the satisfaction of the orthodontist and the proposed target situation finalized, the treatment planning software will store the following information (in addition to the patient records):
1) the virtual model of the current stage or malocclusion;
2) the placement location of the brackets on the malocclusion, including the type and dimensions of the brackets;
3) the orthodontist's selection of a type of archwire (including material and size); and
4) the target situation, including the location of the teeth and brackets in three dimensions at the target situation.

Note that it is not absolutely necessary for the appliance manufacturing step to calculate or even know the shape of the archwire. Archwire geometry is dictated by bracket positions in three-dimensional space when the teeth are in the target situation. This bracket position information is included in the target situation, no. 4) above.

With reference again to FIG. 1, the above information from the treatment planning software is sent over a suitable communications medium 24 in digital form to the precision appliance service center 26. The service center manufactures a customized archwire and a bracket placement tray for placement of the brackets at the intended location on the teeth in the malocclusion.

Basically, the position of the bracket slots, and the shape of the brackets, when the teeth are in a target situation, is information that is ultimately developed and stored by the treatment planning software. This position of the bracket slots and the shape of the slot (e.g., the length) is of course known in three dimensions. From the slot shape, it is possible to derive a three-dimensional set of line segments that represent the shape of an archwire passing through the bracket slots in the target situation, and calculating the optimal shape of bends that connect the bracket slots together. The positions of the straight sections and the bends are fed as an input file to a wire bending robot. The wire bending robot need only know the wire size, the shape and size of the slots, and the positions of the slots in the target situation. From this information, robot commands are generated to bend the archwire into the desired shape.

The bracket placement tray is separately manufactured using stereolithography or other similar technique. The treatment planning software generates items 1) and 2) above, and superimposes the brackets on the teeth to generate a three-dimensional model comprising the three-dimensional tooth objects plus the virtual brackets at their intended locations in the observed stage or malocclusion. This three-dimensional model is supplied to a stereolithography (SLA) instrument. The SLA instrument manufactures a plastic model of the teeth with the brackets superimposed on the teeth. A thermoplastic foil is placed above the SLA model and the model and foil are placed within a pressure chamber. The chamber is pressurized so that the foil envelops the dentition and the brackets. After cooling, the foil is removed from the model. The foil, now in the shape of a transfer tray, has small indentations where the brackets are located. Real brackets are placed in these indentations. The orthodontist uses indirect bonding techniques to bond the brackets to the teeth. The transfer tray positions the brackets on the teeth at the desired location. After the bonding is complete, the orthodontist removes the transfer tray, resulting in the brackets bonded to the teeth at the desired location. A further scan of the dentition can be made at this step to verify the position of the brackets. Any substantial deviation in the bracket position can be accounted for by modification of the archwire, again using the treatment planning features described above.

There will always be some small gap between the bracket base (the part bonded to the tooth) and the tooth, as an off-the-shelf bracket will never precisely match the individual tooth of any given patient. One option is to fill the gap using a surplus of bonding adhesive during bonding. Another option is to equip the base of the bracket with a customized pad made from an adhesive.

Customized bracket pads can be manufactured using a variety of techniques. One possibility is to bond a blob of adhesive to a bracket base, and mill the blob using a milling machine to match the tooth surface. Since the tooth surface is known precisely from the scanning, and the position of the bracket base relative to the surface is also known precisely, a very accurate bracket pad can be manufactured in this fashion. Another technique is to stamp out a bracket pad using stamping machine either in the desired shape or as a blank and milling the stamped pad to the desired shape. A third possibility is creating a negative of the customized pad, forming the pad in a mold, bonding the pad to the bracket and the orthodontist trimming the pad as necessary when the pad is bonded to the tooth.

Once the brackets have been bonded to the teeth, a scan of the bracket placement is made. The scan is compared to the digital template of the expected bracket position. If the bracket is placed incorrectly, the bracket can be re-bonded to the tooth. Alternatively, corrections to the wire may be made if necessary to account for displacement of the brackets from their expected position. Basically, this is done by simulating the position of the teeth with the actual bracket placement at the target situation and correcting the shape of the archwire as necessary, or obtaining a new archwire based on the actual placement of the brackets.

It is also possible to manufacture a transfer tray without the intermediate step of a positive SLA model representing the dentition and the brackets. These trays may be either similar to the plastic sheets and just be fabricated using rapid prototyping methods (SLA, laser sintering, milling, 3-D printing, etc.), or they have more sophisticated geometry including features to hold the brackets and features to provide proper positioning at the dentition. Additionally, bracket placement jigs can be milled from the three-dimensional models of the dentition and the brackets using techniques described in, for example, in the Andreiko patent cited earlier.

As another possibility, the customized bracket bonding pads based on the virtual tooth/bracket geometry can be fabricated. Such bonding pads may include additional material which conforms to the surface of the tooth to act as a placement jig for the tooth to allow the bracket bonding pad to be precisely located on the tooth. Then the bracket is bonded to the bracket bonding pad. The additional material is then removed.

With the above description in mind, it will be appreciated that the treatment planning functions can be performed with the importation of any 3D object from any source. While the preferred embodiment uses the scanned three-dimensional model from the hand-held scanner, this is not necessary or required. The software preferably has import filter for common types of files of 3D objects including STL, DXF, VRML etc.

Additionally, another key aspect of the treatment planning software is that it permits the placing of brackets onto tooth models in an arbitrary manner and virtually "bonding" those brackets to the teeth so that they move together. While the present embodiment has described a landmarking feature by which the user places landmarks on the teeth and the brackets are placed on the landmarks, this may be performed in other ways, including automatically with no user involvement based on parameters such as crown height, bracket type, tooth size, etc.

As indicated above, the software also provides for aligning of the brackets along virtual wire of any shape. Thus, as the user changes the shape of the archwire, the brackets follow this shape, thereby indicating tooth position correction in the target situation. This feature allows the user to drive the treatment planning based on wire shape. Conversely, the wire shape can be dictated by the placement of the brackets on the teeth. Thus, the treatment plan can be one driven by bracket placement. Obviously, wide variety is possible in the shape and design of the wire.

Furthermore, by providing for the simulation of teeth in both maxilla and mandible together, the software provides for a wide variety in defining the maxillary/mandible relationship, the occlusal plane and the mid-line of the teeth.

Another significant aspect of the software is that it provides for virtually unlimited 3D measuring features using the marking icon and measurement feature described earlier. This feature offers a powerful diagnostic tool, as well as a tool for monitoring the progress of treatment and quantifying results.

Because the teeth are represented as complete three-dimensional virtual objects, it is possible to detect the collision between teeth or between teeth and brackets in the simulation of movement of teeth from the current to the target situation. The point cloud representing tooth objects defines a surface, when surfaces come in contact during the tooth movement a collision is simulated. This collision is detected by suitable collision detection algorithms. When the collisions are detected, the user can be notified of the collision and resolve the conflict between teeth, for example by selecting one tooth as a primary tooth and moving that tooth first in an initial stage of treatment, and then moving the other tooth in a secondary stage of treatment. These features are described in further detail in U.S. patent application Ser. No. 09/451,609 filed Nov. 30, 1999, now allowed, the contents of which are incorporated by reference herein.

Another advantage of the instant treatment planning software is that it offer the user real time simulation with immediate feedback on the effect of user specified tooth movement. When a value is entered into a field in the display or the user uses the navigation tools, results are displayed immediately. Further the system offers arbitrary access to every object, including election, navigation and export.

A. Robot Design

Figure 88:
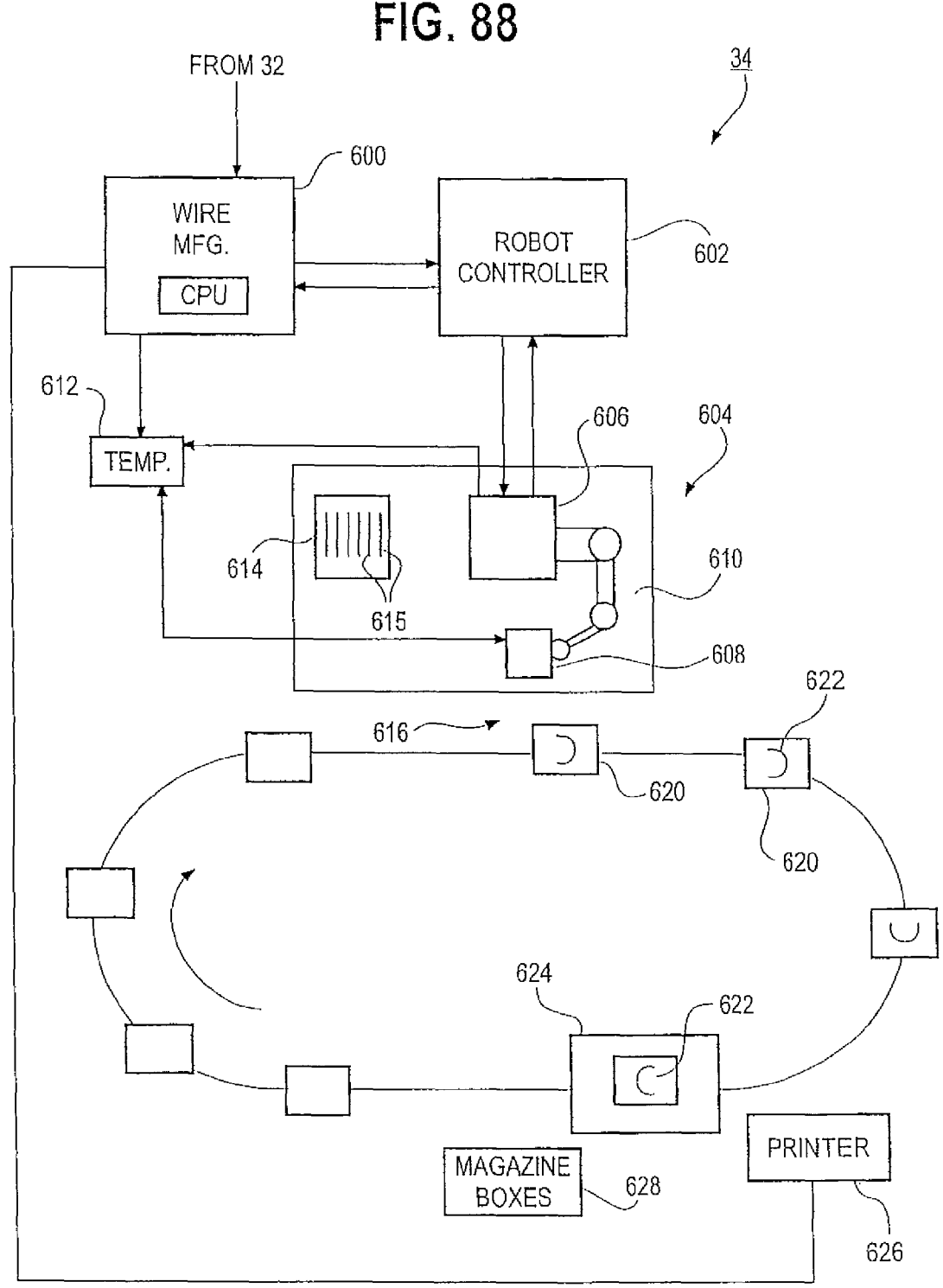
FIG. 88 is a schematic representation of an archwire manufacturing system shown in FIG. 1.
Figure 88A:
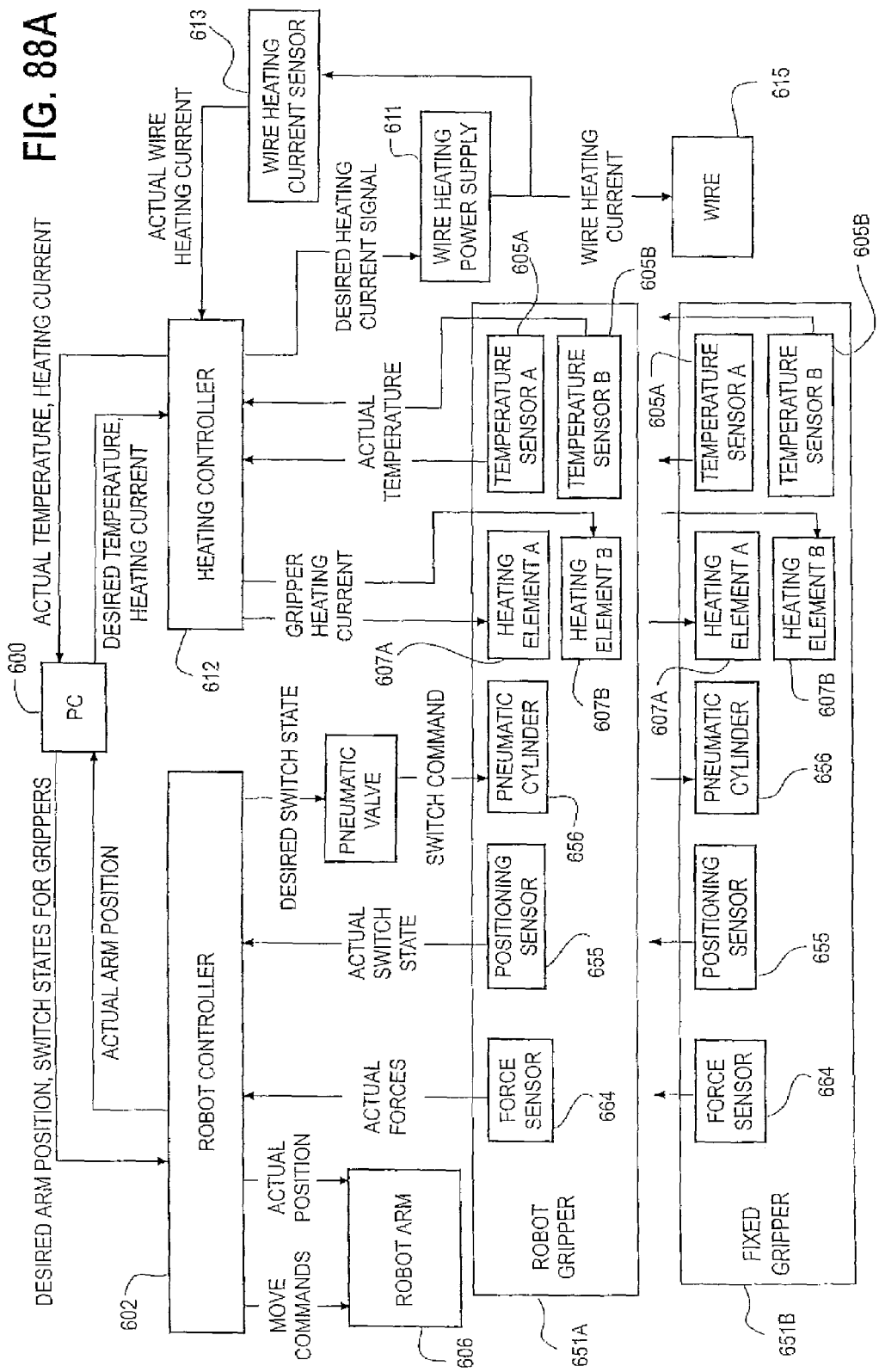
FIG. 88A is a block diagram of the system of FIG. 88.

FIG. 88 is a schematic representation of a presently preferred archwire manufacturing system 34 shown in FIG. 1. The key aspects of the system 34 are shown in block diagram form in FIG. 88A. The system 34 includes a control system for controlling the operation of a wire bending robot 604. The control system in the illustrated embodiment comprises a general purpose computer 600 running a bending program and a robot controller 602. The computer 600 receives an input file from the precision appliance service center computer that contains information as to the location of bracket slots in three dimensions, when the teeth are in a target situation. The computer 600 supplies the robot controller 602 with wire position information corresponding to points along the wire where bends need to be made. This information is translated by the controller 602 into motion commands for the wire bending robot 604.

It will be appreciated that the system works in an analogous fashion when bending other types of medical devices. The computer 600 receives an input file from some source that provides information as to how the medical device in question needs to be bent. The computer 600 supplies the robot controller 602 with position information corresponding to points along the length of the medical device where bends need to be made, and the robot responsively bends a medical device in accordance with the input file.

The wire bending robot 604 consists of a moveable arm 606 having a gripping tool at the distal end thereof. The moveable arm has a proximal end mounted to a table or base 610. The robot also includes a first gripping tool 608. In the illustrated embodiment, the first gripping tool 608 is fixed with respect to the base 610 and mounted to the table. Hence, the first gripper tool 608 will be referred to herein occasionally as the "fixed gripper." It would be possible to place the first gripper tool 608 at the end of second robot arm, in which case the first gripper tool would not necessarily be fixed, but rather would be free to move in space relative to the source of archwires, or the other moveable arm. In such as system, a coordinate system would be defined having an origin at which the first tool is positioned at a known position. The bending commands for the robot would be with respect to this known point.

A wire or other workpiece to be bent is held by the first gripper 608 and the gripping tool at the end of the moveable arm 606, and the arm is moved to a new position in space to thereby bend the workpiece. The details of the construction of the arm 606 and fixed gripper 608 are described in further detail below.

Figure 93:
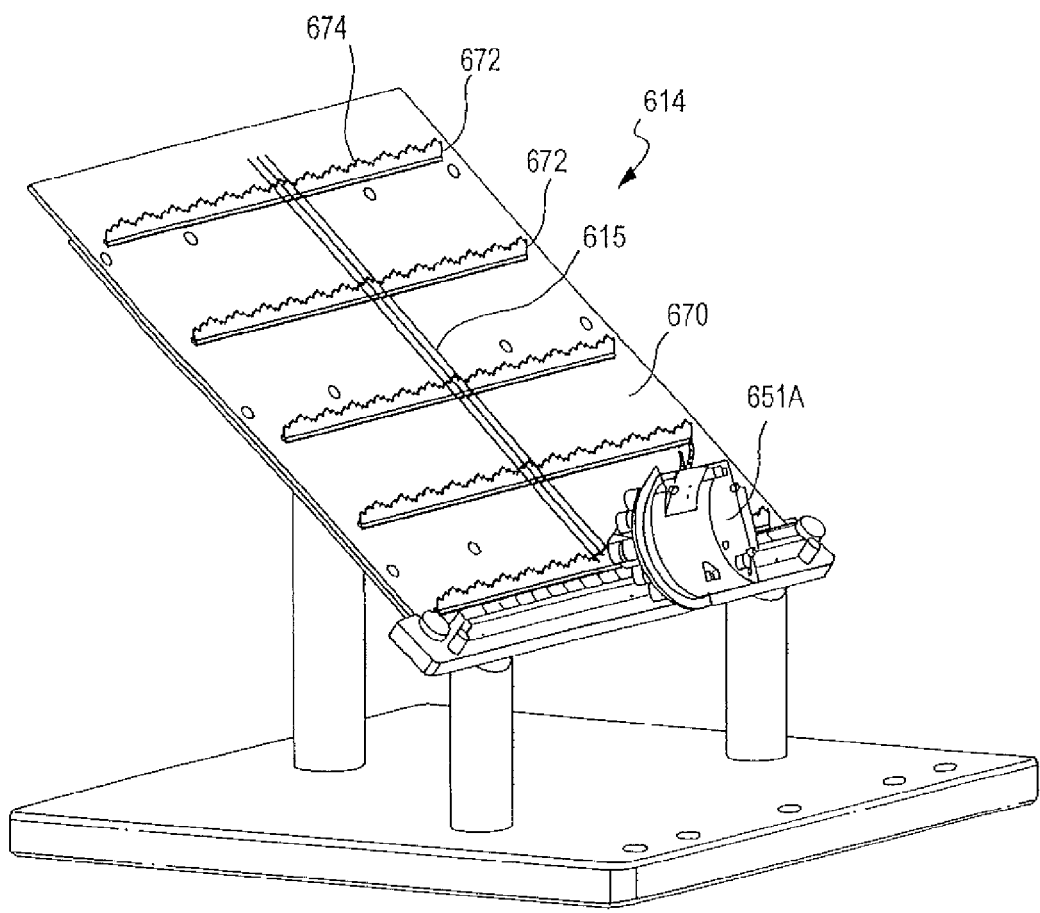
FIG. 93 is a perspective view of a magazine of FIG. 88 that holds a plurality of straight archwires.

The system 34 of FIG. 88 is set up to manufacture customized archwires one after the other continuously, as would be case in a precision appliance service center serving a plurality of clinics. As such, the robot 604 includes a source of archwire material. The source could be a spool of wire in which case a cutting tool is needed to cut lengths of wire for individual archwires. Alternatively, as shown in FIGS. 88 and 93 the source consists of a magazine 614 containing a plurality of straight archwires 615 ready to be grasped by the gripping tool at the end of the moveable arm 606. In an embodiment in which the first gripping tool is mounted to the end of a moveable arm, the first gripping tool could retrieve the next workpiece while the moveable arm places the finished workpiece at an exit location.

After an archwire is bent in accordance with an input file supplied to the computer 600, the moveable gripping tool at the end of the robot arm 606 places the wire (or workpiece being bent) at an exit location indicated at 616. A conveyor system 618 including a plurality of trays 620 is provided for carrying the finished archwires wires 622 from the exit location 616 to a labeling and packaging station 624. The labeling and packaging station 624 includes a printer 626 that prints a label for the archwire and a magazine 628 containing a supply of packages such as boxes or bags for the wires. A worker at the station 624 takes a label from the printer and applies it to the archwire 622 or to the package for the wire. The conveyor system 618 is also based on a commercially available, off-the-shelf conveyor system, such as of the type available from the Montech division of Montrac.

The wire manufacturing system 34 includes a heating controller 612 responsive to commands and settings from the wire manufacturing computer 600. The controller 612 controls the supply of current to heating elements 607A and 607B in the gripping fingers in the gripping tools in the robot, to thereby heat the gripping fingers above ambient temperature. Temperature sensors 605A and 605B detect the temperature of the gripper fingers and are used for feedback control of the heating of the gripper fingers. A direct or indirect system for measuring the temperature of the workpiece may also be provided, such as infrared heat detector. The heating controller 612 also controls a wire heating power supply 611 that supplies a current to the gripping tools when they are bending a wire. The power supply 611 is used when the robot is bending shape memory materials or Titanium Molybdenum Alloys (TMA) materials, or possibly other materials. The current produces a resistive heating in the wire. The current is controlled via a wire heating current sensor 613 so as to produce a wire temperature at which a bend formed in the wire is set into the material. The heating of the gripping fingers avoids excessive heat loss when resistive heating of the wire is performed.

Figure 89:
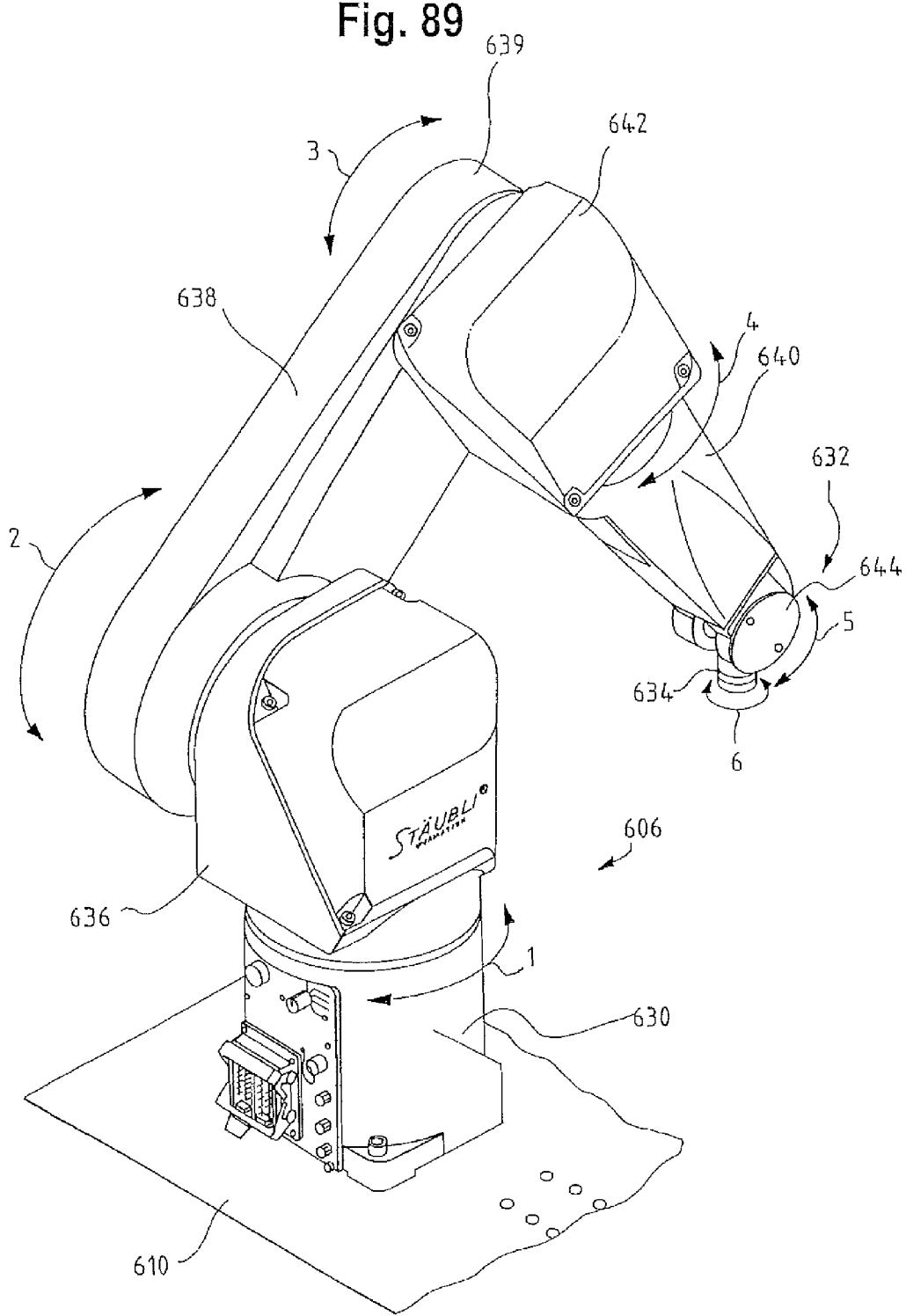
FIG. 89 is a perspective view of a moveable robot arm used in the manufacturing system in FIG. 88.

FIG. 89 is a perspective view of a moveable robot arm 606 used in the manufacturing system in FIG. 88. In FIG. 89, the gripping tool at the distal end 634 of the arm is omitted. In a preferred embodiment, the moveable arm is based on an off-the-shelf six-axis robot arm and fixed tool. A suitable arm, fixed tool, and robot controller for the robot 604 is available from Stäubli Unimation of Germany. The Stäubli robot arm and fixed tool is customized with gripping fingers, heating controller and ancillary systems, software, current heating subsystem, force sensors, and other features as described herein for bending archwires or other suitable medical devices.

Figure 92:
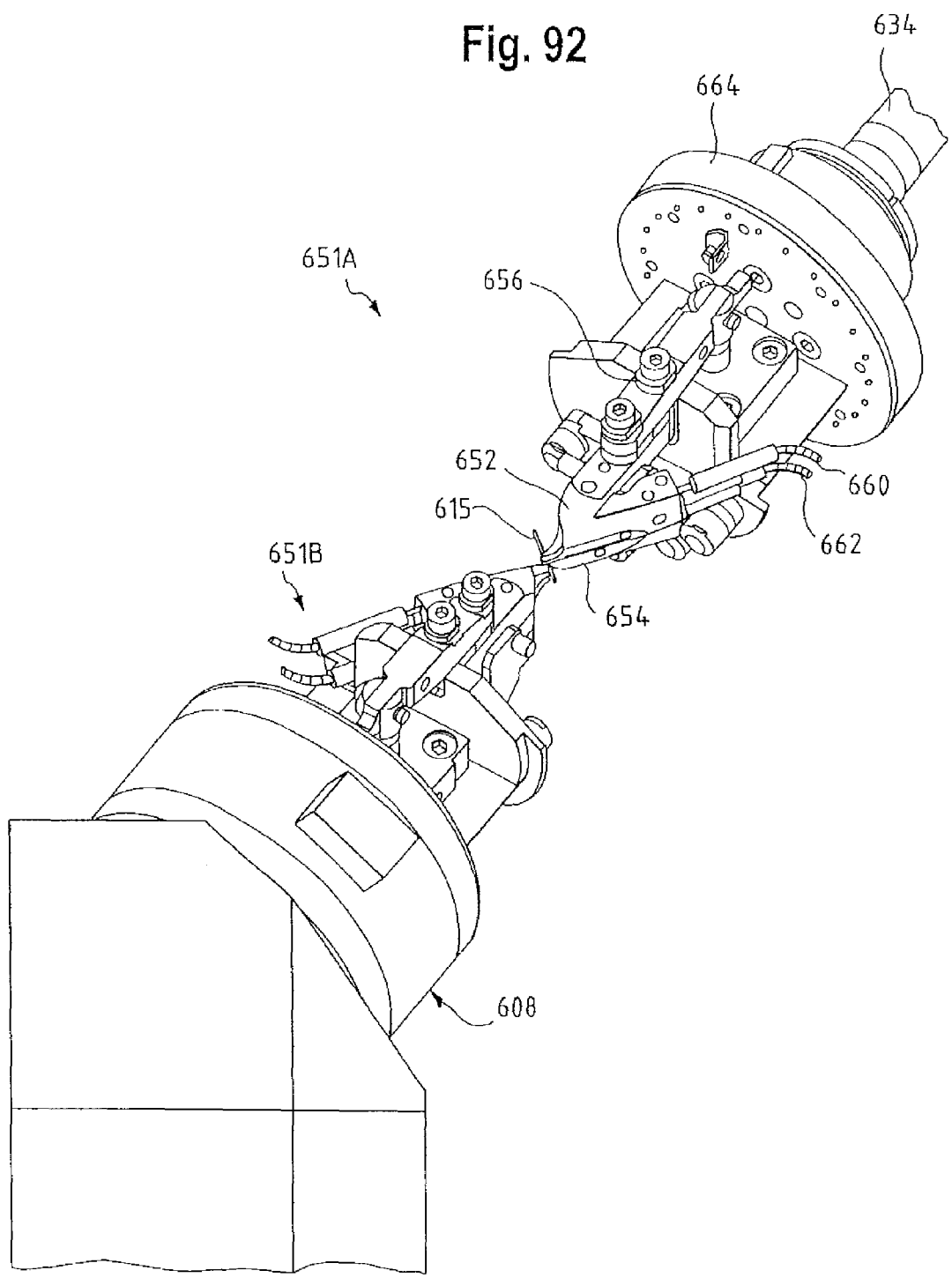
FIG. 92 is a perspective view of the fixed gripping tool of FIG. 88 and the gripping tool of FIG. 91, in which an orthodontic archwire is gripped by the tools.

The arm 606 consists of a proximal end or base 630 which mounts to the table 610 of FIG. 88 and a free distal end 632 consisting of a tool flange 634, where the second gripping tool 651A of FIG. 92 is mounted, as described below. The arm 606 is capable of motion along six different rotational axes, with the directions indicated by the arrows numbered 1-6 in FIG. 89. Thus, the base is fixed with respect to the table 610 and the head portion 636 rotates relative to the base 630. A joint in head portion 636 rotates arm segment 638 about an axis indicated by arrow 2. Similarly, the arm segment 640 is rotated about an axis indicated by arrow 3 by a joint 639. A joint 642 rotates an arm segment 640 about the axis indicated by the arrow 4. A joint 644 attached to the end of arm segment 640 rotates the tool flange 634 about the axis indicated by arrow 5. A sixth joint (not shown) rotates the tool flange 634 about an axis indicated by arrow 6.

Figure 90:
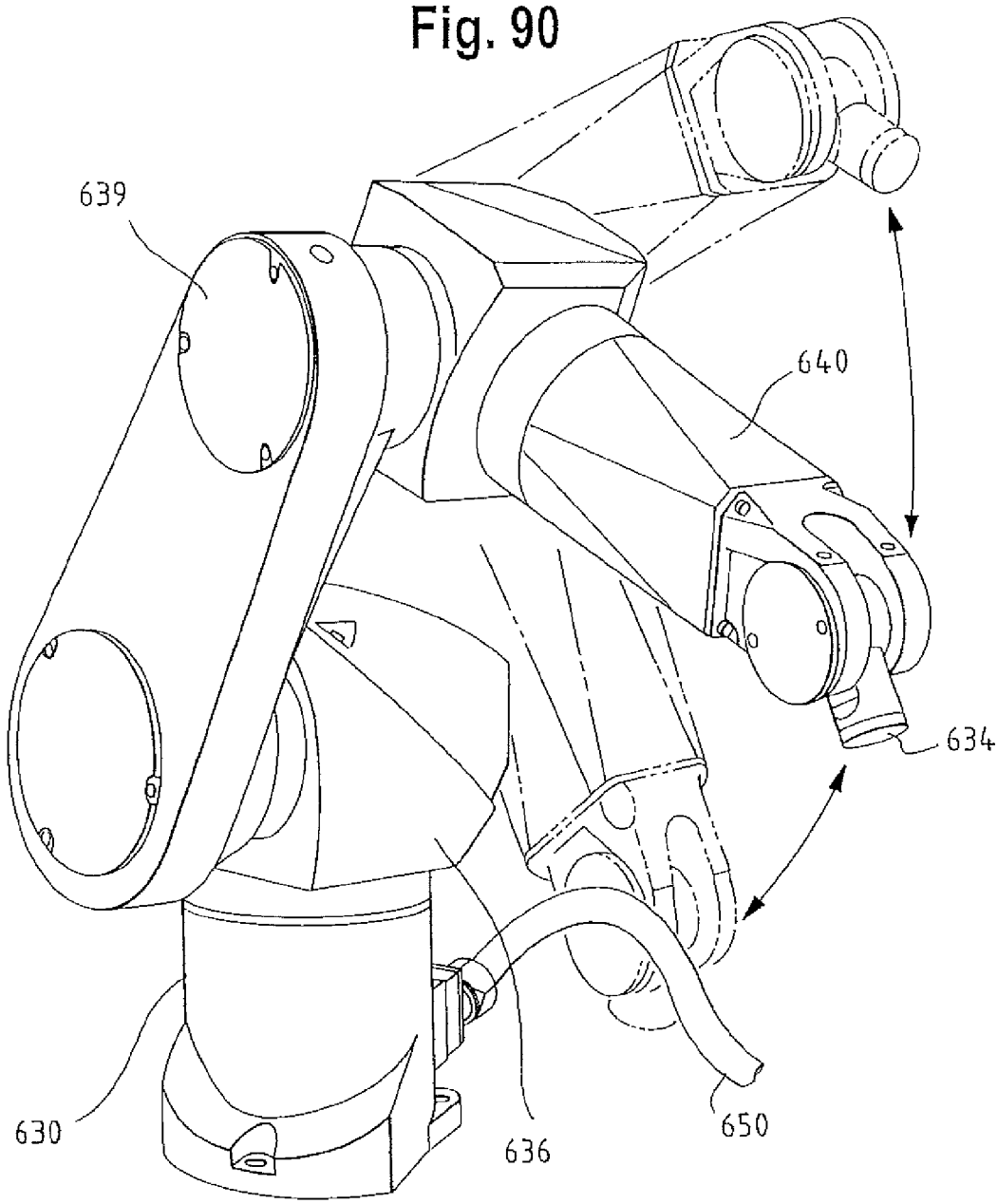
FIG. 90 is perspective view of the robot arm of FIG. 89, showing the movement of one of the arm joints and the corresponding motion of the arm.

FIG. 90 is perspective view of the robot arm of FIG. 89, showing the movement of the arm joint 639 and the corresponding motion of the arm segment 640 and tool flange 634. The motion commands for the robot are supplied from the robot controller 602 along a cable 650 which plugs into the base 630 of the robot.

Figure 91:
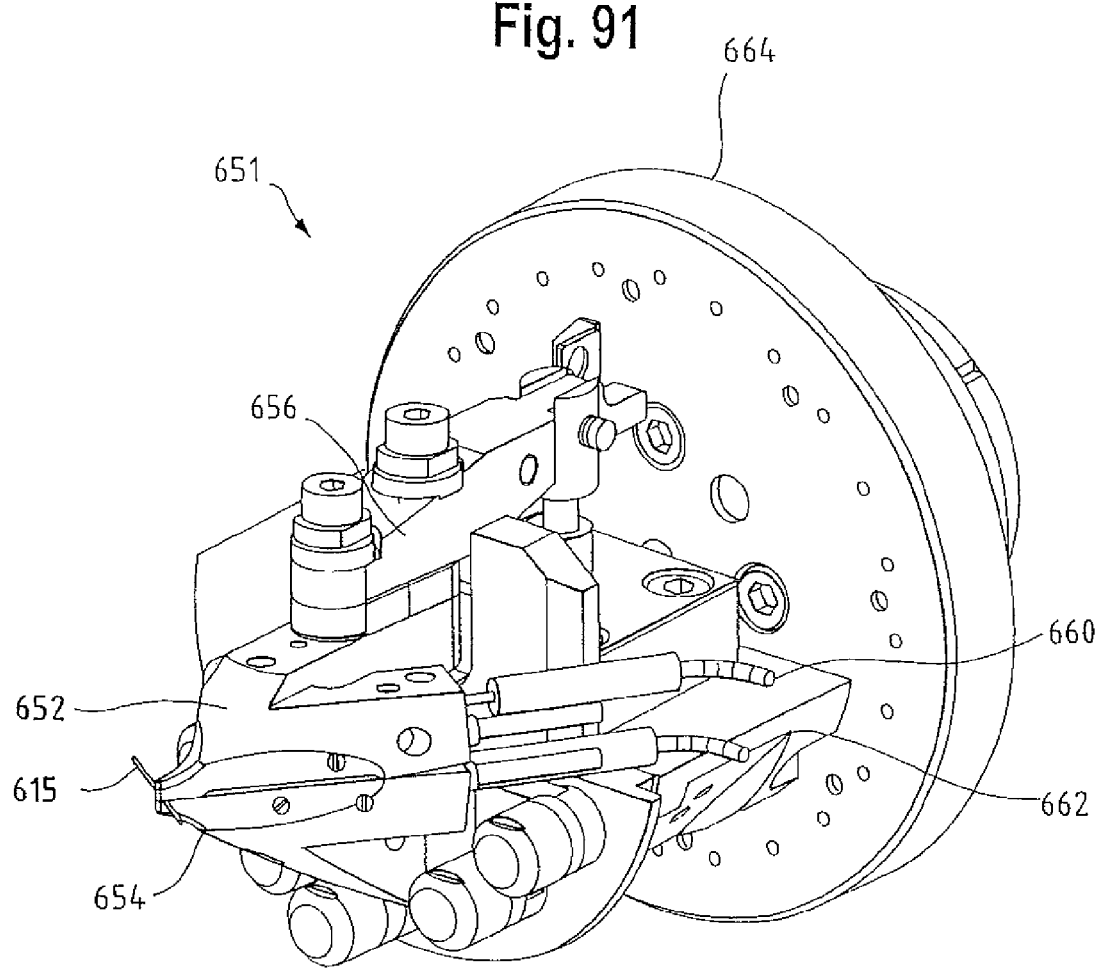
FIG. 91 is a detailed perspective view of the gripping tool that is mounted to the distal end of the moveable robot arm of FIG. 89 and FIG. 90.

FIG. 91 is a detailed perspective view of a preferred gripping tool 651A that is mounted to the tool flange 634 at the distal end of the robot arm 606 of FIG. 89 and FIG. 90. The construction shown in FIG. 91 also applies to the fixed gripper 608 of FIG. 88 and FIG. 92. The gripping tool 651A consists of a pair of opposed gripping fingers 652 and 654 which open and close to grip and release the workpiece, in this case an orthodontic archwire 615. A pneumatic cylinder actuates gripping finger 652 by moving it about an axis relative to finger 654, to thereby permit the fingers 652 and 654 to grip and release a workpiece such as a wire. A positioning sensor 655 (FIG. 88A) detects the position of the fingers.

In a representative embodiment, the archwires are made from a shape memory alloy such as Nitinol, a material based on Nickel and Titanium plus Copper or other alloy. These materials can be heated to retain the shape of a bend formed in the wire. Accordingly, the wire heating power supply 611 of FIG. 88A supplies a current to the gripping fingers of the fixed gripping tool and the moveable gripping tool. The flow of current along the wire creates a resistive heating of the wire sufficient for the material to take a set according to the shape of the wire as it is bent. To avoid dissipation of heat from the wire into the gripping fingers, the gripping fingers 652 and 654 are preferably heated by electrical heating elements 607A and 607B. Conductors 660 and 662 supply current to the heating elements in the gripper fingers.

The gripping tool 651A of FIG. 91 further includes a force sensor 664 in the form of a strain gauge. The force sensor is designed to detect forces that the wire imparts to the gripping fingers after a bend has been placed in the wire or during the bending movement. The forces detected by the force sensor 664 are determined both in magnitude and in direction in three-dimensions. The use of the output from the force sensors to overbend wire is explained in further detail below.

FIG. 92 is a perspective view of the fixed gripper 608 having a gripper tool 651B as shown in FIG. 91 along with a moveable gripping tool 651A located at the distal end 632 of the moveable arm 606. An orthodontic archwire 615 is shown gripped by the gripping tools 651A and 651B. The fixed gripper 608 and gripping tool 651B remain stationary relative to the base 610. The archwire is bent or twisted by the fixed gripping tool 651 grasping the archwire 615 and the moveable gripping tool 651A also grasping the archwire 615, and then moveable gripping tooling 651A bending the wire by moving to a new location in three-dimensional space relative to the fixed gripping tools. The location in space for the moveable arm to move to is determined by the input file fed to the robot computer 600. Basically, the input file consists of a series of point locations in a three dimensional coordinate system which correspond to bracket locations and orientation in a three-dimensional coordinate system for the arch, as described in more detail below. The manner of calculation of these points and generating movement commands (i.e., arm position and switch states for the gripper fingers) for the robot's moveable arm and commands for the fixed gripper to bend the wire will be described in further detail below.

Other possibilities exist for input files and calculation of the bending points. For example, in extraction cases, the wire is needed to close a gap between teeth and the wire serves as a guide or rail for the bracket to slide along to close the teeth. In this situation, a smooth curve is needed between the teeth to allow the brackets to slide the required amount. In this situation, the space between the teeth is divided into small sections, and wire coordinates are obtained for each section. A series of small bends are formed at each section to generate the required smooth curve. It may be helpful in this situation to round the edges of the gripping fingers to help provide the desired smooth shape. As another alternative, free-form curves can be formed by bending the wire between two points which would encompass a plurality of brackets.

While the preferred embodiment of a robot arm is shown in FIG. 89, that is not the only possible arrangement of a robot arm. The robot of FIG. 89 is optimized for complex bends and twists in archwires. However, some medical devices or archwires may need only simple bends, in which case a lesser number of joints may be required. For example, a one, two or three axis robot may be sufficient for some applications.

Figure 95:
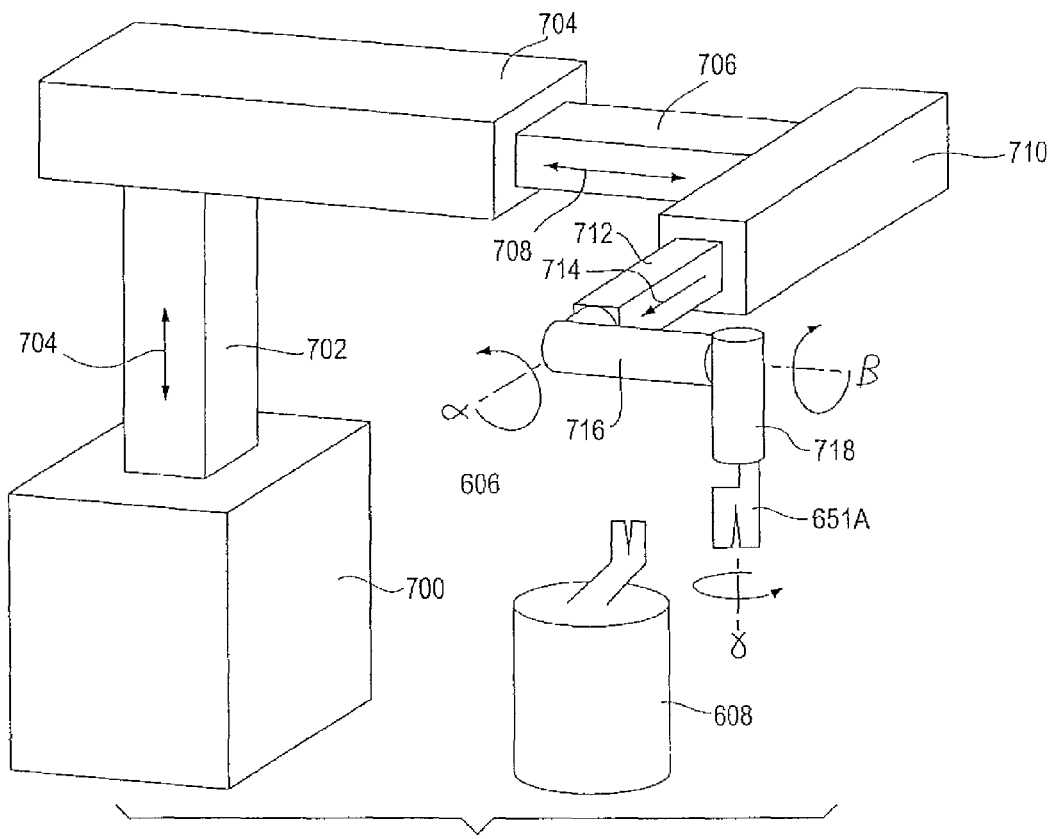
FIG. 95 is a perspective view of an alternative arrangement of a moveable robot arm.

FIG. 95 is a perspective view of an alternative arrangement of a six-axis moveable robot arm. In this embodiment, the robot arm comprises a base 700, a motor that moves arm segment 702 along direction 704, a second section that contains a motor that moves second arm segment 706 along direction 708, and a third section 710 that contains a motor moving the arm section 712 along direction 714. A motor is provided for rotating arm section 712 about axis α. A section 716 is connected to the end of section 712 and includes a motor for rotation of section 716 about an axis indicated by β. A sixth section 718 is rotated about an axis indicated by γ. The gripping tool 651A is mounted to the end of the section 718. Robots of this type are also known and suitable for forming the basis of an orthodontic archwire bending robot. The term "moveable arm" as used in the claims is intended to interpreted broadly to encompass the arm segments of the type shown in FIG. 95 as well as the construction shown in FIG. 90.

The gripping fingers of the gripping tools 651A and 652 preferably optimized, in terms of their physical configuration, for the type and shape of the workpiece being bent. This shape may change depending on the nature of the workpiece, e.g., wire, fixation plate, spectacle frames, etc. In the case of wires, wires come in various cross-sections and sizes. It may be desirable to form a plurality of contours in the gripping fingers so as to enable the gripping fingers to grip several different types and sizes of wires without changing gripping tools. For example, one part of the gripper fingers has a series of rectangular contours to grip wires of rectangular cross-section of varying sizes, and perhaps one or more circular contours to grip round wires.

The force sensors on the gripping tools may also be used to provide feedback for an adjustable gripping force to be applied to the workpiece (e.g., wires). It may be desirable to allow the wire to slide through the gripper fingers if the forces acting from the workpiece to the gripper exceed a certain limit. When these forces are sensed, the fixed gripper loosens its grip on the workpiece and allows it to slide.

Figure 94:
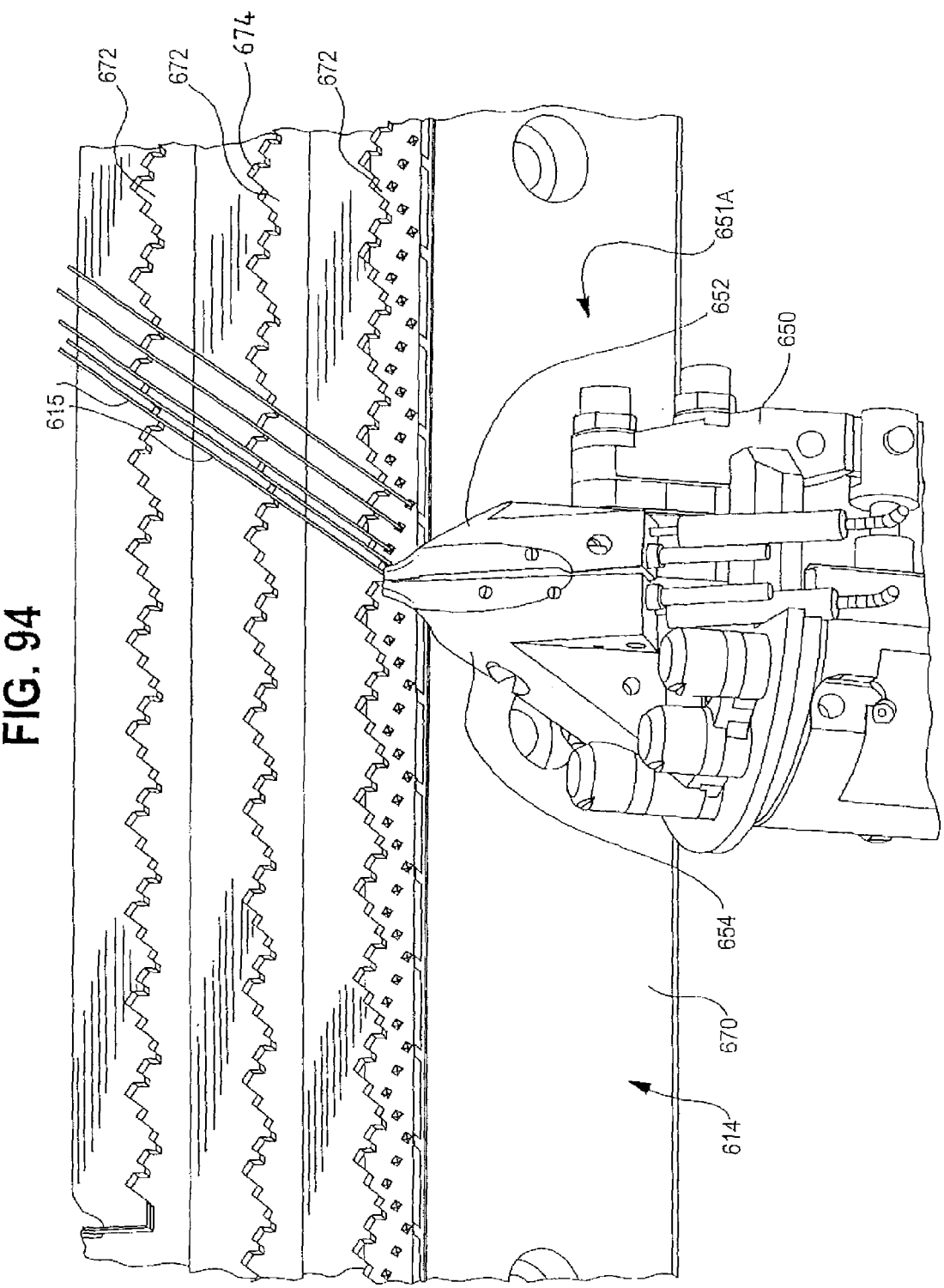
FIG. 94 is a detailed perspective view of the moveable gripping tool grasping one of the archwires from the magazine of FIG. 93.

FIG. 93 is a perspective view of a magazine 614 of FIG. 88 that holds a plurality of straight archwires needing to be bent in an presently preferred embodiment. FIG. 94 is a detailed perspective view of the moveable gripping tool grasping one of the archwires from the magazine of FIG. 93.

The magazine 614 consists of a tray 670 having a set of parallel raised elements 672 that define a series of grooves 674 in the upper surface thereof. The archwires 615 are placed in the grooves 674. The archwires are maintained spaced apart from each other in the tray. This permits the robot's moveable gripping tool 651A to pick up a single archwire at a time from the magazine 614 as shown in FIG. 94 and insert it into the fixed gripping tool to commence a bending operation. Also, the magazine 614 is positioned at a known location and the dimensions of the tray and slot features thereof are known precisely. This location information is supplied to the robot control software and allows the gripping tool 651A to remove the archwires one at a time from the magazine automatically and without human assistance. When the magazine 614 is empty a full one is placed at the same location.

Figure 96A:
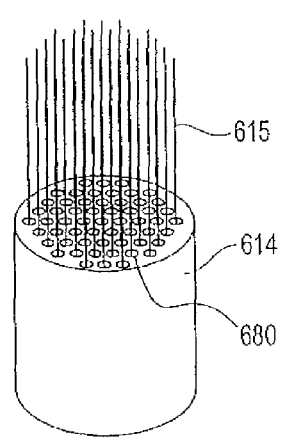
FIGS. 96A and 96B are perspective views of alternative magazine constructions to the magazine of FIG. 93.
Figure 96B:
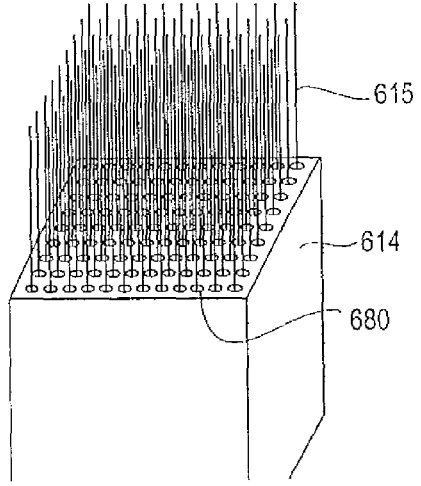

FIGS. 96A and 96B are perspective views of alternative magazine constructions to the magazine of FIG. 7. In FIG. 96A, the magazine 614 consists of a cylindrical holder with a plurality of apertures 680 spaced from each other, each containing a straight archwire 615. In FIG. 96B, the archwires are in a rectangular holder with the apertures arranged in rows and columns. In either case, the moveable arm grips an individual one of the archwires and removes it from the magazine by virtue of the spacing of the wires from each other in the magazine and because the location of each wire in the magazine can be known.

Figure 97:
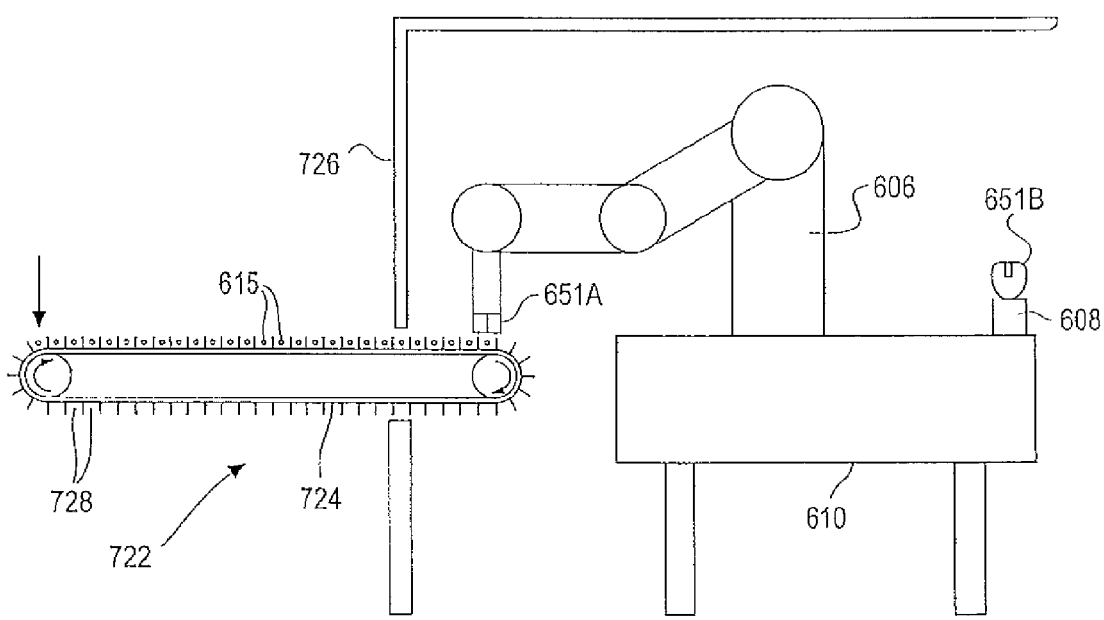
FIG. 97 is a schematic illustration of a conveyor system that carries archwires to the robot arm of FIG. 88.

FIG. 97 is a schematic illustration of a conveyor system 722 including a conveyor belt 724 that carries archwires 615 to the robot. Here, the robot is enclosed within a safety cage 726. A source feeds archwires 615 into slots 728 in the conveyor belt. When a wire has been bent and the robot is ready for a new wire, the belt advances one position and the robot grips the next wire placed on the belt 724. As another alternative, a spool of archwire can be fed to the robot and a cutting tool (not shown) provided for cutting the wire from the spool into a desired length. The cutting tool could be incorporated into the end of a second robot arm, for example. Still further implementations are possible.

It also possible for the archwire manufacturing system to have other workstations or workplaces in which one or more of the following tasks may be performed: loop bending, surface refining, and marking of the wires. These stations could be positioned at locations around the conveyor system 722 or be in separate locations.

It is also possible to enclosed the robotic wire bending system within an enclosure and fill the enclosure with an inert gas such as nitrogen. The inert gas prevents oxidation of the workpiece during bending or oxidation or other chemical reaction affecting the gripping tools.

B. Archwire Manufacture

Figure 98:
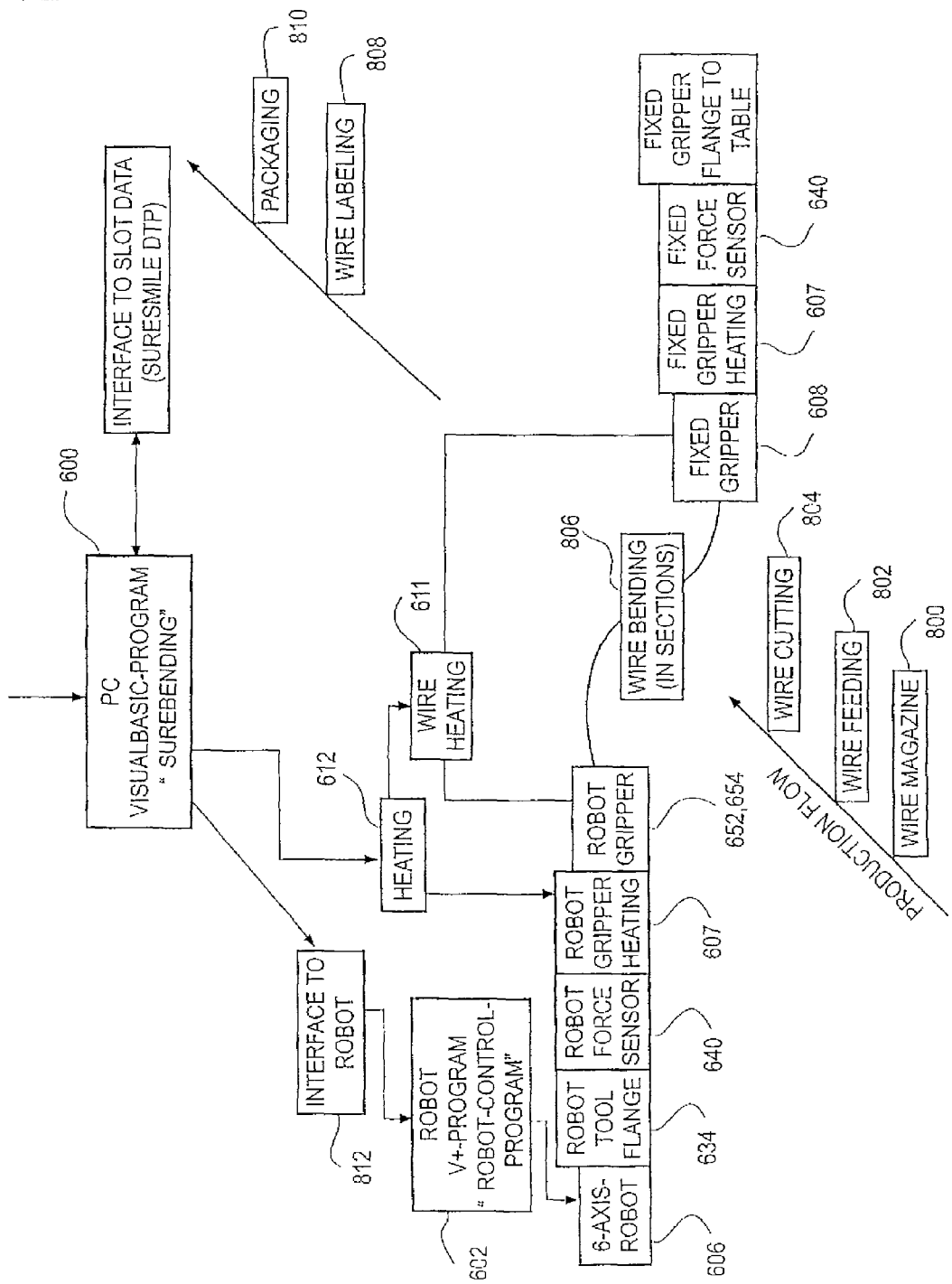
FIG. 98 is a diagram illustrating the robot software as it relates to the production flow in producing orthodontic archwires.
Figure 106A:
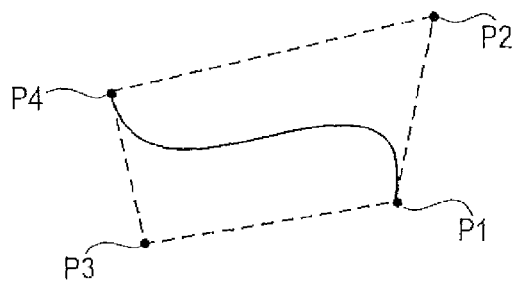
FIG. 106A is an illustration of four points and a curve defined by a Bezier spline, a technique used to calculate the shape of the bend in the wire between points P2 and P3 in FIG. 106.
Figure 106B:
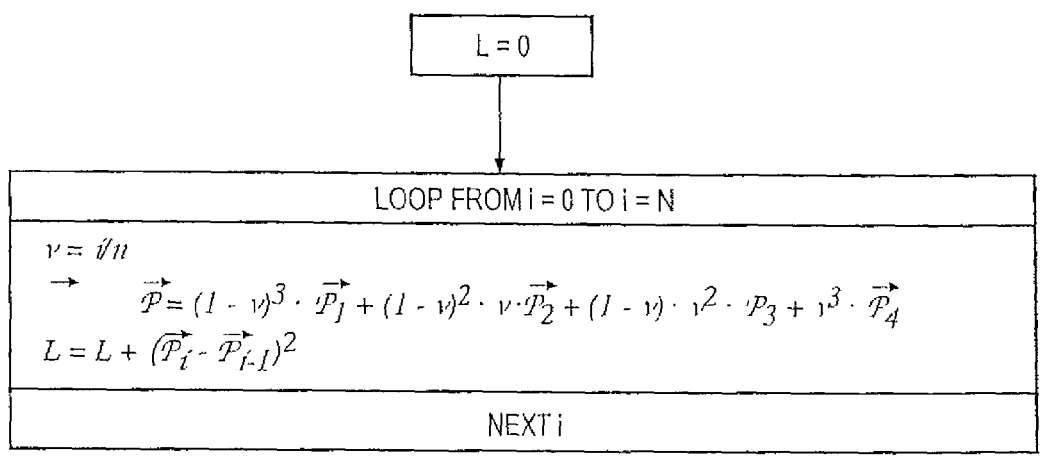
FIG. 106B is a flow chart of an algorithm to calculate the Bezier spline of FIG. 106A and the length of the curve.

The production flow for manufacturing archwires (or other similar appliances) with a representative embodiment of the wire manufacturing system of FIG. 88 is shown in FIG. 98. The production flow includes the step 800 of loading a wire magazine 614, such as spool of wire in an alternative embodiment, feeding the wire to the robot at step 802 and cutting the wire to length at step 804. At step 806, a series of bends are placed in the archwire in accordance with the prescription for the archwire. After the bending is complete, the wires are labeled at the station 624 at step 808 and packaged in a box or other package at step 810.

The bending of the wire at step 806 is based on slot data for bracket slots at described below in conjunction with FIGS. 99-106, or based on some other suitable criteria as explained herein. The wire bending computer 600 receives this slot data from the precision appliance center computer of FIG. 1. The computer 600 executes a bending program that processes the slot data into a set of points in three dimensional space and calculates movements of the moveable arm necessary to achieve the appropriate bends in the wire. The computer 600 has a software interface 812 to the robot controller, which translates position or movement signals for the robot arm into low level instructions for the robot controller 602. The robot controller executes a robot control program (adapted from the control program that comes with the robot) which causes the robot arm 606 to move relative to the fixed gripper 608 to bend and/or twist the wire. Where the archwire is a shape memory alloy, the wire heating power supply 611 supplies current to the gripper fingers 652 and 652 on the moveable arm and the gripper fingers on the fixed gripper 608 to heat the wire while the wire is held in the bent condition, and/or during bending motion, to set the shape of the wire.

Robot Input File

The input file, which dictates the shape of an archwire after bending, will now be discussed in conjunction with FIGS. 99-106. The input file includes a set of matrices, one matrix for each bracket in the arch of the patient. Each matrix consists of a combination of a vector of location of a point on the bracket and a matrix of orientation, indicating the orientation of the bracket in three-dimensional space. Both the vector of location and the matrix of orientation are based on the position of the brackets on the teeth when the teeth are in a target situation. The target situation is developed by the orthodontist from the scan of the dentition and the execution of a treatment planning using the treatment planning software at the clinic.

FIG. 99 illustrates the target situation for one arch 820 a patient. The target situation is a three dimensional virtual model of the teeth 822 in which virtual brackets 824 are placed, for example, on the labial surface of the teeth. A coordinate system is defined for the arch 820 having an origin 826. The coordinate system is in three dimensions, with the X and Y dimensions lying in the plane of the arch and the Z direction pointing out of the page. The location of the origin 826 is not particularly important. In the illustrated embodiment, an average "mass" is assigned to each virtual tooth in the arch, and a center of "mass" is calculated for the arch 820 and the original 826 is located at that center.

As shown in FIGS. 100 and 101, a vector of location 828 is defined for each bracket. The vector 828 extends from the origin 826 to the center of the slot 830 in the bracket along the wall 832 of the bracket slot, i.e., to point 834. The vector of location consists of the X, Y and Z coordinates of the point 834 in the defined arch coordinate system.

The orientation matrix consists of a 3×3 matrix of unit vectors of the form:

1)

$$\begin{matrix} X_1 & Y_1 & Z_1 \\ X_2 & Y_2 & Z_2 \\ X_3 & Y_3 & Z_3 \end{matrix}$$

where $X_1$ $X_2$ and $X_3$ are the X Y and Z components of the X unit vector shown in FIG. 101, $Y_1$ $Y_2$ and $Y_3$ are the X, Y and Z components of the Y unit vector shown in FIG. 101, and $Z_1$ $Z_2$ $Z_3$ are the X, Y and Z components of the Z unit vector shown in FIG. 101. As noted above, the matrix for each bracket thus consists of the combination of the 3×3 orientation matrix and the position matrix, and is thus as follows:

2)

$$\begin{matrix} X_1 & Y_1 & Z_1 & X \\ X_2 & Y_2 & Z_2 & Y \\ X_3 & Y_3 & Z_3 & Z \\ 0 & 0 & 0 & 1 \end{matrix}$$

where X, Y and Z in the right hand column of entries is the position vector.

The robot input file also includes an antitangential value and a tangential value for each bracket. The antitangential value consists of the distance from the center of the bracket slot (point 834) to a point defining the terminus of the previous bend in the wire. The tangential value consists of the distance from the center of the bracket slot to the point defining the terminus of the next bend in the wire. The input file also consists of the thickness of the wire, as measured in the direction of the Y unit vector in FIG. 101.

With reference to FIG. 102, an example of the 4×4 matrix 2) for a rear most molar of a patient will be described. Figure shows the origin 826, the position vector 828, and the X and Y unit vectors which indicate the orientation of the bracket slot. FIG. 102 also shows the scale (in units of millimeters) which gives absolute location and orientation information for the bracket slot. Here, we assume in the example that there is no Z component to the tangential vector X or the normal vector Y. FIG. 103 shows the tangential distance $T_D$ and the antitangential distance $AT_D$ as measured along the centerline of the archwire. The resulting matrix is shown in FIG. 104.

From a set of the matrices as shown in FIG. 104 comprising all the brackets in the arch, the robot bending program extracts a series of line segments in three dimensional space, which are defined by the terminus of the antitangential and tangential distances for each bracket slot. The set of line segments 840 is shown in FIG. 105. The line segments are defined by a set of points P1, P2, P3 . . . Pn having known three dimensional coordinates due to the known location of the bracket slots and the known tangential and antitangential distances. The line segments can also be defined as a set of vectors having a location for the head of the vector and a magnitude and orientation in three directions. The following discussion will use the set of points P1, P2, P3 . . . PN. In FIG. 105, the slashes 842 indicate the end points of the bracket slot 830 of FIG. 101.

The bends need to be placed in the wire before point P1, between points P2 and P3, between points P4 and P5, etc., that is, between the bracket slots. The slot-to-slot bends of the complete archwire are bent section by section. To form one slot-to-slot bend, the wire is fed so that the fixed gripper tool 651B and the robot arm gripper tool 651A can grip the wire in its initial shape. The wire length between fixed gripper and robot arm gripper is equal to the curved length of the wire along the bend. The straight wire sections 840 between the bends have to fit to the bracket slots. To bend the wire into the demanded shape, the main control computer 600 sends signals to the robot controller 602. The robot controller 602 generates signals to move the robot arm 606 with the robot gripper tool 651A into a new position. The movement path is defined by a bending trajectory. The bend is indicated at 844 in FIG. 106.

To form one slot-to-slot bend (e.g., bend 844 between P2 and P3), there might be several of these bending movements necessary. One slot-to-slot bend is considered finished if two consecutive straight wire sections (e.g., between P1 and P2 and between P3 and P4), have the desired relative positions between one another.

To achieve this position, there are different approaches dependent on the wire material properties possible: a) bending material with elastic/plastic properties, such as stainless steel, b) bending material with shape memory properties, and c) bending TMA alloys.

Material with elastic/plastic properties must be overbent to compensate for the elastic part of the deformation. The overbend process, which is described in further detail below, can be defined as a closed loop control. Within the first bending step, the robot arm 606 moves to a new position. Preferably the new position is equal to the planned position or to the planned position plus an amount of overbending. At the end of the move the forces and moments acting on the grippers are measured. They indicate the remaining elastic deformation in the wire. To determine the gripper position which correspond to the released wire shape, the robot arm 606 starts a new move in direction opposite to the acting forces and moments. The forces correspond to a translational move, the moments to a rotational move. By adjusting continuously the movement direction to the measured forces and moments, the robot achieves a position, where the forces and moments are in the order of the measurement resolution (zero-force-position). By choosing an appropriate measurement resolution, the remaining elastic deformation can be neglected and the relative position of the two grippers corresponds to the relative position of the straight wire sections in the released situation. This zero-force-position is compared to the planned position. If the differences are bigger than the tolerance limits, an additional bending step follows to decrease the difference. From the zero-force-position the robot moves now in direction to the planned position and overrides the planned position about the value of the difference between zero-force and planned position. The endpoint of this move is called overbend position. From the overbend position starts again the force and moment controlled move to find the new zero-force-position. If the new zero-force-position is within tolerance limits to the planned position, then the bending process for one slot-to-slot bend is completed and the wire is fed to bend the next slot-to-slot section. If the amount of overbend was too much, the new overbend position is calculated as described above. If the amount of overbend was not sufficient, then the new overbend position is calculated as the former overbend position plus the difference between new zero-force-position and planned position. The described process is repeated within a loop up to the situation, that the difference between zero-force-position and planned position is smaller than the tolerance limit.

Materials with shape memory properties and TMA will be bent to the planned position. To transfer this position into the memory of the alloy, the wire section between the two grippers is heated to a certain temperature for a certain time. The heating is possible e.g. by conductive resistance heating, laser, convection, radiation, or applying warm air or liquid to the material. Heating current and time must be appropriately adjusted to the respective alloy, the wire section length and the wire shape. To warm-up the wire, the wire heating can start already during the bending movement to the planned position. To avoid a heat sink effect at the gripper fingers and to ensure that the complete inter-bracket section of the wire obtains the necessary heating, the gripper fingers 652, 654 (FIG. 91) or at least the contact areas of gripper and wire are heated too. The grippers may be heated continuously during the production process of the whole archwire. To compensate for an incomplete transition of the bending position to the alloy memory, there can be defined a certain amount of overbending.

In bending TMA materials, the material can be heated to a high temperature where there is no springback, however when the material cools, it retains its springback properties. The procedure for bending such materials is as follows: 1) heat the gripper fingers; 2) bend the wire to the desired configuration; 3) heat the wire up to the temperature where the springback tendency no longer exists; 4) turn off the heat source and allow the wire to cool, and 5) advance the wire to the next position for bending; and then repeat steps 1)-5).

The bending of the wire from one section to the next requires that the location and alignment of one straight wire section (i), for example P3 to P4, is defined in reference to the previous straight wire section (i–1) in the counting order defined in the bending system. The origin of the bending system is defined at the end of the straight wire section (i–1), which aims towards the following straight section (i). The x-axis is equal to the direction of the straight wire section (i–1) directed to section (i). For wires with rectangular cross-section the y-axis is perpendicular to x and in direction to the wider dimension of the wire. For quadratic or circular cross-section the y-axis must be perpendicular to x and can be chosen according to practical reasons. The x,y,z-axis follow the right hand rule.

The bracket slot data as described above needs to be transformed to bending data for use by the robot controller 602. This is done by calculation, from the position of the bracket center point 834 (FIG. 100) to the position of the straight wire section center point (located along the middle of the wire, point 840 in FIG. 105).

Next, there needs to be a calculation of the bent wire shape and length. In FIG. 30, this is shown as the shape of the wire between points P2 and P3. For each bending step, the robot gripper grips the wire in a certain distance from the fixed gripper corresponding to the length of the wire between points P2 and P3. The wire section between the two grippers will be bent. To minimize the bending forces and moments and to ensure that the bending forces and moments don't exceed limits, which may cause damage to the equipment or to the wire, the gripped wire length should be approximately the "natural" length of the wire in its bent shape. If the length is too short, the wire will be torn and there will be high tensional forces, if it's too long, the wire will tend to kink.

The robot computer 600 therefore calculates the approximate shape of the bent wire using an appropriate algorithm. One way is deriving a second or third order curve representing the shape of the wire using numerical techniques. Another would be using a regular spline algorithm. Ideally, there should be no sharp bends in the wire. In the illustrated embodiment, a Bezier spline algorithm is used. The algorithm gives an analytical description of a smooth curve and generates a set of points along the length of the curve. The length of the curve is obtained by summing up the distance (in three dimensions) along each segment of the curve. The separation distance between each point in the segments can be set arbitrarily and in the illustrated embodiment is 0.05 mm. The algorithm is as follows:

Input:

Centerpoint location and alignment of two neighbored straight wire sections (given as 4×4 matrice with local vector $\vec{l}$, tangential vector $\vec{t}$ normal vector $\vec{n}$ and vertical vector $\vec{v}$) These matrices correspond to the 4×4 matrix described earlier.

tangential and antitangential distances $s_t$ and $s_{at}$

Bezier-distance $b_d$ (empirical value)

The Bezier formula, as known by literature, is described by four points as shown in FIG. 20A. The points of the spline curve are given by:

$$\vec{P} = (1-v)^3 \cdot \vec{P_1} + (1-v)^2 \cdot v \cdot \vec{P_2} + (1-v) \cdot v^2 \cdot \vec{P_3} + v^3 \cdot \vec{P_4}$$
$$v \in \{0, \ldots, 1\}$$

Here it will be noted that the Bezier points $P_1$ to $P_4$ in FIG. 20A are not necessarily the points P1-P4 of the wire segments shown in FIG. 19, but rather are the points used to calculate the Bezier spline length and shape.

To describe the curved wire shape between the straight wire sections from slot (i−1) to slot i, the Bezier points $\vec{P}_1$, $\vec{P}_2$, $\vec{P}_3$, $\vec{P}_4$ are calculated by:

$$\vec{P}_1 = \vec{l}_{i-1} + s_{t,i-1} \cdot \vec{t}_{i-1}$$

$$\vec{P}_2 = \vec{l}_{i-1} + (s_{t,i-1} + b_d) \cdot \vec{t}_{i-1}$$

$$\vec{P}_3 = \vec{l}_i - (s_{t,i} + b_d) \cdot \vec{t}_i$$

$$\vec{P}_4 = \vec{l}_i - s_{at,i} \cdot \vec{t}_i$$

The wire length L and the N intermediate spline points can be calculated by the algorithm shown in FIG. 20B.

The empirical value Bezier-distance $b_d$ must be set to make the calculated and actual bent wire shape tally. For orthodontic wires, a good assumption is $b_d = 1 \times \ldots 2\times$ the larger wire cross-section dimension.

The bending trajectory needs to be calculated for each bend. The bending trajectory is a number of positions of the moveable arm's gripper 651A in relation to the fixed gripper 651B, which connect the start position and the destination position of a bending movement. In general there are translational and rotational movement components from each bending trajectory position to the next.

Figure 115A:
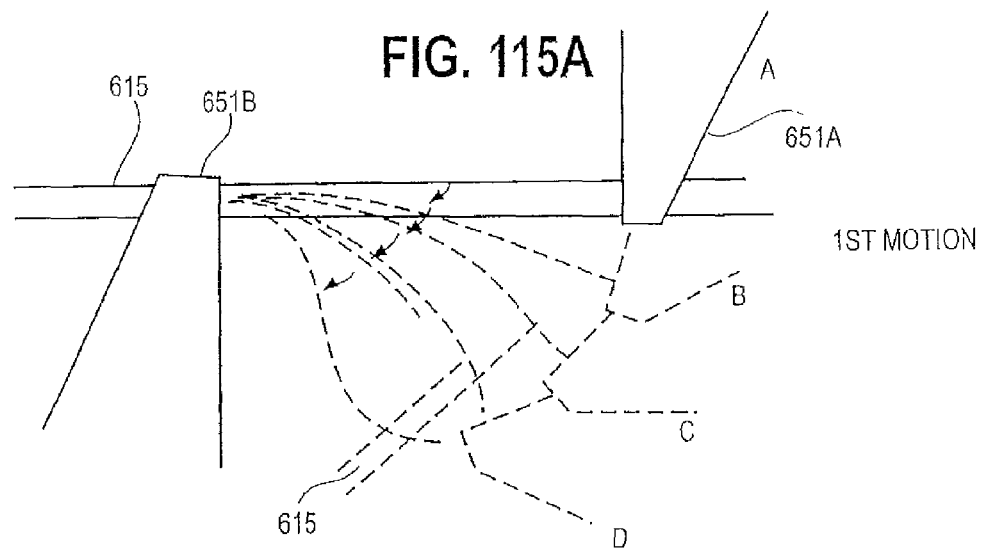

For each bending trajectory position the calculated length of the curved wire must be equal to the calculated length in the planned position. To avoid kinking condition for the wire the movement can be divided into two parts:
1. Initial movement to steer the wire into a distinctly deformed shape. The initial movement is defined as a rotational transformation around an axis through the endpoint of the fixed gripper perpendicular to the connecting vector of the start position and the end position. This is indicated in FIG. 115A by the rotational motion of the moveable gripping tool 651B and movements a, b, c, and d.
2. Finish movement to destination position. The finish movement is a gradual approach from the start position (or if there is an initial movement from the end position of the initial movement) to the destination position. The translational and rotational parts of the whole bending movement are split up steadily to the individual bending trajectory positions. Between two bending trajectory positions, the movement path of the robot gripper is defined by a linear translational movement along the straight line connection of the two positions and by steadily divided rotational movement. The distance between two bending trajectory positions must be small enough to avoid kinking of the wire and inadmissible forces and moments. These movements are indicated at positions d, e, f, and g in FIG. 115B.

Figure 109:
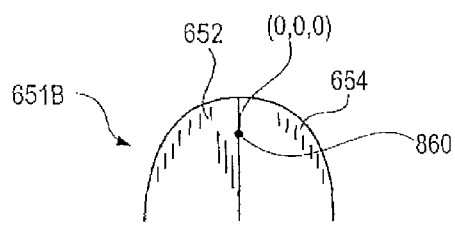
FIG. 109 is an elevational view of the gripping fingers of the fixed gripping tool of FIG. 92, showing the origin of a coordinate system used by the robot in bending wire.
Figure 110:
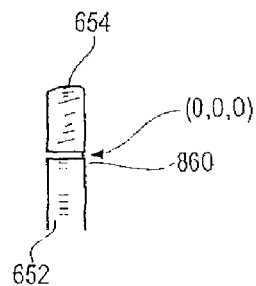
FIG. 110 is a top view of the gripping fingers of FIG. 109.

In bending wire as described herein, the robot system 604 of FIG. 88 has a coordinate system in which an origin 860 is defined as shown in FIGS. 109 and 110. The wire passes through the fixed gripping tool 651B through a small gap formed when the fingers are in an open position. The origin 860 is defined as the along the center of the axis of the wire at the planar edge of the fixed gripping tool 651B. The robot controller software knows the location of the moveable gripping tool relative to the fixed gripping tool in this coordinate system at all times. Furthermore, the wire is gripped by the moveable gripping tool at a precise point on the moveable gripping tool. Therefore, when the wire is held by the fixed gripping tool and the moveable gripping tool, the distance between the two is known exactly. This allows the bending shown in FIG. 115A-115C to be executed without stretching or contracting the wire. In particular, the distance as measured along the wire between the fixed and moveable gripping tools at the point of attachment to the wire is constantly maintained a distance equal to the calculated Bezier distance for the wire as bent between the points P2 and P3 of FIGS. 105 and 106, and of course for subsequent bends.

To advance the wire between bends or to place the wire in condition for the first bend, there are at least two possibilities. One is that the moveable gripper tool grips the wire and pulls it through the fixed gripping tool (with the fixed gripping tool opened to allow the sliding of the wire with respect to the gripping tool). As an alternative, the wire could be on a spool or coil, and the spool rotated by a motor to advance the wire through the fixed gripping tool. In the later embodiment, a cutting tool will need to be provided to cut the wire after the bending is completed. Archwire manufacturers sell wires in bulk already cut to length and the present description is made in the embodiment in which the wire segment is advanced by the moveable gripping tool advancing the wire through the fixed gripping tool.

Having the bent wire between the two grippers in a tensed state, the robot gripper is moved to a new position, where no forces and moments are acting on the gripper. The force sensors 640 on the fixed and moveable gripping tools are used to determine the position. This position is called the zero force position and corresponds to the released state of the wire. Forces, moments and the movements components are calculated in the main robot coordinate system of FIGS. 109 and 110.

Depending on the nature of the material, some overbending of the wire may be needed. This would be indicated for example if the zero force position is not the same as the calculated position for the robot's moveable arm 606. To better understand the overbending principles, attention is directed to FIGS. 108 and 108.

Figure 107:
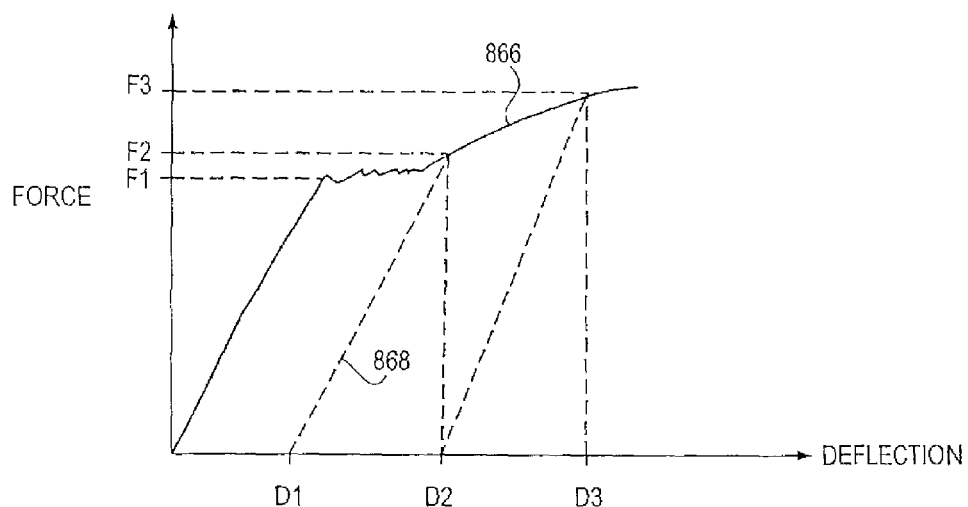
FIG. 107 is a graph of force as a function of deflection for a workpiece such as a wire. The graph illustrates that that when a certain amount of force, F1, is applied to the workpiece and then released, a deflection D2 results. When the force is released, the amount of remaining deflection, D1, is less than the deflection observed when the force is applied to the wire, D2, since the wire has elastic properties.

FIG. 107 illustrates the relationship between force and deflection of wire. The solid line 866 indicates how much force is needed to give a certain deflection of the wire. Where the force is less than F1, when the force is released the wire returns to its initial state and experiences no deflection due to elastic properties of the wire. At force level F1, some permanent deformation, i.e., plastic deformation, of the wire starts to take place. With a force level of F2, the wire is deflected an amount D2, but when the force is release from the wire the wire bends back to a deflection amount D1, with the relaxation curve 868 essentially parallel to the curve 866 up to force level F1, as shown. Thus, some level of force indicated at F3 is required to be applied to the wire such that when the force is removed the required deflection Ds is achieved in the wire. The fact that F3 is greater than F2 and that the deflection D3 is greater than D2 illustrates that some overbending is generally needed to yield the proper shape of the wire after the bending forces are removed.

Figure 108:
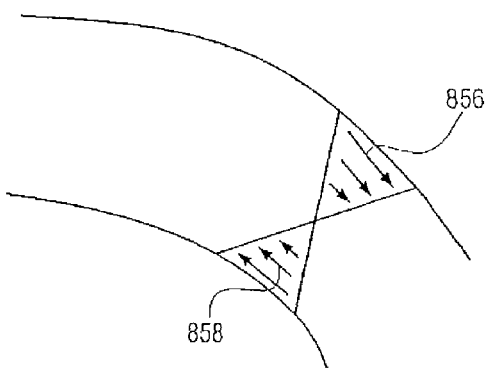
FIG. 108 is an illustration of the stresses found in a wire when it is bent.

FIG. 108 illustrates the stresses involved with wire material when it is bent. The wire has one portion experiencing elongation stress, as indicated at 856, while compression stresses are experienced at locations 858, with the length of the arrows indicating the relative magnitude of the stress. With small bends, the forces at the center of the wire are small enough such that only elastic deformation occurs, while at the outside portion of the wire some plastic deformation may occur. The result is that bending wire is a mixture of elastic and plastic deformation, the character of which is determined by the amount of the bend, the wire material, and the cross-sectional shape.

To determine the amount of required overbending, there are several possibilities. One is a purely analytical solution like finite element analysis of wire. Alternatively, a piece of wire can be tested to determine its response to known forces, and the result stored as a calibration table of bends. Basically, the curves in FIG. 107 are obtained experimentally. A more preferred approach uses force sensors 640 (FIG. 88A) on the fixed and moveable gripping tools to sense the zero force position of the wire and compare the location of the moveable gripper in this position with the intended position. A geometrical or deformation approach is another alternative. In this approach, the wire is bent some amount and then released, the relaxation position noted, the wire bent some more, the wire released, etc. the process continuing until the wire is bent to the desired position.

With a force based system, perhaps augmented by an adaptive, self-learning artificial intelligence type learning program or calibration table based on previous bends of similar wire, the resulting configuration of the wire can usually be achieved more quickly. Basically, for every bend performed in the wire, information is stored as to the movement necessary to result in a specific bend. For example, to achieve a 13 degree bend in the wire of type T and cross-sectional shape W, the wire had to be bent 15.5 degrees, and this information is stored. With enough data, a mathematical relationship can be derived that that represents curves 866 and 868 for the wire of type T (at least in the portion of the curve of interest), and this mathematical relationship can be used, in conjunction with force sensors, to quickly and accurately place the required bends in the wire.

In either situation, an optical system such as a camera could be used for detecting the position of the wire in the relaxed position is used to determine the actual shape of the wire after any given bend.

Figure 111:
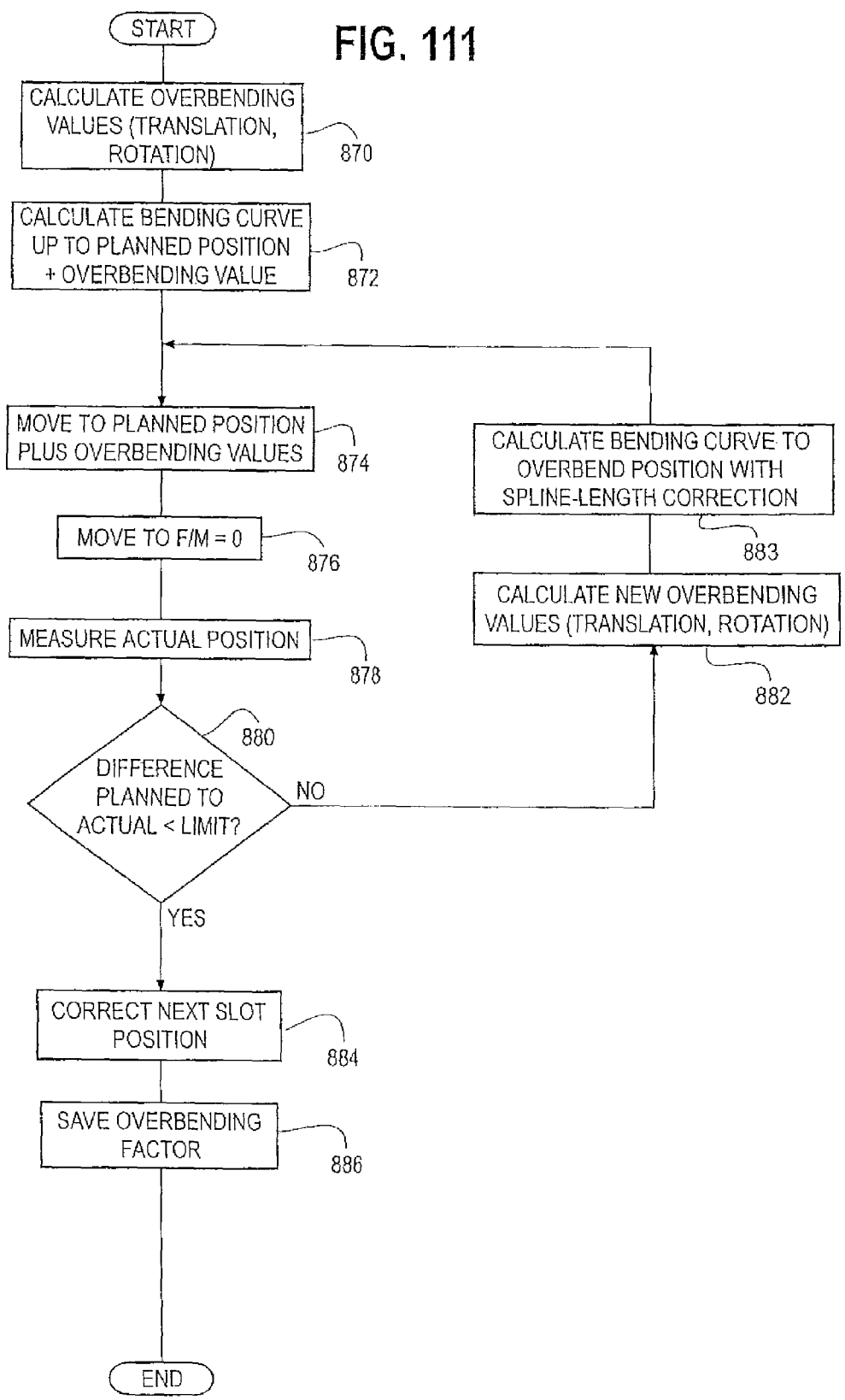
FIG. 111 is flowchart illustrating a deformation-controlled overbending procedure, which may be used to compensate for the elastic properties of the wire demonstrated by FIG. 107.

FIG. 111 is a flow chart of a deformation controlled overbending process that can be used with stainless steel or other wires, including shape memory wires where some overbending is still required.

At step 870, a calculation is made of overbending values in both a translation and rotational aspect. This calculation could be performed for example using finite elements methods, using a calibration table, using a derived mathematical relationship between force and bending, using stored values for overbending from previous bends, or some combination of the above.

At step 872, the bending curve is calculated up to the planned position and including the overbending values. This involves the Bezier spline algorithm set forth previously.

At step 874, the moveable gripping tool is moved to the position indicated by the sum of the planned position plus the overbending position. This forms a bend in the wire. Again, this position is determined in reference to the robot coordinate system and in reference to the spatial relationship between the points where a bend needs to be placed in the wire (P3 and P2 in FIG. 105, for example).

At step 876, the force sensors are used to measure the residual forces imparted by the wire onto the gripping tools, and if the forces are greater than some threshold, the moveable gripping tool 651A is moved to the position where the force measurement is zero or substantially zero.

At step 878 the actual position of the moveable gripping tool is measure using the position sensors in the moveable robot arm.

At step 880, a check is made to see if the difference between the actual position and the planned position is less than a limit. If not, new overbending values are calculated (step 882), and a new bending curve is calculated to overbend the wire an additional amount, in the desired direction, to bring the wire closer to the desired shape (step 883).

Steps 874-883 are repeated until the difference between the actual position of the moveable gripping tool and the planned position is less than a limit.

At step 884, the error in the actual position relative to the planned position is noted and compensated for by correcting the next slot position. In particular, the next slot position represented by the next pair of points in the set of points in FIG. 105 is translated in three dimensions by the amount of the error. This correction of the next slot position is needed so as to avoid propagation of an error in any given bend to all subsequent bends.

At step 886, the overbending results from steps 874-882 are saved in memory and used in an adaptive technique for estimating future overbending requirements as explained above.

Figure 112:
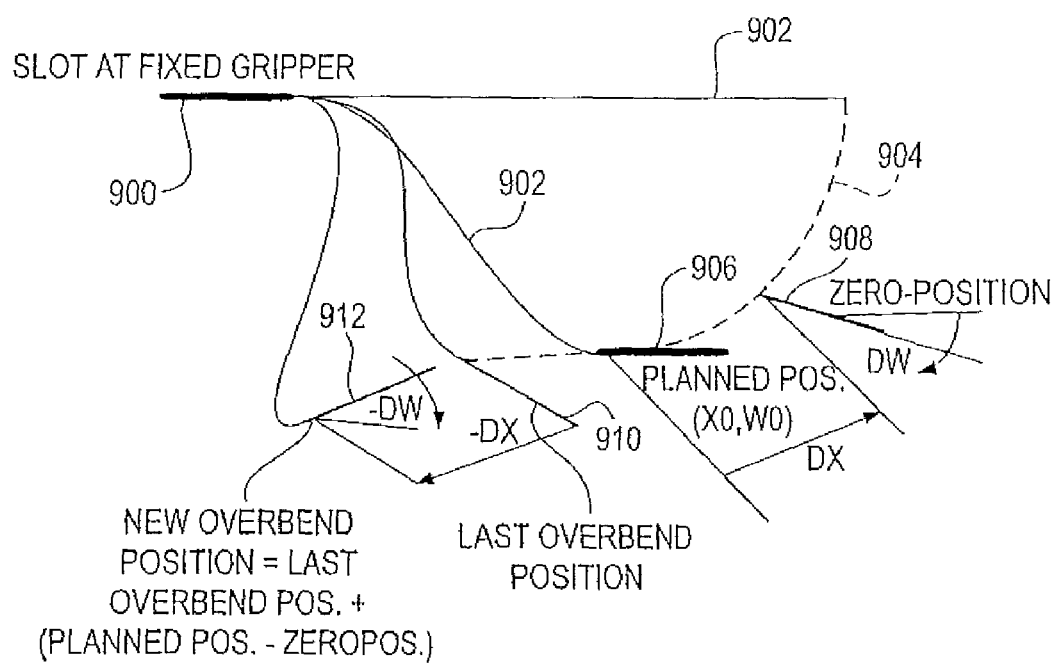

FIG. 112 is a schematic representation of the overbending performed by the method of FIG. 111. The line 900 represents the slot between the fingers of the fixed gripper and the line 902 represents the wire in various stages of bending. The dashed line 904 indicates the movement of step 874, with line 906 representing the slot of the moveable gripping tool between the gripping fingers where the wire is gripped in the planned position. The zero force position where the moveable gripper is moved to is indicated at 908 (step 876 in FIG. 111). There is both a rotational (dw) and translational (dx) aspect to the difference between the zero force position and the planned position. The last overbend position is shown as position 910 (the overbend calculated at step 870). The required correction is shown by the position 912. This new overbend position, calculated at step 880 in FIG. 111 is equal to the last overbend position 910 plus the planned position 906 minus the zero position 908. This new overbend position includes both translational and rotational aspects as indicated by −dx and −dw.

Figure 113A:
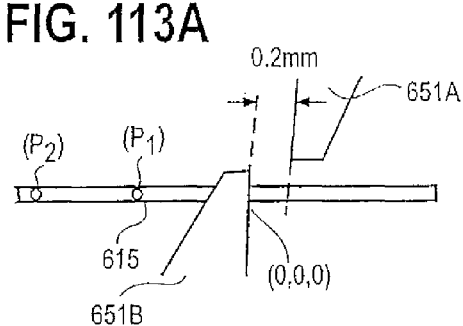
Figure 113B:
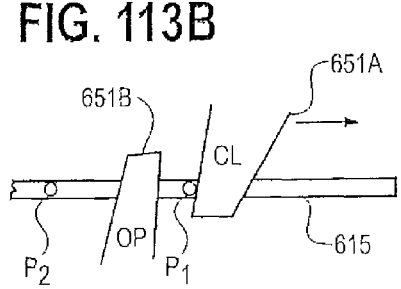
Figure 113C:
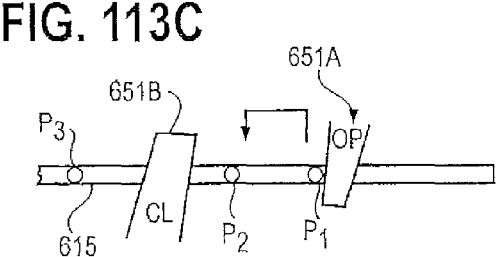
Figure 113D:
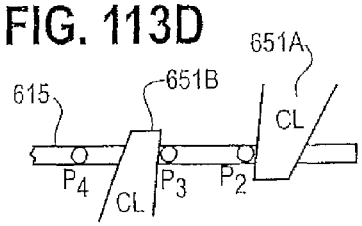

One possible example of actual robot gripper movements to feed the wire through the grippers and execute a representative bend will be explained conjunction with FIG. 113A-113E. As shown in FIG. 113A, the wire is thread through the fixed gripper tool 651B or placed there by the moveable gripping tool such that some length of wire is extending beyond the end of the fixed gripping tool 651B. The points P1 and P2 along the wire segment are indicated. The moveable gripper tool 651A is positioned above and slightly to the right of the fixed gripping tool, here 0.2 mm away. The moveable gripping fingers open and the moveable gripper moves down to clamp the wire. The 0.2 mm distance is merely chosen so that the fingers to not collide and can vary from the illustrated embodiment. The fingers cooperate with each other by translation movements of the moveable gripping tool and releasing and closing the fixed and moveable grippers such that the wire is advanced through the fixed gripping tool. This is also indicated by FIG. 113B, showing the fixed gripping tool 651B open (OP) to allow the wire to be slid through a slot formed between the fingers of the tool 651B. The moveable gripping tool moves to the right to draw the wire through the fixed gripping tool until the point P2 is to the right of the fixed gripping tool (as shown in FIG. 113C), where it can be grasped by the moveable gripping tool. As shown in FIGS. 113C and 113D, the moveable gripping tool opens and releases its grip on the wire (indicated by OP) and moves to the position where it closes (CL) and grasps the wire at location P2. Then moveable gripping tool 651A draws the wire through the fixed gripping tool while gripping the wire at point P2, such that point P3 is located at the origin of the robot coordinate system, as shown in FIG. 113D. Since the planned location of both P2 and P3 after a bend in the wire is made is known in the robot coordinate system, the moveable gripping tool 651A moves to the position shown in FIG. 113B to place a bend in the wire. At this point, if further overbending is called for, the process of, e.g., FIGS. 111 and 112 is performed to place the required overbend in the wire. The movements of FIG. 113B-113D could be combined to one movement if the distance is small enough, and depending on the thickness of the wire.

Figure 113E:
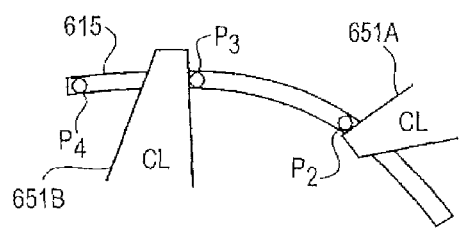
Figure 114:
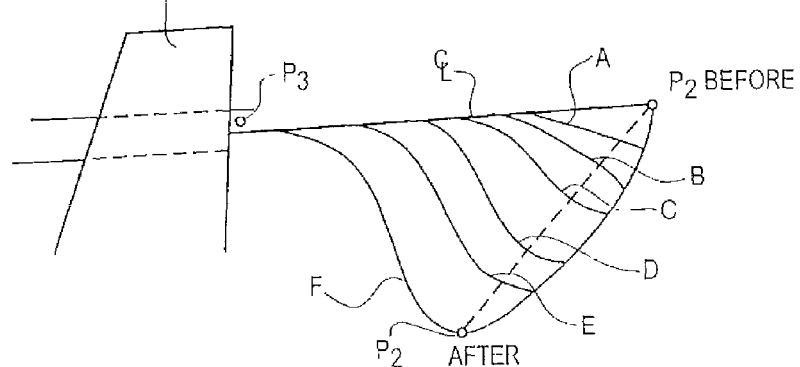
Figure 115B:
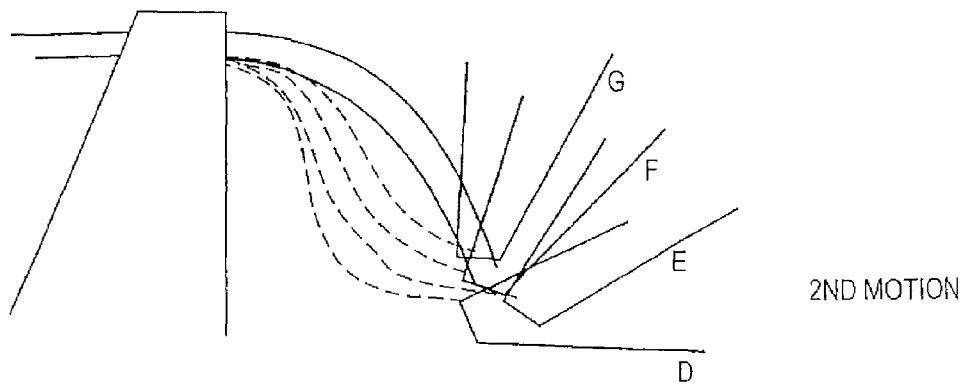
Figure 115C:
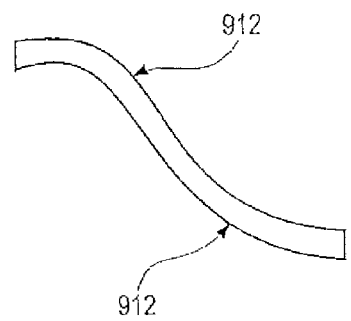
Figure 118:
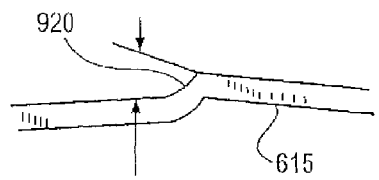

FIG. 118 illustrates before and after positions of the wire when the bending of FIG. 113E occurs. The figure illustrates that the movement of FIG. 113E is not a straight line movement which might cause excessive elongation or kinking of the wire. Rather, the movement of the gripper is illustrated as steps a, b, c, d, e, f such that the distance, as measured along the length of the wire, is maintained constant. The movement may performed in two stages (such as shown in FIGS. 115A and 115B). The result is that two bends 912 are placed in the wire, as shown in FIG. 115C. Of course, a twist could also be performed in the wire if required by the prescription.

Figure 116A:
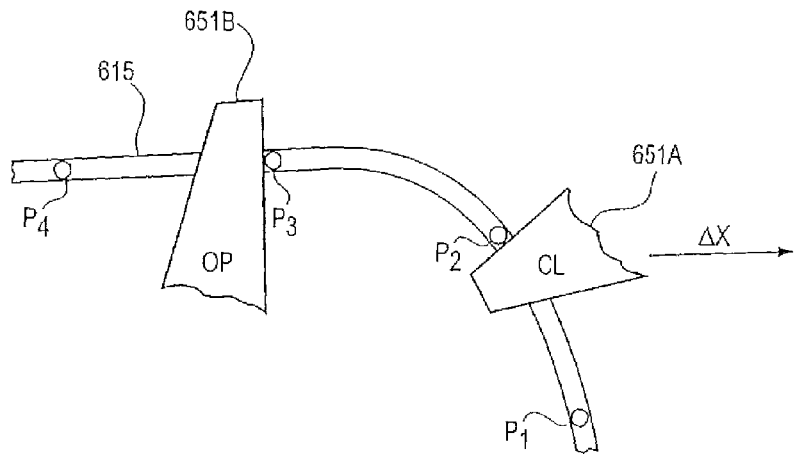
Figure 116B:
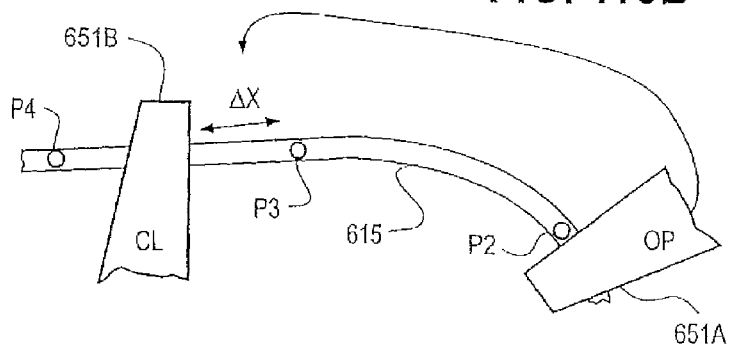
Figure 116C:
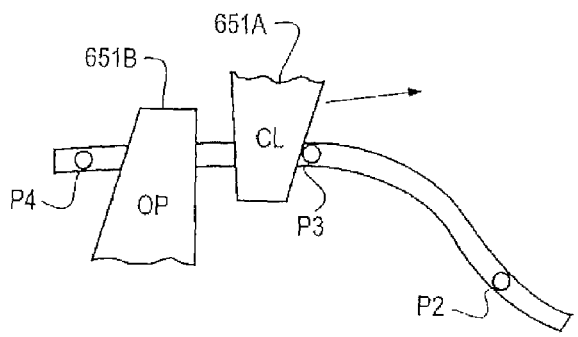
Figure 116D:
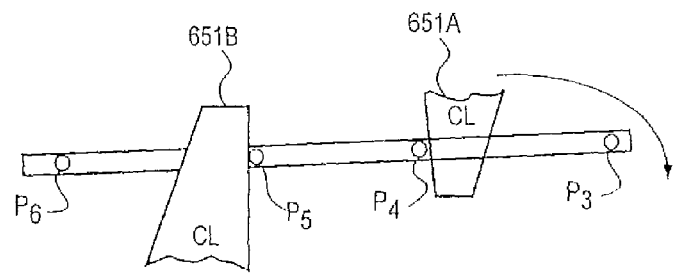

After the bend has been placed in the wire, the steps shown in FIG. 116A-116D are performed to advance the wire along to the position of the next bend. First, as indicated at FIG. 116A, the moveable gripping tool 651A is translated to the right an amount indicated by ΔX. This moves point P3 to the right of the fixed gripping tool by an amount ΔX, as shown in FIG. 116B. Then, the moveable gripping tool releases the wire and re-grips the wire to the right of the fixed gripping tool as shown in FIG. 116C and again translates to the right an amount sufficient to move point P4 to the right of the fixed gripping tool. The moveable gripping tool releases the wire again and grips the wire at point P4. The wire is again translated to the right such that the situation shown in FIG. 116D is obtained. The wire is now in position for a bend in the wire between P4 and P5. The process of FIGS. 111 and 112 occurs again to calculate new bending and overbending positions and the bend is formed in the wire. The process of FIG. 116A-116D continues until all the bends have been formed in the archwire. When the final bend is complete, the wire is released from the moveable gripper at the exit location of the wire manufacturing system, and carried by conveyor to the labeling and packaging station described earlier.

Shape memory alloy materials require heating to take on the shape given by the bend produced in FIG. 113E. Thus, for these wires, while the wire is held in the position shown by FIG. 113E, heat is applied to the wire to raise the temperature of wire to the value needed to take the set. The temperature varies with the type of material. In the illustrated embodiment, a resistance heating system is used as described previously. The current is adjusted until the proper temperature is reached. The heat treating is deemed complete when the force sensors read zero (or less than some limit) when the wire is held by the grippers in the planned position. The amount of current and time applied to the wire is again stored information that can be used for future heating of the same type of wire.

For some softer shape memory materials, e.g., NiTi, the force sensor 640 (FIG. 88A) provided in the gripping tools must be very sensitive to detect the small forces involved. While shape memory materials may not require force sensors at all, they can be used to give information as to the effectiveness of the heating process.

In a preferred embodiment, two force sensors are used. A coarser force sensor, used for measuring larger forces during bending, is fitted to the moveable gripping tool. A finer force sensor, with a higher resolution, low noise and higher sensitivity, e.g., with a sensitivity of less than 0.0005N, is fitted to the fixed gripping tool, in order to detect the zero force position. The force sensors are both based on strain gauge technology and can be readily adapted from commercially available strain gauges or off the shelf units. For example, the finer force sensor may have different amplifiers or other modifications to the circuitry to have greater sensitivity, signal to noise ratio and force resolution. Other types of force sensors, such as those based on piezo technology, would be suitable. Suitable off-the-shelf strain gauge force sensors are available from JR3 Inc. of Woodland Calif., model nos. 45E15A-U760 (fixed gripping tool) and 67M25A-I40 (moveable gripping tool).

Other types of heating systems could be adopted for archwires and other types of workpieces to be bent, such as laser, flame, infrared, conductive or radiant heating. Some springback may still be observed in shape memory materials even when heating is performed unless the wire is heated close to the maximum permitted temperature of the wire. Therefore, with some shape memory materials it may be desirable to perform some overbending in order to lower the temperature needed to set the new shape into the wire. Again, the required amount of overbending at a given wire temperature can be stored in memory and used to derive a relationship between temperature, overbending and resulting position for the material, which can be used for subsequent bends in the wire.

Due to the complexities of wire deformation and twisting in wire that can occur when wire of a rectangular cross section is bent, and the difficulty in controlling the resulting shape of the wire (particularly when complex bends and twists are formed in the wire), the usage of force measuring devices, and position sensors to detect the shape of the wire when the wire is in a zero force condition, gives accurate information as to the shape of the wire after a bend. Thus, a force based approach to overbending is a preferred embodiment. The actual position of the wire in the zero force condition can be obtained by position sensors on the robot arm (which makes no contribution to the measurement of forces), or better yet, by releasing the wire from the moveable arm and detecting the position of the wire with a camera or other optical system. Basically, the camera would image the wire immediately in front of the fixed gripping tool. Pattern recognition and image processing algorithms are used to determine the edge of the wire, and thereby calculate its shape. More than one camera could be used if necessary to image the wire sufficiently to calculate twist in the wire. The effects of gravity would have to be compensated for in any position measuring system in which the wire is not held by the moveable gripping tool.

Thus, in one possible embodiment the robot further comprises an optical sensor system such as a CCD camera detecting the shape of the orthodontic appliance after the bend in said orthodontic appliance has been made, such as by releasing the appliance from the moveable gripping tool and allowing the appliance to take its natural position, and then using the optical system to detect the shape of the appliance.

It is also possible to use both the force measuring systems and the optical system as a final check on the shape. The force sensor system (e.g., coupled to the fixed and/or moveable gripping tools) detects forces generated by the orthodontic appliance after the orthodontic appliance has been bent. The moveable arm is operated to move the orthodontic appliance to a zero-force position in which the forces detected by the force system are below a predetermined threshold. The optical sensor system detects the shape of the orthodontic appliance in the zero-force position. The position detected by the optical sensor system can be used as a feedback mechanism for further wire bending if the zero force position is not the intended or desired configuration of the appliance. An optional type of sensor system would be calipers that contact the workpiece and responsively provide position information as to the location (i.e., bend) formed in the workpiece.

Figure 117:
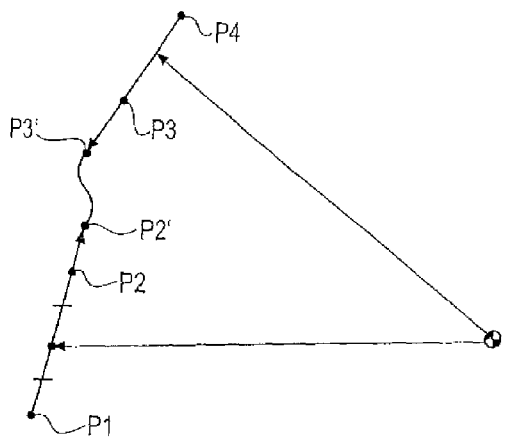

For stainless steel wires, there is generally no need for heat treatment of the wire. It is simply bent into the desired position, with overbending performed as required. The shorter the distance between endpoints of a bend, the greater the deformation in the wire, therefore the greater the predictability in the deformation. With orthodontic archwires, the situation can occur where there is a relatively long distance between bracket slots (particularly in the region of the molars) and it can be difficult to obtain a stable bending result. A preferred solution here is to make this distance shorter by adding on some length to the tangential distance of one slot position and the antitangential distance of the next slot position, as shown in FIG. 117. Here, point P2 is extended in space to point P2', and point P3 is brought closer to point P2 by moving it to point P3'. The required bending of the wire is now calculated relative to points P3' and P2'. The bend placed between P3' and P2' is now sufficiently short that it can be formed with enough control.

Figure 119:
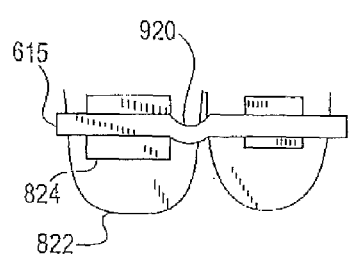

In practice, it known that after an archwire has been fitted to the patient's brackets, the archwire imparts forces to move the teeth to the desired position. However, after a certain amount of time, some small amount of bend remains in the wire but it is insufficient to cause any further tooth movement. Consequently, the teeth are not moved to their desired position. This can be compensated for by adding an additional amount of bend to the wire so that when the wire is installed, it will continue to exert forces until the teeth have been moved all the way to their desired position. As shown in FIG. 118, this small additional bend is shown as 920. FIG. 33 shows the wire of FIG. 118 installed in the brackets of a patient. The bend 920 of FIG. 32 is in addition to other bends that may be placed between the brackets 824. FIG. 119 illustrates that enough residual force exists by virtue of bend 920 to move the teeth 822 to their desired position.

Figure 120:
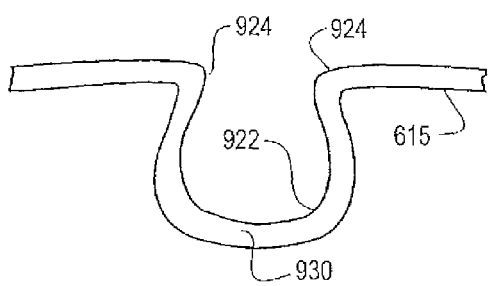
Figure 121A:
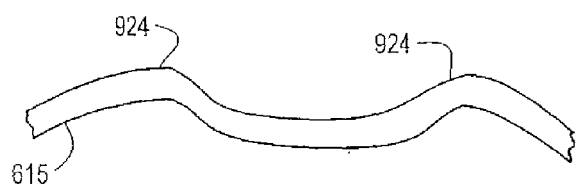
Figure 121B:
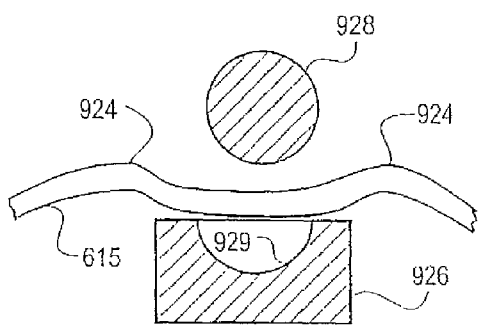

In certain orthodontic situations, loops may need to be bent in the wires. FIG. 120 illustrates a loop 922 formed in a wire 615. The loop may be formed by the robot of FIG. 90. Alternatively, only the peripheral corners 924 of the loop 920 are formed by the bending robot, as shown in FIG. 121A, with the remainder of the loop formed by placing the wire over a die 926 having a shape 928 matching the shape of the bottom portion 930 of the loop 920. A forming tool 928 is moved against the wire and die 926 to form the bottom portion of the loop as indicated in FIG. 121B.

The robot may also include a separate arm or tooling by which stops, or other features are bonded to the wire by suitable techniques such as welding. For example, the robot can be fitted with other tools for forming a Herbst appliance or expansion devices. Alternatively, different types of wires could be joined together by welding.

The robot may also be used to bend clear, transparent wires made from polymeric or plastic materials, such as thermoplastics, duroplastics, polyacrylic plastics, epoxy plastics, thermoplastics, fiber reinforced composites, glass fiber containing materials or other similar materials suitable for an orthodontic archwire. These plastics archwires may require heating during bending, but current sources may not be suitable heating devices. Recommended techniques for heating the plastic wire include blowing hot air over the wires during bending, using heated pliers, placing a heat conductive material onto the wire, using a laser to heat the wire, or spraying a hot vapor or liquid onto the wire.

As noted above, additional possibilities are presented for bending fixation plates, orthotic devices, prosthetic devices, endodontic devices, surgical guidewires, surgical archbars, implants or surgical tools with the robot manufacturing system. The gripper fingers and associated structures may be optimized depending on the workpiece or appliance in question. However, the principles of operation are basically the same.

For example, the robot of the present invention is particularly useful for bending fixation plates, rods, compression plates and the like, for example facial, cranial, spinal, hand, and long bone and other osteosynthesis plates, such as, for example, the titanium appliances provided by Leibinger Gmbh of Germany. These fixation plates may consists of, for example, an elongate skeletal frame having a plurality of apertures for receiving screws, arranged in straight lengths, C, Y, J H, T or other shape configurations, or a long cylindrical rod. At the present, these appliances are manually bent by the surgeon to the shape of the bone in the operating room using special manual bending tools. It is possible to automate this process and bend the plates in advance using the principles of the present invention. In particular, the shape of the bone or bone fragments is obtained a CAT scan, from a scan of the exposed bone using a hand-held scanner (such as described above. Once a three-dimensional virtual model of the bone is obtained, e.g., from CAT scan data, the virtual model is manipulated using a computer to fuse the bones together in the desired position. The surgeon then overlays the three-dimensional virtual implant in the desired location on the virtual model, and bends the virtual implant using the user interface of a general purpose computer storing the virtual model of the bone and implant. The required shape of the implant to fit the bone in the desired location is derived.

Alternatively, a physical model of the bone in the desired configuration can be manufactured from the virtual model using stereolithography (SLA), three-dimensional lithography, or other known technology, and the shape of the implant derived from the physical model.

As another alternative, a SLA physical model of the bones (e.g., skull) is made from a CT scan or other source, and the surgeon performs a simulated surgery on the physical model to place the bones in the desired condition. The model is then scanned with an optical scanner and a virtual model of the bones in the desired condition is obtained, as described in the patent application of Rudger Rubbert et al., cited above. The virtual fixation device is then compared or fitted to the virtual model of the bones to arrive at a desired shape of the fixation device.

In either situation, the shape of the implant is then translated to the robot controller as a series of straight sections and bends of known geometry (and specifically position commands for the moveable gripping tool relative to the fixed gripping tool). The moveable and fixed gripping tools of the bending device grip the implant or fixation device at one end and then either bend the appliance or advance the position of the implant to the location of the next bend, and continue along the length of the device to form the device in the desired configuration. Obviously, some modification to the gripping tools may be needed from the disclosed embodiment depending on the physical characteristics of the device being bent, and such modifications are within the ability of persons skilled in the art.

The bending apparatus described above is also adaptable to generic workpieces, such as tubes, cylinders, wires or other types of structures.

The bending apparatus may use resistive heating, force sensors, overbending, and the other features described at length in the context of orthodontic archwires, depending on the application for other workpieces.

Bonding Pads

Customized bracket pads can be manufactured using a variety of techniques. One possibility is to bond a blob of adhesive to a bracket base, and mill the blob using a milling machine to match the tooth surface. Since the tooth surface is known precisely from the scanning, and the position of the bracket base relative to the surface is also known precisely, a very accurate bracket pad can be manufactured in this fashion. Another technique is to stamp out a bracket pad using stamping machine either in the desired shape or as a blank and milling the stamped pad to the desired shape. A third possibility is creating a negative of the customized pad, forming the pad in a mold, bonding the pad to the bracket and the orthodontist trimming the pad as necessary when the pad is bonded to the tooth.

Since the treatment planning software gives precise information as to the location of the bracket relative to the tooth surface in three dimension, the shape of the customized bonding pad can be determined with high precision. This shape is transferred to a suitable milling machine using known techniques and the pad is milled in accordance with the desired shape. The pad is then affixed to the bracket (either at the precision appliance center or at the orthodontic clinic and the bracket+pad bonded to the tooth.

While presently preferred embodiments of the invention have been described for purposes of illustration of the best mode contemplated by the inventors for practicing the invention, wide variation from the details described herein is foreseen without departure from the spirit and scope of the invention. This true spirit and scope is to be determined by reference to the appended claims. The term "bend", as used in the claims, is interpreted to mean either a simple translation movement of the workpiece in one direction or a twist (rotation) of the workpiece, unless the context clearly indicates otherwise.

The invention claimed is:

1. A method of generating a 3-dimensional virtual model of a bite for a patient, comprising the steps of:
   obtaining individual virtual tooth models for teeth of a patient in upper jaw and in lower jaw;
   scanning surface of said teeth of said patient in a clenched condition thereby generating a series of frames of images of said scanned surface; and
   registering said frames using a frame-to-frame registration algorithm with said individual virtual tooth models; thereby generating said 3-dimensional virtual model of said bite for said patient.

2. The method of claim 1, wherein said scanning is performed in-vivo.

3. The method of claim 1, wherein said scanning is performed by a hand-held scanner.

4. The method of claim 3, wherein said hand-held scanner is adapted for intra-oral scanning and comprises a light source, an electronic imaging device and a pattern source, said light source projecting a pattern onto said dentition, said electronic imaging device converting incident radiation into a two dimensional image of the pattern as reflected from said dentition.

5. The method of claim 4, wherein said hand-held scanner further comprises a continuous illumination light source providing general illumination of the dentition during scanning.

6. The method of claim 1, wherein said scanning is performed using a CAT scan.

7. The method of claim 1, wherein said 3-dimensional virtual model is refined using a cumulative registration algorithm.

8. The method of claim 7, wherein said 3-dimensional virtual model comprises two or more segments, and wherein said segments are registered using a segment registration algorithm.

9. The method of claim 1, wherein a clipping plane is utilized in order to view a cross-section of said 3-dimensional virtual model of said bite.

10. The method of claim 9, wherein viewing said cross-section enables inspecting contact points between said teeth in the upper jaw and in the lower jaw.

11. The method of claim 1, wherein a user can adjust said 3-dimensional virtual model of said bite.

12. The method of claim 1, wherein a user can move or rotate said teeth in the lower jaw relative to the upper jaw.

13. The method of claim 1, wherein a user can simulate a chewing motion of said teeth in the upper jaw and the lower jaw.

14. The method of claim 13, wherein during the simulation the lower jaw moves from side to side and up and down to simulate a chewing motion.

* * * * *